US006878733B1

(12) United States Patent
Shenoy et al.

(10) Patent No.: US 6,878,733 B1
(45) Date of Patent: Apr. 12, 2005

(54) FORMULATIONS FOR PHARMACEUTICAL AGENTS IONIZABLE AS FREE ACIDS OR FREE BASES

(75) Inventors: Narmada Shenoy, Sunnyvale, CA (US); Waranush Sorasuchart, Bangkok (TH); Arun Koparkar, San Jose, CA (US)

(73) Assignee: Sugen, Inc., South San Francisco, CA (US)

( * ) Notice: Subject to any disclaimer, the term of this patent is extended or adjusted under 35 U.S.C. 154(b) by 295 days.

(21) Appl. No.: 09/716,332

(22) Filed: Nov. 21, 2000

Related U.S. Application Data

(60) Provisional application No. 60/167,544, filed on Nov. 24, 1999.

(51) Int. Cl.$^7$ .............................................. A61K 31/415
(52) U.S. Cl. ....................... 514/397; 514/406; 514/418; 514/422; 514/426
(58) Field of Search .............................. 514/397, 418, 514/422, 426, 406

(56) References Cited

U.S. PATENT DOCUMENTS

| | | | | |
|---|---|---|---|---|
| 4,002,749 | A | 1/1977 | Rovnyak et al. | 424/246 |
| 4,053,613 | A | 10/1977 | Rovnyak et al. | 424/246 |
| 4,966,849 | A | 10/1990 | Vallee et al. | 435/199 |
| 5,217,999 | A | 6/1993 | Levitzki et al. | 514/613 |
| 5,302,606 | A | 4/1994 | Spada et al. | 514/357 |
| 5,330,992 | A | 7/1994 | Eissenstat et al. | 514/312 |
| 5,786,488 | A | 7/1998 | Tang et al. | 548/455 |
| 5,792,783 | A | * 8/1998 | Tang et al. | 514/397 |
| 5,840,745 | A | 11/1998 | Buzzetti et al. | 514/414 |
| 5,880,141 | A | 3/1999 | Tang et al. | 514/339 |
| 5,883,113 | A | 3/1999 | Tang et al. | 514/418 |
| 5,883,116 | A | 3/1999 | Tang et al. | 514/418 |
| 5,886,020 | A | 3/1999 | Tang et al. | 514/418 |
| RE36,256 | E | 7/1999 | Spada et al. | 514/249 |

FOREIGN PATENT DOCUMENTS

| | | |
|---|---|---|
| EP | 0 252 731 A2 | 1/1988 |
| EP | 0 304 493 | 3/1989 |
| EP | 0 566 226 A1 | 10/1993 |
| EP | 0 934 931 A2 | 8/1999 |
| EP | 0 934 931 A3 | 8/1999 |
| FR | 1 599 772 | 7/1970 |
| WO | 91/13055 | 9/1991 |
| WO | 91/15495 | 10/1991 |
| WO | 92/07830 | 5/1992 |
| WO | 92/20642 | 11/1992 |
| WO | 92/21660 | 12/1992 |
| WO | 93/01182 | 1/1993 |
| WO | 93/23040 | 11/1993 |
| WO | 94/03427 | 2/1994 |
| WO | 94/10202 | 5/1994 |
| WO | 94/14808 | 7/1994 |
| WO | 95/01349 | 1/1995 |
| WO | 95/14667 | 6/1995 |
| WO | 95/24190 | 9/1995 |
| WO | 96/00226 | 1/1996 |
| WO | 96/16964 | 6/1996 |
| WO | 96/22976 | 8/1996 |
| WO | 96/32380 | 10/1996 |
| WO | 96/40116 | 12/1996 |
| WO | 98/07695 | 2/1998 |
| WO | 98/07835 | 2/1998 |
| WO | 98/24432 | 6/1998 |
| WO | 98/38984 | 9/1998 |
| WO | 98/45708 | 10/1998 |
| WO | 98/50356 | 11/1998 |
| WO | 98/56376 | 12/1998 |
| WO | 99/10325 | 3/1999 |
| WO | 99/19325 | 4/1999 |
| WO | 99/48868 | 9/1999 |
| WO | 99/61422 | 12/1999 |
| WO | 00/08202 | 2/2000 |
| WO | 00/35908 | 6/2000 |
| WO | 00/38519 | 7/2000 |
| WO | 00/56709 | 9/2000 |

OTHER PUBLICATIONS

Stein, Jay, Editor–in–Chief, Internal Medicine, 4$^{th}$ Edition, Chapters 71–72, pp. 699–715, 1994.*

Akbasak and Sunar–Akbasak., "Oncogenes: cause or consequence in the development of glial tumors," *J. Neurol. Sci.* 111:119–133 (1992).

Andreani et al., "Synthesis and potential coanthracyclinic activity of substituted 3–(5–imidazo2,1–bithiazolylmethylene)–2–indolinones," *Eur. J. Med. Chem.* 32:919–924 (1997) ©Elsevier, Paris.

Andreani et al., "In vivo cardiotonic activity of pyridylmethylene–2–indolinones" *Arzneimittel–Forschung Drug Research* 48(II): 727–729 (1998).

Andreani et al., "Synthesis and cardiotonic activity of 2–indolinones," *Eur. J. Med. Chem.* 25(2):187–190 (1990).

Arteaga et al., "Blockade of the Type 1 Somatomedin Receptor Inhibits Growth of Human Breast Cancer Bells in Athymic Mice," *J. Clin. Invest.* 84:1418–1423 (1989) ©The American Society for Clinical Investigation, Inc.

(Continued)

*Primary Examiner*—Dwayne C. Jones
(74) *Attorney, Agent, or Firm*—Beth A. Burrous; Foley & Lardner

(57) ABSTRACT

The present invention features formulations of indolinones which compounds are ionizable as free acids or free bases. The formulation is suitable for parenteral or oral administration, wherein the formulation comprises an ionizable substituted indolinone, and a pharmaceutically acceptable carrier therefor. The term "ionizable substituted indolinone" includes pyrrole substituted 2-indolinones which, in addition to being otherwise optionally substituted on both the pyrrole and 2-indolinone portions of the compound, are necessarily substituted on the pyrrole moiety with one or more hydrocarbon chains which themselves are substituted with at least one polar group. The formulations and the compounds themselves are useful for the treatment of protein kinase related disorders as discussed herein.

73 Claims, No Drawings

OTHER PUBLICATIONS

Arvidsson et al., "Try–716 in the Platelet–Derived–Growth–Factor β–Receptor Kinase Insert is Involved in GRB2 Binding and Ras Activation," *Molecular and Cellular Biology* 14(10):6715–6726 (1994) ©The American Society for Microbiology.

Baserga, "Oncogenes and the Strategy of Growth Factors," *Cell* 79:927–93 (1994) ©Cell Press.

Baserga, "The Insulin–like Growth Factor I Receptor: A Key to Tumor Growth?" *Cancer Research* 55:249–252 (1995).

Bolen et al., "The Src family of tyrosine protein kinases in hemopoietic signal transduction," *FASEB J.* 6:3403–3409 (1992).

Bolen, "Nonreceptor tyrosine protein kinases," *Oncogene* 8:2025–2031 (1993) ©MacMillan Press Ltd.

Bonner et al., "Structure and Biological Activity of Human Homologs of a raf–mil Oncogene," *Molecular and Cellular Biology* 5:1400–1407 (1985) ©The American Society for Microbiology.

Cance et al., "Novel Protein Kinases Expressed in Human Breast Cancer," *Int. J. Cancer* 54:571–577 (1993) ©Wiley–Liss, Inc.

Carpenedo et al., "Identification and Measurement of Oxindole (2–Indolinone) in the Mammalian Brain and Other Rat Organs" *Analytical Biochemistry* 244:74–79 (1997) ©Academic Press, Inc.

Chen et al., "Effects of 3,3–Dipyridylmethyl–1–Phenyl–2–Indolinone on γ–Aminobutyric Acid Elicited Chloride Current of Snail Central Neuron" *Chinese Journal of Physiology* 40(3):149–156 (1997).

Claesson–Welsh, "Signal Transduction by the PDGF Receptor," *Progress in Growth Factor Research* 5:37–54 (1994) ©Elsevier Science Ltd.

Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994) ©The American Society for Microbiology.

Damiani et al., "Inhibition of Copper–Mediated Low Density Lipoprotein Peroxidation by Quinoline and Indolinone Nitroxide Radicals," *Biochemical Pharmacology* 48(6):1155–1161 (1994) ©Elsevier Science Ltd.

Davis et al., "Synthesis and microbiological properties of 3–Amino–1–Hydroxy–2–Indolinone and Related Compounds," *Journal of Medicinal Chemistry* 16(9):1043–1045 (1973) ©American Chemical Society.

De Vries et al., "The fms–Like Tyrosine Kinase, a Receptor for Vascular Endothelial Growth Factor," *Science* 255:989–991, 1991.

Decker and Lohmann–Matthes, "A quick and simple method for the quantitation of lactate deydrogenase release in measurements of cellular cytotoxicity and tumor necrosis factor (TNF) activity," *J. Immunol. Methods* 15:61–69 (1988) ©Elsevier.

Decodts et al., "Suicide inhibitors of proteases. Lack of activity of halomethyl derivatives of some aromatic lactams," *Eur. J. Med. Chem.—Chim. Ther.*, 18(2):107–111 (1983).

Dickson et al., "Tyrosine kinase receptor—nuclear protooncogene interactions in breast cancer," *Cancer Treatment Res.* 61:249–273 (1992) ©Kluwer Academic Publishers.

Fantl et al., "Distinct Phosphotyrosines on a Growth Factor Receptor Bind to Specific Molecules that Mediate Different Signaling Pathways," *Cell* 69:413–423 (1992) ©Cell Press.

Fendly et al., "Characterization of Murine Monoclonal Antibodies Reactive to Either the Human Epidermal Growth Factor Receptor or HER2–neu Gene product," *Cancer Research* 50:1550–1558 (1990) (mistakenly referred to as Fendley).

Ferrara and Henzel, "Pituitary Fillicular Cells Secrete a Novel Heparin–Binding Growth Factor Specific for Vascular Endothelial Cells," *Biochemical and Biophysical Research Communications* 161:851–858 (1989) ©Academic Press, Inc.

Fingl and Woodbury, "Chapter 1—General Principles," in *The Pharmacological Basis of Therapeutics* $5^{th}$ edition, Goodman and Gilman editors, MacMillan Publishing Co., Inc., New York, pp. 1–46 (1975) ©MacMillam Publishing Co., Inc.

Floege et al., "Heparin suppresses mesangial cell proliferation and matrix expansion in experimental mesangioproliferative glomerulonephritis," *Kidney International* 43:369–380 (1993) ©International Society of Nephrology.

Floege et al., "Factors involved in the regulation of mesangial cell proliferation in vitro and in vivo," *Kidney International* 43:S47–S54 (1993) ©International Society of Nephrology.

Folkman and Shing, "Angiogenesis," *J. Bio. Chem.* 267:10931–10934 (1992) ©The American Society for Biochemistry and Molecular Biology.

Folkman, "Ch. 24. Angiogenesis," *Congress of Thrombosis and Haemostasis* (Verstraete et al., eds.) Leuven University Press, Leuven pp. 583–596 (1987).

Folkman, "Tumor Angiogenesis, Therapeutic Implications," *New England J. Medicine* 285:1182–1186 (1971).

Folkman, "What Is Evidence that Tumors Are Angiogenesis Dependent?" *Journal of National Cancer Institute* 82:4–6 (1990).

Gazit et al., "Tyrphostins. 2. Heterocyclic and alpha–substituted benzylidenmalononitrile tyrphostins as potent inhibitors of EGF receptor and ErbB2–neu tyrosine kinases," *J. Med. Chem.* 34(6):1896–1907 (1991) ©American Chemical Society.

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301–326 (1991).

Graziani et al., "Hepatocyte Growth Factor/Scatter Factor Stimulates the Ras–Guanine Nucleotide Exchanger," *The Journal of Biological Chemistry* 268(13):9165–9168 (1993) ©American Society for Biochemistry and Molecular Biology.

Hayler, et al., "Development of Large–Scale Synthesis of Ropinirole in the Pursuit of a Manufacturing Process," *Org. Process Res. Dev.* 2:(1):3–9 (1998) ©The American Chemical Society and Royal Society of Chemistry.

Hirao et al., "Rhodium–catalyzed carbonylation of 2–alkynylanillines: stynctheses of 1,3–dihydroindol–2–ones," *Tetrahedron Lett.* 36(35):6243–6246 (1995) ©Pergamon.

Honegger et al., "Point Mutation at the ATP Binding Site of EGF Receptor Abolishes Protein–Tyrosine Kinase Activity and Alters Cellular Routing," *Cell* 51:199–209 (1987) ©Cell Press.

Houck et al. "Dual Regulation of Vascular Endothelial Growth Factor Bioavailability by Genetic and Proteolytic Mechanisms," *J. Biol. Chem.* 267:26031–26037 (1992) ©American Society for Biochemistry and Molecular Biology, Inc.

Hu et al., "Interaction of Phosphatidylinositol 3–Kinase–Associated p85 with Epidermal Growth Factor and Platelet–Derived Growth Factor Receptors," *Molecular and Cellular Biology* 12(3):981–990 (1992) ©Am. Soc. Microbiol.

Jellinek et al., "Inhibition of Receptor Binding by High–Affinity RNA Ligands to Vascular Endothelial Growth Factor," *Biochemistry* 33:10450–10456 (1994) ©Am. Chemical Society.

Kashishian and Cooper, Phosphorylation Sites at the C–terminus of the Platelet–Derived Growth Factor Receptor Bind Phospholipase Cγ1, *Molecular Biology of the Cell* 4:49–57 (1993) ©The American Society for Cell Biology.

Kashishian et al., "Phosphorylation Sites in the PDGF receptor with Different Specificities for Binding GAP and P13 Kinae in vivo," *The EMBO Journal* 11(4):1373–1382 (1992).

Millauer et al., "High Affinity VEGF Binding and Developmental Expression Suggest Flk–1 as a Major Regulator of Vasculogenesis and Angiogenesis," *Cell* 72:835–846 (1993) ©Cell press.

Mohammadi et al., "Structures of the tyrosine kinase domain of fibroblast growth factor receptor in complex with inhibitors," *Science* 276(5314):955–960 (1997) ©American Association for the Advancement of Science.

Moreto et al. "3,3–bis–(4–hydroxyphenyl)–7–methyl–2–indolinone (BHMI), the active metabolite of the laxative sulisatin" *Arzneimittel–Forschung Drug Research* 29(II):1561–1564 (1979).

Moreto et al., "Study of the laxative properties of the disodium salt of the sulfiuric diester of bis–(4–hydroxyphenyl)–7–methyl–2indolinone (Dan–603) in the rat," *European Journal of Pharmacology* 36:221–226 (1976) ©North–Holland Publishing Company.

Morrison et al., "Signal Transdution from Membrane to Cytoplasm: Growth Factors and Membrane–Bound Oncogene Products Increases Raf–1 Phosphorylation and Associated Protein Kinase Activity," *Proc. Natl. Acad. Sci. USA* 85; 8855–8859 (1988).

Mosmann, "Rapid Colorimetric Assay for Cellular Growth and Survival: Application to Proliferation and Cytotoxicity Assays," *J. Immunol. Methods* 65:55–63 (1983) ©Elsevier Publishers B.V.

Nishimura et al., "Two Signaling Molecules Share a phosphotyrosine–Containing Binding Site in the Platelet–Derived Growth Factor Receptor," *Molecular and Cellular Biology* 13:6889–6896 (1993).

Plowman et al., "Receptor Tyrosine Kinases as Targets for Drug Intervention," *DN&P* 7(6):334–339 (1994).

Quinn et al., "Fetal Liver Kinase 1 as a Receptor for Vascular Endothelial Growth Factor and is Selectively Expressed in Vascular Endothelium," *Proc. Natl. Acad. Sci. USA* 90:7533–7537 (1993).

Rozakis–Adcock et al., "Association of the Shc and Grb2–Sem5 SH2–containing proteins is implicted in activation of the Ras pathway by tyrosine kinases," *Nature* 360:689–692 (1992).

Rygaard and Povlsen, "Heterotransplantation of a Human Malignant Tumor to 'Nude' Mice," *Acta path. microbiol. scand.* 77:758–760 (1969).

Sainsbury, et al., "Electrochemical oxidation of aromatic ethers. Part 5. Further studies of the coupling reactions of alkoxylated aralkyl and aryl amides," *J. Chem. Soc.*, 1:108–114 (1979).

Sandberg–Nordqvist et al., "Characterization of Insulin–Like Growth Factor 1 in Human Primary Brain Tumors," *Cancer Research* 53:2475–2478 (1993).

Schlessinger and Ullrich, "Growth Factor Signalling by Receptor Tyrosine Kinases," *Neuron* 9:383–391 (1992) ©Cell Press.

Shibuya et al., "Nucleotide Sequence and Expression of a Novel Human Receptor–Type Tyrosine Kinase Gene (flt) closely related to the fms fmaily", *Oncogene* 5:519–524 (1990).

Singh et al., "Indolinone derivatives as potential antimicrobial agents," *Zentralbl. Mikrobiol.* 144:105–109 (1989) ©VEB Gastav Fischs veslag.jena.

Singh et al., "Synthesis and Anticonvulsant Activity of New 1–Substituted 1'–Methyl–3–Chloro–2–Oxosprio (Azetidin–3', 4–Indol–2' Ones)," *Bollettino Chimico Farmaceutico*133:76–79 (1994).

Slamon et al., "Studies of the HER–2–neu Proto–oncogene in Human Breast and Ovarian Cancer," *Science* 244:707–712 (1989).

Soldi et al., "Platelet–activating factor (PAF) induces the early tyrosine phosphorylation of focal adhesion kinase ($p125^{FAX}$) in human endothelial cells," *Oncogene* 13(3):515–525 (1996) ©Stockton Press.

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993) ©Elsevier Science.

Kazlauskas et al., "The 64–kDa Protein That Associates with the Platelet–Derived Growth Factor Receptor β Subunit via Tyr–1009 Is The SH2–Containing Phosphotyrosine Phosphatase Syp," *Proc. Natl. Acad. Sci. USA* 90:6939–6942 (1993).

Kendall and Thomas, "Inhibition of vascular endothelial cell growth factor activity by an endogenously encoded soluble receptor," *Proc. Natl. Acad. Sci. USA* 90:10705–10709 (1993).

Kikumoto, et al., "Reactions of oxindoles an disatin with nitrobenzyl chlorides. Formation of 2'–hydroxyspiro'2H–indole–2, 3' –3'H–indole!," *Tetrahedron* 22(10):3337–3343 (1966) ©Pergamon Press Ltd.

Kim et al., "Inhibition of vascular endothelial growth factor–induced angiogenesis suppressed tumor growth in vivo," *Nature* 362–841–844 (1993).

Kinsella et al., "Protein Kinase C Regulates Endothelial Cell Tube Formation on Basement Membrane Matrix, Matrigel," *Exp. Cell Research* 199:56–62 (1992) ©Academic Press Inc.

Klagsburn and Soker, "VEGF–VPF: The Angiogenesis Factor Found?" *Current Biology* 3:699–702 (1993) ©Current Biology.

Koch et al., "SH2 and SH3 Domains: Elements That Control Interactions of Cytoplasmic Signaling Proteins," *Science* 252:668–674 (1991).

Komada and Kitamura, "The cell dissociation and motility triggered by scatter factor–hepatocyte growth factor are mediated through the cytoplasmic domain of the c–Met receptor," *Oncogene* 8:2381–2390 (1993).

Korc et al., "Overexpression of the Epidermal Growth Factor Receptor in Human Pancreatic Cancer is Associated with Concomitant increases in the Levels of Epidermal Growth Factor and Transforming Growth Factor Alpha," *J. Clin. Invest.* 90:1352–1360 (1992) ©The American Society for Clinical Investigation, Inc.

Korzeniewski and Callewaert,"An Enzyme–Release Assay for Natural Cytotoxicity," *J. Immunol. Methods* 64:313–320 (1983) ©Elsevier Science Publishers.

Kumabe et al., "Amplification of α–platelet–derived growth factor receptor gene lacking an exon coding for a portion of the extracellular region in a primary brain tumor of glial origin," *Oncogene* 7:627–633 (1992).

Lal et al., "Novel diuretic agents. Syntheses of substituted isatylidenes and 3–alkyl or 3–arylalkyl–2–oxindoles," *Indian J. Chem* 13(9):898–903 (1975).

Lee and Donoghue, "Intracellular retention of membrane–anchored v–sis protein abrogates autocrine signal transduction," *Journal of Cell Biology* 118:1057–1070 (1992) ©The Rockefeller University Press.

Levitzki et al., "Tyrosine kinase inhibition: An approach to drug development," *Science* 267:1782–1788 (1995).

Maass et al., "Viral resistance to the thiazolo–iso–indolinoes, a new class of nonnucleoside inhibitors of human immunodeficiency virus type 1 reverse transcriptase," *Antimocrobial Agents and Chemotherapy* 37(12)2612–2617 (1993) ©American Society for Microbiology.

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," *Experimental Therapeutics—Proceedings of the American Association for Cancer Research* 35:381 at abstract No. 2268 (Mar. 1994).

Songyang et al., "SH2 Domain Recognize Specific Phosphopeptide Sequences," *Cell* 72:767–778 (1993) ©Cell Press.

Songyang et al., "Specific Motifs Recognized by the SH2 Domains of Csk, 3PB2, fps–fes, GBR–2, HCP, SHC Syk and Vav," *Molecular and Cellular Biology* 14:2777–2785 (1994) ©American Society for Microbiology.

Spada et al., "Small molecule inhibitors of tyrosine kinase activity," *Expert Opinion on Therapuetic Patents* 5(8):805–817 (1995) ©Ashley Publications.

Sun et al., "Synthesis and biological evaluations of 3–substituted indolin–2–ones: A novel class of tyrosine kinase inhibitors that exhibit selectivity toward particular receptor tyrosine kinases," *J. Med. Chem.* 41(14):2588–2603 (1998) ©The American Chemical Society.

Sun et al., "Design, Synthesis, and Evaluations of Substituted 3–[(3–or4–Carboxyethyipyrrol–2–yl)methylidenyl] indolin–2–ones as Inhibitors of VEGF, FGF, and PDGF Receptor Tyrosine Kinases," *J. Med. Chem.*, (42):5120–5130 (1999). ©American Chemical Society.

Superti–Furga et al., "A functional screen in yeast for regulators and antagonizers of heterologous protein tyrosine kinases," *Nature Biotech* 14:600–605 (1996).

Superti–Furga et al., "Csk inhibition of c–Src activity requires both the SH2 and SH3 domains of Src," *EMBO J.* 12:2625–2634 (1993) ©Oxford University Press.

Takano et al., "Inhibition of antiogenesis by a novel diaminoanthraquinone that inhibits protein kinase C," *Mol. Bio. Cell* 4:358A at abstract No. 2076 (1993).

Thio et al., "Interconversion of 2–(2–aminophenyl)–3–piperoliidinone and 3–(2–piperidylmethyl)–2–indolinone. Reversible N.dbr.N' transacylation" *J. Heterocycl. Chem.*, 8(3):479–482 (1971).

Torp et al., "Expression of the Epidermal Growth Factor Receptor Gene in Human Brain Metastases," *AMPIS* 100:713–719 (1992).

Traxler, "Protein tyrosine kinase inhibitors in cancer treatment," *Expert Opinion on Therapeutic Patents* 7(6):571–588 (1997) ©Ashley Publications Ltd.

Tsai et al., "The effect of 3,3–Di–Pyridyl–Methyl–1–Phenyl–2–indoline on the nerve Terminal Currents of Mouse Skeletal Muscles," *Neuropharmacology* 31(9):943–947 (1992) ©Pergamon Press.

Tuzi et al., "Expression of growth factor receptors in human brain tumours," *Br. J. Cancer* 63:227–233 (1990).

Twamley–Stein et al., "The Src Family Tyrosine Kinases are Required for Platelet–Derived Growth Factor–Mediated Signal Transduction in NIH 3T3 Cells," *Proc. Natl. Acad. Sci.*, 90:7696–7700 (1993).

Vaisman et al., "Characterization of the Receptors for Vascular Endothelial Growth Factor," *J. Biol. Chem.* 265:19461–19466 (1990) ©The American Society for Biochemistry and Molecular Biology.

Varma and Gupta, "Nucleophilic Reactions of 2–Methyl–3–(4'–carbomethoxyphenyl)–4–quinazolinones with 2–Indolinones," *J. Indian Chem. Soc.* 66:804–805 (1989) ©The Indian Chemical Society.

Voller et al., "Ch. 45—Enzyme–Linked Immunosorbent Assay," in *Manual of Clinical Immunology*, $2^{nd}$ edition, Rose and Friedman editors, American Society of Microbiology, Washington, D.C., pp. 359–371 (1980).

Walker, "The Reduction of Insoindogenides, Nitro Compounds, and Pyridines in a Series of 2–Indolinones," *J. Med. Chem.* 8(5):626–637 (1965).

Weidner et al. "Tumor Angiogenesis and Metastasis–Correlation in Invasive Breast Carcinoma," *New England Journal of Medicine* 324(1):1–8 (1991) ©Massachusetts Medical Society.

Wright et al., "Inhibition of Angiogenesis in Vitro and In Ovo With an Inhibitor of Cellular Protein Kinases, MDL 27032," *J. Cellular Physiology* 152:448–457 (1992).

Zaman et al., "Tyrosin Kinase Activity of Purified Recombinant Cytoplasmic Domain of Platelet–Derived Growth Factor β–Receptor (β–PDGFR) and Discovery of a Novel Inhibitor of Receptor Tyrosine Kinases," *Biochemical Pharmacology* 57(1):57–64 (1999) ©Elsevier Science Inc.

Zhang et al., "Microtubule Effects of Weivistatin, a Cyanobacterial Indolinone that Circumvents Multiple Drug Resistance," *Molecular Pharmacology* 49:228–294 (1996) ©The American Society for Pharmacology and Experimental Pharmaceutics.

\* cited by examiner

FORMULATIONS FOR PHARMACEUTICAL AGENTS IONIZABLE AS FREE ACIDS OR FREE BASES

The present application claims priority to U.S. app. Ser. No. 60/167,544, filed Nov. 24, 1999, which is hereby incorporated by reference.

FIELD OF THE INVENTION

The instant invention provides formulations for compounds, such as pyrrole substituted 2-indolinones, which compounds are ionizable as free acids or free bases. Also provided are methods of making and using the formulations of the invention.

BACKGROUND OF THE INVENTION

The following description of the background of the invention is provided to aid in understanding the invention, but is not admitted to describe or constitute prior art to the invention. Various methods are available for administering therapeutic agents to a patient. Such methods include parenteral, oral, ocular, nasal, topical, and transmucosal administration. Variations of these different types of administrations exist. For example, parenteral administration includes intravenous, subcutaneous, intraperitoneal, intramuscular, intraosseous, and intramedullary injection. The chosen mode of administration should take into account the nature of the therapeutic compound and the illness being treated.

Certain potential pharmaceuticals are hydrophobic and typically have very low aqueous solubility and hence low oral bioavailability. Different techniques concerned with solubilizing hydrophobic compounds include those described by Praveen et al., U.S. Pat. No. 5,314,685, and Fernandes et al., U.S. Pat. No. 4,992,271, both of which are hereby incorporated by reference herein in their entirety, including any figures, tables, and drawings.

One measure of the potential usefulness of an oral formulation of a new pharmaceutical agent is the bioavailability observed after oral administration of the formulation. Various factors can affect the oral bioavailability of the drug. These factors include aqueous solubility, drug absorption throughout the gastrointestinal track, drug stability in gastrointestinal tract, and first pass effect. Aqueous solubility is one of the most important factors. The oral bioavailability of an aqueous solution formulation of a drug is generally used as the standard or the idea bioavailability against which other oral formulations are measured. Formulations of drugs that increase the relative bioavailability of the drug as compared to an aqueous solution are desirable, especially with hydrophobic compounds.

SUMMARY OF THE INVENTION

The instant invention features formulations for compounds, such as indolinones, which compounds are ionizable as free acids or free bases.

In one aspect, the invention features a formulation suitable for parenteral or oral administration, said formulation comprising an ionizable substituted indolinone, and a pharmaceutically acceptable carrier therefor.

The term "ionizable substituted indolinone" as used herein includes pyrrole substituted 2-indolinones which, in addition to being otherwise optionally substituted on both the pyrrole and 2-indolinone portions of the compound, are necessarily substituted on the pyrrole moiety with one or more hydrocarbon chains which themselves are substituted with at least one polar group. Physiologically acceptable salts and prodrugs of the claimed compounds are also within the scope of this invention.

A "hydrocarbon chain" refers to an alkyl, alkenyl or alkynyl group, as defined herein.

A "polar" group refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), ammonium, amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like.

While not being bound to any particular theory, applicants at this time believe that the polar groups may interact electronically, for example, but without limitation, through hydrogen bonds, Van der Walls forces and/or ionic bonds (but not covalent bonding), with the amino acids at a protein tyrosine kinsase (PTK) active site. The PTK active site is involved with ligand binding (or similar interaction) that contributes to cellular response. These interactions may assist the molecules of this invention to bind to an active site with sufficient tenacity to interfere with or prevent the natural substrate from entering the site. Polar groups may also contribute to the selectivity of the compounds; i.e:, one polar group may have greater affinity for a PTK binding domain than other polar groups so that the compound containing the first particular polar group is more potent than the compounds containing the other polar groups.

Thus, the "pyrrole substituted 2-indolinones" contemplated for use in the present invention include compounds having the following chemical structure:

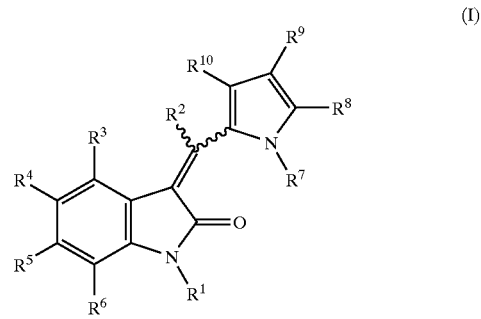

(I)

$R^1$ is selected from the group consisting of hydrogen, alkyl, alkenyl, alkynyl, cyloalkyl, aryl, hydroxy, alkoxy, C-carboxy, O-carboxy, acetyl, C-amido, C-thioamido, sulfonyl and trihalomethanesulfonyl.

$R^2$ is selected from the group consisting of hydrogen, halo, alkyl, cycloalkyl, aryl, heteroaryl and heteroalicyclic.

$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$.

R$^{11}$ and R$^{12}$ are independently selected from the group consisting of hydrogen, alkyl, cycloalkyl, aryl, heteroaryl, carbonyl, acetyl, sulfonyl, trifluoromethanesulfonyl and, combined, a five- or six-member heteroalicyclic ring.

R$^3$ and R$^4$, R$^4$ and R$^5$, and R$^6$ may combine to form a six-member aryl ring, a methylenedioxy group or an ethylenedioxy group.

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl.

R$^8$, R$^9$ and R$^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino and —NR$^{11}$R$^{12}$, providing, however that at least one of R$^8$, R$^9$ or R$^{10}$ is a group having the formula -(alk$_1$)Z. Alternatively, R$^8$ and R$^9$ or R$^9$ and R$^{10}$ may combine to form a six-members alicyclic ring.

Alk$_1$ is selected from the group consisting of alkyl, alkenyl, or alkynyl.

Z is a polar group.

In an embodiment of an oil suspension formulation, the active compound comprises a compound of formula I:

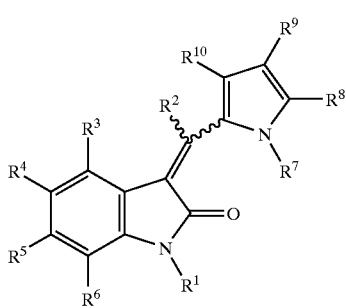

(I)

R$^1$ is selected from the group consisting of hydrogen, alkyl, alkenyl, alkynyl, cycloalkyl, aryl, hydroxy, alkoxy, C-carboxy, O-carboxy, acetyl, C-amido, C-thioamido, sulfonyl and trihalomethanesulfonyl.

R$^2$ is selected from the group consisting of hydrogen, halo, alkyl, cycloalkyl, aryl, heteroaryl and heteroalicyclic.

R$^3$, R$^4$, R$^5$ and R$^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$.

R$^{11}$ and R$^{12}$ are independently selected from the group consisting of hydrogen, alkyl, cycloalkyl, aryl, heteroaryl, carbonyl, acetyl, sulfonyl, trifluoromethanesulfonyl and, combined, a five- or six-member heteroalicyclic ring.

R$^3$ and R$^4$, R$^4$ and R$^5$, R$^5$ and R$^6$ may combine to form a six-member aryl ring, a methylenedioxy group or an ethylenedioxy group.

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl.

R$^8$, R$^9$ and R$^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino and —NR$^{11}$R$^{12}$. Alternatively, R$^8$ and R$^9$ or R$^9$ and R$^{10}$ may combine to form a six-members alicyclic ring.

Alk$_1$ is selected from the group consisting of alkyl, alkenyl or alkynyl.

Z is a polar group.

As used herein, the term "alkyl" refers to a saturated aliphatic hydrocarbon including straight chain and branched chain groups. Preferably, the alkyl group has 1 to 20 carbon atoms (whenever a numerical range; e.g. "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When the alkyl group is substituted, the substituent group(s) is preferably one or more individually selected from oxo, cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^{11}$R$^{12}$, with R$^{11}$ and R$^{12}$ as defined above.

A "cycloalkyl" group refers to an all-carbon monocyclic or fused ring (i.e., rings which share an adjacent pair of carbon atoms) group wherein one or more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and cycloheptatriene. A cycloalkyl group may be substituted or unsubstituted. When the cycloalkyl group is substituted, the substituent group(s) is preferably one or more individually selected from alkyl, aryl, heteroaryl, heteroalycyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^{11}$R$^{12}$, with R$^{11}$ and R$^{12}$ as defined above.

An "alicyclic" group refers to an all carbon monocyclic ring group without π conjugation.

An "alkenyl" group refers to an alkyl group, as defined herein, consisting of at least two carbon atoms and at least one carbon—carbon double bond.

An "alkynyl" group refers to an alkyl group, as defined herein, consisting of at least two carbon atoms and at least one carbon—carbon triple bond.

An "aryl" group refers to an all-carbon monocyclic or fused-ring polycyclic (i.e., rings which share adjacent pairs of carbon atoms) groups have a completely conjugated pi-electron system. Examples, without limitation, or aryl groups are phenyl, naphthalenyl and anthracenyl. The acryl group may be substituted or unsubstituted. When the aryl group is substituted, the substituted group(s) is preferably one or more selected from halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $—NR^{11}R^{12}$, with $R^{11}$ and $R^{12}$ as defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophen, imidazole, oxazole, thiazole, pyrazole, pyridine, pyrimidine, quinoline, isoquinoline, purine and carbazole. The heteroaryl group may be substituted or unsubstituted. When the heteroaryl group is substituted, the substituted group(s) is preferably one or more selected from alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and $—NR^{11}R^{12}$ with $R^{11}$ and $R^{12}$ as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conugated pi-electron system. The heteroalicyclic ring may be substituted or unsubstituted. When the heteroalicyclic group is substituted, the substituted group(s) is preferably one or more selected from alkyl, cycloaklyl, halo, trihalomethyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $—NR^{11}NR^{12}$ with $R^{11}$ and $R^{12}$ as defined above.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "mercapto" group refers to an —SH group.

A "alkylthio" group refers to both an S-alkyl and an —S-cycloalkyl group, as defined herein.

A "arylthio" group refers to both an —S-aryl and an —S-heteroaryl group, as defined herein.

A "carbonyl" group refers to a —C(=O)—R" group, where R" is selected from the group consisting of hydrogen, alkyl, cycloalkyl, aryl, heteroaryl and heteroalicyclic (bonded through a ring carbon), as defined herein.

An "aldehyde" group refers to a carbonyl group where R" is hydrogen.

A "silyl" group refers to a Si—$R_3$ group, where each R is independently selected from the group consisting of hydrogen, alkyl, cycloalkyl, aryl, heteroaryl (bonded through a ring carbon) and heteroalicycle (bonded through a ring carbon), as defined herein.

A "thiocarbonyl" group refers to a —C(=S)—R" group, with R" as defined herein.

A "C-thioamido" group refers to a —C(=S)—$NR^{11}R^{12}$ group, with $R^{11}$ and $R^{12}$ as defined herein.

A "carboxy" group includes both a C-carboxy and an O-carboxy.

A "C-carboxy" group refers to a —C(=O)O—R" group, with R" as defined herein.

An "O-carboxy" group refers to a —OC(=O)R" group, with R" as defined herein.

An "ester" group refers to a —C(=O)O—R" group, with R" as defined herein except that R" cannot be hydrogen.

A "sulfhydryl" group refers to a —SH group.

An "acetyl" group refers to a —C(=O)$CH_3$ group.

A "carboxylic acid" group refers to a C-carboxy group in which R" is hydrogen.

A "halo" group refers to fluorine, chlorine, bromine or iodine.

A "trihaloalkyl" group refers to an -(alkyl)$X_3$, wherein X is a halo group as defined herein, and a "trihalomethyl" group refers to a —$CX_3$ group wherein X is a halo group as defined herein.

A "trihalomethanesulfonyl" group refers to a $X_3$CS-$(=O)_2—$ groups with X as defined above, and a "trihalomethane-sulfonamido" group refers to a $X_3$CS-$(=O)_2—NR^{11}R^{12}$ group, with X, $R^{11}$ and $R^{12}$ as defined herein.

A "cyano" group refers to a —C/N group.

A "sulfinyl" group refers to a —S(=O)—R" group wherein, in addition to being as defined above, R" may also be a hydroxy group.

A "sulfonyl" group refers to a —S(=O)$_2$R" group wherein, in addition to being as defined above, R" may also be a hydroxy group.

A "methylenedioxy" group refers to a —$OCH_2O$— group where the two oxygen atoms are bonded to adjacent carbon atoms.

An "ethylenedioxy" group refers to a —$OCH_2CH_2O$— where the two oxygen atoms are bonded to adjacent carbon atoms.

A "sulfonamido" group includes both a S-sulfonamido and a N-sulfonamido.

An "S-sulfonamido" group refers to a —S(=O)$_2NR^{11}R^{12}$ group, with $R^{11}$ and $R^{12}$ as defined herein.

An "N-sulfonamido" group refers to a —$NR^{11}S(=O)_2$ $R^{12}$ group, with $R^{11}$ and $R^{12}$ as defined herein.

An "O-carbamyl" group refers to a —OC(=O)$NR^{11}R^{12}$ group with $R^{11}$ and $R^{12}$ as defined herein.

An "N-carbamyl" group refers to a $R^{12}$OC(=O)$NR^{11}$— group, with $R^{11}$ and $R^{12}$ as defined herein.

An "O-thiocarbamyl" group refers to a —OC(=S) $NR^{11}R^{12}$ group with $R^{11}$ and $R^{12}$ as defined herein.

An "N-thiocarbamyl" group refers to a $R^{12}$OC(=S) $NR^{11}$— group, with $R^{11}$ and $R^{12}$ as defined herein.

An "amino" group refers to an —$NR^{11}R^{12}$ group, wherein $R^{11}$ and $R^{12}$ are both hydrogen.

An "amido" group includes both a C-amido and a N-amido.

A "C-amido" group refers to a —C(=O)$NR^{11}R^{12}$ group with $R^{11}$ and $R^{12}$ as defined herein.

An "N-amido" group refers to a $R^{12}$C(=O)$NR^{11}$— group, with $R^{11}$ and $R^{12}$ as defined herein.

An "ammonium" group refers to a —$^+NHR^{11}R^{12}$ group wherein $R^{11}$ and $R^{12}$ are independently selected from group consisting of alkyl, cycloalkyl, aryl, and heteroaryl.

A "ureido" group refers to a —$NR^{11}C(=O)NR^{12}R^{13}$ group, with $R^{11}$ and $R^{12}$ as defined herein and $R^{13}$ defined the same as $R^{11}$ and $R^{12}$.

A "guanidino" group refers to a —$R^{11}NC(=N)NR^{12}R^{13}$ group, with $R^{11}$, $R^{12}$ and $R^{13}$ as defined herein.

An "amidino" group refers to a $R^{11}R^{12}NC(=N)—$ group, $R^{11}$ and $R^{12}$ as defined herein.

A "nitro" group refers to a $—NO_2$ group.

A "phosphonyl" or "phosphono" group refers to a $—OP(=O)_2OR"$, with R" as defined herein.

A "morpholino" group refers to a group having the chemical structure:

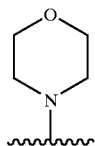

A "piperazinyl" group refers to a group having the chemical structure:

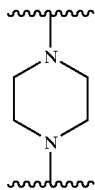

A "tetrazolo" group refers to a group having the chemical structure:

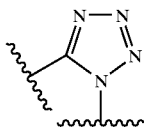

Preferred "pyrrole substituted 2-indolinones" contemplated for use in the present invention have the following features.

It is a presently preferred feature of the "pyrrole substituted 2-indolinones" contemplated for use in this invention that $R^1$ is hydrogen.

It is also a presently preferred feature of "pyrrole substituted 2indolinones" contemplated for use in this invention that $R^2$ is hydrogen.

It is likewise a presently preferred feature of "pyrrole substituted 2-indolinones" contemplated for use in this invention that $R^7$ is hydrogen.

It is a presently preferred feature of "pyrrole substituted 2-indolinones" contemplated for use in this invention that all three of the above limitations exist in the same molecule; i.e., that, in a compound of this invention, $R^1$, $R^2$ and $R^7$ are hydrogen.

It is also a presently preferred feature of "pyrrole substituted 2-indolinones" contemplated for use in this invention that $R^3$, $R^4$, $R^5$ and $R^6$ are selected from the group consisting of hydrogen, unsubstituted lower alkyl, lower alkyl substituted with a group selected from the group consisting of hydroxy, halo, C-carboxy substituted with a group selected from the group consisting of hydrogen and unsubstituted lower alkyl, amino, or $—NR^{11}R^{12}$, unsubstituted lower alkyl alkoxy, lower alkoxy substituted with one or more halo groups, lower alkoxy substituted with a group consisting of unsubstituted aryl or aryl substituted with one or more groups independently selected from the group consisting of unsubstituted lower alkyl, hydroxy, unsubstituted lower alkyl alkoxy, halo, amino, unsubstituted lower alkyl S-sulfonamido or $—NR^{11}R^{12}$, unsubstituted aryl or aryl substituted with one or more groups independently selected from the group consisting of unsubstituted lower alkyl, unsubstituted lower alkyl alkoxy, lower alkoxy substituted with one or more halo groups, lower alkoxy substituted with a group selected from the group consisting of unsubstituted aryl or aryl substituted with one or more groups independently selected from the group consisting of unsubstituted lower alkyl, hydroxy, unsubstituted lower alkyl alkoxy, halo, amino, unsubstituted lower alkyl S-sulfonamido or $—NR^{11}R^{12}$, hydroxy, amino, unsubstituted lower alkyl sulfonamido, C-carboxy substituted with a groups selected from the group consisting of hydrogen or unsubstituted lower alkyl, morpholino, $—NR^{11}R^{12}$, trihalomethyl, aryl, aryl substituted with one or more groups independently selected from group consisting of hydroxy, halo, trihalomethyl, amino, $—NR^{11}R^{12}$, sulfonamido, C-carboxy substituted with a group selected from the group consisting of hydrogen or unsubstituted lower alkyl, unsubstituted lower alkyl or lower alkyl substituted with a group selected from the group consisting of hydroxy, halo, C-carboxy substituted with a group selected from the group consisting of hydrogen or unsubstituted lower alkyl, amino or $—NR^{11}R^{12}$, unsubstituted heteroalicyclic, heteroalicyclic substituted with one or more groups independently selected from the group consisting of halo, hydroxy, unsubstituted lower alkyl, unsubstituted lower alkyl carbonyl, hydroxy, unsubstituted lower alkyl alkoxy or alkoxy substituted with one or more halo groups, unsubstituted aryloxy, aryloxy substituted with one or more groups independently selected from the group consisting of unsubstituted lower alkyl, trihalomethyl, halo, hydroxy, amino or $—NR^{11}R^{12}$, mercapto, unsubstituted lower alkyl alkylthio, unsubstituted arylthio, arylthio substituted with one or more groups selected from the group consisting of halo, hydroxy, amino or $—NR^{11}R^{12}$, C-carboxy substituted with a group selected from the group consisting of hydrogen and unsubstituted lower alkyl, unsubstituted lower alkyl O-carboxy, unsubstituted lower alkyl S-sulfonamido, nitro, unsubstituted lower alkyl C-amido, unsubstituted lower alkyl N-amido, amino and $—R^{11}R^{12}$.

In another presently preferred aspect of "pyrrole substituted 2-indolinones" contemplated for use in this invention, $R^3$, $R^4$, $R^5$ and $R^6$ are independently selected from the group consisting of hydrogen, halo, unsubstituted lower alkyl, lower alkyl, substituted with one or more groups selected from the group consisting of hydroxy, halo, C-carboxy substituted with a group selected from the group consisting of hydrogen or unsubstituted lower alkyl, amino or $—NR^{11}R^{12}$, unsubstituted lower alkyl alkoxy, lower alkyl alkoxy substituted with one or more halo groups, unsubstituted aryloxy, aryloxy substituted with one or more groups independently selected from the group consisting of unsubstituted lower alkyl, lower alkyl substituted with one or more halo groups, hydroxy, unsubstituted lower alkyl alkoxy, halo, amino or $—NR^{11}NR^{12}$, S-sulfonamido wherein $R^{11}$ and $R^{12}$ are independently selected from the group consisting of hydrogen and unsubstituted lower alkyl, unsubstituted aryl, aryl substituted with one or more groups independently selected from the group consisting of halo, unsubstituted lower alkyl, lower alkyl substituted with one or more halo groups, unsubstituted lower alkyl alkoxy, amino or $—NR^{11}R^{12}$, unsubstituted heteraryl, heteroaryl substituted with one or more groups independently selected from the group consisting of unsubstituted lower alkyl, lower alkyl substituted with one or more halo groups, unsubstituted lower alkyl alkoxy, hydroxy, halo, amino or $—NR^{11}R^{12}$, unsubstituted heteroalicyclic, heteroalicyclic substituted with one or more groups independently selected from the group consisting of halo, hydroxy, unsubstituted lower alkyl, lower alkyl substituted with one or more halo groups, unsubstituted lower alkyl alkoxy, amino or —NR$^{11}$R$^{12}$, unsubstituted lower alkyl O-carboxy, C-amido wherein R$^{11}$ and R$^{12}$ are independently selected from the group consisting of hydrogen, unsubstituted lower alkyl and unsubstituted aryl, and, N-amido wherein R$^{11}$ and R$^{12}$ are independently selected from the group consisting of hydrogen, unsubstituted lower alkyl and unsubstituted aryl.

It is a presently preferred feature of "pyrrole substituted 2-indolinones" contemplated for use in this invention that one of R$^8$, R$^9$ and R$^{10}$ is -(alk$_1$)Z while the other two are independently selected from the group consisting of hydrogen, hydroxy, unsubstituted lower alkyl, unsubstituted lower alkenyl, unsubstituted lower alkynyl, unsubstituted lower alkyl alkoxy, lower alkoxy substituted with one or more halo groups, unsubstituted aryl alkoxy, amino, —NR$^{11}$R$^{12}$, halo, C-carboxy substituted with a groups selected from the group consisting of hydrogen or unsubstituted lower alkyl, unsubstituted lower alkyl O-carboxy, unsubstituted lower alkyl C-amido, unsubstituted lower alkyl N-amido, acetyl, unsubstituted lower alkyl S-sulfonamido, unsubstituted aryl or aryl substituted with a group selected from the group consisting of halo, hydroxy, unsubstituted lower alkyl alkoxy, alkoxy substituted with one or more halo groups, C-carboxy substituted with a groups selected from the group consisting of hydrogen or unsubstituted lower alkyl, unsubstituted lower alkyl O-carboxy, amino, and unsubstituted lower alkyl S-sulfonamido and —NR$^{11}$R$^{12}$. In a presently preferred aspect, R$^9$ is -(alk$_1$)Z.

In a particularly preferred embodiment the "pyrrole substituted 2-indolinones" are:

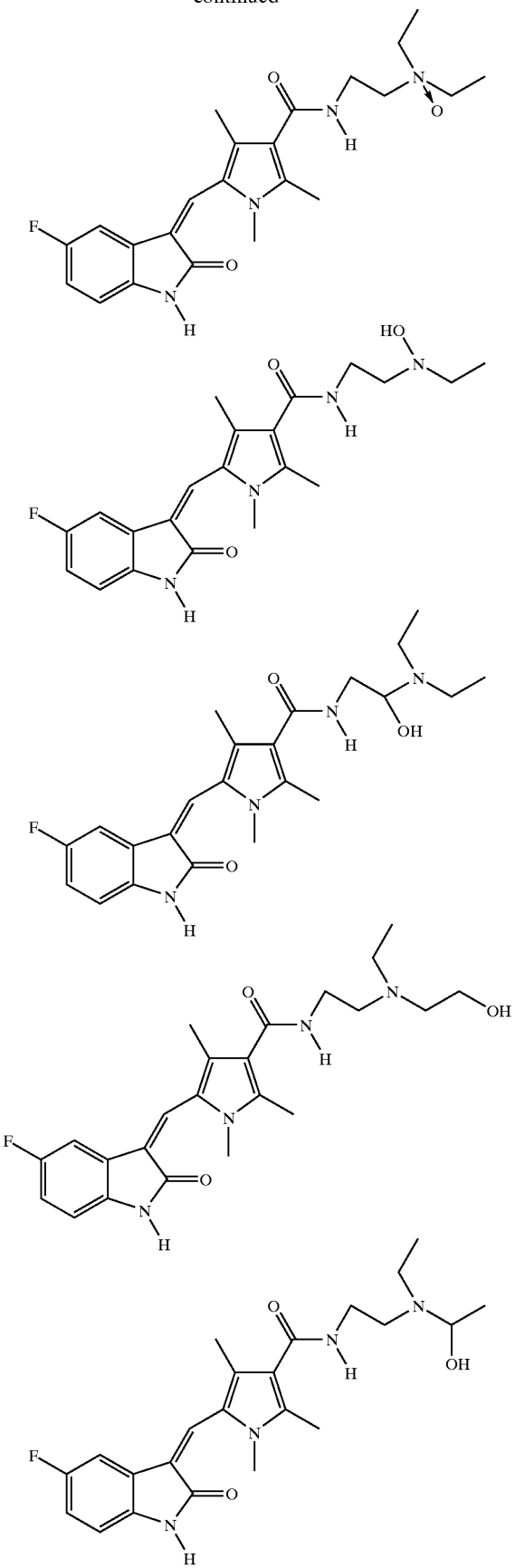

-continued

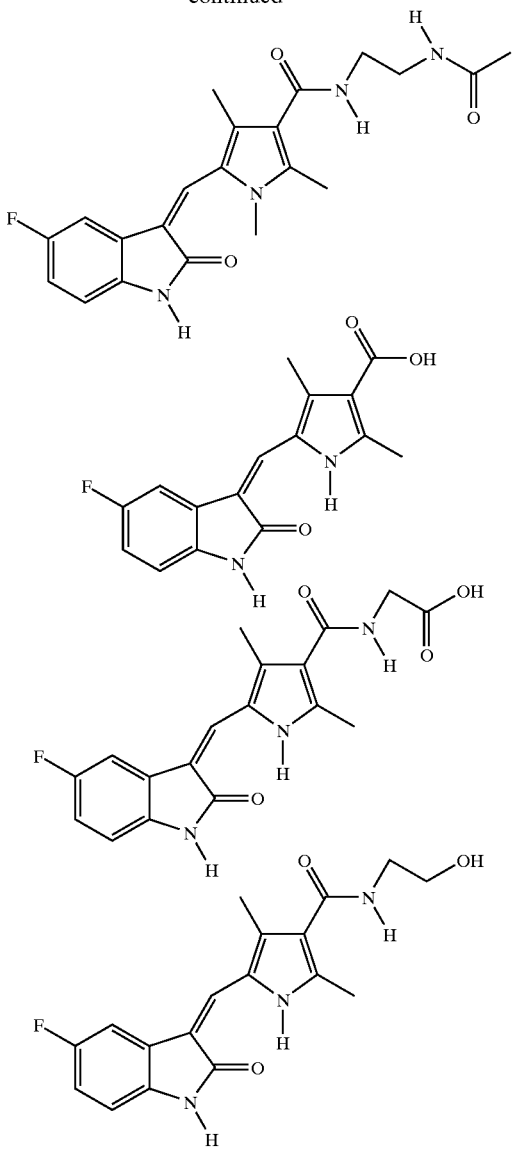

It is a presently preferred feature of "pyrrole substituted 2-indolinones" contemplated for use in this invention that $R^8$ and $R^{10}$ are selected from the group consisting of hydrogen and unsubstituted lower alkyl.

It is also a presently preferred feature of "pyrrole substituted 2-indolinones" contemplated for use in this invention that $alk_1$ is an unsubstituted lower alkyl group.

In yet another presently preferred aspect of "pyrrole substituted 2-indolinones" contemplated for use in this invention, Z is selected from the group consisting of hydroxy, amino, —$NR^{11}R^{12}$, quarternary ammonium, C-carboxy substituted with a group selected from the group consisting of hydrogen or unsubstituted lower alkyl, C-amido substituted with groups selected from the group consisting of hydrogen and unsubstituted lower alkyl, morpholino, piperadinyl, tetrazolo and phosphonyl.

A further presently preferred feature of "pyrrole substituted 2-indolinones" contemplated for use in this invention is that $alk_1$ is a two to four carbon unsubstituted lower alkyl group and Z is a carboxylic acid.

It is presently preferred feature of "pyrrole substituted 2-indolinones" contemplated for use in this invention that $R^9$ is $alk_1$-Z.

It is likewise a presently preferred feature of "pyrrole substituted 2-indolinones" contemplated for use in this invention that $R^{11}$ and $R^{12}$ are independently selected from the group comprising hydrogen, unsubstituted lower alkyl, hydroxy, unsubstituted lower alkyl alkoxy, unsubstituted lower alkyl carbonyl, unsubstituted lower alkyl O-carboxy and acetyl.

In another presently preferred aspect of "pyrrole substituted 2-indolinones" contemplated for use in this invention $R^1$, $R^2$, $R^3$, $R^4$, $R^5$, $R^6$ and $R^7$ are hydrogen, $R^8$ and $R^{10}$ are methyl and $R^9$ is —$CH_2CH_2C(=O)OH$.

It is also a presently preferred aspect of "pyrrole substituted 2-indolinones" contemplated for use in this invention that $R^1$, $R^2$, $R^3$, $R^4$, $R^5$, $R^6$, $R^7$ and $R^8$ are hydrogen, $R^{10}$ is methyl and $R^9$ is —$CH_2CH_2C(=O)OH$.

In yet another presently preferred aspect of "pyrrole substituted 2-indolinones" contemplated for use in this invention, $R^7$ is selected from the group consisting of: hydrogen, unsubstituted lower alkyl, and lower alkyl substituted with a group selected from the group consisting of unsubstituted cycloalkyl, unsubstituted aryl, and aryl substituted with a group selected from hydroxy, unsubstituted lower alkyl alkoxy and halo.

It is also a presently preferred aspect of "pyrrole substituted 2-indolinones" contemplated for use in this invention that Z is selected from the group consisting of —C(=O)$NR^{13}R^{14}$ wherein $R^{13}$ and $R^{14}$ are independently selected from the group consisting of hydrogen, unsubstituted lower alkyl, lower alkyl substituted with a group selected from the group consisting of amino and —$NR^{11}R^{12}$, unsubstituted aryl, aryl substituted with one or more groups selected from the group consisting of halo, hydroxy, unsubstituted lower alkyl alkoxy and trihalomethyl, unsubstituted heteroaryl, unsubstituted heteroalicyclic, and, combined, a five-member or a six-member unsubstituted heteroalicyclic, and, —$NR^{11}R^{12}$, wherein, $R^{11}$ and $R^{12}$ are independently selected from the group consisting of unsubstituted lower alkyl and, combined, a five-member or a six-member unsubstituted heteroalicyclic ring.

Yet another presently preferred aspect of "pyrrole substituted 2-indolinones" contemplated for use in this invention is that $R^7$ is selected from the group consisting of unsubstituted lower alkyl, lower alkyl substituted with one or more groups selected from the group consisting of unsubstituted cycloalkyl, unsubstituted aryl, aryl substituted with one or more groups independently selected from the group consisting of halo and unsubstituted lower alkyl alkoxy and unsubstituted lower alkyl carboxyalkyl, and Z is selected from the group consisting of unsubstituted C-carboxy and unsubstituted lower alkyl C-carboxy.

Finally, it is a presently preferred aspect of "pyrrole substituted 2-indolinones" contemplated for use in this invention that $R^3$ $R^4$, $R^5$, and $R^6$ are independently selected from the group consisting of hydrogen, halo, unsubstituted lower alkyl, lower alkyl substituted with one or more hydroxy groups, unsubstituted lower alkoxy, unsubstituted aryl, aryl substituted with one or more unsubstituted lower alkoxy groups, and —$S(O)_2NR^{11}R^{12}$, $R^5$ is hydrogen, $R^6$ is —$NR^{11}R^{12}$, and $R^{11}$ and $R^{12}$ are independently selected from the group consisting of hydrogen, unsubstituted lower alkyl and, combined, a five-member or a six-member unsubstituted heteroalicyclic ring.

The chemical formulae referred to herein may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate receptor tyrosine kinase (RTK), cellular tyrosine kinase (CTK) and/or serine tyrosine kinase (STK) activity and is not limited to any one tautomeric or structural isomeric form.

In addition, "pyrrole substituted 2-indolinones" contemplated for use in this invention include compounds of the combinatorial library of 3-pyrrolidinyl-2-indolinone compounds formed by reacting oxindoles of structure II with aldehydes of structure III.

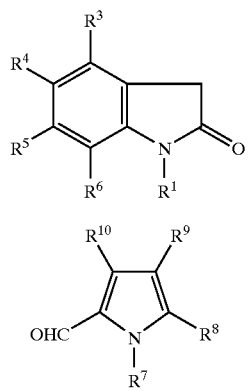

wherein $R^1$–$R^{10}$ have the meanings set forth above.

As used herein, a "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles suitable for use in the formation of "pyrrole substituted 2-indolinones" contemplated for use in this invention, and the second dimension represents all the aldehydes suitable for use in the formation of "pyrrole substituted 2-indolinones" contemplated for use in this invention. Each oxindole may be reacted with each and every aldehyde in order to form a 3-pyrrolindinyl-2-indolinone compound. All 3-pyrrolindinyl-2-indolinone compounds formed in this way are within the scope of the "pyrrole substituted 2-indolinones" contemplated for use in this invention.

The oxindole in the above combinatorial library is preferably selected from the group consisting of oxindole itself and substituted oxindoles such as, without limitation, 6-bromooxindole, 5-hydroxyoxindole, 5-methoxyoxindole, 6-methoxyoxindole, 5-phenylaminosulfonyloxindole, 4-[2-(2-isopropylphenoxy)-ethyl]oxindole, 4-[2-(3-isopropylphenoxy)ethyl]oxindole 4-[2-4-isopropylphenoxy)ethyl]oxindole, 5-fluorooxindole, 6-fluorooxindole, 7-fluorooxindole, 6-trifluoromethyloxindole, 5-chlorooxindole, 6-chlorooxindole, indole-4-carboxylic acid, 5-bromooxindole, 6-(N-acetamido)-oxindole, 4-methyloxindole, 5-methyloxindole, 4-methyl-5-chlorooxindole, 5-ethyloxindole, 6-hydroxyoxindole, 5-acetyloxindole, oxindole-5-carboxylic acid, 5-methoxyoxindole, 6-methoxyoxindole, 5-aminooxindole, 6-aminooxindole, 4-(2-N-morpholinoethyl)oxindole, 7-azaoxindole, oxindole-4-carbamic acid t-butyl ester, oxindole-6-carbamic acid t-butyl ester, 4-(2-carboxyethyl)oxindole, 4-n-butyloxindole, 4,5-dimethyloxindole, 6-(methanesulfonamido)oxindole, 6-(benzamido)oxindole, 5-ethoxyoxindole, 6-phenyloxindole, 6-(2-methoxyphen-1-yl)oxindole, 6-(3-methoxyphen-1-yl)oxindole, 6-(4-methoxyphen-1-yl)oxindole, 5-aminosulfonyloxindole, 5-isopropylaminosulfonyloxindole, dimethylaminosulfonyloxindole, 5-(N-morpholinosulfonyl)oxindole and 4-(2-hydroxyethyl)oxindole.

The aldehyde in the above combinatorial library is preferably selected from the group consisting of, without limitation, 3-(5-formyl-2,4-dimethyl-1H-pyrrol-3-yl) propionic acid, 3-(5-formyl-4-methyl-1H-pyrrol-3-yl) propionic acid, 3-(1-benzyl-5-formyl-2,4-dimethyl-1H-pyrrol-3-yl) propionic acid, 3-(5-formyl-1-methoxycarbonylmethyl-2,4-dimethyl-1H-pyrrol-3-yl) propionic acid, 3-(5-formyl-1,2,4-trimethyl-1H-pyrrol-3-yl) propionic acid, 3-[5-formyl-1-(3-methoxy-benzyl)-2,4-dimethyl-1H-pyrrol-3-yl]propionic acid methyl ester, 3-(1-cyclohexylmethyl-5-formyl-2, 4dimethyl-1H-pyrrol-3-yl) propionic acid methyl ester, 3-[1-(2,2-dimethyl-propyl)-5-formyl-2,4-dimethyl-1H-pyrrol-3-yl]propionic acid methyl ester, 1,3,5-trimethyl-4-(3-morpholin-4-yl-3-oxo-propyl)-1H-pyrrole-2-carbaldehyde, 3-(5-formyl-1,2,4-trimethyl-1H-pyrrol-3-yl)-N-(2-morpholin-4-yl-ethyl)propionamide, 3-(5-formyl-1,2,4-trimethyl-1H-pyrrol-3-yl)-N-phenylpropionamide, 1,3,5-trimethyl-4-(3-oxo-3-piperidin-1-yl-propyl)-1H-pyrrole-2-carbaldehyde, 1,3,5-trimethyl-4-(3-oxo-3-pyrrolidin-1-yl-propyl)-1H-pyrrole-2-carbaldehyde, 3-(5-formyl-1,2,4-trimethyl-1H-pyrrol-3-yl)-N-(4-methoxy-phenyl) propionamide, N-(4-fluoro-phenyl)-3-(5-formyl-1,2,4-trimethyl-1H-pyrrol-3-yl)propionamide, 3-(5-formyl-1,2,4-trimethyl-1H-pyrrol-3-yl)-N-(4-trifluoromethyl-phenyl) propionamide, 3-[5-formyl-1-(3-methoxy-benzyl)-2,4-dimethyl-1H-pyrrol-3-yl]propionic acid, 3-(1-cyclohexylmethyl-5-formyl-2,4-dimethyl-1H-pyrrol-3-yl) propionic acid, 3-[1-(3-fluoro-benzyl)-5-formyl-2,4-dimethyl-1H-pyrrol-3-yl]propionic acid methyl ester, 3-(1-benzyl-5-formyl-2,4-dimethyl-1H-pyrrol-3-yl) propionic acid, 3-[1-(4-fluorobenzyl)-5-formyl-2,4-dimethyl-1H-pyrrol-3-yl]propionic acid methyl ester, 3-[1-(4-fluoro-benzyl)-5-formyl-2,4-dimethyl-1H-pyrrol-3-yl]propionic acid, 3-[1-(3-fluoro-benzyl)-5-formyl-2,4-dimethyl-1H-pyrrol-3-yl]propionic acid, 3,5-dimethyl-4-(3-morpholin-4-yl-propyl)-1H-pyrrole-2-carbaldehyde, 4-(3-dimethylamino-propyl)-3,5-dimethyl-1H-pyrrole-2-carbaldehyde, 5-formyl-2,4-dimethyl-1H-pyrrole-3-carboxylic acid, 3,5-dimethyl-4-(4-methyl-piperazine-1-carbonyl)-1H-pyrrole-2-carbaldehyde, 5-formyl-2,4-dimethyl-1H-pyrrole-3-carboxylic acid (2-dimethylamino-ethyl) amide.

A method for the synthesis of a 3-pyrrolidinyl-2-indolinone of formula 1 suitable for use as a "pyrrole substituted 2-indolinones" in this invention comprises reacting an oxindole of formula 2 with an aldehyde of formula 3 in a solvent, preferably in the presence of a base.

The reaction may be carried out in the presence of a base. The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo[5.4.1]undec-7-ene, pyrrolidine and piperidine.

Examples of inorganic bases are, without limitation, ammonia, alkali metal or alkaline earth hydroxides, phosphates, carbonates, bicarbonates, bisulfates and amides. The alkali metal include, lithium, sodium and potassium while the alkaline earths include calcium, magnesium and barium.

In a presently preferred aspect of this method, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydro- furan, dimethylsulfoxide and dimethylformamide.

In a present referred aspect of this method, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10° C. of the indicated temperature, more preferably within 5° C. of the indicated temperature and, most preferably, within 2° C. of the indicated temperature. Thus, for example, by "about 75° C." is meant 75° C.±10° C., preferably 75° C.±5° C. and most preferably, 75° C.±2° C.

A compound selected from the group consisting of:
3-(3,5-Diisopropyl-4-methoxybenzylidene)-1,3-dihydroindol-2-one
5-Chloro-3-(3,5-diisopropyl-4-methoxybenzylidene)-1,3-dihydroindol-2-one
N-[3-(3,5-Diisopropyl-4-methoxybenzylidene)-2-oxo-2,3-dihydro-1H-indol-6-yl]-acetamide
3-(3,5-Diisopropyl-4-methoxybenzylidene)-6-hydroxy-1,3-dihydroindol-2-one
5-Acetyl-3-(3,5-diisopropyl-4-methoxybenzylidene)-1,3-dihydroindol-2-one
3-(3,5-Diisopropyl-4-methoxybenzylidene)-2-oxo-2,3-dihydro-1H-indole-5-carboxylic acid methyl ester
3-(3-Isopropyl-4-methoxybenzylidene)-1,3-dihydroindol-2-one
3-(5-Isopropyl-4-methoxybenzylidene)-1,3-dihydroindol-2-one
5-Chloro-3-(5-isopropyl-4-methoxy-2-methylbenzylidene)-1,3-dihydroindol-2-one
3-(3-Cyclopentyl-4-methoxybenzylidene)-1,3-dihydroindol-2-one
3-(3-Cyclopentyl-4-methoxybenzylidene)-5-fluoro-1,3-dihydroindol-2-one
3-(3-Cyclohexyl-4-methoxybenzylidene)-1,3-dihydroindol-2-one
5-Bromo-3-(6-methoxybiphenyl-3-ylmethylene)-1,3-dihydroindol-2-one
5-Chloro-3-(2,3-dihydrobenzofuran-5-ylmethylene)-1,3-dihydroindol-2-one
5-Chloro-3-(2,2-dimethylchroman-6-ylmethylene)-1,3-dihydroindol-2-one
N-{3-[3-Cyclohexyl-4-(2-morpholin-4-ylethoxy)-benzyidene]-2-oxo-2,3-dihydro-1H-indol-6-yl}-acetamide
3-(3,5-Diisopropyl-4-methoxybenzylidene)-5-methoxy-1,3-dihydroindol-2-one
N-[3-(4-Methoxy-3-thiophen-3-ylbenzylidene)-2-oxo-2,3-dihydro-1H-indol-6-yl]-acetamide
3-(3,5-Diisopropyl-4-methoxybenzylidene)-5-methyl-1,3-dihydroindol-2-one
5-Amino-3-(3,5-diisopropyl-4-methoxybenzylidene)-1,3-dihydroindol-2-one
5-Chloro-3-(4-methoxy-3,5-dimethylbenzylidene)-1,3-dihydroindol-2-one
3-(3,5-Diisopropyl-4-methoxybenzylindene)6-fluoro-1,3-dihydroindol-2-one
3-(2,2-Dimethylchroman-6-ylmethylene)-5-fluoro-1,3-dihydroindol-2-one
5-Chloro-3-[3,5-diisopropyl-4-(2-morpholin-4-ylethoxy)-benzylidene]-1,3-dihydroindol-2-one
3-(3,5-Diisopropyl-4-methoxybenzylidene)-7-fluoro-1,3-dihydroindol-2-one
3-(4-Methoxy-3-thiophen-3-ylbenzylidene)-5-(2-morpholin-4-ylethyl)-1,3-dihydroindol-2-one
N-[3-(5-Isopropyl-4-methoxy-2-methylbenzylidene)-2-oxo-2,3-dihydro-1H-indol-6-yl]-acetamide
3-(3,5-Diisopropyl-4-methoxybenzylidene)-5-ethyl-1,3-dihydroindol-2-one
N-[2'-Methoxy-5'-(2-oxo-1,2-dihydroindol-3-ylidenemethyl)-biphenyl-3-yl]-acetamide
5-Fluoro-3-(5-isopropyl-4-methoxy-2-methylbenzylidene)-1,3-dihydroindol-2-one
N-[3-(4-Methoxy-3-thiophen-2-ylbenzylidene)-2-oxo-2,3-dihydro-1H-indol-6-yl]-acetamide
6-Amino-3-(3,5-diisopropyl-4-methoxybenzylidene)-1,3-dihydroindol-2-one
N-[3-(2,2-Dimethylchroman-6-ylmethylene)-2-oxo-2,3-dihydro-1H-indol-6-yl]-acetamide
5-Bromo-3-(2,2-dimethylchroman-6-ylmethylene)-1,3-dihydroindol-2-one
3-(4-Methoxy-3-thiophen-3ylbenzylidene)-1,3-dihydroindol-2-one
5-Bromo-3-(5-isopropyl-4-methoxy-2-methylbenzylidene)-1,3-dihydroindol-2-one
5-Fluoro-3-(6-methoxybiphenyl-3-ylmethylene)-1,3-dihydroindol-2-one
3-(3-Isopropyl-4-methoxybenzylidene)-4-methyl-1,3-dihydroindol-2-one
3-(4,5-Dimethoxy-2-thiophen-2-ylbenzylidene)-1,3-dihydroindol-2-one
N-{3-[4-(2-Morpholin-4-ylethoxy)-3-thiophen-2-ylbenzylidene]-2-oxo-2,3-dihydro-1H-indol-6yl}-acetamide
3-(2,2-Dimethylchroman-6-ylmethylene)-4-methyl-1,3-dihydroindol-2-one
3-(2,3-Dihydrobenzofuran-5-ylmethylene)-5-fluoro-1,3-dihydroindol-2-one
3-(3-Cyclohexyl-4-methoxybenzylidene)-5-fluoro-1,3-dihydroindol-2-one
5-Fluoro-3-(3-isopropyl-4-methoxybenzylidene)-1,3-dihydroindol-2-one
3-(5-Isopropyl-4-methoxy-2-methylbenzylidene)-1,3-dihydropyrrolo[2,3-b]pyridin-2-one
3-(3'-Ethoxy-6-methoxybiphenyl)-3-ylmethylene)-1,3-dihydroindol-2-one
3-(3-Cyclopentyl-4-methoxyenzylidene)-1,3-dihydropyrrolo[2,3-b]pyridin-2-one
3-(3-Cyclopentyl-4-methoxybenzylidene)-4-methyl-1,3-dihydroindol-2-one
3-(4,5,2'-Trimethoxybiphenyl-2-ylmethylene)-1,3-dihydroindol-2-one N-{3-[4-(2-Morpholin-4-ylethoxy)-3-thiophen-3-ylbenzylidene]-2-oxo-2,3-dihydro-1H-indol-6-yl}-acetamide
5-Chloro-3-(3-cyclohexyl-4-methoxybenzylidene)-1,3-dihydroindol-2-one
[3-(3,5-Diisopropyl-4-methoxybenzylidene)-2-oxo-2,3-dihydro-1H-indol-6-yl]-carbamic acid tert-butyl ester
3-(3,5-Diisopropyl-4-methoxybenzylidene)-4-methyl-1,3-dihydroindol-2-one
5-Bromo-3-(3,5-diisopropyl-4-methoxybenzylidene)-1,3-dihydroindol-2-one
N-{3-[3-tert-Butyl-4-(2-morpholin-4-ylethoxy)-benzylidene]-2-oxo-2,3-dihydro-1H-indol-6-yl}-acetamide
3-(4-Methoxy-3,5-dimethylbenzylidene)-1,3-dihydropyrrolo[2,3-b]pyridin-2-one
5-Bromo-3-[3,5-diisopropyl-4-(2-morpholin-4-ylethoxy)-benzylidene]-1,3-dihydroindol-2-one
3-(3'-Ethoxy-4,5-dimethoxybiphenyl-2-ylmethylene)-1,3-dihydroindol-2-one
5-Chloro-3-(4-methoxy-3-thiophen-2-ylbenzylidene)-1,3-dihydroindol-2-one
5-Chloro-3-(4-methoxy-3-pyridin-3-ylbenzylidene)-1,3-dihydroindol-2-one
5-Chloro-3-(4,5,3'-trimethoxybiphenyl-2-ylmethylene)-1,3-dihydroindol-2-one
3-(4,5-Dimethoxy-2-naphthalen-2-ylbenzylidene)-1,3-dihydroindol-2-one
N-[3-(3'-Acetylamino-6-methoxybiphenyl-3-ylmethylene)-2-oxo-2,3-dihydro-1H-indol-6-yl]-acetamide
6-Methoxy-3-(4-methoxy-3-thiophen-3-ylbenzylidene)-1,3-dihydroindol-2-one
3-(6Methoxybiphenyl-3-ylmethylene)-1,3-dihydroindol-2-one
3-(2,3-Dihydrobenzofuran-5ylmethylene)-1,3-dihydroindol-2-one
5-Chloro-3-(6-methoxybiphenyl-3-ylmethyl)-1,3-dihydroindol-2-one
3-(3-Cyclohexyl-4-methoxybenzylidene)-4-methyl-1,3-dihydroindol-2-one
3-(2,3-dihydrobenzofuran-5-ylmethylene)-4-methyl-1,3-dihydroindol-2-one
3-(3-Isopropyl-4-methoxybenzylidene)-1,3-dihydropyrrolo[2,3-b]pyridin-2-one
3-(6-Methoxybiphenyl-3-ylmethylene)-1,3-dihydropyrrolo[2,3-b]pyridin-2-one
3-(3-Cyclohexyl-4-methoxybenzylidene)-1,3-dihydropyrrolo[2,3-b]pyridin-2-one
3-(2,3-Dihydrobenzofuran-5-ylmethylene)-1,3-dihydropyrrolo[2,3-b]pyridin-2-one
3-(3,5-Diisopropyl-4-methoxybenzylidene)-1,3-dihydropyrrolo[2,3-b]pyridin-2-one
5-Bromo-3-(3-isopropyl-4-methoxybenzylidene)-1,3-dihydroindol-2-one
5-Bromo-3-(3-cyclopentyl-4-methoxybenzylidene)-1,3-dihydroindol-2-one
5-Chloro-3-(3-cyclopentyl-4-methoxybenzylidene)-4-methyl-1,3-dihydroindol-2-one
5-Chloro-3-(6-methoxybiphenyl-3-ylmethylene)-4-methyl-1,3-dihydroindol-2-one
5-Chloro-3-(5-isopropyl-4-methoxy-2-methylbenzylidene)-4-methyl-1,3-dihydroindol-2-one
5-Chloro-3-(4-methoxy-3,5-dimethylbenzylidene)-4-methyl-1,3-dihydroindol-2-one
3-(3,5-Diisopropyl-4-methoxybenzylidene)-6-trifluoromethyl-1,3-dihydroindol-2-one
6-Chloro-3-(3,5-diisopropyl-4-methoxybenzylidene)-1,3-dihydroindol-2-one
3-[3-(3,5-Diisopropyl-4-methoxybenzylidene)-2-oxo-2,3-dihydro-1H-indol-5-yl]-propionic acid
3-(3,5-Diisopropyl-4-methoxybenzylidene)-6-methoxy-1,3-dihydroindol-2-one
5-Butyl-3-(3,5-diisopropyl-4-methoxybenzylidene)-1,3-dihydroindol-2-one
3-(3,5-Diisopropyl-4-methoxybenzylidene)-2-oxo-2,3-dihydro-1H-indol-2,3-dihydro-1H-indole-4-carboxylic acid
3-(3,5-Diisopropyl-4-methoxybenzylidene)-6-(3-methoxyphenyl)-1,3-dihydroindol-2-one
7-Chloro-3-(3,5-diisopropyl-4-methoxybenzylidene)-5-methyl-1,3-dihydroindol-2-one
3-(3,5-Diisopropyl-4-methoxybenzylidene)-2-oxo-2,3-dihydro-1H-indol-5-yl]-carbamic acid tert-butyl ester
5-Chloro-3-(3-isopropyl-4-methoxybenzylidene)-1,3-dihydroindol-2-one
5-Chloro-3-(3-cyclopentyl-4-methoxybenzylidene)-1,3-dihydroindol-2-one
3-(6-Methoxybiphenyl-3-ylmethylene)-4-methyl-1,3-dihydroindol-2-one
3-(5-Isopropyl-4-methoxy-2-methylbenzylidene)-4-methyl-1,3-dihydroindol-2-one
5-Bromo-3-(2,3-dihydrobenzofuran-5-ylmethylene)-1,3-dihydroindol-2-one
5-Chloro-3-(3-isopropyl-4-methoxybenzylidene)-4-methyl-1,3-dihydroindol-2-one
5-Chloro-3-(3,5-diisopropyl-4-methoxybenzylidene)-4-methyl-1,3-dihydroindol-2-one
5-Chloro-3-(2,2-dimethylchroman-6-ylmethylene)-4-methyl-1,3-dihydroindol-2-one
3-(3,5-Diisopropyl-4-methoxybenzylidene)-2-oxo-2,3-dihydro-1H-indole-5-carboxylic acid
3-(3,5-Diisopropyl-4-methoxybenzylidene)-5,6-dimethoxy-1,3-dihydroindol-2-one
N-[3-(3,5-Diisopropyl-4-methoxybenzylidene)-2-oxo-2,3-dihydro-1H-indol-6-yl]-methanesulfonamide
N-[3-(3,5-Diisopropyl-4-methoxybenzylidene)-2-oxo-2,3-dihydro-1H-indol-6-yl]-benzamide
3-(3,5-Diisopropyl-4-methoxybenzylidene)-6-(3-ethoxyphenyl)-1,3-dihydroindol-2-one
3-(3,5-Diisopropyl-4-methoxybenzylidene)-6-phenyl-1,3-dihydroindol-2-one
3-(3,5-Diisopropyl-4-methoxybenzylidene)-5-fluoro-1,3-dihydroindol-2-one
5-Fluoro-3-(4-methoxy-3,5-dimethylbenzylidene)-1,3-dihydroindol-2-one
3-(2,2-dimethylchroman-6-ylmethylene)-1,3-dihydroindol-2-one
is also a preferred embodiment of this invention.
Likewise, a compound selected from the group consisting of:
5-methyl-3-(3-methyl-1H-indol-2-ylmethylene)-1,3-dihydroindol-2-one,
3-(3-methyl-1H-indol-2-ylmethylene)-2-oxo-2,3-dihydro-1H-indol-5-sulfonic acid amide,
3(3-methyl-1H-indol-2-ylmethylene)-2-oxo-2,3-dihydro-1H-indole-5-sulfonic acid methylamide,
3-(3-methyl-1H-indole-2-ylmethylene)-2-oxo-2,3-dihydro-1H-indole-5-sulfonic acid dimethylamide, 3-(3-methyl-1H-indol-2-ylmethylene)-2-oxo-2,3-dihydro-1H-indole-5-carboxylic acid,
5-acetyl-3-(3-methyl-1H-indol-2-ylmethylene)-1,3-dihydroindol-2-one,
5-acetyl-3-(1H-indol-2-ylmethylene)-1,3-dihydroindol-2-one,
3-(1H-indol-2-ylmethylene)-2-oxo-2,3-dihydro-1H-indol-5-sulfonic acid amide,
5-amino-3-(1H-indol-2-ylmethylene)-1,3-dihydroindol-2-one,
3-(1H-indol-2-ylmethylene)-2-oxo-2,3-dihydro-1H-indole-5-carboxylic acid,
6-chloro-3-(1H-indol-2-ylmethylene)-1,3-dihydroindol-2-one,
3-(1H-indol-2-ylmethylene)-1,3-dihydroindol-2-one,
5-chloro-3-(1H-indol-2-ylmethylene)-1,3-dihydroindol-2-one,
5-bromo-3-(1H-indol-2-ylmethylene)-1,3-dihydroindol-2-one,
3-(1H-indol-2-ylmethylene)-4-methyl-1,3-dihydroindol-2-one,
3-(3-methyl-1H-indol-2-ylmethylene)-1,3-dihydroindol-2-one,
5-chloro-3-(3-methyl-1H-indol-2-ylmethylene)-1,3-dihydroindol-2-one,
5-bromo-3-(3-methyl-1H-indol-2-ylmethylene)-1,3-dihydroindol-2-one,
4-methyl-3-(3-methyl-1H-indol-2-ylmethylene)-1,3-dihydroindol-2-one, and
3-(1H-indol-2-ylmethylene)-5[(1H-indol-2-ylmethylene)amino]-1,3-dihydroindol-2-one
is also a presently preferred "pyrrole substituted-2-indolinone" contemplated for use in this inventory.

Finally, presently preferred "pyrrole substituted-2-indolinone" compounds contemplated for use in the invention comprise compounds selected from the group consisting of:
3-[2-(2-oxo-1,2-dihydro-indol-3-ylidenemethyl)-4,5,6,7-tetrahydro-1H-indol-3-yl]-propionic acid,
3-[2-(5-chloro-2-oxo-1,2-dihydro-indol-3-ylidenemethyl)-4,5,6,7-tetrahydro-1H-indol-3-yl]-propionic acid,
3-2-(5-bromo-2-oxo-1,2-dihydro-indol-3-ylidenemethyl)-4,5,6,7-tetrahydro-1H-indol-3-yl]-propionic acid,
3-[2-(4-methyl-2-oxo-1,2-dihydro-indol-3-ylidenemethyl)-4,5,6,7-tetrahydro-1H-indol-3-yl]-propionic acid,
3-[2-(5-methyl-2-oxo-1,2-dihydro-indol-3-ylidenemethyl)-4,5,6,7-tetrahydro-1H-indol-3-yl]-propionic acid,
3-[2-(6-chloro-2-oxo-1,2-dihydro-indol-3-ylidenemethyl)-4,5,6,7-tetrahydro-1H-indol-3-yl]-propionic acid,
3-[2-(6-methoxy-2-oxo-1,2-dihydro-indol-3-ylidenemethyl)-4,5,6,7-tetrahydro-1H-indol-3-yl]-propionic acid,
N,N-dimethyl-3-[2-(2-oxo-1,2-dihydro-indol-3-ylidenemethyl)-4,5,6,7-tetrahydro-1H-indol-3-yl]-propionamide,
3-[3-(3-dimethylamino-propyl)-4,5,6,7-tetrahydro-1H-indol-2-ylmethylene]-1,3-dihydro-indol-2-one,
3-[2-(2-oxo-1,2-dihydro-indol-3-ylidenemethyl)-4,5,6,7-tetrahydro-1H-indol-3-yl]-propionamide,
3-[3-(3-morpholin-4-yl-3-oxo-propyl)-4,5,6,7-tetrahydro-1H-indol-2-ylmethylene]-1,3-dihydro-indol-2-one,
N-methyl-3-[2-(2-oxo-1,2-dihydro-indol-3-ylidenemethyl)-4,5,6,7-tetrahydro-1H-indol-3-yl]-propionamide,
N-(2-morpholin-4-yl-ethyl)-3-[2-(2-oxo-1,2-dihydro-indol-3-ylidenemethyl)-4,5,6,7-tetrahydro-1H-indol-3-yl]-propionamide,
3-[2-(2-oxo-1,2-dihydro-pyrrolo[2,3-b]pyridin-3-ylidenemethyl)-4,5,6,7-tetrahydro-1H-indol-3-yl]-propionic acid,
3-{2-[6-(3-methoxy-phenyl)-2-oxo-1,2-dihydro-indol-3-ylidenemethyl]-4,5,6,7-tetrahydro-1H-indol-3-yl}-propionic acid,
3-{2-[6-(4-methoxy-phenyl)-2-oxo-1,2-dihydro-indol-3-ylidenemethyl]-4,5,6,7-tetrahydro-1H-indol-3-yl}-propionic acid,
3-[2-(2-oxo-6-phenyl-1,2-dihydro-indol-3-ylidenemethyl)-4,5,6,7-tetrahydro-1H-indol-3-yl]-propionic acid,
3-{2-[6-(2-methoxy-phenyl)-2-oxo-1,2-dihydro-indol-3-ylidenemethyl]-4,5,6,7-tetrahydro-1H-indol-3-yl}-propionic acid,
3-[2-(5-isopropylsulfamoyl-2-oxo-1,2-dihydro-indol-3-ylidenemethyl)-4,5,6,7-tetrahydro-1H-indol-3-yl]-propionic acid,
3-[2-(6-morpholin-4-yl-2-oxo-1,2-dihydro-indol-3-ylidenemethyl)-4,5,6,7-tetrahydro-1H-indol-3-yl]-propionic acid,
3-[2-(5-chloro-4-methyl-2-oxo-1,2-dihydro-indol-3-ylidenemethyl)-4,5,6,7-tetrahydro-1H-indol-3-yl]-propionic acid,
3-[2-(5-bromo-4-methyl-2-oxo-1,2-dihydro-indol-3-ylidenemethyl)-4,5,6,7-tetrahydro-1H-indol-3-yl]-propionic acid,
3-[2-(5-bromo-2-oxo-1,2-dihydro-indol-3-ylidenemethyl)-4,5,6,7-tetrahydro-1H-indol-3-yl]-N-(2-morpholin-4-yl-ethyl)-propionamide,
3-[2-(5-chloro-2-oxo-1,2-dihydro-indol-3-ylidenemethyl)-4,5,6,7-tetrahydro-1H-indol-3-yl]-N-(2-morpholin-4-yl-ethyl)-propionamide, and
3-[2-(2-oxo-1,2-dihydro-indol-3-ylidenemethyl)-phenyl]-propionic acid.

In a preferred embodiment of the invention formulation, the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred embodiment of the invention formulation, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

Compound IV

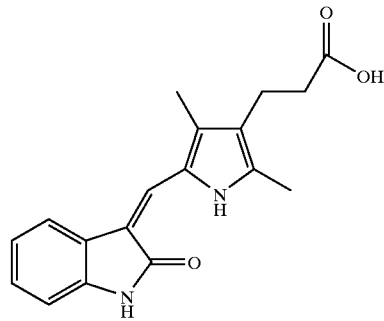

Further examples of some preferred compounds are:

TABLE 1

| Example | Structure | Name |
|---|---|---|
| 1 | 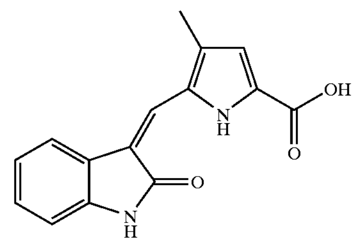 | 4-Methyl-5-(2-oxo-1,2-dihydroindol-3-ylidenemethyl)-1H-pyrrole-2-carboxylic acid. |
| 2 | 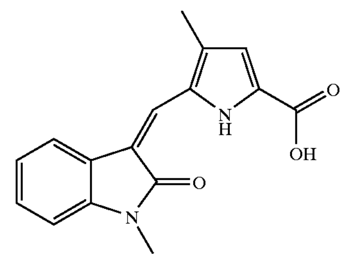 | 4-Methyl-5-(1-methyl-2-oxo-1,2-dihydroindol-3-ylidenemethyl)-1H-pyrrole-2-carboxylic acid |
| 3 | 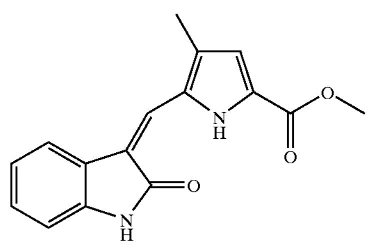 | 4-Methyl-5-(2-oxo-1,2-dihydroindol-3-ylidenemethyl)-1H-pyrrole-2-carboxylic acid methyl ester |
| 4 | 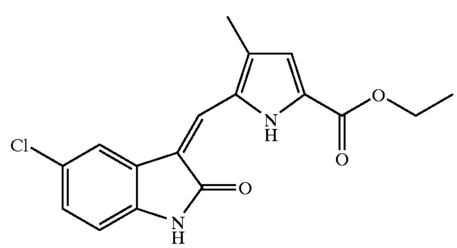 | 5-(5-Chloro-2-oxo-1,2-dihydroindol-3-ylidenemethyl)-4-methyl-1H-pyrrole-2-carboxylic acid ethyl ester |
| 5 | 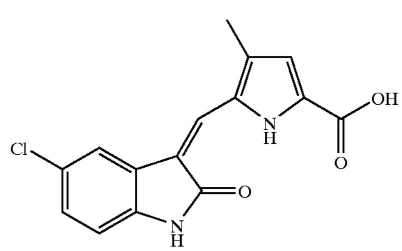 | 5-(5-Chloro-2-oxo-1,2-dihydroindol-3-ylidenemethyl)-4-methyl-1H-pyrrole-2-carboxylic acid |
| 6 | 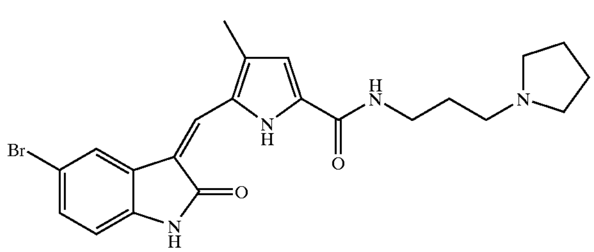 | 5-(5-Bromo-2-oxo-1,2-dihydroindol-3-ylidenemethyl)-4-methyl-1H-pyrrole-2-carboxylic acid (3-pyrrolidin-1-ylpropyl)amide |

TABLE 1-continued

| Example | Structure | Name |
|---|---|---|
| 7 | 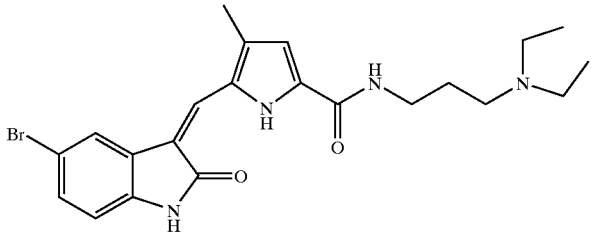 | 5-(5-Bromo-2-oxo-1,2-dihydroindol-3-ylidenemethyl)-4-methyl-1H-pyrrole-2-carboxylic acid (3-diethylaminopropyl)amide |
| 8 | 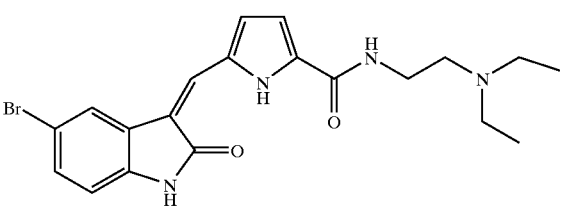 | 5-(5-Bromo-2-oxo-1,2-dihydroindol-3-ylidenemethyl)-1H-pyrrole-2-carboxylic acid (2-diethylaminoethyl)amide |
| 9 | 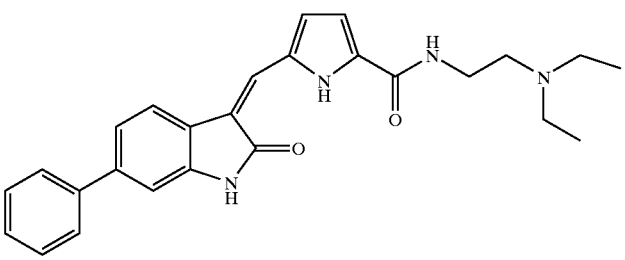 | 5-(2-Oxo-6-phenyl-1,2-dihydroindol-3-ylidenemethyl)-1H-pyrrole-2-carboxylic acid (2-diethylaminoethyl)amide |
| 10 | 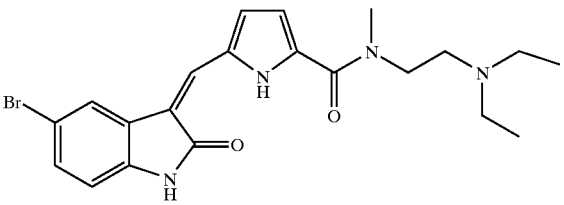 | 5-(5-Bromo-2-oxo-1,2-dihydroindol-3-ylidenemethyl)-1H-pyrrole-2-carboxylic acid (2-diethylaminoethyl)methylamide |
| 11 | 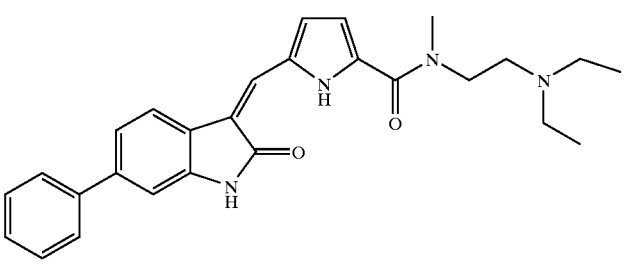 | 5-(2-Oxo-6-phenyl-1,2-dihydroindol-3-ylidenemethyl)-1H-pyrrole-2-carboxylic acid (2-diethylaminoethyl)methylamide |
| 12 | 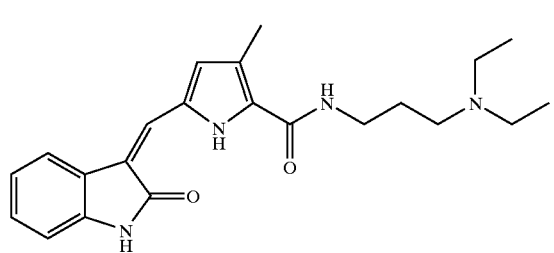 | 3-Methyl-5-(2-oxo-1,2,dihydroindol-3-ylidenemethyl)-1H-pyrrole-2-carboxylic acid (3-diethylaminopropyl)amide |

TABLE 1-continued

| Example | Structure | Name |
|---|---|---|
| 13 | 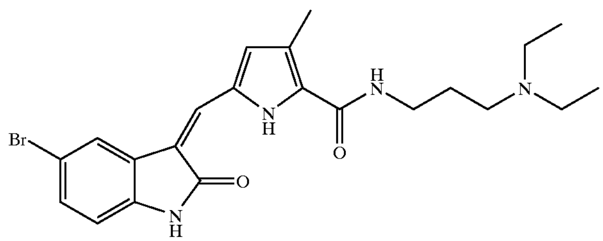 | 5-(5-Bromo-2-oxo-1,2-dihydroindol-3-ylidenemethyl)-3-methyl-1H-pyrrole-2-carboxylic acid (3-diethylaminopropyl)amide |
| 14 | 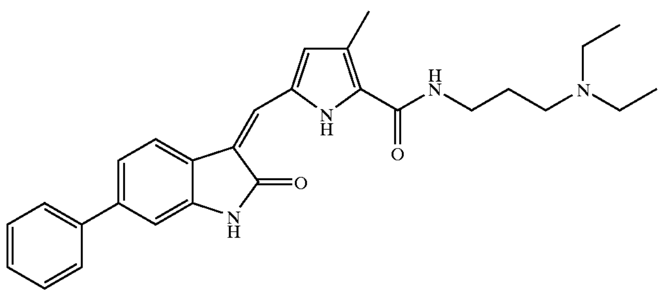 | 3-Methyl-5-(2-oxo-6-phenyl-1,2-dihydroindol-3-ylidenemethyl)-1H-pyrrole-2-carboxylic acid (3-diethylaminopropyl)amide |
| 15 | 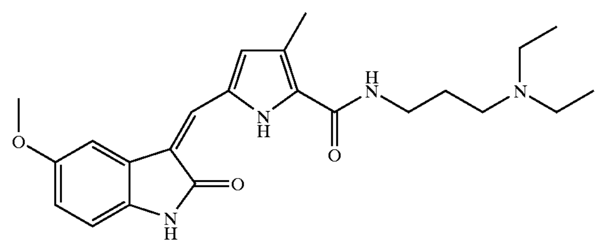 | 5-(5-Methoxy-2-oxo-1,2-dihydroindol-3-ylidenemethyl)-3-methyl-1H-pyrrole-2-carboxylic acid (3-diethylaminopropyl)amide |
| 16 | 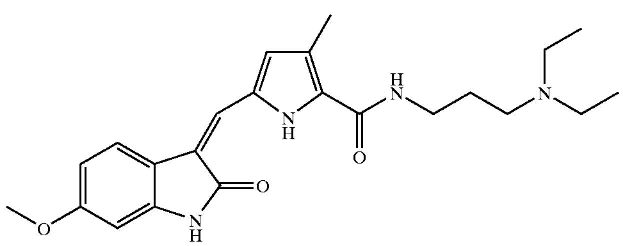 | 5-(6-Methoxy-2-oxo-1,2-dihydroindol-3-ylidenemethyl)-3-methyl-1H-pyrrole-2-carboxylic acid (3-diethylaminopropyl)amide |
| 17 | 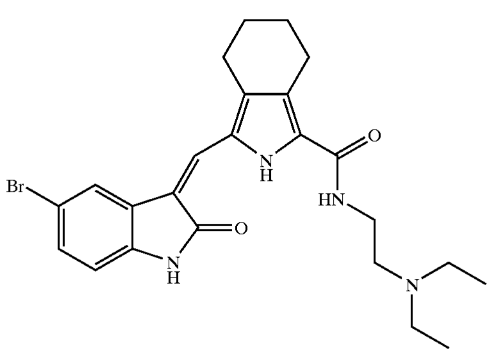 | 3-(5-Bromo-2-oxo-1,2-dihydroindol-3-ylidenemethyl)-4,5,6,7-tetrahydro-2H-isoindole-1-carboxylic acid (2-diethylamino-ethyl)amide |

TABLE 1-continued

| Example | Structure | Name |
|---|---|---|
| 18 | 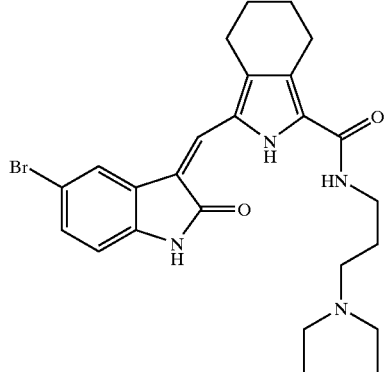 | 3-(5-Bromo-2-oxo-1,2-dihydroindol-3-ylidenemethyl)-4,5,6,7-tetrahydro-2H-isoindole-1-carboxylic acid (3-diethylaminopropyl)amide |
| 19 | 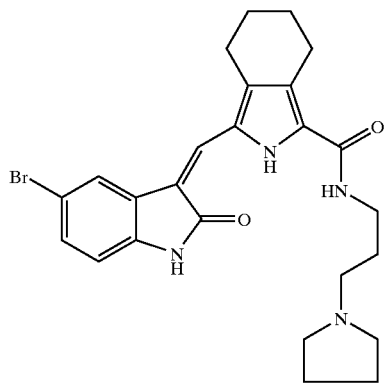 | 3-(5-Bromo-2-oxo-1,2-dihydroindol-3-ylidenemethyl)-4,5,6,7-tetrahydro-2H-isoindole-1-carboxylic acid (3-pyrrolidin-1-ylpropyl)amide |
| 20 | 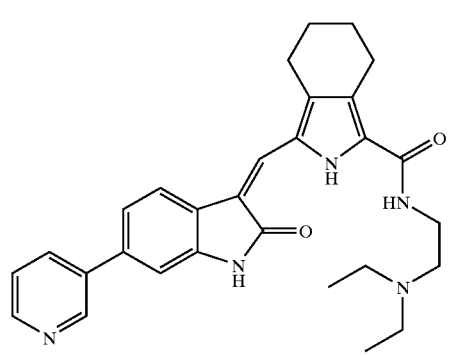 | 3-(2-Oxo-6-pyridin-3-yl-1,2-dihydroindol-3-ylidenemethyl)-4,5,6,7-tetrahydro-2H-isoindole-1-carboxylic acid (2-diethylaminoethyl)amide |
| 21 | 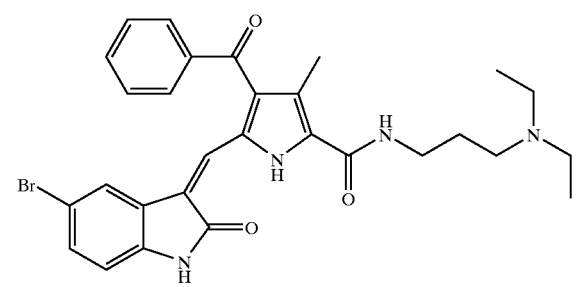 | 4-Benzoyl-5-(5-bromo-2-oxo-1,2-dihydroindol-3-ylidenemethyl)-3-methyl-1H-pyrrole-2-carboxylic acid (3-diethylaminopropyl)amide |

TABLE 1-continued

| Example | Structure | Name |
|---|---|---|
| 22 | 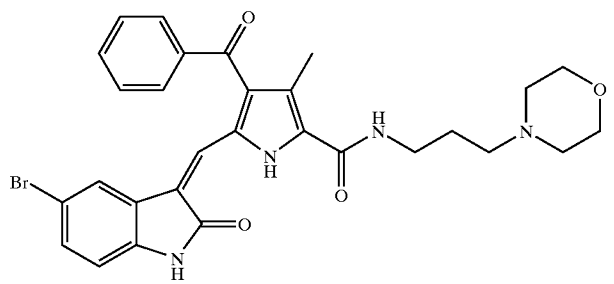 | 4-Benzoyl-5-(5-bromo-2-oxo-1,2-dihydroindol-3-ylidenemethyl)-3-methyl-1H-pyrrole-2-carboxylic acid (3-morpholin-4-ylpropyl)amide |
| 23 | 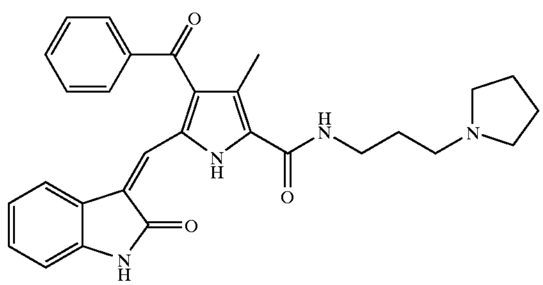 | 4-Benzoyl-3-methyl-5-(2-oxo-1,2-dihydroindol-3-ylidenemethyl)-1H-pyrrole-2-carboxylic acid (3-pyrrolidin-1-ylpropyl)amide |
| 24 | 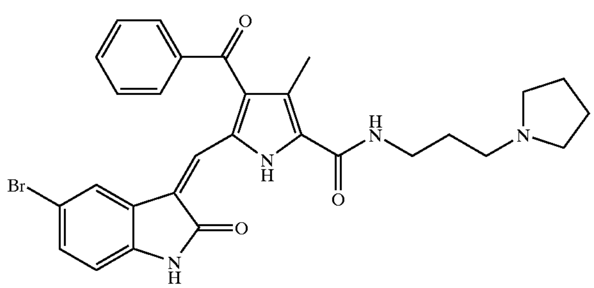 | 4-Benzoyl-5-(5-bromo-2-oxo-1,2-dihydroindol-3-ylidenemethyl)-3-methyl-1H-pyrrole-2-carboxylic acid (3-pyrrolidin-1-ylpropyl)amide |
| 25 | 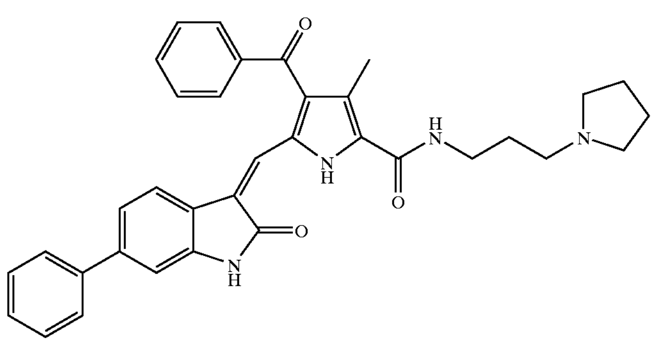 | 4-Benzoyl-3-methyl-5-(2-oxo-6-phenyl-1,2-dihydroindol-3-ylidenemethyl)-1H-pyrrole-2-carboxylic acid (3-pyrrolidin-1-ylpropyl)amide |
| 26 | 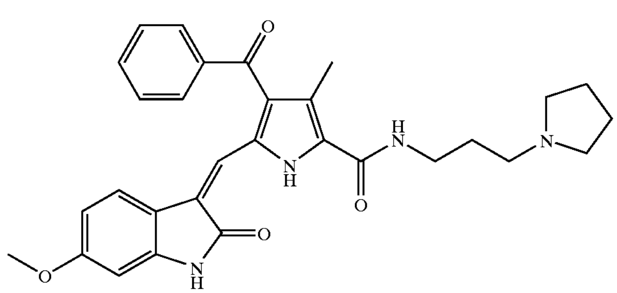 | 4-Benzoyl-5-(6-methoxy-2-oxo-1,2-dihydro-indol-3-ylidenemethyl)-3-methyl-1H-pyrrole-2-carboxylic acid (3-pyrrolidin-1-ylpropyl)amide |

TABLE 1-continued

| Example | Structure | Name |
|---|---|---|
| 27 | 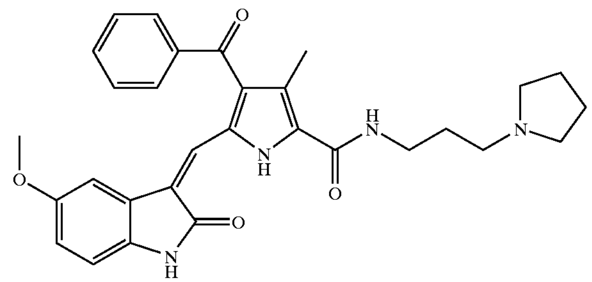 | 4-Benzoyl-5-(5-methoxy-2-oxo-1,2-dihydro-indol-3-ylidenemethyl)-3-methyl-1H-pyrrole-2-carboxylic acid (3-pyrrolidin-1-ylpropyl)amide |
| 28 | 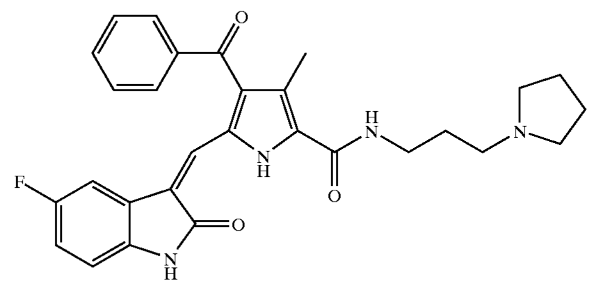 | 4-Benzoyl-5-(5-fluoro-2-oxo-1,2-dihydro-indol-3-ylidenemethyl)-3-methyl-1H-pyrrole-2-carboxylic acid (3-pyrrolidin-1-ylpropyl)amide |
| 29 | 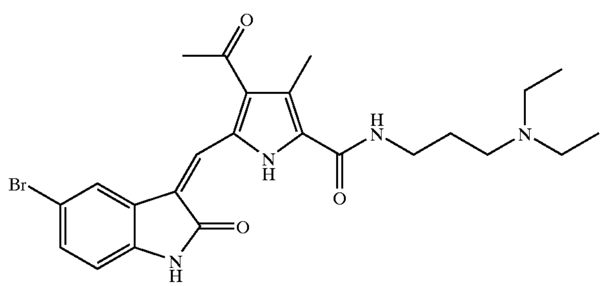 | 4-Acetyl-5-(5-bromo-2-oxo-1,2-dihydroindol-3-ylidenemethyl)-3-methyl-1H-pyrrole-2-carboxylic acid (3-diethylaminopropyl)amide |
| 30 | 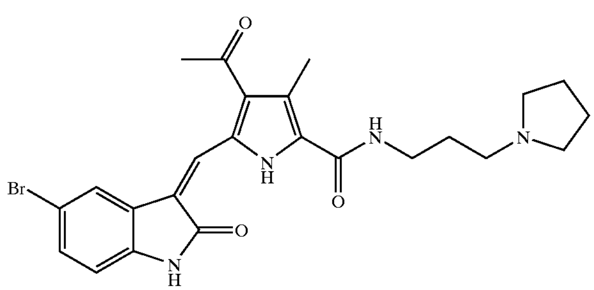 | 4-Acetyl-5-(5-bromo-2-oxo-1,2-dihydroindol-3-ylidenemethyl)-3-methyl-1H-pyrrole-2-carboxylic acid (3-pyrrolidin-1-ylpropyl)amide |
| 31 | 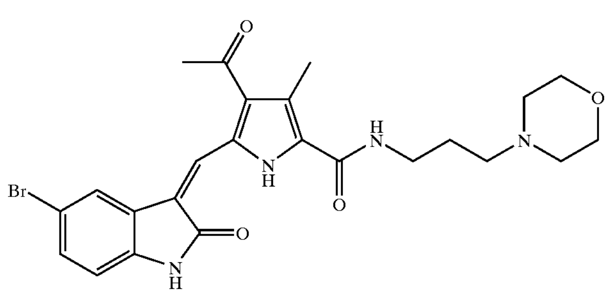 | 4-Acetyl-5-(5-bromo-2-oxo-1,2-dihydroindol-3-ylidenemethyl)-3-methyl-1H-pyrrole-2-carboxylic acid (3-morpholin-4-ylpropyl)amide |

TABLE 1-continued

| Example | Structure | Name |
|---|---|---|
| 32 | 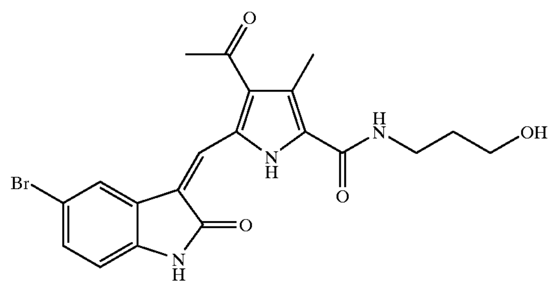 | 4-Acetyl-5-(5-bromo-2-oxo-1,2-dihydroindol-3-ylidenemethyl)-3-methyl-1H-pyrrole-2-carboxylic acid (3-hydroxy-propyl)amide |
| 33 | 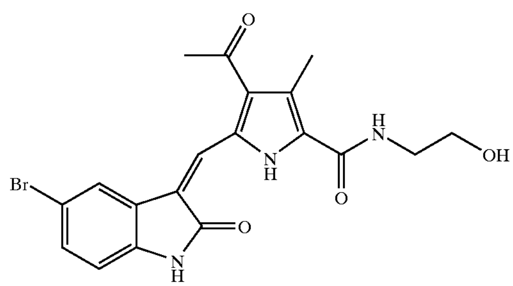 | 4-Acetyl-5-(5-bromo-2-oxo-1,2-dihydroindol-3-ylidenemethyl)-3-methyl-1H-pyrrole-2-carboxylic acid (2-hydroxy-ethyl)amide |
| 34 | 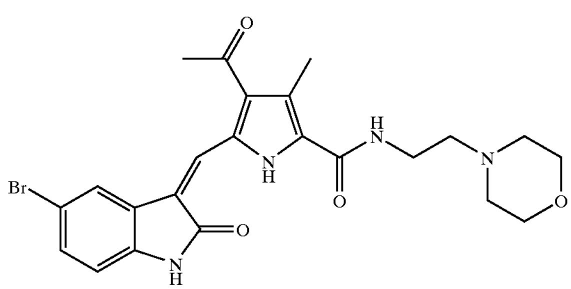 | 4-Acetyl-5-(5-bromo-2-oxo-1,2-dihydroindol-3-ylidenemethyl)-3-methyl-1H-pyrrole-2-carboxylic acid (2-morpholin-4-yl-ethyl)amide |
| 35 | 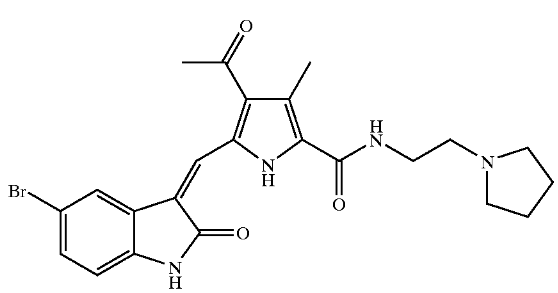 | 4-Acetyl-5-(5-bromo-2-oxo-1,2-dihydroindol-3-ylidenemethyl)-3-methyl-1H-pyrrole-2-carboxylic acid (2-pyrrolidin-1-yl-ethyl)amide |
| 36 | 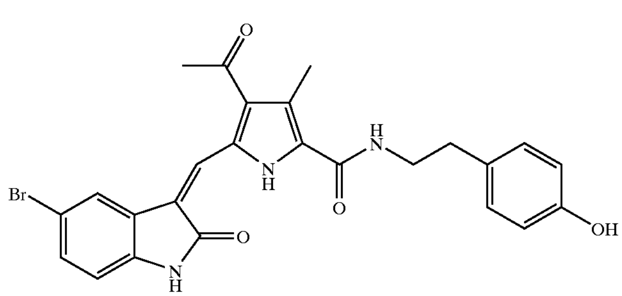 | 4-Acetyl-5-(5-bromo-2-oxo-1,2-dihydroindol-3-ylidenemethyl)-3-methyl-1H-pyrrole-2-carboxylic acid [2-(4-hydroxy-phenyl)-ethyl]amide |

TABLE 1-continued

| Example | Structure | Name |
|---|---|---|
| 37 | 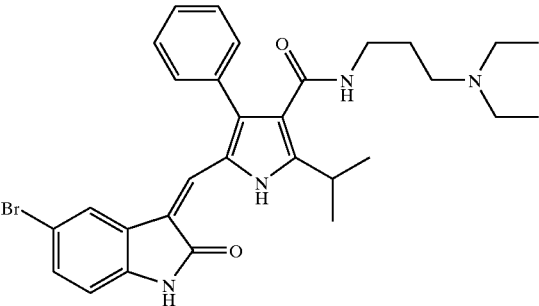 | 5-(5-Bromo-2-oxo-1,2-dihydroindol-3-ylidenemethyl)-2-isopropyl-4-phenyl-1H-pyrrole-3-carboxylic acid (3-diethylamino-propyl)amide |
| 38 | 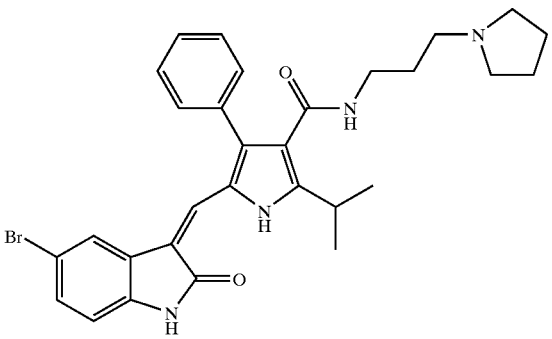 | 5-(5-Bromo-2-oxo-1,2-dihydroindol-3-ylidenemethyl)-2-isopropyl-4-phenyl-1H-pyrrole-3-carboxylic acid (3-pyrrolidin-1-ylpropyl)amide |
| 39 | 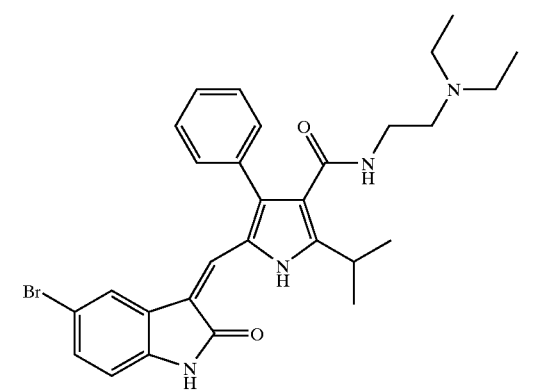 | 5-(5-Bromo-2-oxo-1,2-dihydroindol-3-ylidenemethyl)-2-isopropyl-4-phenyl-1H-pyrrole-3-carboxylic acid (2-diethylamino-ethyl)amide |
| 40 | 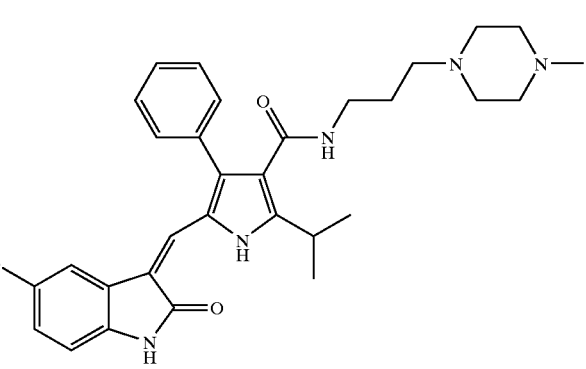 | 5-(5-Bromo-2-oxo-1,2-dihydroindol-3-ylidenemethyl)-2-isopropyl)-4-phenyl-1H-pyrrole-3-carboxylic acid [3-(4-methyl-piperazin-1-yl)-propyl]amide |

TABLE 1-continued

| Example | Structure | Name |
| --- | --- | --- |
| 41 | 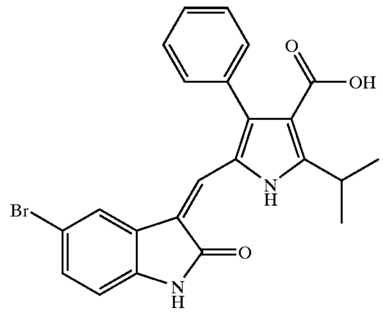 | 5-(5-Bromo-2-oxo-1,2-dihydroindol-3-ylidenemethyl)-2-isopropyl-4-phenyl-1H-pyrrole-3-carboxylic acid |
| 42 | 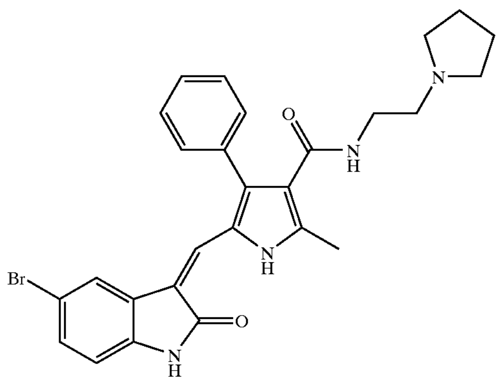 | 5-(5-Bromo-2-oxo-1,2-dihydroindol-3-ylidenemethyl)-2-methyl-4-phenyl-1H-pyrrole-3-carboxylic acid (2-pyrrolidin-1-yl-ethyl)amide |
| 43 | 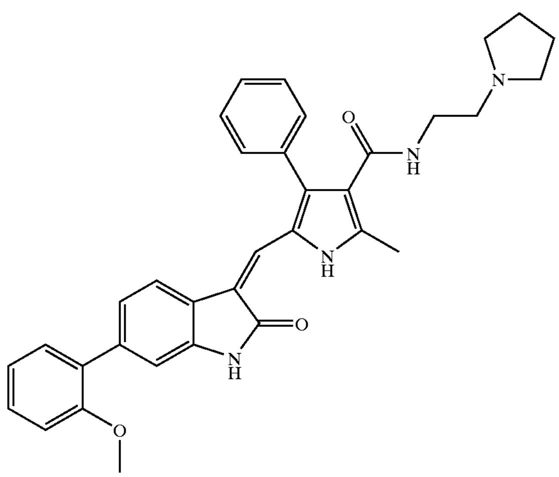 | 5-[6-(2-Methoxy-phenyl)-2-oxo-1,2-dihydroindol-3-ylidenemethyl]-2-methyl-4-phenyl-1H-pyrrole-3-carboxylic acid (2-pyrrolidin-1-yl-ethyl)amide |
| 44 | 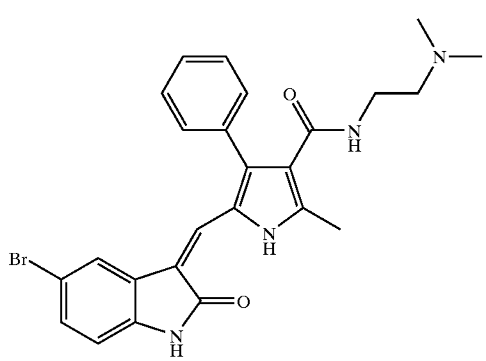 | 5-(5-Bromo-2-oxo-1,2-dihydroindol-3-ylidenemethyl)-2-methyl-4-phenyl-1H-pyrrole-3-carboxylic acid (2-dimethylamino-ethyl)amide |

TABLE 1-continued

| Example | Structure | Name |
|---------|-----------|------|
| 45 | 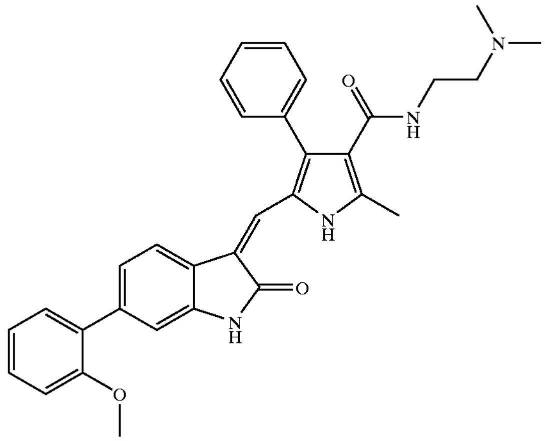 | 5-[6-(2-Methoxy-phenyl)-2-oxo-1,2-dihydroindol-3-ylidenemethyl]-2-methyl-4-phenyl-1H-pyrrole-3-carboxylic acid (2-dimethylamino-ethyl)amide |
| 46 | 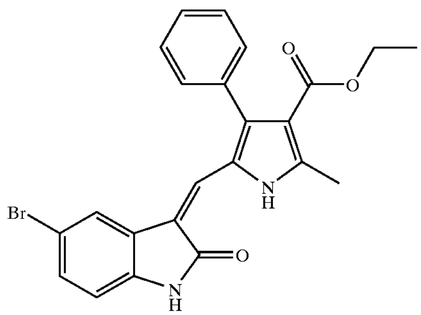 | 5-(5-Bromo-2-oxo-1,2-dihydroindol-3-ylidenemethyl)-2-methyl-4-phenyl-1H-pyrrole-3-carboxylic acid ethyl ester |
| 47 | 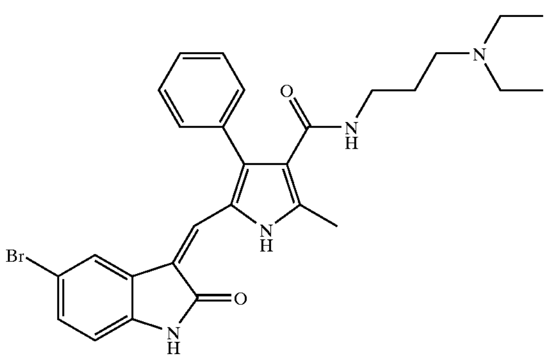 | 5-(5-Bromo-2-oxo-1,2-dihydroindol-3-ylidenemethyl)-2-methyl-4-phenyl-1H-pyrrole-3-carboxylic acid (3-diethylamino-propyl)amide |
| 48 | 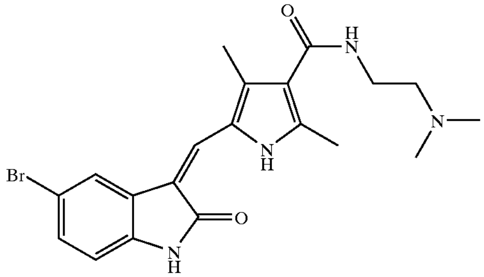 | 5-(5-Bromo-2-oxo-1,2-dihydroindol-3-ylidenemethyl)-2,4-dimethyl-1H-pyrrole-3-carboxylic acid (2-dimethylamino-ethyl)amide |

TABLE 1-continued

| Example | Structure | Name |
|---|---|---|
| 49 | 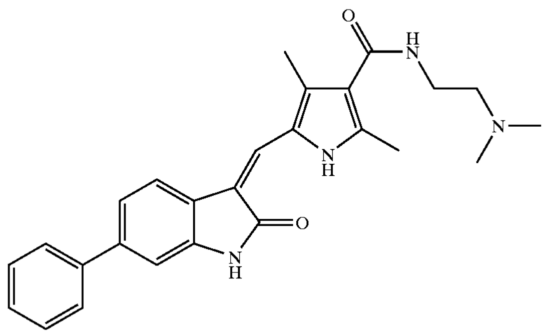 | 2,4-Dimethyl-5-(2-oxo-6-phenyl-1,2-dihydro-indol-3-ylidenemethyl)-1H-pyrrole-3-carboxylic acid (2-dimethylamino-ethyl)amide |
| 50 | 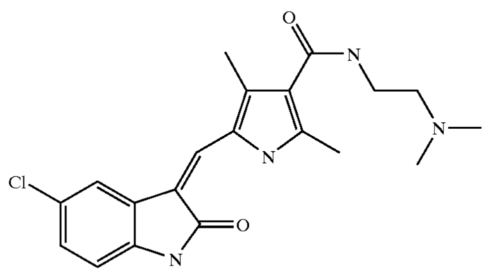 | 5-(5-Chloro-2-oxo-1,2-dihydroindol-3-ylidenemethyl)-2,4-dimethyl-1H-pyrrole-3-carboxylic acid (2-dimethylamino-ethyl)amide |
| 51 | 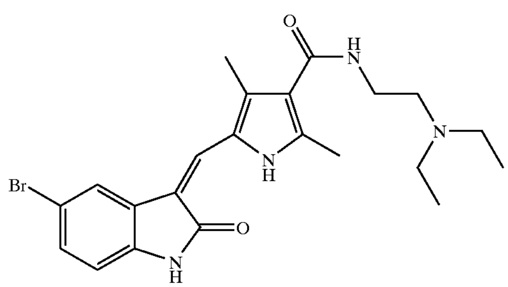 | 5-(5-Bromo-2-oxo-1,2-dihydroindol-3-ylidenemethyl)-2,4-dimethyl-1H-pyrrole-3-carboxylic acid (2-diethylaminoethyl)amide |
| 52 | 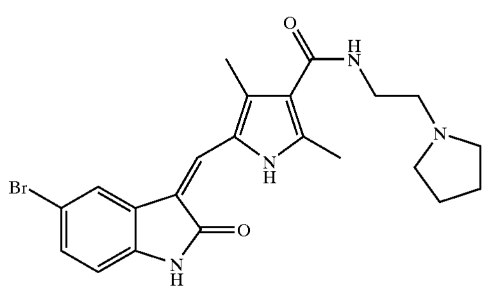 | 5-(5-Bromo-2-oxo-1,2-dihydroindol-3-ylidenemethyl)-2,4-dimethyl-1H-pyrrole-3-carboxylic acid (2-pyrrolidin-1-yl-ethyl)amide |
| 53 | 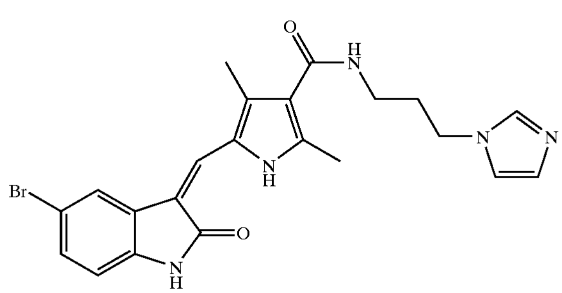 | 5-(5-Bromo-2-oxo-1,2-dihydroindol-3-ylidenemethyl)-2,4-dimethyl-1H-pyrrole-3-carboxylic acid (3-imidazol-1-ylpropyl)amide |

TABLE 1-continued

| Example | Structure | Name |
|---|---|---|
| 54 | 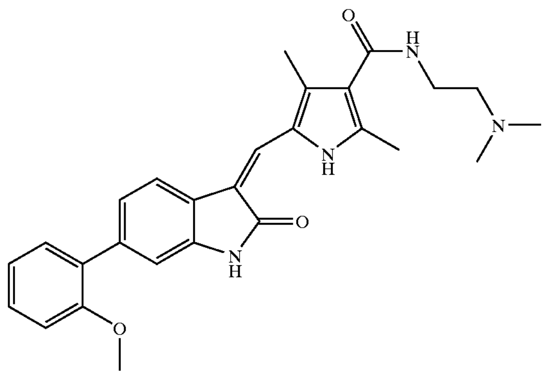 | 5-[6-(2-Methoxy-phenyl)-2-oxo-1,2-dihydroindol-3-ylidenemethyl)-2,4-dimethyl-1H-pyrrole-3-carboxylic acid (2-dimethyl-amino-ethyl)amide |
| 55 | 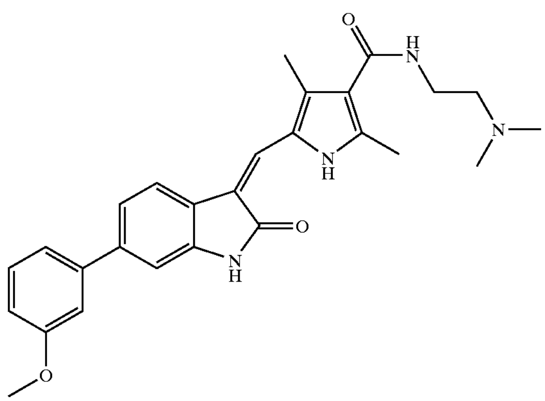 | 5-[6-(3-Methoxy-phenyl)-2-oxo-1,2-dihydroindol-3-ylidenemethyl]-2,4-dimethyl-1H-pyrrole-3-carboxylic acid (2-dimethyl-amino-ethyl)amide |
| 56 | 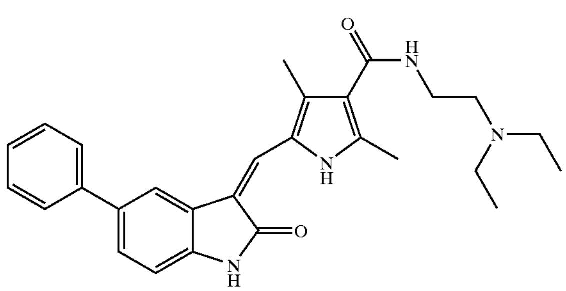 | 2,4-Dimethyl-5-(2-oxo-5-phenyl-1,2-dihydroindol-3-ylidenemethyl)-1H-pyrrole-3-carboxylic acid (2-diethylaminoethyl)amide |
| 57 | 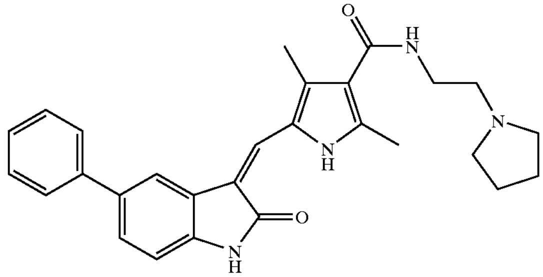 | 2,4-Dimethyl-5-(2-oxo-5-phenyl-1,2-dihydroindol-3-ylidenemethyl)-1H-pyrrole-3-carboxylic acid (2-pyrrolidin-1-yl-ethyl)amide |

TABLE 1-continued

| Example | Structure | Name |
|---|---|---|
| 58 | 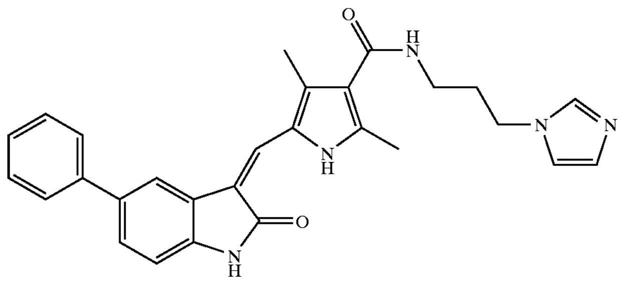 | 2,4-Dimethyl-5-(2-oxo-5-phenyl-1,2-dihydroindol-3-ylidenemethyl)-1H-pyrrole-3-carboxylic acid (3-imidazol-1-ylpropyl)amide |
| 59 | 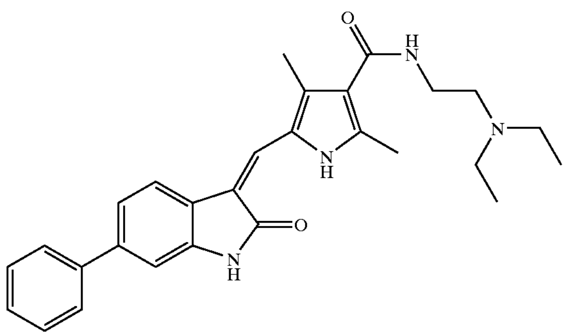 | 2,4-Dimethyl-5-(2-oxo-6-phenyl-1,2-dihydroindol-3-ylidenemethyl)-1H-pyrrole-3-carboxylic acid (2-diethylaminoethyl)amide |
| 60 | 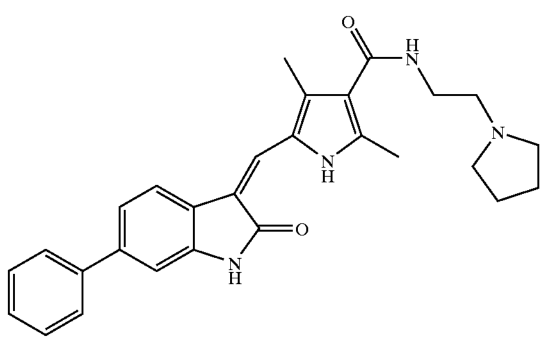 | 2,4-Dimethyl-5-(2-oxo-6-phenyl-1,2-dihydroindol-3-ylidenemethyl)-1H-pyrrole-3-carboxylic acid (2-pyrrolidin-1-yl-ethyl)amide |
| 61 | 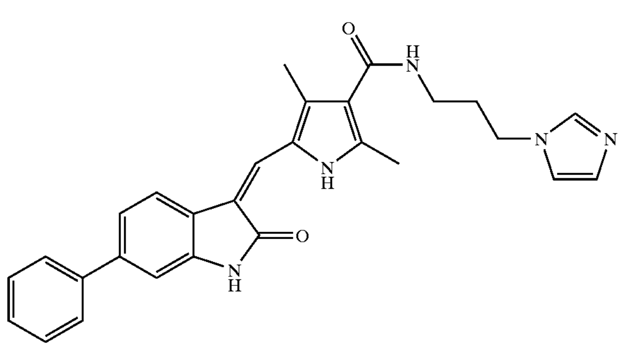 | 2,4-Dimethyl-5-(2-oxo-6-phenyl-1,2-dihydroindol-3-ylidenemethyl)-1H-pyrrole-3-carboxylic acid (3-imidazol-1-ylpropyl)amide |

TABLE 1-continued

| Example | Structure | Name |
|---------|-----------|------|
| 62 | 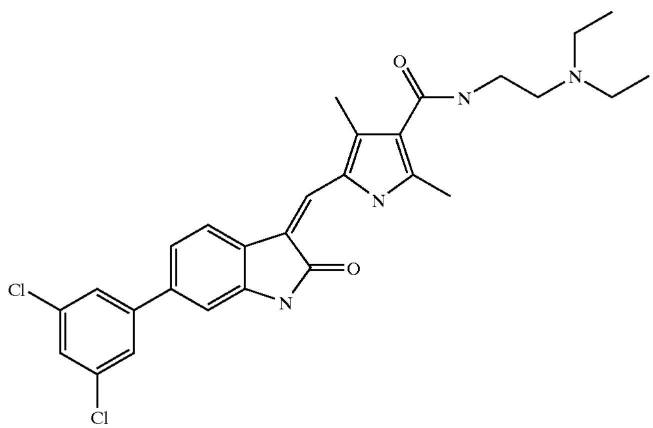 | 5-[6-(3,5-Dichloro-phenyl)-2-oxo-1,2-dihydroindol-3-ylidenemethyl]-2,4-dimethyl-1H-pyrrole-3-carboxylic acid (2-diethylamino-ethyl)amide |
| 63 | 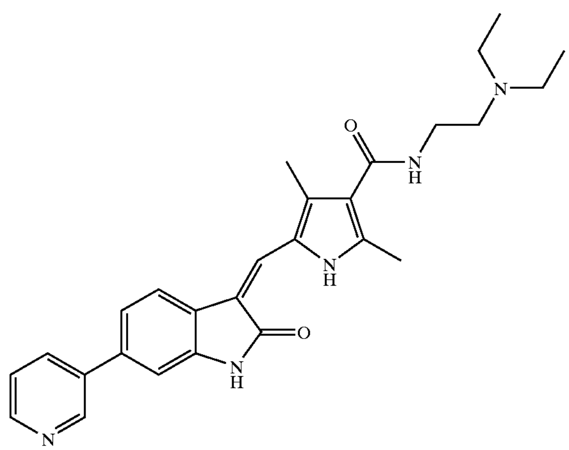 | 2,4-Dimethyl-5-(2-oxo-6-pyridin-3-yl-1,2-dihydroindol-3-ylidenemethyl)-1H-pyrrole-3-carboxylic acid (2-diethylaminoethyl)amide |
| 64 | 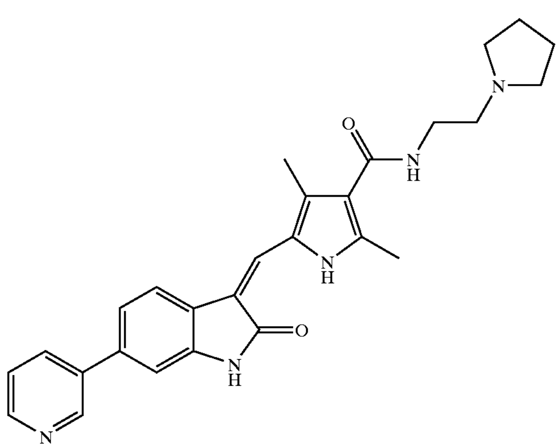 | 2,4-Dimethyl-5-(2-oxo-6-pyridin-3-yl-1,2-dihydroindol-3-ylidenemethyl)-1H-pyrrole-3-carboxylic acid (2-pyrrolidin-1-yl-ethyl)amide |

TABLE 1-continued

| Example | Structure | Name |
|---|---|---|
| 65 | 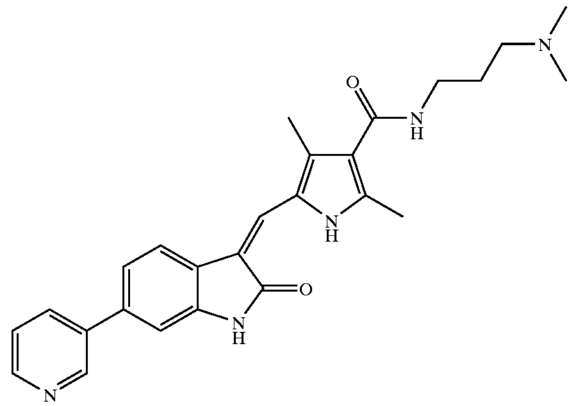 | 2,4-Dimethyl-5-(2-oxo-6-pyridin-3-yl-1,2-dihydroindol-3-ylidenemethyl)-1H-pyrrole-3-carboxylic acid (3-dimethylamino-propyl)amide |
| 66 | 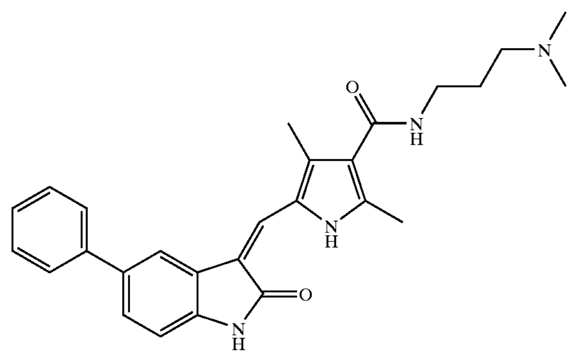 | 2,4-Dimethyl-5-(2-oxo-5-phenyl-1,2-dihydroindol-3-ylidenemethyl)-1H-pyrrole-3-carboxylic acid (3-dimethylamino-propyl)amide |
| 67 | 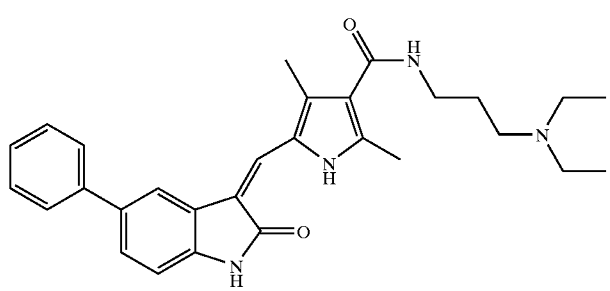 | 2,4-Dimethyl-5-(2-oxo-5-phenyl-1,2-dihydroindol-3-ylidenemethyl)-1H-pyrrole-3-carboxylic acid (3-diethylaminopropyl)amide |
| 68 | 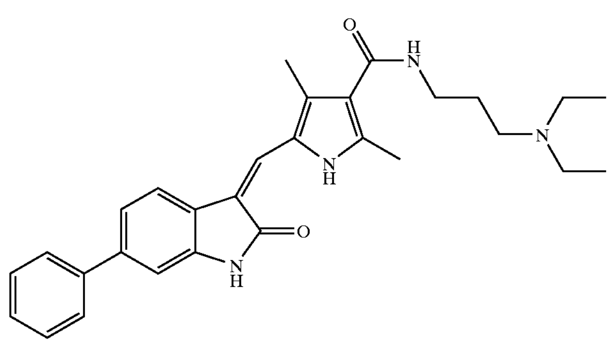 | 2,4-Dimethyl-5-(2-oxo-6-phenyl-1,2-dihydroindol-3-ylidenemethyl)-1H-pyrrole-3-carboxylic acid (3-diethylamino-propyl)amide |

TABLE 1-continued

| Example | Structure | Name |
|---|---|---|
| 69 | 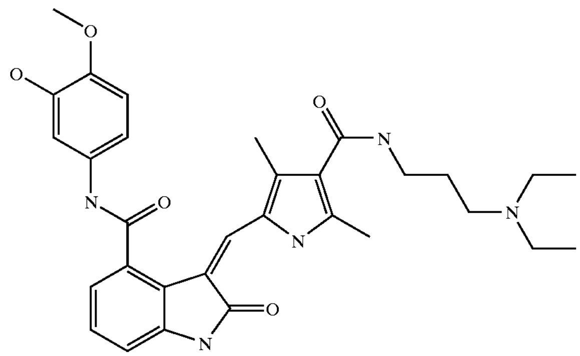 | 3-[4-(3-Diethylamino-propylcarbamoyl)-3,5-dimethyl-1H-pyrrol-2-ylmethylene]-2-oxo-2,3-dihydro-1H-indole-4-carboxylic acid (3-chloro-4-methoxy-phenyl)amide |
| 70 | 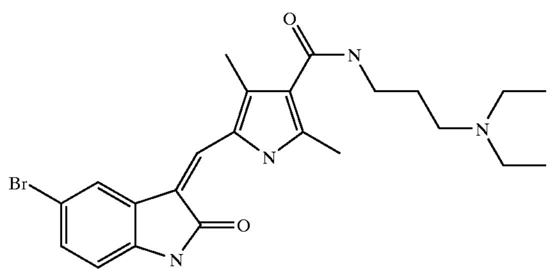 | 5-(5-Bromo-2-oxo-1,2-dihydroindol-3-ylidenemethyl)-2,4-dimethyl-1H-pyrrole-3-carboxylic acid (3-diethylaminopropyl)amide |
| 71 | 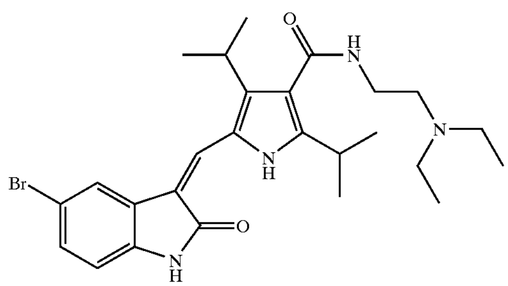 | 5-(5-Bromo-2-oxo-1,2-dihydroindol-3-ylidenemethyl)-2,4-diisopropyl-1H-pyrrole-3-carboxylic acid (2-diethylaminoethyl)amide |
| 72 | 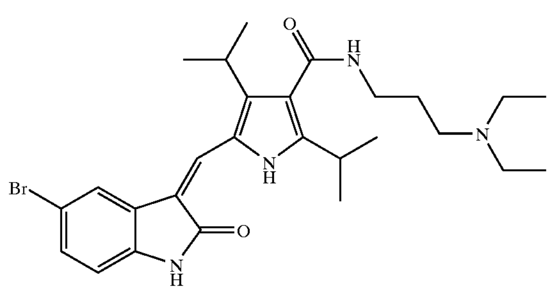 | 5-(5-Bromo-2-oxo-1,2-dihydroindol-3-ylidenemethyl)-2,4-diisopropyl-1H-pyrrole-3-carboxylic acid (3-diethylaminopropyl)amide |
| 73 | 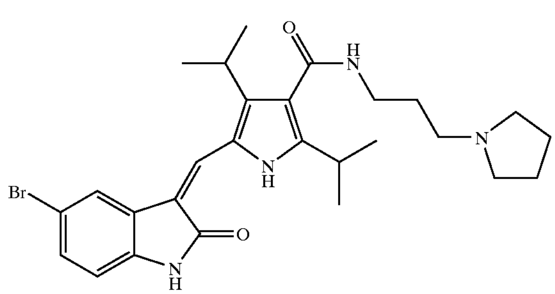 | 5-(5-Bromo-2-oxo-1,2-dihydroindol-3-ylidenemethyl)-2,4-diisopropyl-1H-pyrrole-3-carboxylic acid (3-pyrrolidin-1-ylpropyl)amide |

TABLE 1-continued

| Example | Structure | Name |
|---|---|---|
| 74 | 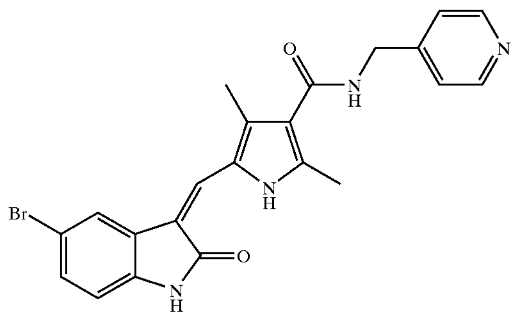 | 5-(5-Bromo-2-oxo-1,2-dihydroindol-3-ylidenemethyl)-2,4-dimethyl-1H-pyrrole-3-carboxylic acid (pyridin-4-ylmethyl)amide |
| 75 | 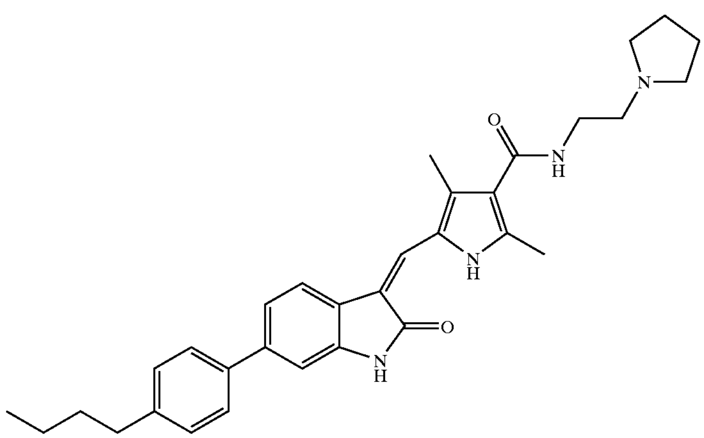 | 5-[6-(4-Butyl-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 76 | 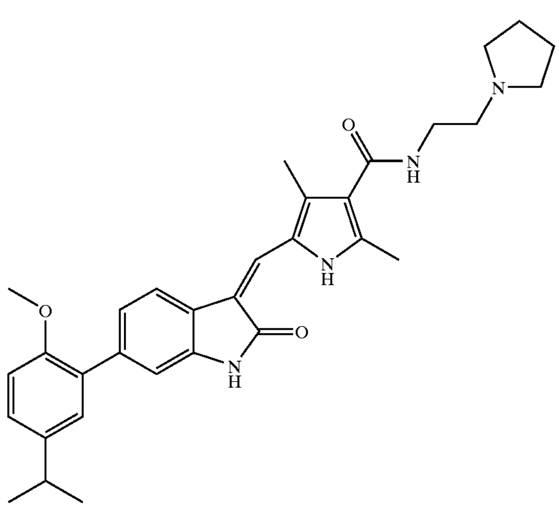 | 5-[6-(5-Isopropyl-2-methoxy-phenyl)-2-oxo-1,2-dihydroindol-3-ylidenemethyl]-2,4-dimethyl-1H-pyrrole-3-carboxylic acid (2-pyrrolidin-1-yl-ethyl)amide |

TABLE 1-continued

| Example | Structure | Name |
|---|---|---|
| 77 | 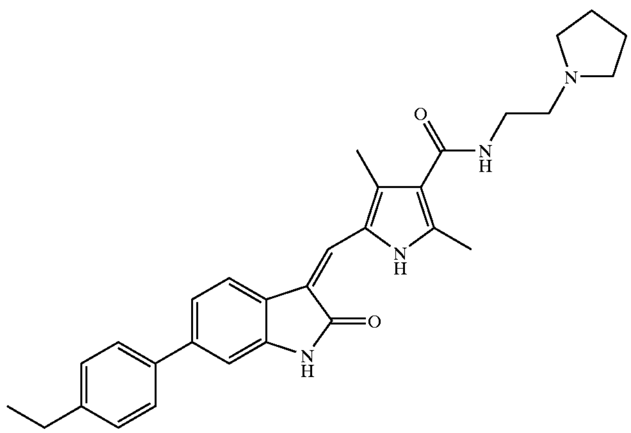 | 5-[6-(4-Ethyl-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 78 | 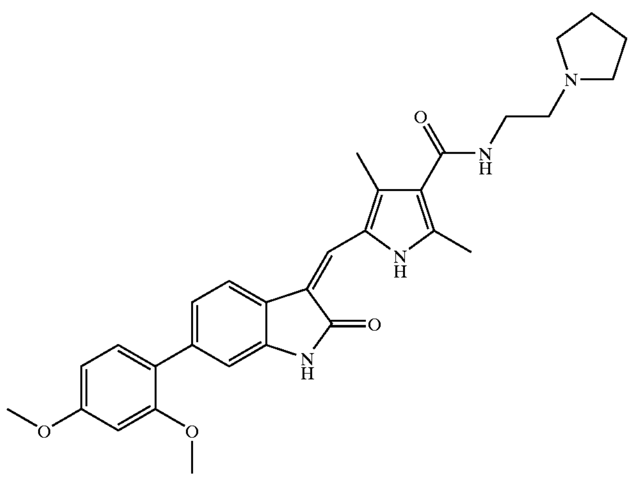 | 5-[6-(2,4-Dimethoxy-phenyl)-2-oxo-1,2-dihydroindol-3-ylidenemethyl]-2,4-dimethyl-1H-pyrrole-3-carboxylic acid (2-pyrrolidin-1-yl-ethyl)amide |
| 79 | 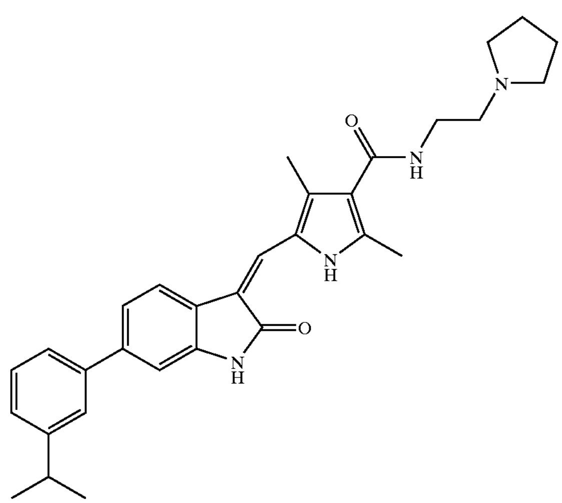 | 5-[6-(3-Isopropyl-phenyl)-2-oxo-1,2-dihydroindol-3-ylidenemethyl]-2,4-dimethyl-1H-pyrrole-3-carboxylic acid (2-pyrrolidin-1-yl-ethyl)amide |

TABLE 1-continued

| Example | Structure | Name |
|---|---|---|
| 80 | 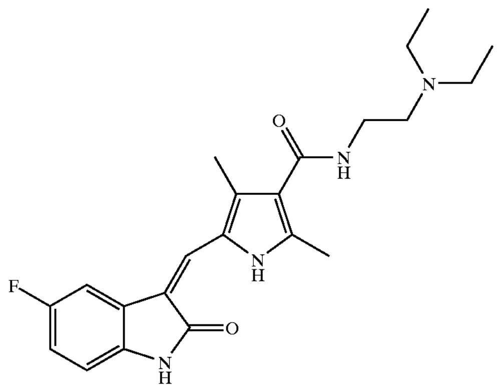 | 5-(5-Fluoro-2-oxo-1,2-dihydroindol-3-ylidenemethyl)-2,4-dimethyl-1H-pyrrole-3-carboxylic acid (2-diethylaminoethyl)amide |
| 81 | 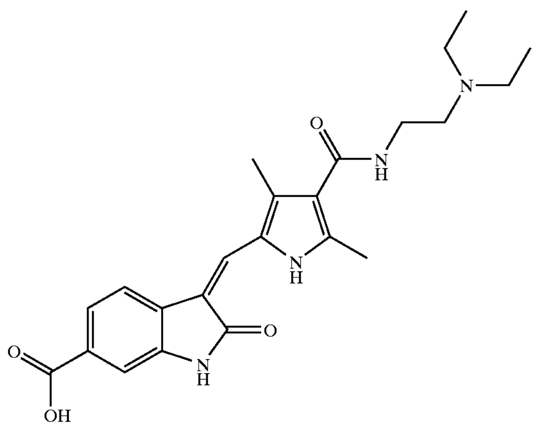 | 3-[4-(2-diethylaminoethylcarbamoyl)-3,5-dimethyl-1H-pyrrol-2-ylmethylene]-2-oxo-2,3-dihydro-1H-indole-6-carboxylic acid |
| 82 | 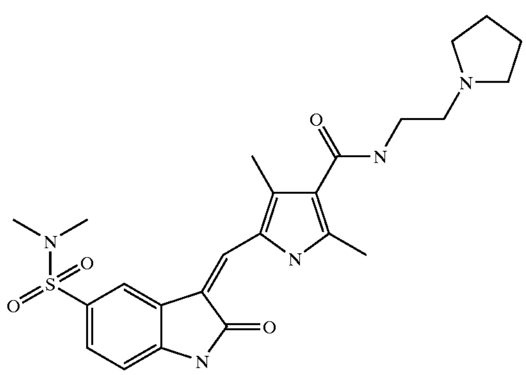 | 5-(5-Dimethylsulfamoyl-2-oxo-1,2-dihydroindol-3-ylidenemethyl)-2,4-dimethyl-1H-pyrrole-3-carboxylic acid (2-pyrrolidin-1-yl-ethyl)amide |
| 83 | 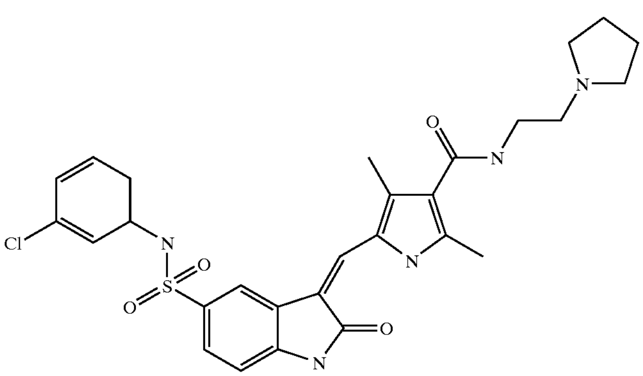 | 5-[5-(3-Chloro-phenylsulfamoyl)-2-oxo-1,2-dihydroindol-3-ylidenemethyl]-2,4-dimethyl-1H-pyrrole-3-carboxylic acid (2-pyrrolidin-1-yl-ethyl)amide |

TABLE 1-continued

| Example | Structure | Name |
| --- | --- | --- |
| 84 | 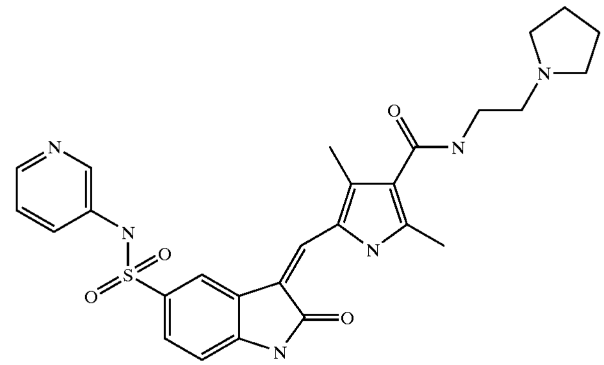 | 2,4-Dimethyl-5-[2-oxo-5-(pyridin-3-ylsulfamoyl)-1,2-dihydroindol-3-ylidenemethyl]-1H-pyrrole-3-carboxylic acid (2-pyrrolidin-1-yl-ethyl)amide |
| 85 | 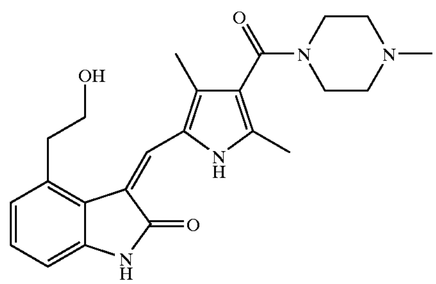 | 3-[3,5-Dimethyl-4-(4-methyl-piperazine-1-carbonyl)-1H-pyrrol-2-ylmethylene]-4-(2-hydroxy-ethyl)-1,3-dihydroindol-2-one |
| 86 | 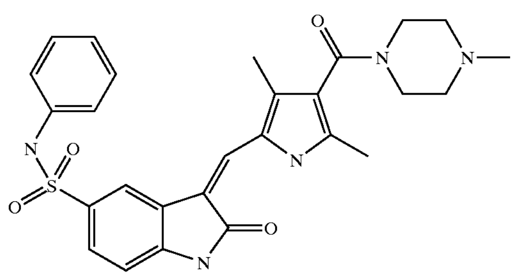 | 3-[3,5-Dimethyl-4-(4-methyl-piperazine-1-carbonyl)-1H-pyrrol-2-ylmethylene]-2-oxo-2,3-dihydro-1H-indole-5-sulfonic acid phenylamide |
| 87 | 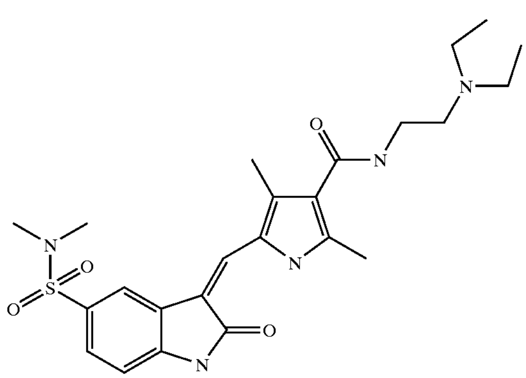 | 5-(5-Dimethylsulfamoyl-2-oxo-1,2-dihydroindol-3-ylidenemethyl)-2,4-dimethyl-1H-pyrrole-3-carboxylic acid (2-diethylamino-ethyl)amide |

TABLE 1-continued

| Example | Structure | Name |
|---|---|---|
| 88 | 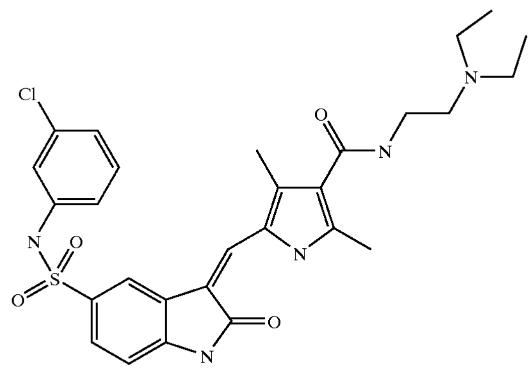 | 5-[5-(3-Chloro-phenylsulfamoyl)-2-oxo-1,2-dihydroindol-3-ylidenemethyl]-2,4-dimethyl-1H-pyrrole-3-carboxylic acid (2-diethylamino-ethyl)amide |
| 89 | 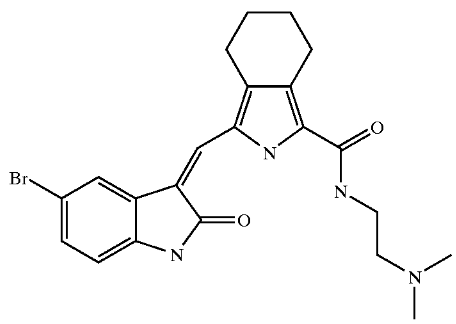 | 3-(5-Bromo-2-oxo-1,2-dihydro-indol-3-ylidenemethyl)-4,5,6,7-tetrahydro-2H-isoindole-1-carboxylic acid (2-dimethylamino-ethyl)-amide |
| 90 | 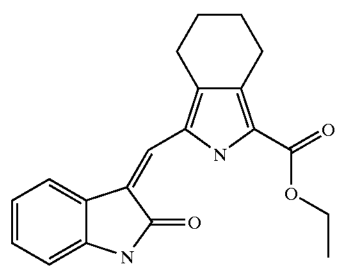 | 3-(2-Oxo-1,2-dihydro-indol-3-ylidenemethyl)-4,5,6,7-tetrahydro-2H-isoindole-1-carboxylic acid ethyl ester |
| 91 | 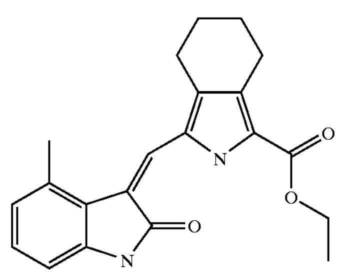 | 3-(4-Methyl-2-oxo-1,2-dihydro-indol-3-ylidenemethyl)-4,5,6,7-tetrahydro-2H-isoindole-1-carboxylic acid ethyl ester |
| 92 | 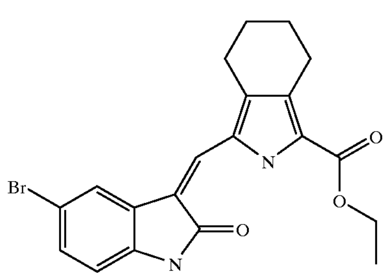 | 3-(5-Bromo-2-oxo-1,2-dihydro-indol-3-ylidenemethyl)-4,5,6,7-tetrahydro-2H-isoindole-1-carboxylic acid ethyl ester |

TABLE 1-continued

| Example | Structure | Name |
|---|---|---|
| 93 | 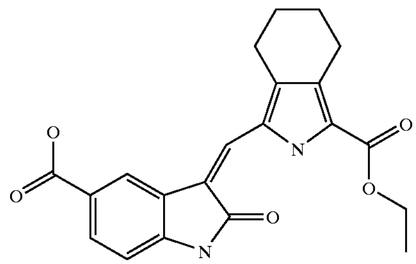 | 3-(3-Ethoxycarbonyl-4,5,6,7-tetrahydro-2H-isoindol-1-ylmethylene)-2-oxo-2,3-dihydro-1H-indole-5-carboxylic acid |
| 94 | 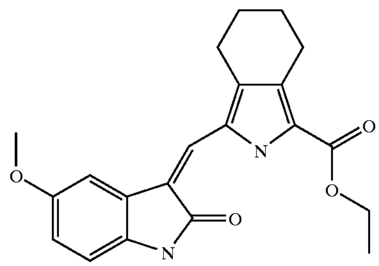 | 3-(5-Methoxy-2-oxo-1,2-dihydro-indol-3-ylidenemethyl)-4,5,6,7-tetrahydro-2H-isoindole-1-carboxylic acid ethyl ester |
| 95 | 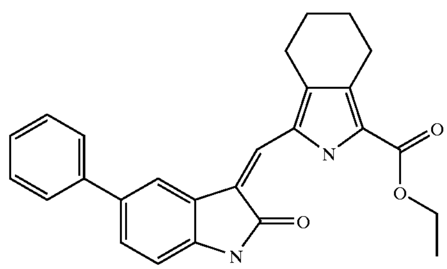 | 3-(2-Oxo-5-phenyl-1,2-dihydro-indol-3-ylidenemethyl)-4,5,6,7-tetrahydro-2H-isoindole-1-carboxylic acid ethyl ester |
| 96 | 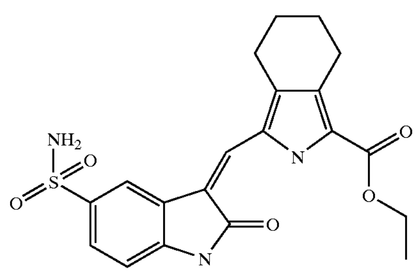 | 3-(2-Oxo-5-sulfamoyl-1,2-dihydro-indol-3-ylidenemethyl)-4,5,6,7-tetrahydro-2H-isoindole-1-carboxylic acid ethyl ester |
| 97 | 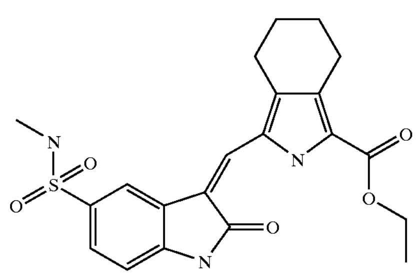 | 3-(5-Methylsulfamoyl-2-oxo-1,2-dihydro-indol-3-ylidenemethyl)-4,5,6,7-tetrahydro-2H-isoindole-1-carboxylic acid ethyl ester |

TABLE 1-continued

| Example | Name |
|---|---|
| 98 | 3-(5-Dimethylsulfamoyl-2-oxo-1,2-dihydro-indol-3-ylidenemethyl)-4,5,6,7-tetrahydro-2H-isoindole-1-carboxylic acid ethyl ester |
| 99 | 3-(2-Oxo-5-phenylsulfamoyl-1,2-dihydro-indol-3-ylidenemethyl)-4,5,6,7-tetrahydro-2H-isoindole-1-carboxylic acid ethyl ester |
| 100 | 3-(6-Bromo-2-oxo-1,2-dihydro-indol-3-ylidenemethyl)-4,5,6,7-tetrahydro-2H-isoindole-1-carboxylic acid ethyl ester |
| 101 | 3-(2-Oxo-6-phenyl-1,2-dihydro-indol-3-ylidenemethyl)-4,5,6,7-tetrahydro-2H-isoindole-1-carboxylic acid ethyl ester |
| 102 | 3-(3-Ethoxycarbonyl-4,5,6,7-tetrahydro-2H-isoindol-1-ylmethylene)-2-oxo-2,3-dihydro-1H-indole-6-carboxylic acid |

TABLE 1-continued

| Example | Structure | Name |
| --- | --- | --- |
| 103 | 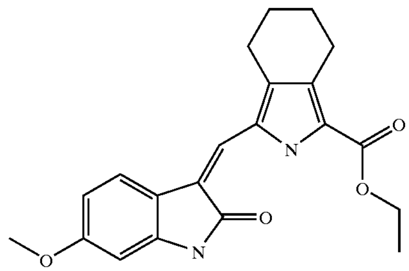 | 3-(6-Methoxy-2-oxo-1,2-dihydro-indol-3-ylidenemethyl)-4,5,6,7-tetrahydro-2H-isoindole-1-carboxylic acid ethyl ester |
| 104 | 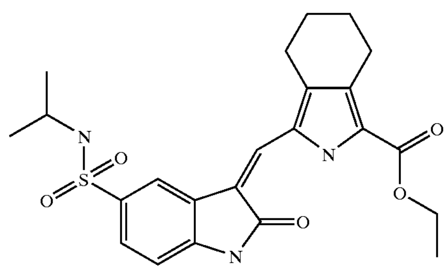 | 3-(5-Isopropylsulfamoyl-2-oxo-1,2-dihydro-indol-3-ylidenemethyl)-4,5,6,7-tetrahydro-2H-isoindole-1-carboxylic acid ethyl ester |
| 105 | 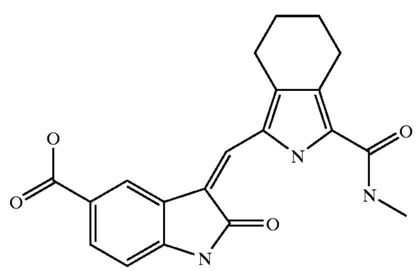 | 3-(3-Methylcarbamoyl-4,5,6,7-tetrahydro-2H-isoindol-1-ylmethylene)-2-oxo-2,3-dihydro-1H-indole-5-carboxylic acid |
| 106 | 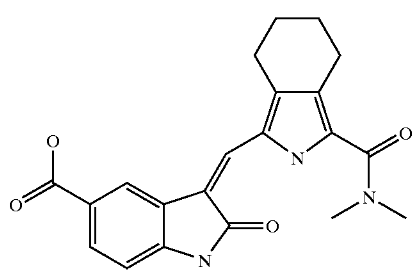 | 3-(3-Dimethylcarbamoyl-4,5,6,7-tetrahydro-2H-isoindol-1-ylmethylene)-2-oxo-2,3-dihydro-1H-indole-5-carboxylic acid |
| 107 | 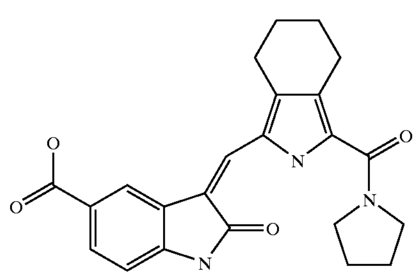 | 2-Oxo-3-[3-(pyrrolidine-1-carbonyl-4,5,6,7-tetrahydro-2H-isoindol-1-ylmethylene]-2,3-dihydro-1H-indole-5-carboxylic acid |

TABLE 1-continued

| Example | Structure | Name |
| --- | --- | --- |
| 108 | 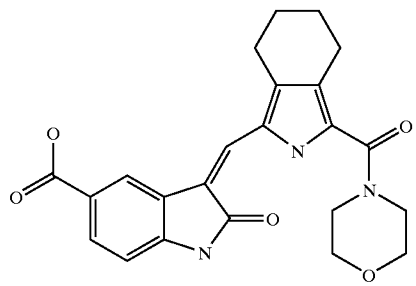 | 3-[3-(Morpholine-4-carbonyl)-4,5,6,7-tetra-hydro-2H-isoindol-1-ylmethylene]-2-oxo-2,3-dihydro-1H-indole-5-carboxylic acid |
| 109 | 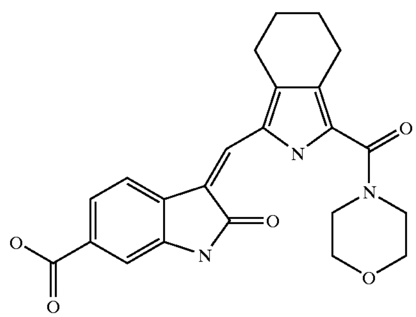 | 3-[3-(Morpholine-4-carbonyl)-4,5,6,7-tetra-hydro-2H-isoindol-1-ylmethylene]-2-oxo-2,3-dihydro-1H-indole-6-carboxylic acid |
| 110 | 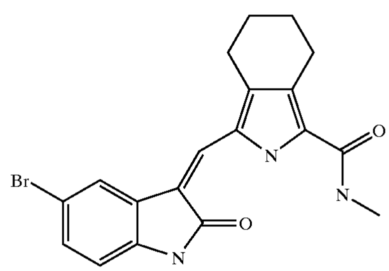 | 3-(5-Bromo-2-oxo-1,2-dihydro-indol-3-ylidenemethyl)-4,5,6,7-tetrahydro-2H-isoindole-1-carboxylic acid methylamide |
| 111 | 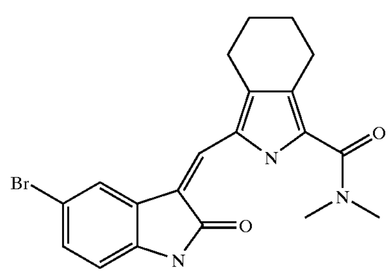 | 3-(5-Bromo-2-oxo-1,2-dihydro-indol-3-ylidenemethyl)-4,5,6,7-tetrahydro-2H-isoindole-1-carboxylic acid dimethylamide |
| 112 | 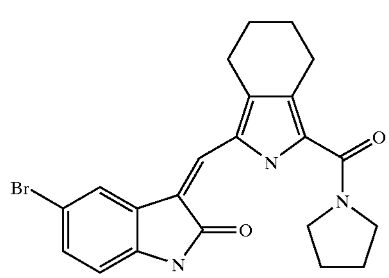 | 5-Bromo-3-[3-(pyrrolidine-1-carbonyl)-4,5,6,7-tetrahydro-2H-isoindol-1-ylmethylene]-1,3-dihydro-indol-2-one |

TABLE 1-continued

| Example | Structure | Name |
|---|---|---|
| 113 | 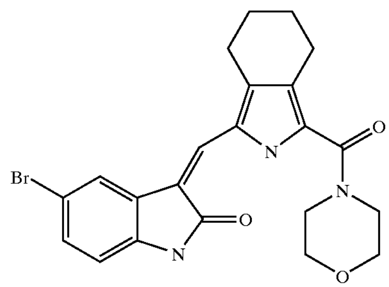 | 5-Bromo-3-[3-(morpholine-4-carbonyl)-4,5,6,7-tetrahydro-2H-isoindol-1-ylmethylene]-1,3-dihydro-indol-2-one |
| 114 | 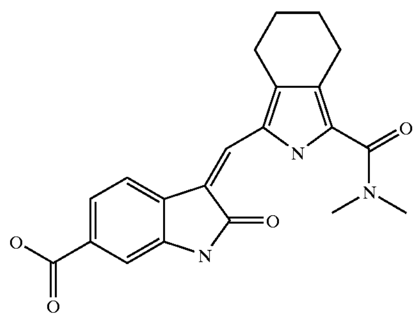 | 3-(3-Dimethylcarbamoyl-4,5,6,7-tetrahydro-2H-isoindol-1-ylmethylene)-2-oxo-2,3-dihydro-1H-indole-6-carboxylic acid |
| 115 | 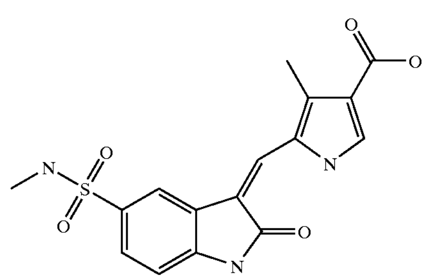 | 4-Methyl-5-(5-methylsulfamoyl-2-oxo-1,2-dihydro-indol-3-ylidenemethyl)-1H-pyrrole-3-carboxylic acid |
| 116 | 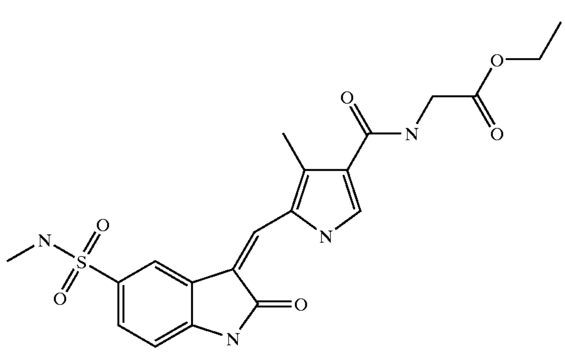 | {[4-Methyl-5-(4-methyl-5-methylsulfamoyl-2-oxo-1,2-dihydro-indol-3-ylidenemethyl)-1H-pyrrole-3-carbonyl]-amino}-acetic acid ethyl ester |

TABLE 1-continued

| Example | Structure | Name |
|---|---|---|
| 117 | 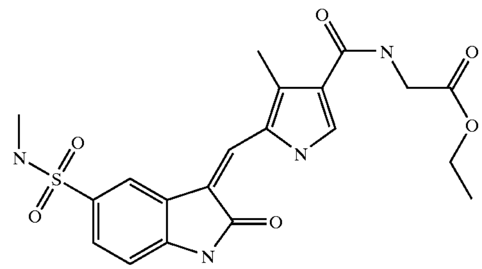 | {[4-Methyl-5-(5-methylsulfamoyl-2-oxo-1,2-dihydro-indol-3-ylidenemethyl)-1H-pyrrole-3-carbonyl]-amino}-acetic acid ethyl ester |
| 118 | 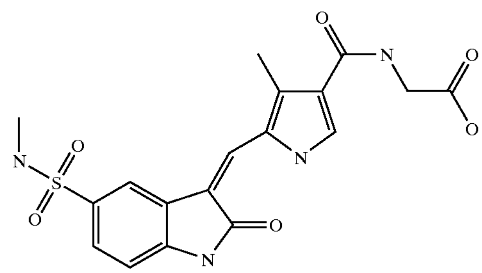 | {[4-Methyl-5-(5-methylsulfamoyl-2-oxo-1,2-dihydro-indol-3-ylidenemethyl)-1H-pyrrole-3-carbonyl]-amino}-acetic acid |
| 119 | 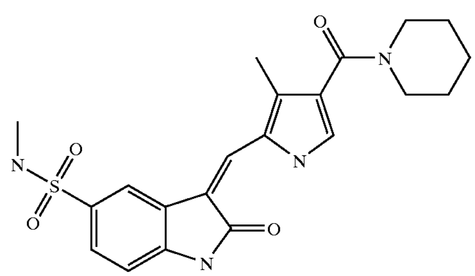 | 3-[3-Methyl-4-(piperidine-1-carbonyl)-1H-pyrrol-2-ylmethylene]-2-oxo-2,3-dihydro-1H-indole-5-sulfonic acid methylamide |
| 120 | 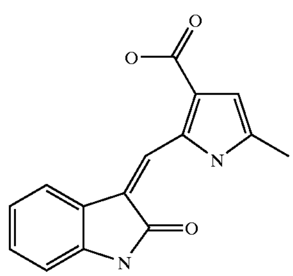 | 5-Methyl-2-(2-oxo-1,2-dihydro-indol-3-ylidenemethyl)-1H-pyrrole-3-carboxylic acid |
| 121 | 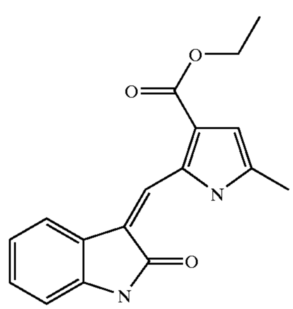 | 5-Methyl-2-(2-oxo-1,2-dihydro-indol-3-ylidenemethyl)-1H-pyrrole-3-carboxylic acid ethyl ester |

TABLE 1-continued

| Example | Structure | Name |
|---|---|---|
| 122 | 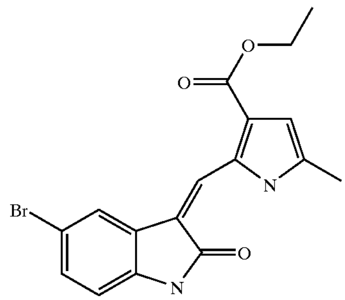 | 2-(5-Bromo-2-oxo-1,2-dihydro-indol-3-ylidenemethyl)-5-methyl-1H-pyrrole-3-carboxylic acid ethyl ester |
| 123 | 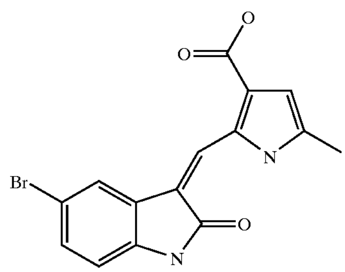 | 2-(5-Bromo-2-oxo-1,2-dihydro-indol-3-ylidenemethyl)-5-methyl-1H-pyrrole-3-carboxylic acid |
| 124 | 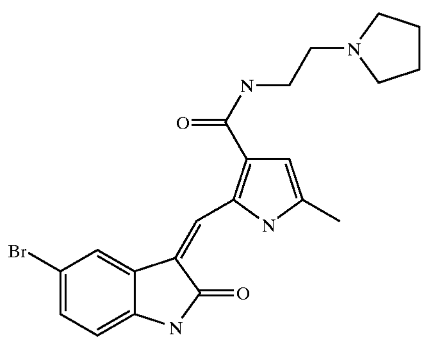 | 2-(5-Bromo-2-oxo-1,2-dihydro-indol-3-ylidenemethyl)-5-methyl-1H-pyrrole-3-carboxylic acid (2-pyrrolidin-1-yl-ethyl)-amide |
| 125 | 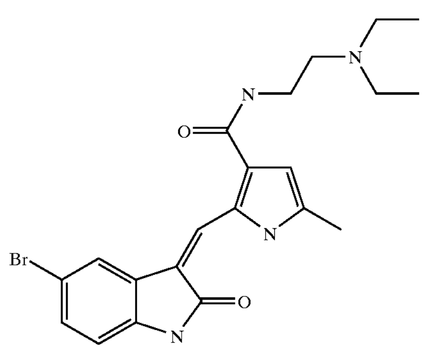 | 2-(5-Bromo-2-oxo-1,2-dihydro-indol-3-ylidenemethyl)-5-methyl-1H-pyrrole-3-carboxylic acid (2-diethylamino-ethyl)-amide |

Some representative "pyrrole substituted-2-indolinone" compounds contemplated for use in this invention are shown in Table 1. The compounds shown are examples only and are not to be construed as limiting the scope of this invention in any manner whatsoever.

TABLE 2
| Compound | Structures | Names |
|---|---|---|
| 126 | 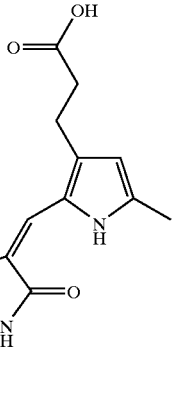 | 3-{2-[6-(4-Fluoro-phenyl)-2-oxo-1,2-dihydroindol-3-ylidenemethyl]-5-methyl-1H-pyrrol-3-yl}-propionic acid |
| 127 | 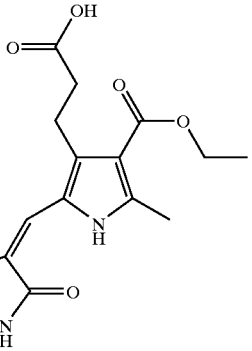 | 4-(2-Carboxy-ethyl)-5-[6-(4-fluoro-phenyl)-2-oxo-1,2-dihydroindol-3-ylidenemethyl]-2-methyl-1H-pyrrole-3-carboxylic acid ethyl ester |
| 128 | 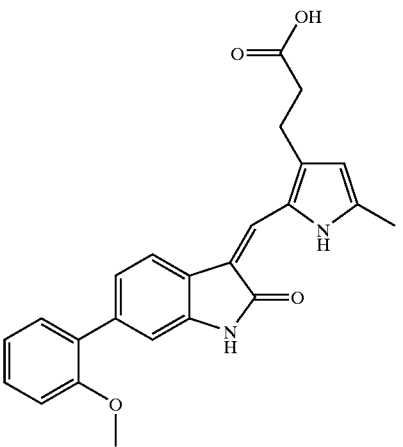 | 3-{2-[6-(2-Methoxy-phenyl)-2-oxo-1,2-dihydroindol-3-ylidenemethyl]-5-methyl-1H-pyrrol-3-yl}-propionic acid |

TABLE 2-continued

| Compound | Structures | Names |
|---|---|---|
| 129 | 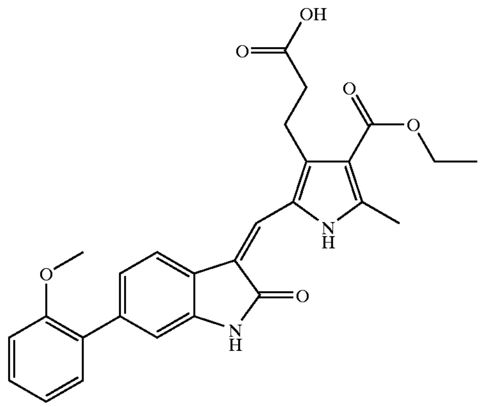 | 4-(2-Carboxy-ethyl)-5-[6-(2-methoxy-phenyl)-2-oxo-1,2-dihydroindol-3-ylidenemethyl]-methyl-1H-pyrrole-3-carboxylic acid ethyl ester |
| 130 | 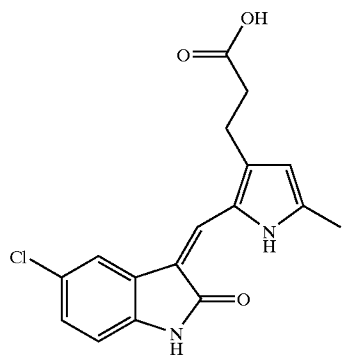 | 3-[2-(5-Chloro-2-oxo-1,2-dihydroindol-3-ylidenemethyl)-5-methyl-1H-pyrrol-3-yl]-propionic acid |
| 131 | 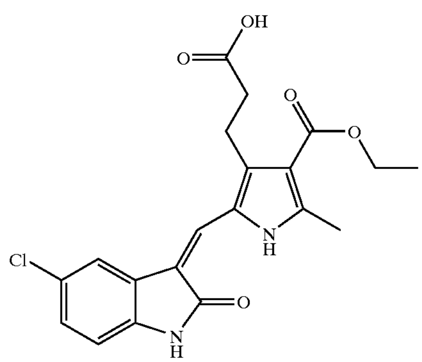 | 4-(2-Carboxy-ethyl)-5-(5-chloro-2-oxo-1,2-dihydroindol-ylidenemethyl)-2-methyl-1H-pyrrole-3-carboxylic acid ethyl ester |
| 132 | 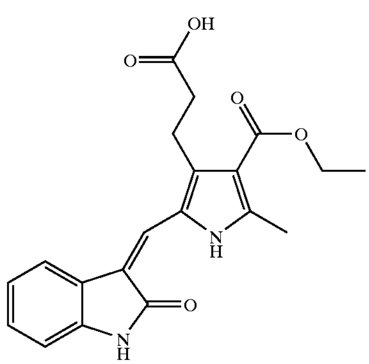 | 4-(2-Carboxy-ethyl)-2-methyl-5-(2-oxo-1,2-dihydroindol-3-ylidenemethyl)-1H-pyrrole-3-carboxylic acid ethyl ester |

TABLE 2-continued

| Compound | Structures | Names |
|---|---|---|
| 133 | 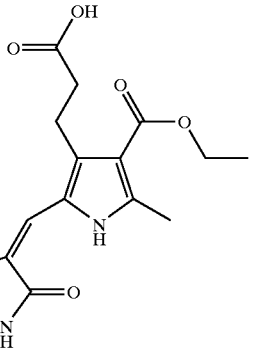 | 5-(5-Bromo-2-oxo-1,2-dihydroindol-3-ylidenemethyl)-4-(2-carboxy-ethyl)-2-methyl-1H-pyrrole-3-carboxylic acid ethyl ester |
| 134 | 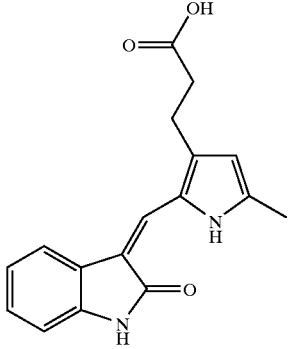 | 3-[5-Methyl-2-(2-oxo-1,2-dihydroindol-3-ylidenemethyl)-1H-pyrrol-3-yl]-propionic acid |
| 135 | 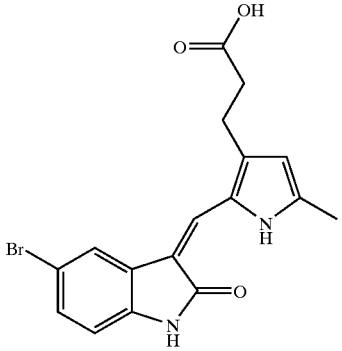 | 3-[2-(5-Bromo-2-oxo-1,2-dihydroindol-3-ylidenemethyl)-5-methyl-1H-pyrrol-3-yl]-propionic acid |
| 136 | 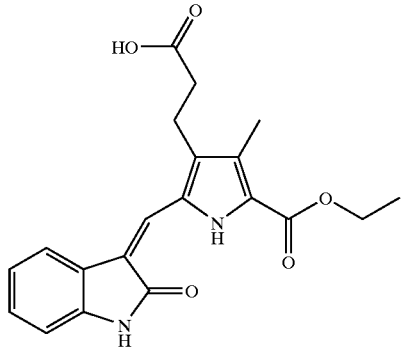 | 4-(2-Carboxy-ethyl)-3-methyl-5-(2-oxo-1,2-dihydroindol-3-ylidenemethyl)-1H-pyrrole-2-carboxylic acid ethyl ester |

TABLE 2-continued

| Compound | Structures | Names |
|---|---|---|
| 137 | 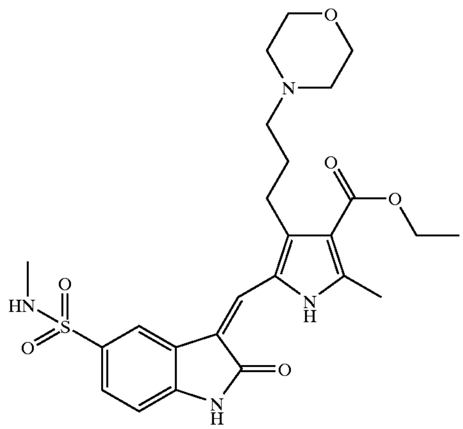 | 2-Methyl-5-(5-methylsulfamoyl-2-oxo-1,2-dihydroindol-3-ylidenemethyl)-4-(3-morpholin-4-yl-propyl)-1H-pyrrole-3-carboxylic acid ethyl ester |
| 138 | 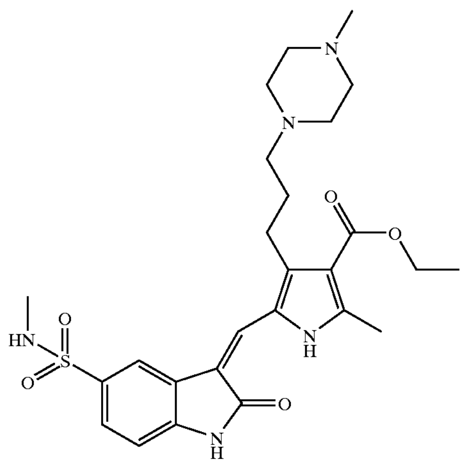 | 2-Methyl-4-[3-(4-methyl-piperazin-1-yl)-propyl]-5-(5-methylsulfamoyl-2-oxo-1,2-dihydroindol-3-ylidenemethyl)-1H-pyrrole-3-carboxylic acid ethyl ester |
| 139 | 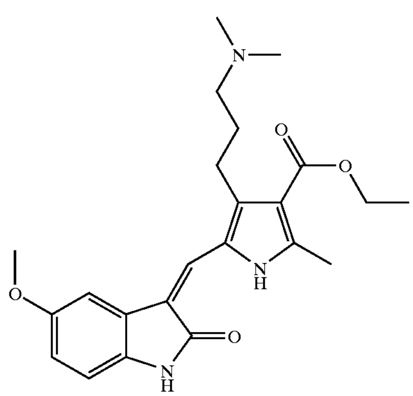 | 4-(3-Dimethylamino-propyl)-5-(methoxy-2-oxo-1,2-dihydroindol-3-ylidenemethyl)-2-methyl-1H-pyrrole-3-carboxylic acid ethyl ester |

TABLE 2-continued

| Compound | Structures | Names |
|---|---|---|
| 140 | 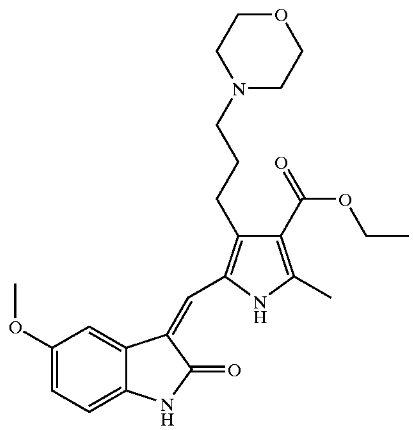 | 5-(5-Methoxy-2-oxo-1,2-dihydroindol-3-ylidenemethyl)-2-methyl-4-(3-morpholin-4-yl-propyl)-1H-pyrrole-3-carboxylic acid ethyl ester |
| 141 | 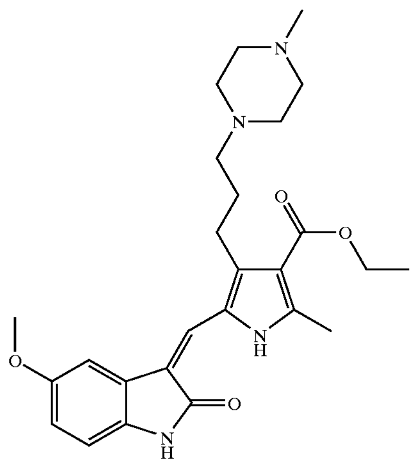 | 5-(5-Methoxy-2-oxo-1,2-dihydroindol-3-ylidenemethyl)-2-methyl-4-[3-(4-methyl-piperazin-1-yl)-propyl]-1H-pyrrole-3-carboxylic acid ethyl ester |
| 142 | 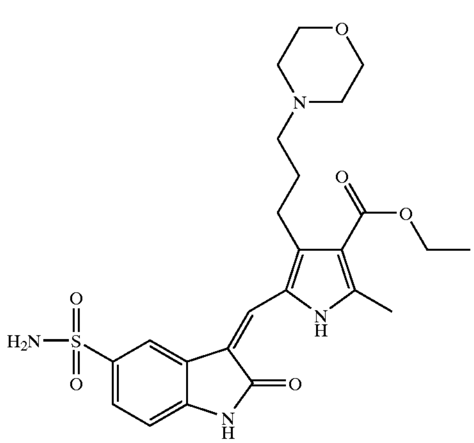 | 2-Methyl-4-(3-morpholin-4-yl-propyl)-5-(2-oxo-5-sulfamoyl-1,2-dihydroindol-3-ylidenemethyl)-1H-pyrrole-3-carboxylic acid ethyl ester |

TABLE 2-continued

| Compound | Structures | Names |
|---|---|---|
| 143 | 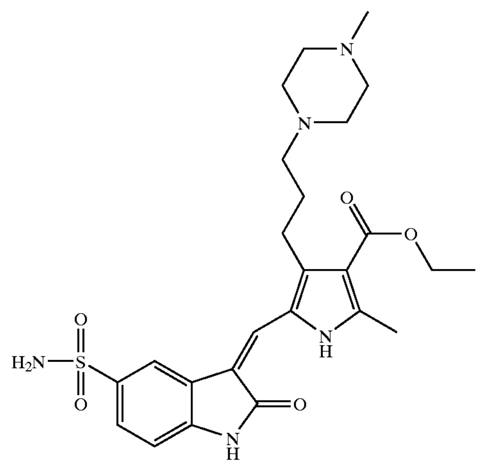 | 2-Methyl-4-[3-(4-methyl-piperazin-1-yl)-porpyl]-5-(2-oxo-5-sulfamoyl-1,2-dihydroindol-3-ylidenemethyl)-1H-pyrrole-3-carboxylic acid ethyl ester |
| 144 | 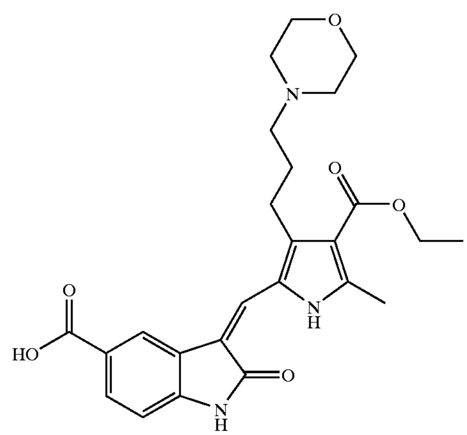 | 3-[4-Ethoxycarbonyl-5-methyl-3-(3-morpholin-4-yl-propyl)-1H-pyrrol-2-ylmethylene]-2-oxo-2,3-dihydro-1H-indole-5-carboxylic acid |
| 145 | 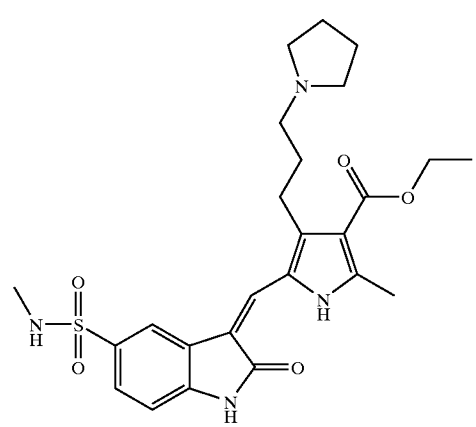 | 2-Methyl-5-(5-methylsulfamoyl-2-oxo-1,2-dihydroindol-3-ylidenemethyl)-4-(3-pyrrolidin-1-yl-propyl)-1H-pyrrole-3-carboxylic acid ethyl ester |

TABLE 2-continued

| Compound | Structures | Names |
|---|---|---|
| 146 | 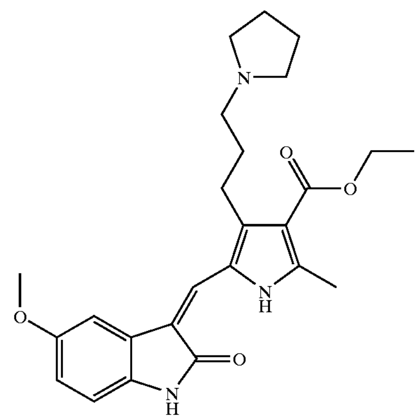 | 5-(5-Methoxy-2-oxo-1,2-dihydroindol-3-ylidenemethyl)-2-methyl-4-[3-pyrrolidin-1-yl-propyl]-1H-pyrrole-3-carboxylic acid ethyl ester |
| 147 | 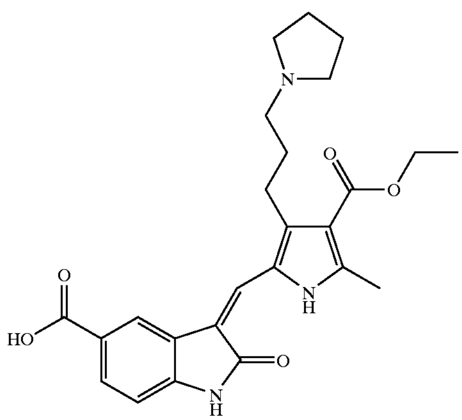 | 3-[4-Ethoxycarbonyl-5-methyl-3-(3-pyrrolin-1-yl-propyl)-1H-pyrrol-2-ylmethylene]-2-oxo-2,3-dihydro-1H-indole-5-carboxylic acid |
| 148 | 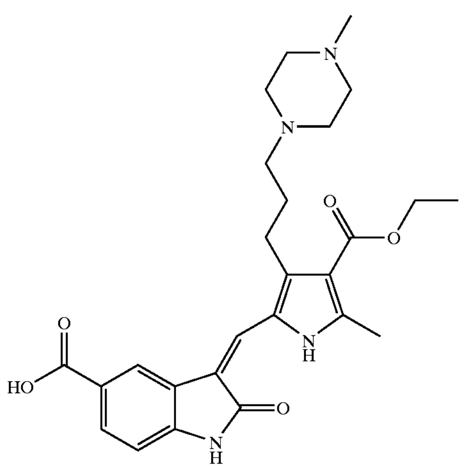 | 3-{4-Ethoxycarbonyl-5-methyl-3-[3-(4-methyl-piperazin-1-yl)-propyl]-1H-pyrrol-2-ylmethylene}-2-oxo-2,3-dihydro-1H-indole-5-carboxylic acid |

TABLE 2-continued

| Compound | Structures | Names |
|---|---|---|
| 149 | 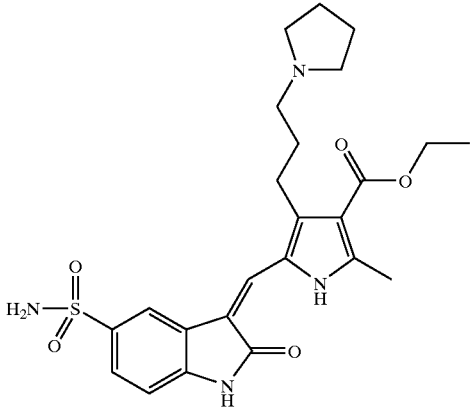 | 2-Methyl-5-(2-oxo-5-sulfamoyl-1,2-dihydroindol-3-ylidenemethyl)-4-(3-pyrrolidin-1-yl-propyl)-1H-pyrrole-3-carboxylic acid ethyl ester |
| 150 | 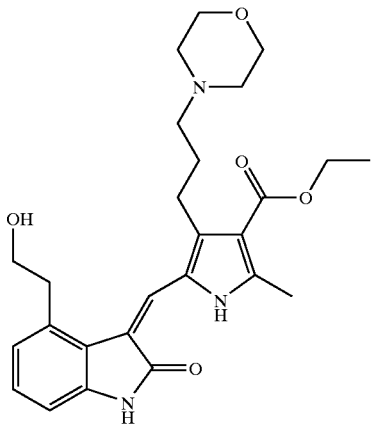 | 5-[4-(2-Hydroxy-ethyl)-2-oxo-1,2-dihydroindol-3-ylidenemethyl-2-methyl-4-(3-morpholin-4-yl-propyl)-1H-pyrrole-3-carboxylic acid ethyl ester |
| 151 | 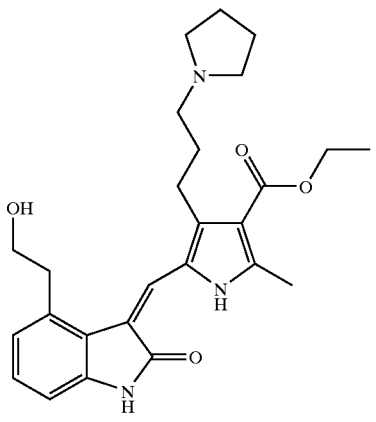 | 5-[4-(2-Hydroxy-ethyl)-2-oxo-1,2-dihydroindol-3-ylidenemethyl-4-(3-pyrrolidin-1-yl-propyl)-1H-pyrrole-3-carboxylic acid ethyl ester |

TABLE 2-continued

| Compound | Structures | Names |
|---|---|---|
| 152 | 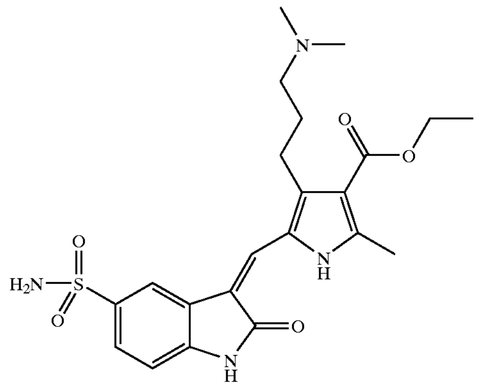 | 4-(3-Dimethylamino-propyl)-2-methyl-5-(2-oxo-5-sulfamoyl-1,2-dihydroindol-3-ylidenemethyl)-1H-pyrrole-3-carboxylic acid ethyl ester |
| 153 | 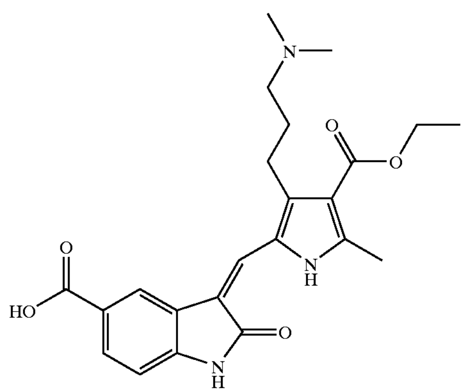 | 3-[3-(3-Dimethylamino-propyl)-4-ethoxycarbonyl-5-methyl-1H-pyrrol-2-ylmethylene]-2-oxo-2,3-dihydro-1H-indole-5-carboxylic acid |
| 154 | 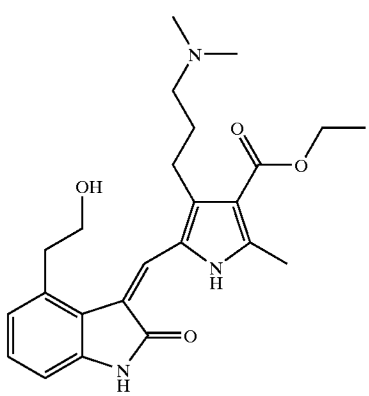 | 4-(3-Dimethylamino-propyl)-5-[4-(2-hydroxy-ethyl)-2-oxo-1,2-dihydroindol-3-ylidenemethyl]-2-methyl-1H-pyrrole-3-carboxylic acid ethyl ester |

TABLE 2-continued

| Compound | Structures | Names |
|---|---|---|
| 155 | 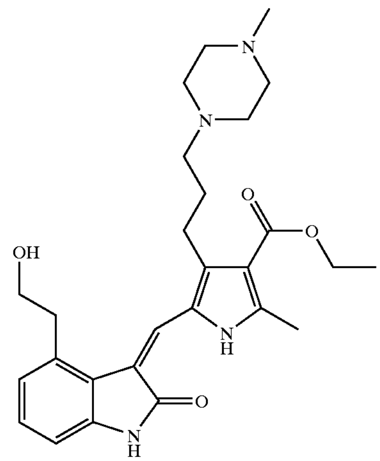 | 5-[4-(2-Hydroxy-ethyl)-2-oxo-1,2-dihydroindol-3-ylidenemethyl]-2-methyl-4-[3-(4-methyl-piperazin-1-yl)-propyl]-1H-pyrrole-3-carboxylic acid ethyl ester |
| 156 | 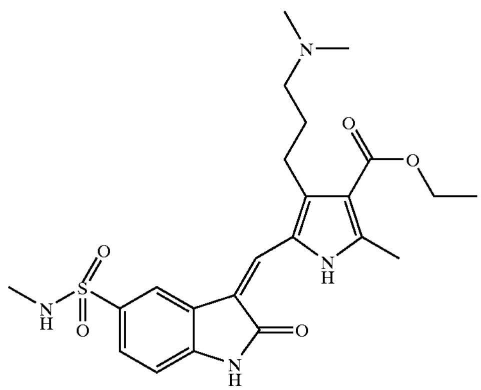 | 4-(3-Dimethylamino-propyl)-2-methyl-5-(5-methylsulfamoyl-2-oxo-1,2-dihydroindol-3-ylidenemnethyl)-1H-pyrrole-3-carboxylic acid ethyl ester |
| 157 | 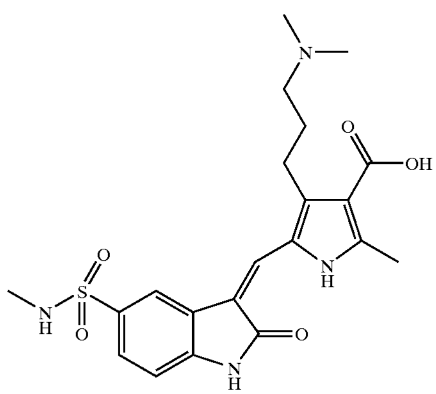 | 4-(3-Dimethylamino-propyl)-2-methyl-5-(5-methylsulfamoyl-2-oxo-1,2-dihydroindol-3-ylidenemethyl)-1H-pyrrole-3-carboxylic acid |
| 158 | 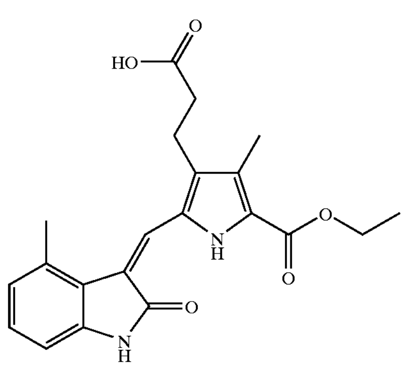 | 4-(2-Carboxy-ethyl)-3-methyl-5-(4-methyl-2-oxo-1,2-dihydroindol-3-ylidenemethyl)-1H-pyrrole-2-carboxylic acid ethyl ester |

TABLE 2-continued

| Compound | Structures | Names |
|---|---|---|
| 159 | 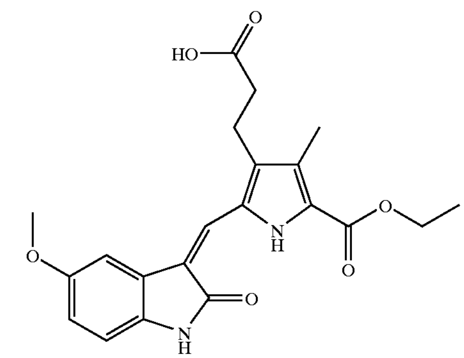 | 4-(2-Carboxy-ethyl)-5-(5-methoxy-2-oxo-1,2-dihydroindol-3-ylidenemethyl)-1H-pyrrole-2-carboxylic acid ethyl ester |
| 160 | 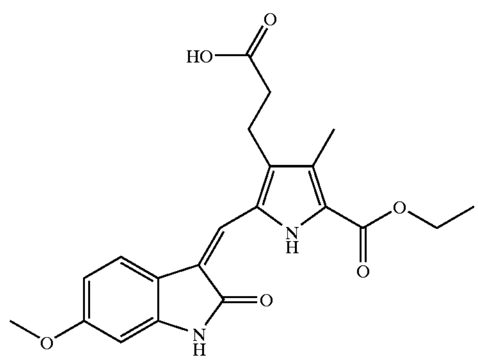 | 4-(2-Carboxy-ethyl)-5-(6-methoxy-2-oxo-1,2-dihydroindol-3-ylidenemethyl)-1H-pyrrole-2-carboxylic acid ethyl ester |
| 161 | 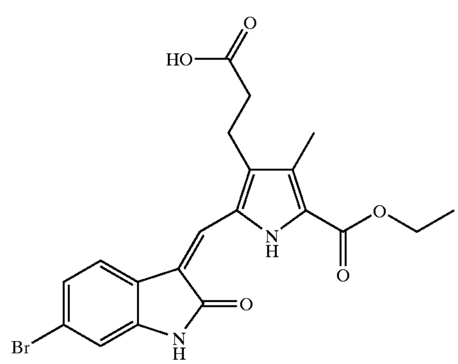 | 5-(6-Bromo-2-oxo-1,2-dihydroindol-3-ylidenemethyl)-3-(2-carboxy-ethyl)-3-methyl-1H-pyrrole-2-carboxylic acid ethyl ester |
| 162 | 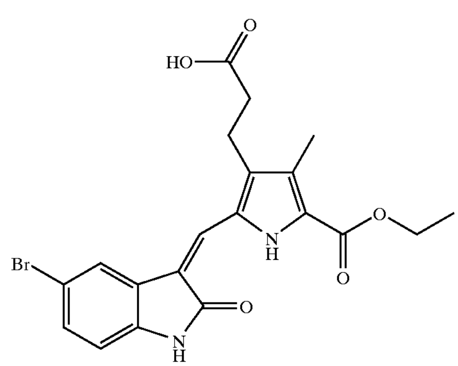 | 5-(5-Bromo-2-oxo-1,2-dihydroindol-3-ylidenemethyl)-3-(2-carboxy-ethyl)-3-methyl-1H-pyrrole-2-carboxylic acid ethyl ester |

TABLE 2-continued

| Compound | Structures | Names |
|---|---|---|
| 163 | 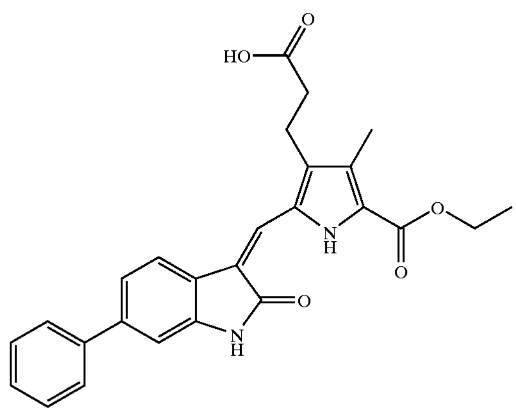 | 4-(2-Carboxy-ethyl)-3-methyl-5-(2-oxo-6-phenyl-1,2-dihydroindol-3-ylidenemethyl)-1H-pyrrole-2-carboxylic acid ethyl ester |
| 164 | 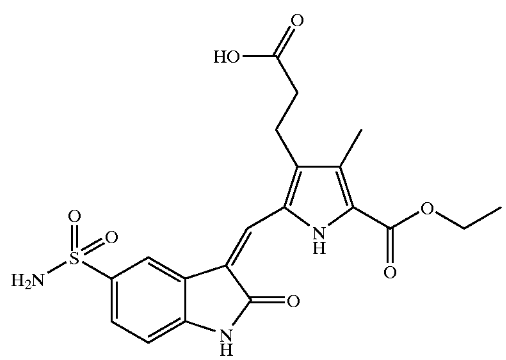 | 4-(2-Carboxy-ethyl)-3-methyl-5-(2-oxo-5-sulfamoyl-1,2-dihydroindol-3-ylidenemethyl)-1H-pyrrole-2-carboxylic acid ethyl ester |
| 165 | 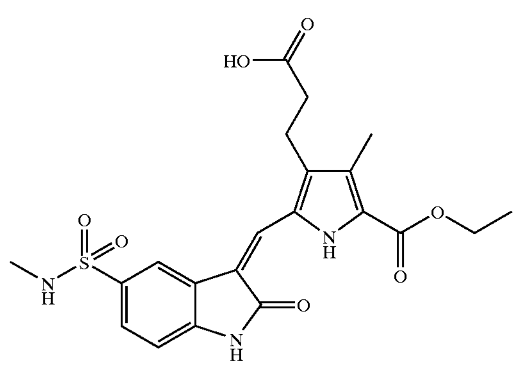 | 4-(2-Carboxy-ethyl)-3-methyl-5-(5-methylsulfamoyl-2-oxo-1,2-dihydroindol-3-ylidenemethyl)-1H-pyrrole-2-carboxylic acid ethyl ester |
| 166 | 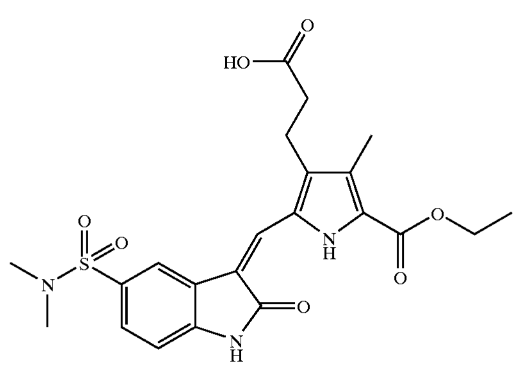 | 4-(2-Carboxy-ethyl)-5-(dimethylsulfamoyl-2-oxo-1,2-dihydroindol-3-ylidenemethyl)-3-methyl-1H-pyrrole-2-carboxylic acid ethyl ester |

TABLE 2-continued

| Compound | Structures | Names |
|---|---|---|
| 167 | 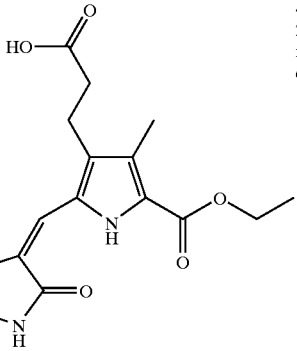 | 4-(2-Carboxy-ethyl)-5-(5-isopropylsulfamoyl-2-oxo-1,2-dihydroindol-3-ylidenemethyl)-3-methyl-1H-pyrrole-2-carboxylic acid ethyl ester |
| 168 | 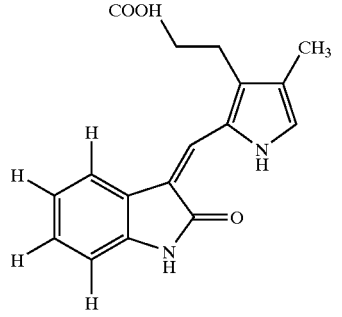 | 3-[4-Methyl-2-(2-oxo-1,2-dihydroindol-3-ylidenemethyl)-1H-pyrrol-3-yl]-propionic acid |
| 169 | 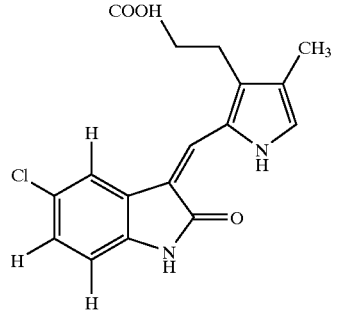 | 3-[2-(5-Chloro-2-oxo-1,2-dihydroindol-3-ylidenemethyl)-4-methyl-1H-pyrrol-3-yl]-propionic acid |
| 170 | 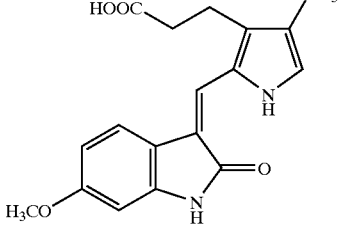 | 3-[2-(6-Methoxy-2-oxo-1,2-dihydroindol-3-ylidenemethyl)-4-methyl-1H-pyrrol-3-yl]-propionic acid |
| 171 | 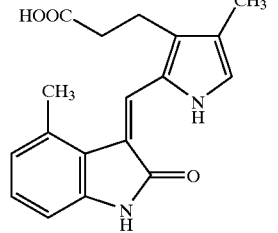 | 3-[2-(4-Methyl-2-oxo-1,2-dihydroindol-3-ylidenemethyl)-4-methyl-1H-pyrrol-3-yl]-propionic acid |

TABLE 2-continued

| Compound | Structures | Names |
|---|---|---|
| 172 | 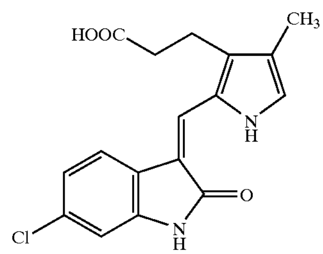 | 3-[2-(6-Chloro-2-oxo-1,2-dihydroindol-3-ylidenemethyl)-4-methyl-1H-pyrrol-3-yl]-propionic acid |
| 173 | 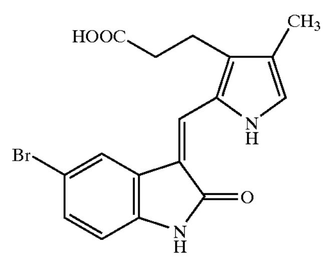 | 3-[2-(5-Bromo-2-oxo-1,2-dihydroindol-3-ylidenemethyl)-4-methyl-1H-pyrrol-3-yl]-propionic acid |
| 174 | 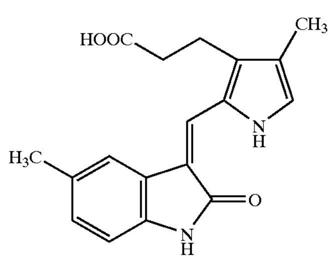 | 3-[2-(5-Methyl-2-oxo-1,2-dihydroindol-3-ylidenemethyl)-4-methyl-1H-pyrrol-3-yl]-propionic acid |
| 175 | 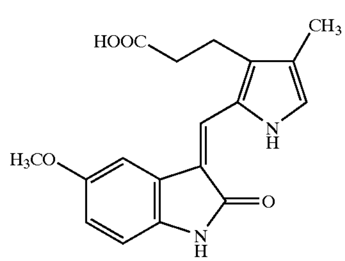 | 3-[2-(5-Methoxy-2-oxo-1,2-dihydroindol-3-ylidenemethyl)-4-methyl-1H-pyrrol-3-yl]-propionic acid |
| 176 | 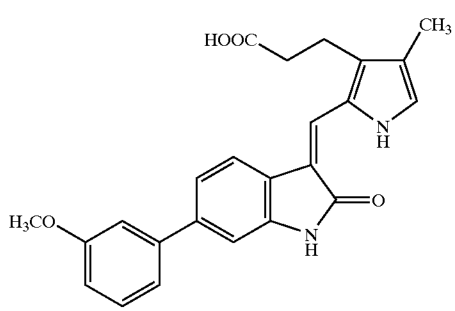 | 3-{2-[6-(3-Methoxyphenyl)-2-oxo-1,2-dihydroindol-3-ylidenemethyl]-4-methyl-1H-pyrrol-3-yl}-propionic acid |

TABLE 2-continued

| Compound | Structures | Names |
|---|---|---|
| 177 | 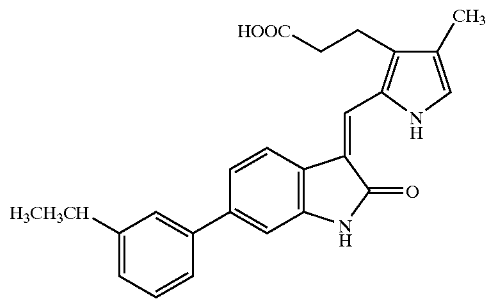 | 3-{2-[6-(3-Ethoxyphenyl)-2-oxo-1,2-dihydroindol-3-ylidenemethyl]-4-methyl-1H-pyrrol-3-yl}-propionic acid |

In addition to the above substances, the following compounds are useful in the present invention.

107
-continued
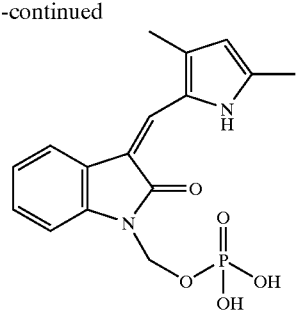
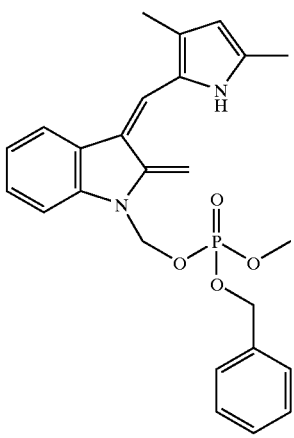
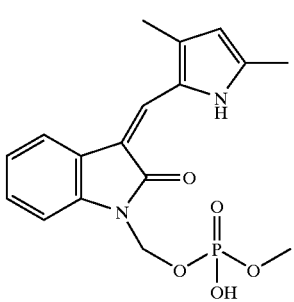
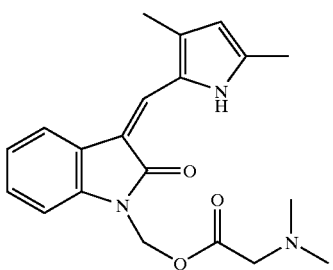
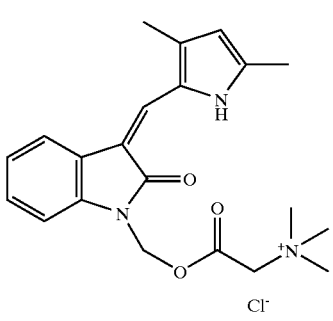
108
-continued
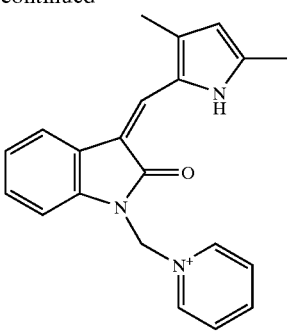
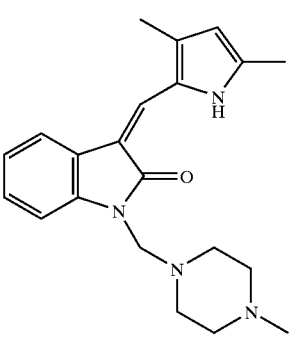
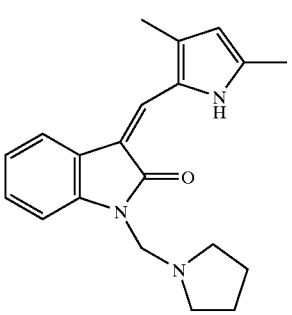
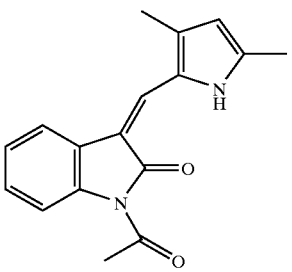
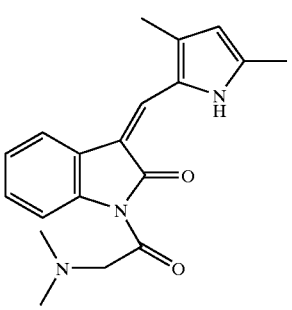

-continued
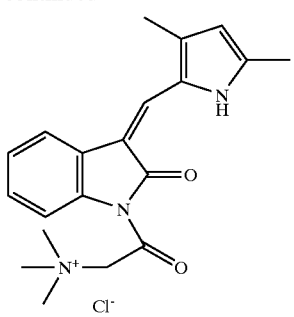
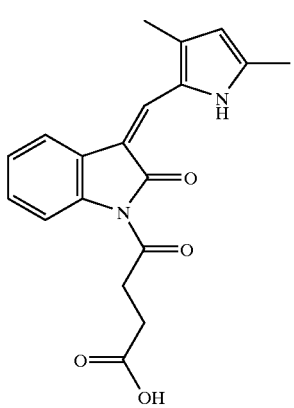
-continued
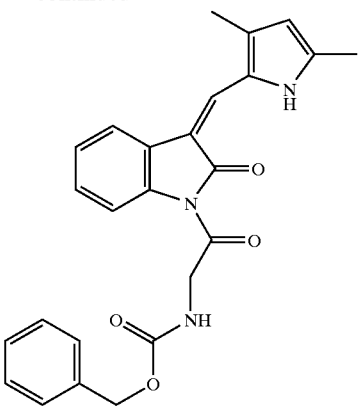
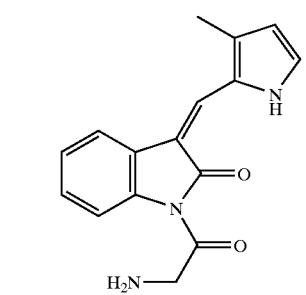
TABLE 3
| Example # | Structure |
| --- | --- |
| 1 | ![structure] |
| 2 | ![structure] |

TABLE 3-continued
| Example # | Structure |
|---|---|
| 3 | 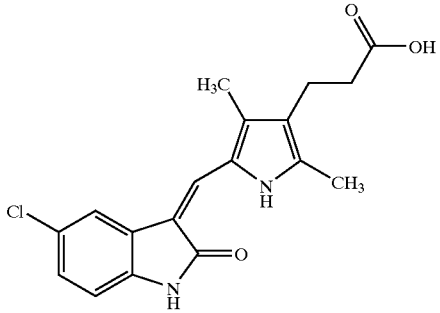 |
| 4 | 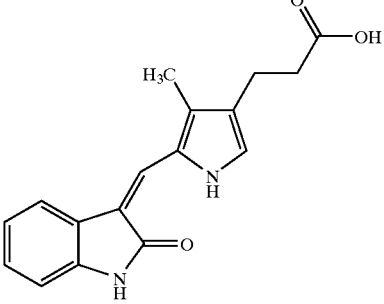 |
| 5 | 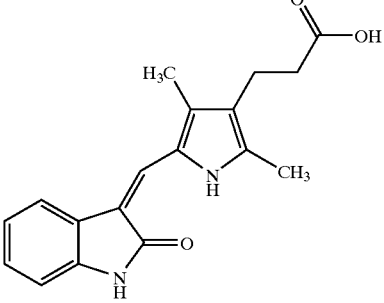 |
| 6 | 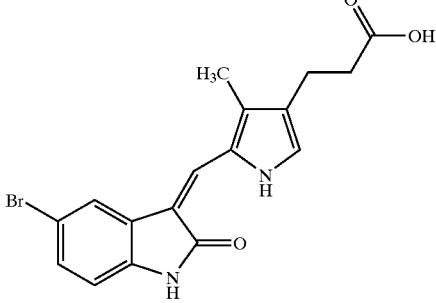 |

TABLE 3-continued
| Example # | Structure |
|---|---|
| 7 | 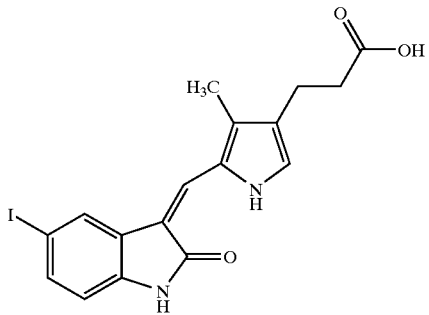 |
| 8 | 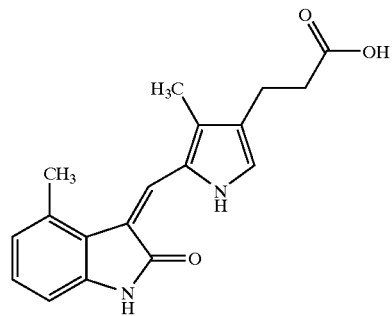 |
| 9 | 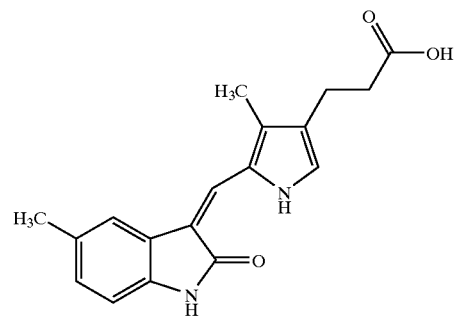 |
| 10 | 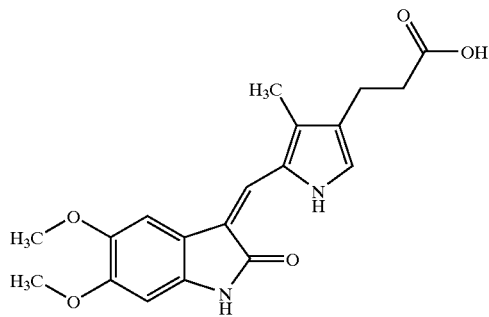 |

TABLE 3-continued

| Example # | Structure |
|---|---|
| 11 | 3-[5-[(6-chloro-2-oxo-1,2-dihydro-3H-indol-3-ylidene)methyl]-4-methyl-1H-pyrrol-3-yl]propanoic acid |
| 12 | 3-[5-[(5-methoxycarbonyl-2-oxo-1,2-dihydro-3H-indol-3-ylidene)methyl]-4-methyl-1H-pyrrol-3-yl]propanoic acid |
| 13 | 3-[5-[(5-carboxy-2-oxo-1,2-dihydro-3H-indol-3-ylidene)methyl]-4-methyl-1H-pyrrol-3-yl]propanoic acid |
| 14 | 3-[5-[(5-sulfamoyl-2-oxo-1,2-dihydro-3H-indol-3-ylidene)methyl]-4-methyl-1H-pyrrol-3-yl]propanoic acid |

TABLE 3-continued

| Example # | Structure |
|---|---|
| 15 | 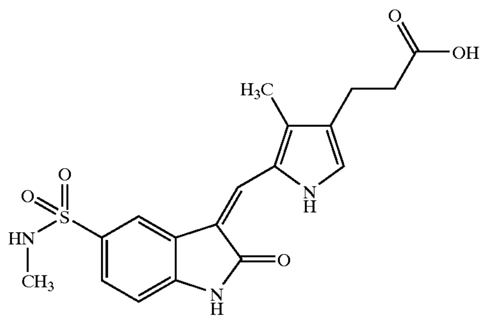 |
| 16 | 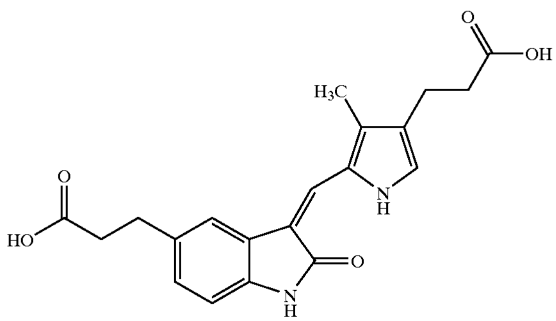 |
| 17 | 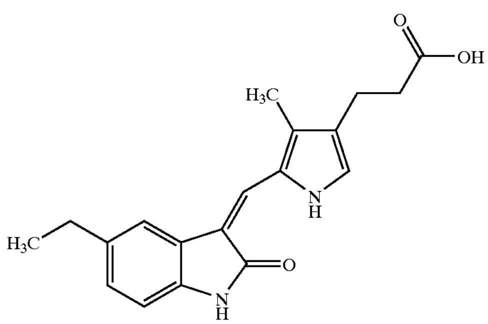 |
| 18 | 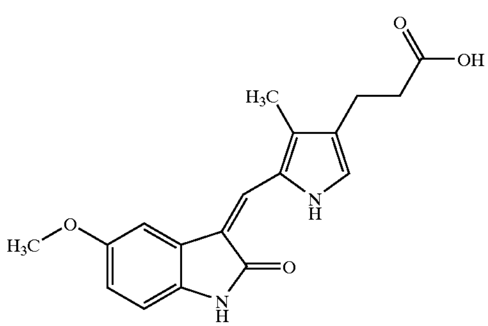 |

TABLE 3-continued

| Example # | Structure |
|---|---|
| 19 | 5-bromo-3-[(2,4-dimethyl-3-(2-carboxyethyl)-1H-pyrrol-5-yl)methylene]-2-indolinone |
| 20 | 5-iodo-3-[(2,4-dimethyl-3-(2-carboxyethyl)-1H-pyrrol-5-yl)methylene]-2-indolinone |
| 21 | 4-methyl-3-[(2,4-dimethyl-3-(2-carboxyethyl)-1H-pyrrol-5-yl)methylene]-2-indolinone |
| 22 | 5-methyl-3-[(2,4-dimethyl-3-(2-carboxyethyl)-1H-pyrrol-5-yl)methylene]-2-indolinone |

TABLE 3-continued

| Example # | Structure |
|---|---|
| 23 | 3-{5-[(6-hydroxy-2-oxo-1,2-dihydro-indol-3-ylidene)-methyl]-2,4-dimethyl-1H-pyrrol-3-yl}-propionic acid |
| 24 | 3-{5-[(6-methoxy-2-oxo-1,2-dihydro-indol-3-ylidene)-methyl]-2,4-dimethyl-1H-pyrrol-3-yl}-propionic acid |
| 25 | 3-{5-[(6-hydroxy-2-oxo-1,2-dihydro-indol-3-ylidene)-methyl]-4-methyl-1H-pyrrol-3-yl}-propionic acid |
| 26 | 3,5-dimethoxybenzyl 3-{5-[(6-hydroxy-2-oxo-1,2-dihydro-indol-3-ylidene)-methyl]-4-methyl-1H-pyrrol-3-yl}-propionate |

TABLE 3-continued

| Example # | Structure |
|---|---|
| 27 | 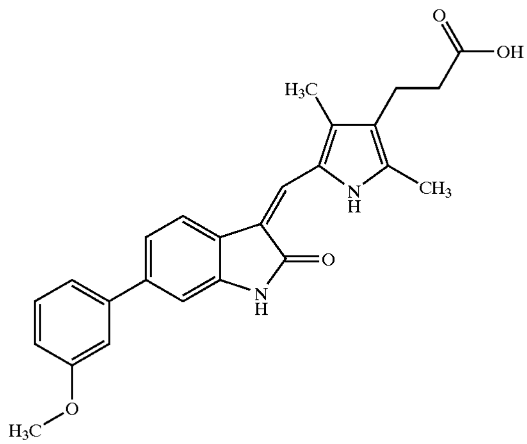 |
| 28 | 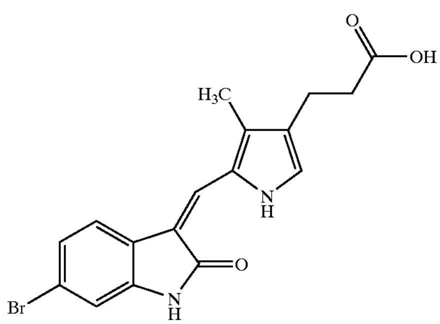 |
| 29 | 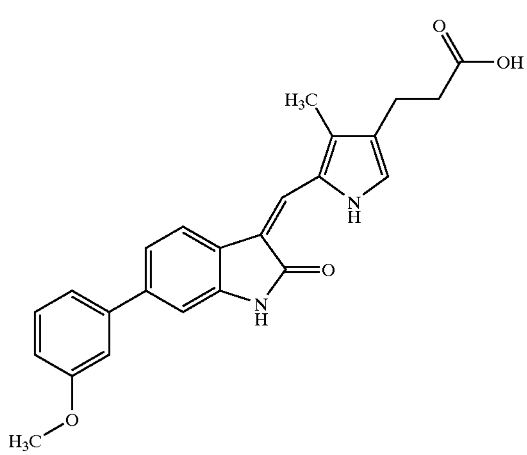 |

TABLE 3-continued
| Example # | Structure |
|---|---|
| 30 | 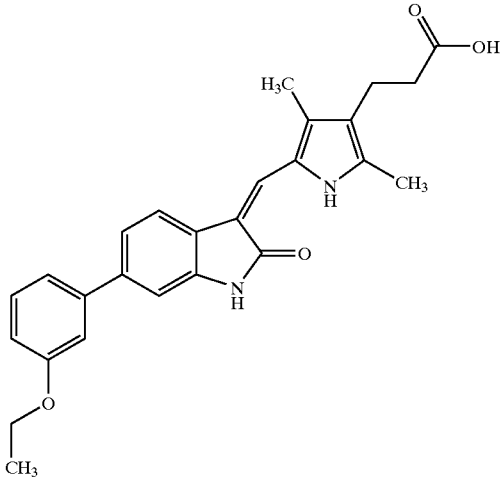 |
| 31 | 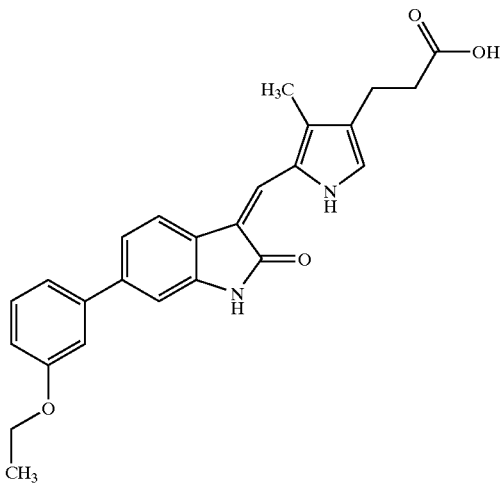 |
| 32 | 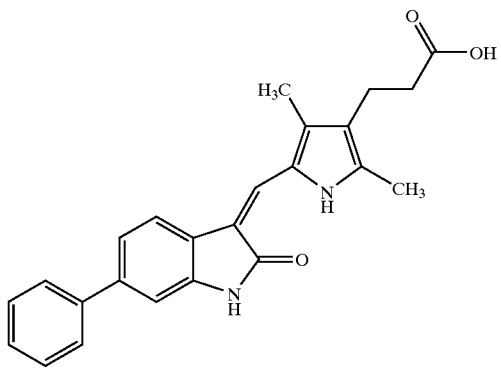 |

TABLE 3-continued

| Example # | Structure |
|---|---|
| 33 | 3-{5-[(6-phenyl-2-oxo-1,2-dihydro-indol-3-ylidene)-methyl]-4-methyl-1H-pyrrol-3-yl}-propionic acid |
| 34 | 3-{5-[(6-(4-methoxyphenyl)-2-oxo-1,2-dihydro-indol-3-ylidene)-methyl]-4-methyl-1H-pyrrol-3-yl}-propionic acid |
| 35 | 3-{5-[(6-(4-methoxyphenyl)-2-oxo-1,2-dihydro-indol-3-ylidene)-methyl]-2,4-dimethyl-1H-pyrrol-3-yl}-propionic acid |
| 36 | 3-{5-[(6-(2-methoxyphenyl)-2-oxo-1,2-dihydro-indol-3-ylidene)-methyl]-4-methyl-1H-pyrrol-3-yl}-propionic acid |

TABLE 3-continued

| Example # | Structure |
|---|---|
| 37 | 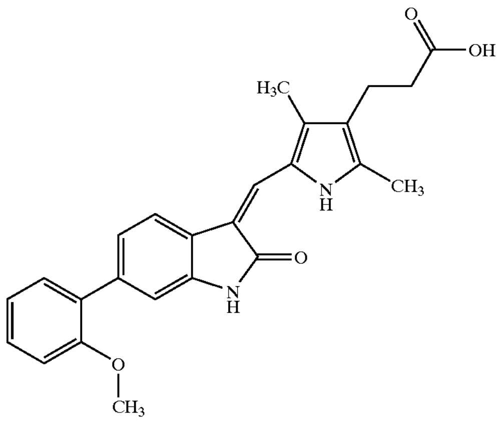 |
| 38 | 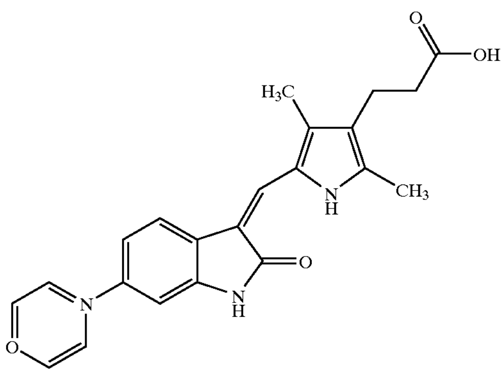 |
| 39 | 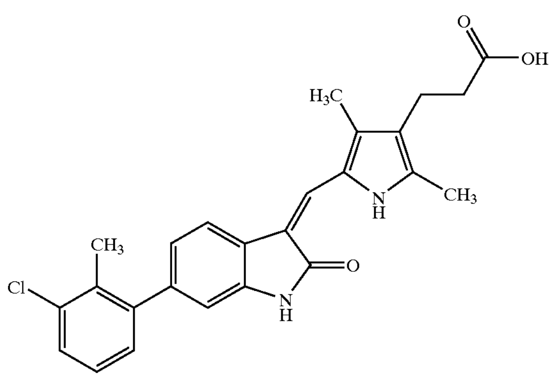 |
| 40 | 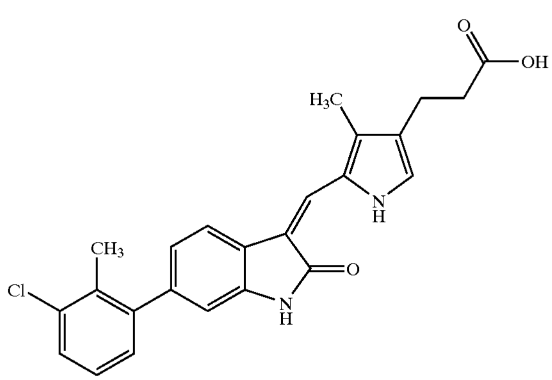 |

TABLE 3-continued
| Example # | Structure |
|---|---|
| 41 | 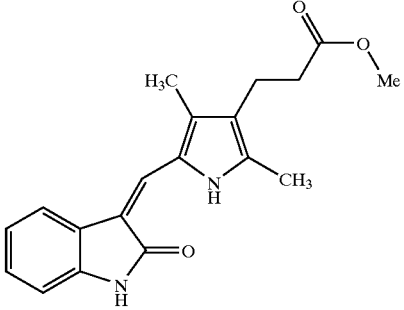 |
| 42 | 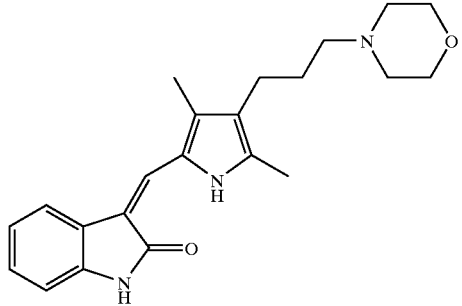 |
| 43 | 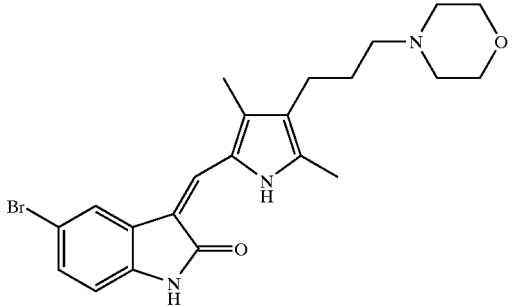 |
| 44 | 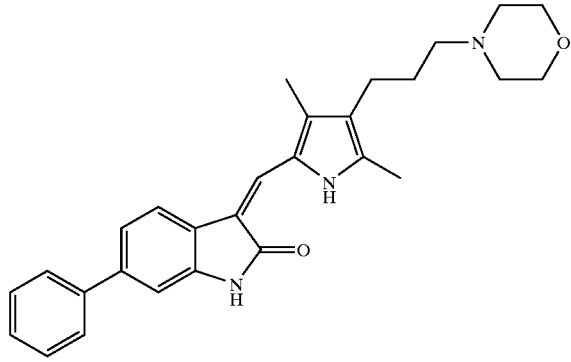 |

TABLE 3-continued
| Example # | Structure |
|---|---|
| 45 | 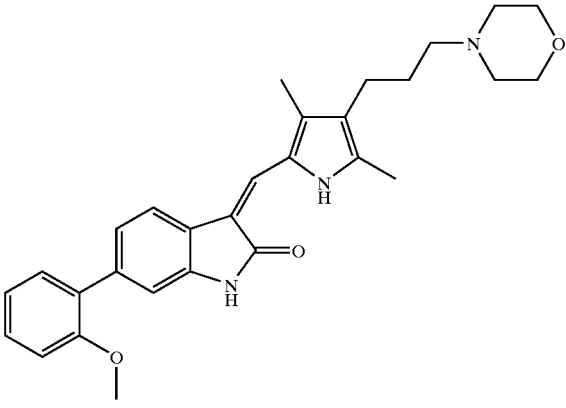 |
| 46 | 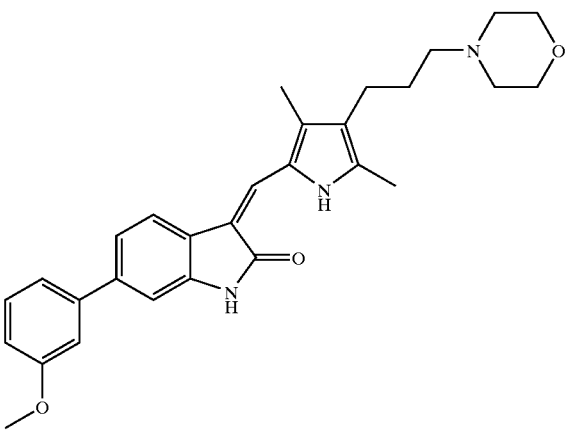 |
| 47 | 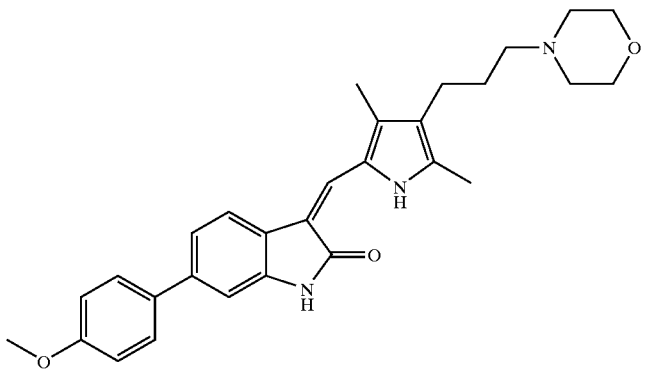 |
| 48 | 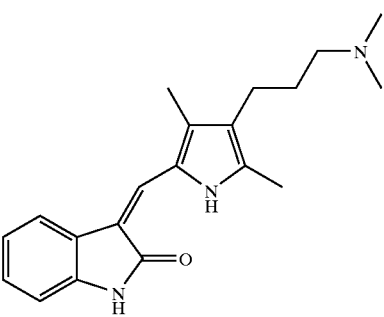 |

TABLE 3-continued

| Example # | Structure |
| --- | --- |
| 49 | 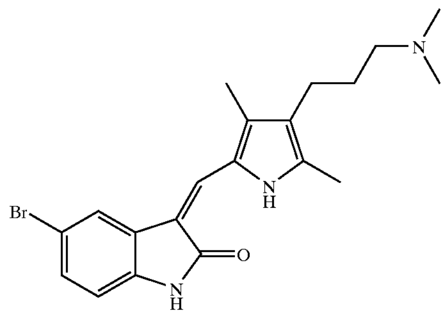 |
| 50 | 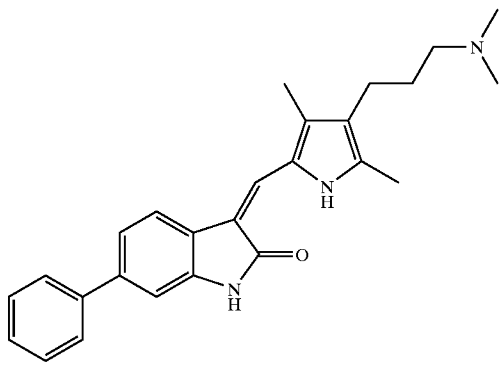 |
| 51 | 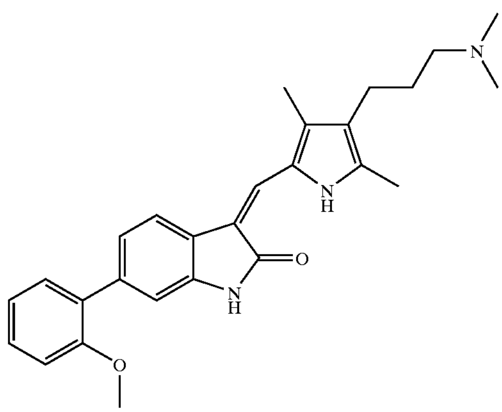 |
| 52 | 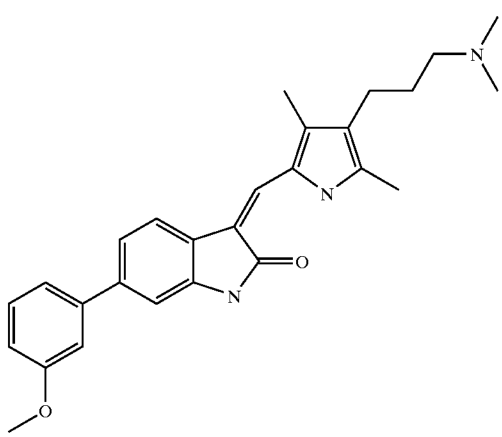 |

TABLE 3-continued
| Example # | Structure |
|---|---|
| 53 | 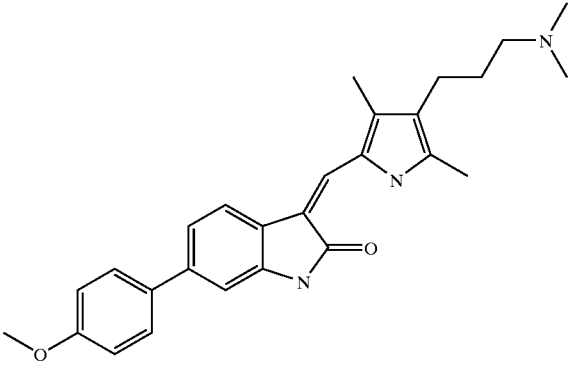 |
| 54 | 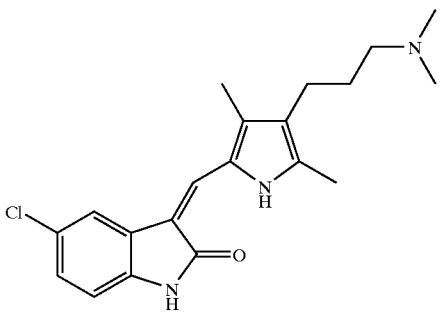 |
| 55 | 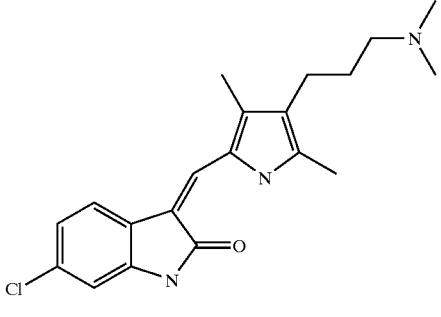 |
| 56 | 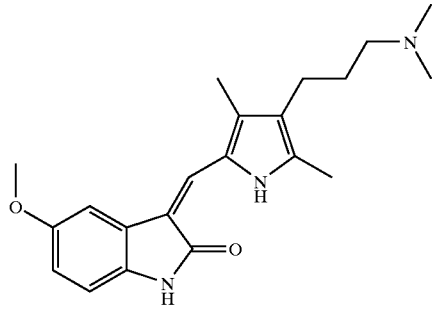 |

TABLE 3-continued

| Example # | Structure |
| --- | --- |
| 57 | 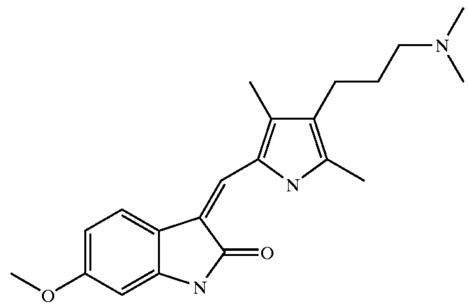 |
| 58 | 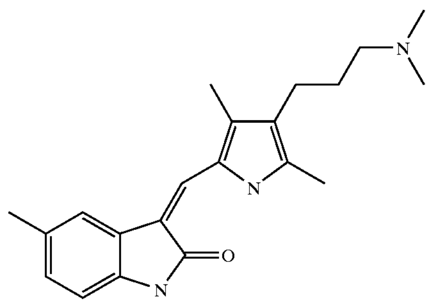 |
| 59 | 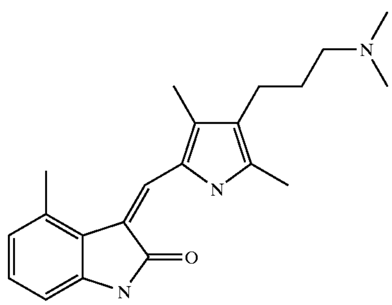 |
| 60 | 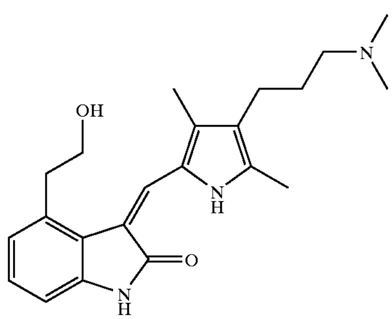 |
| 61 | 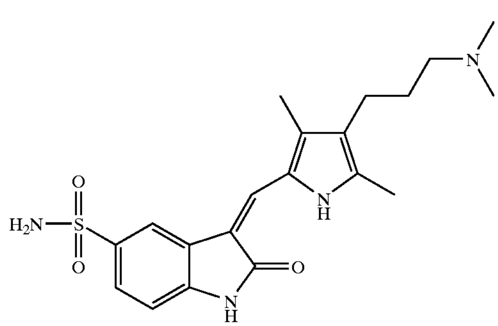 |

TABLE 3-continued

| Example # | Structure |
|---|---|
| 62 | 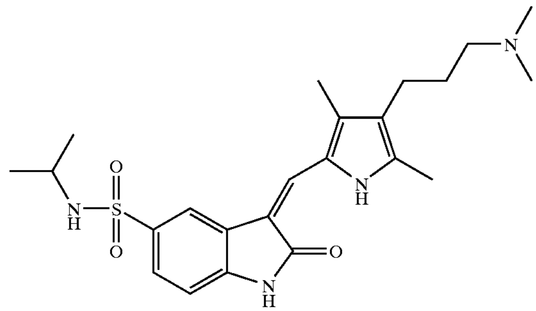 |
| 63 | 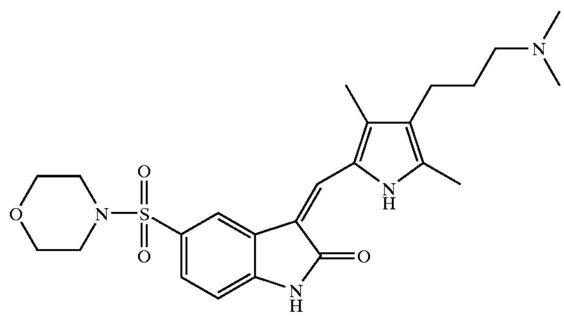 |
| 64 | 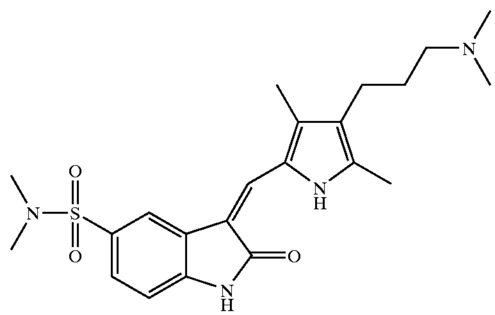 |

Also included within the ionizable substituted indolinones contemplated for use in the present invention are pharmaceutically acceptable salts, prodrugs, derivatives, and analogs of the above-identified pyrrole substituted 2-indolinones.

As utilized herein, the term "pharmaceutically acceptable salt" includes formulations of a compound that do not abrogate the biological activity and properties of the compound. Pharmaceutically acceptable salts can be obtained by reacting a pyrrole substituted 2-indolinone contemplated for use in the invention with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like, or with inorganic or organic bases such as sodium hydroxide, potassium hydroxide, ammonium hydroxide, calcium hydroxide, choline, n-methyl glucamine, diethylamine, procaine and the like. The pharmaceutically acceptable salts which the compounds of this invention may form include the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), calcium hydroxide (Ca(OH)2), etc). As utilized herein, "quaternary ammonium" includes a quaternized nitrogen (e.g., —NRR'R", where each of R, R' and R" is independently selected from H, aryl, alkyl, and the like), a quaternized nitrogen containing heterocyclic aryl, and the like.

As utilized herein, the term "prodrug" includes any compounds that, when administered to a biological system, are converted into the active ionizable substituted indolinone contemplated for use in the invention either as a result of spontaneous chemical reaction(s), enzyme catalyzed reaction(s), metabolic reaction(s), or the like. A "prodrug" also refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water solubility is beneficial. A further example of a prodrug might be a short polypeptide bonded to a carboxy group wherein metabolic removal of the polypeptide group releases the active compound.

In one aspect of the invention formulation, a therapeutically effective amount of the ionizable substituted indolinone is utilized in the invention formulation.

As used herein, a "pharmaceutically acceptable carrier" refers to a carrier or diluent that does not abrogate the biological activity and/or properties of the administered compound while facilitating administration by, for example, stabilizing or solubilizing the compound. Suitable pharmaceutically acceptable carriers include, without limitation, one or more polyoxyhydrocarbyl compounds, one or more buffers, one or more pharmaceutically acceptable surfactants, one or more pharmaceutically acceptable preservatives, one or more antioxidants, one or more pharmaceutically acceptable alcohols, one or more pharmaceutically acceptable aqueous solutions, one or more pharmaceutically acceptable oils, liposomes, one or more polyglycolized lipids, one or more pharmaceutically acceptable granulating agents, one or more pharmaceutically acceptable diluents, one or more pharmaceutically acceptable binders, one or more pharmaceutically acceptable disintegrants, one or more pharmaceutically acceptable lubricants, one or more pharmaceutically acceptable flow enhancers, one or more pharmaceutically acceptable suspending agents, and suitable combinations of any two or more thereof.

The term "pharmaceutically acceptable" or "pharmaceutical" as used herein refers to solutions or components of the formulation that do not prevent the therapeutic compound from exerting a therapeutic effect and do not cause unacceptable adverse side effects. Examples of pharmaceutically acceptable reagents are provided in *The United States Pharmacopeia The National Formulary,* United States Pharmacopeial Convention, Inc., Rockville, Md. 1990 and *FDA Inactive Ingredient Guide* 1990, 1996 issued by the Division of Drug Information Resources (both are hereby incorporated by reference herein, including any drawings). Unacceptable side effects vary for different diseases. Generally, the more severe the disease the more toxic effects which will be tolerated. Unacceptable side effects for different diseases are known in the art.

Although all permutations of specific components within the invention formulations are contemplated to be within the scope of the present invention, the following combinations of one or more specific pharmaceutically acceptable carrier(s) and specific ionizable substituted indolinones are preferred in one aspect of the invention.

In one aspect of the invention formulation, the formulation is suitable for parenteral administration. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

In another aspect of the invention formulation suitable for parenteral or oral administration, the pharmaceutically acceptable carrier comprises one or more polyoxyhydrocarbyl compounds. A preferred embodiment of this aspect has the ionizable substituted indolinone be a pyrrole substituted 2-indolinone of Formula I having $R^9$ be -(alk$_1$)Z$_1$ and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

In another aspect of the invention, the formulation includes permeability and penetrating enhancers. These include ionic compounds (e.g., 3,5-diidosalicylate sodium) dimethylsulfoxide and related compounds (e.g., decylmethyl sulfoxide) azone, and related compounds (e.g., N-alkyl-dihydro-1,4-oxazepine-5,7-diones), solvents, and related compounds (e.g., ethanol, dimethyl acetamide, dimethylformamide) fatty alcohols, fatty acids and enzymes (e.g., acid phosphatase and papin). These are other examples of permeability and pentration enhancers can be found in Pharmaceutical Skin Penetration Enhancement, K. A. Walters and J. Hadgraft, Eds. (Dekker, New York, 1993).

The term "polyoxyhydrocarbyl compound" as used herein includes without limitation water soluble carbohydrates (such as glucose, sucrose, maltotriose, and the like); water soluble carbohydrate derivatives (such as gluconic acid and mannitol and oligosaccharides, and the like); water soluble polypeptides; water soluble polymers (such as polyvinylpyrrolidone, poly(vinyl alcohol), and in particular, polyethers such as other polyoxyalkylenes including poly (ethylene glycol) and the like); water soluble mixed oxyalkylene polymers; and the polymeric forms of ethylene glycol; and the like; and suitable combinations of two or more thereof. Although polyoxyhydrocarbyl compounds preferably contain more than one carbon, oxygen, and hydrogen atom, some molecules such as poly (ethyleneimine) are also included.

A particularly preferred class of solubilizing polyoxyhydrocarbyl compounds comprises poly(ethylene glycol) (PEG) and PEG derivatives, such as PEG monomethyl ether. Other suitable PEG derivatives include PEG-silicon derived ethers. Many of these polymers are commercially available in a variety of molecular weights. Others may be conveniently prepared from commercially available materials, such as by coupling of an amino-PEG moiety to a haloalkyl silyl or silane moiety.

Suitable PEGs may vary in molecular weight from about 200 g/mol to about 20,000 g/mol or more, more preferably 200 g/mol to 5,000 g/mol, even more preferably 250 g/mol to 1,000 g/mol, and most preferably 250 g/mol to 500 g/mol. The choice of a particular molecular weight may depend on the particular ionizable substituted indolinone chosen and its molecular weight and degree of hydrophobicity, as well as the particular application for which the formulation is to be used.

Thus, the one or more polyoxyhydrocarbyl compounds can be selected from the group consisting of polyethylene glycol 300, polyethylene glycol 400, propylene glycol, and glycerin, and the like, and suitable combinations of two or more hereof. Preferably, each of the one or more polyoxyhydrocarbyl compounds is polyethylene glycol 300.

In another aspect of the invention formulation suitable for parenteral or oral administration, the ionizable substituted indolinone is solubilized by combining it with a molar equivalent of a base solution or an acid solution. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound III), and pharmaceutically active salts, prodrugs, derivatives, and analogs thereof.

The term "solubilized" as used herein refers to dissolving of a substance in a fluid and/or adsorption of fluid molecules on the surface of the substance to assist in such dissolving. In one aspect, "solubilized" refers to hydration of a substance in water.

The term "molar equivalent" as used herein refers to equal or similar molar amounts of a test substance as compared to a reference substance.

The term "base solution" as used herein refers to a basic solution, typically one which has a pH higher than 7 and is capable of reacting with an acidic solution. Preferably the base in the base solution is selected from the group consisting of sodium hydroxide, ammonium hydroxide, triethylamine, ethylenediamine, N-methyl-D-glucamine, choline, triethanolamine, and the like, and suitable combinations of two or more hereof.

The term "acid solution" as used herein refers to an acidic solution, typically one which has a pH lower than 7 and is capable of reacting with a basic solution. Preferably the acid in the acid solution is selected from the group consisting of hydrochloric acid, sulfuric acid, formic acid, lactic acid, malic acid, succinic acid, acetic acid, methane sulfonic acid, benzene sulfonic acid, phosphoric acid, and the like, and suitable combinations of two or more hereof.

In another aspect of the invention formulation suitable for parenteral or oral administration, the pharmaceutically acceptable carrier further comprises one or more buffers. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

The term "buffer" as used herein refers to a substance, preferably in a solution, that resists a change of quality. Preferably a buffer is a solution that resists a change to a pH, such as a substance in a solution capable of neutralizing both acids and bases and therefore maintaining an original acidity or basicity of a solution. Suitable buffers include acetate, citrate, phosphate buffer, ascorbate, hydrochloric acid buffer, Tris-HCl buffer, sodium phosphate, sodium carbonate, sodium hydroxide, glutamate, glycine, Tris base buffers, and the like, and suitable combinations of two or more hereof. Most preferably, the buffer is sodium phosphate buffer.

In one embodiment, the buffer pH is three pH units higher than the pka of the ionizable substituted indolinone, or three pH units lower than the pkb of the ionizable substituted indolinone. Preferably, the buffer has a molarity (i.e., molar concentration, measured in moles per liter (M)) between 0.01 M and 0.1 M.

The term "pka" as used herein refers to the negative logarithm of the acidity constant, the acidity constant being the product of the concentration of the hydronium ion and the concentration of the conjugated base, divided by the concentration of the acid (the acidity constant is also sometimes referred to as the equilibrium constant).

The term "pkb" as used herein refers to the negative logarithm of the basicity constant, the basicity constant being the product of the concentration of the hydroxyl ion and the concentration of the conjugated acid, divided by the concentration of the base (the basicity constant is also sometimes referred to as the equilibrium constant).

In another aspect of the invention formulation suitable for parenteral or oral administration, the pharmaceutically acceptable carrier further comprises one or more pharmaceutically acceptable surfactants. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

The term "pharmaceutically acceptable surfactant" as used herein with respect to both oral and parenteral formulations refers to a compound that can solubilize hydrophobic compounds into aqueous solutions. Suitable surfactants include non-ionic surfactants, anionic surfactants, and the like, and suitable combinations of two or more thereof.

Preferably for parenteral formulations, the surfactant is a non-ionic surfactant. Examples of pharmaceutically acceptable non-ionic surfactants include but are not limited to polyoxyethylene sorbitan fatty acid esters (e.g., POLYSORBATE 80®, and the like), glyceryl monooleate, sorbitan monooleate, lecithin, polyvinyl alcohol, ethylene oxide copolymers (such as PLURONIC™ (a polyether), TETRONIC™ (BASF), and the like), polyol moieties, sorbitan esters, and the like, and suitable combinations of two or more hereof. Preferably ethoxylated castor oils, such as CREMOPHOR EL®, are used for the formulation of hydrophobic pharmaceutical agents, such as ionizable substituted indolinones contemplated for use in the present invention. The term "ethoxylated castor oil" as used herein refers to castor oil that is modified with at least one oxygen containing moiety. In particular the term refers to castor oil comprising at least one ethoxyl moiety.

Further, the term "pharmaceutically acceptable surfactant", as used herein in reference to oral formulations, includes pharmaceutically acceptable non-ionic surfactants such as copolymers of ethylene glycol nd propylene glycol (for example, polyoxyethylenepolypropylene glycols (such as POLOXAMER® 68 (BASF Corp.)) or a mono fatty acid ester of polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), polyoxyethylene (20) sorbitan monolaurate (TWEEN® 20), and the like); polyoxyethylene castor oil derivatives (such as polyoxyethyleneglycerol-triricinoleate, polyoxyl 35 castor oil (CREMOPHOR® EL, BASF Corp.), and the like); polyoxyethyleneglycerol oxystearate (such as CREMOPHOR® RH 40 (polyethyleneglycol 40 hydrogenated castor oil), CREMOPHOR® RH 60 (polyethyleneglycol 60 hydrogenated castor oil), BASF Corp.), and the like); and the like); pharmaceutically acceptable anionic surfactants, e.g., sodiumlauryl sulfate (SLS); and the like; and suitable combinations of two or more hereof.

In a further aspect of the invention formulation suitable for parenteral or oral administration, the pharmaceutically acceptable carrier further comprises one or more pharmaceutically acceptable preservatives. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

Preferably, each of the one or more pharmaceutically acceptable preservatives is selected from the group consisting of benzyl alcohol, methyl paraben, ethyl paraben, propyl paraben, phenol, and the like, and suitable combinations of two or more hereof. A most preferred preservative is benzyl alcohol.

In yet another aspect of the invention formulation suitable for parenteral or oral administration, the pharmaceutically acceptable carrier further comprises one or more antioxidants. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

The term "antioxidant" as used herein refers to a substance that inhibits oxidation or reactions promoted by, for example, oxygen or peroxides. Suitable antioxidants include sodium meta-bisulfite, EDTA, sodium ascorbate, ascorbic acid, ascorbic acid palmitate, benzyl alcohol, alpha-tocopherol and the like, and suitable combinations of two or more hereof. Preferably the antioxidant is alpha-tocopherol.

In yet a further aspect of the invention formulation suitable for parenteral or oral administration, the pharmaceutically acceptable carrier further comprises one or more pharmaceutically acceptable alcohols. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

The term "pharmaceutically acceptable alcohol" as used herein refers to alcohols which are liquids at about room temperature (approximately 20° C.). These include propylene glycol, ethanol, 2-(2-ethoxyethoxy)ethanol (TRANSCUTOL®, Gattefosse, (Westwood, N.J.)), benzyl alcohol, glycerol, and the like, and suitable combinations of two or more hereof. Preferably, each of the one or more pharmaceutically acceptable alcohols is independently selected from the group consisting of ethanol, benzyl alcohol, propylene glycol, 2-(2-ethoxyethoxy)ethanol, and glycerol. Most preferably, each of the pharmaceutically acceptable alcohols is ethanol or polyethylene glycol.

The formulation including one or more pharmaceutically acceptable alcohols should be dissolved in a sufficient amount of a pharmaceutically acceptable aqueous solution prior to patient administration to avoid toxic effects due to the alcohol content. The added amount of a pharmaceutically acceptable aqueous solution should be sufficient to avoid hemolysis. Examples of suitable pharmaceutically acceptable aqueous solutions such as WFI (water for injection) and solutions containing isotonic saline are known in the art. Pharmaceutically acceptable aqueous solutions include 0.45% N saline, WFI (water for injection), D5W (5% dextrose in water), D5W 0.45% N saline, and the like, and suitable combinations of two or more hereof.

In a separate aspect of the invention is a formulation suitable for parenteral (especially subcutaneous for intramuscular) or oral administration, the pharmaceutically acceptable carrier further comprises one or more pharmaceutically acceptable oils. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

Suitable pharmaceutically acceptable oils include mineral oils, vegetable oils (e.g., safflower oil, peanut oil, olive oil, sesame oil, coconut oil, and the like, and suitable combinations of two or more hereof, fractionated coconut oil, propyleneglycol monolaurate, and mixed triglycerides with caprylic acid and capric acid, and the like, and suitable combinations of two or more hereof. In a preferred embodiment, the oil is Miglyol 812 (a mixture of triestyer of glycerin and caprylic and capric acids-capric/caprylic triglyceride). In another preferred embodiment, the oil is sesame oil.

In a particular aspect, the invention features a formulation suitable for parenteral administration, the formulation comprising: (a) 3-[2,4-dimethyl-5-(2-oxo-1,2-dihydro-indol-3-ylidenemethyl)-1H-pyrrol-3-yl]-propionic acid; (b) polyethylene glycol 300; and (c) sodium phosphate buffer. In preferred embodiments, the parenteral formulation also contains benzyl alcohol, and 3-[2,4-dimethyl-5-(2-oxo-1,2-dihydro-indol-3-ylidenemethyl)-1H-pyrrol-3-yl]-propionic acid is solubilized with sodium hydroxide.

In a further aspect of the invention formulation; the formulation comprising an ionizable substituted indolinone and a pharmaceutically acceptable carrier is suitable for oral administration. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

In one aspect of the invention formulation suitable for oral administration, the pharmaceutically acceptable carrier comprises one or more polyoxyhydrocarbyl compounds. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H- pyrrol-3-yl]-propionic acid (compound IV), and pharmaceutically active salts, prodrugs, derivatives, and analogs thereof.

In preferred embodiments of this aspect of the invention formulation suitable for oral administration, the one or more polyoxyhydrocarbyl compounds are independently selected from the group consisting of: water soluble carbohydrates, water soluble carbohydrate derivatives, polypeptides, water soluble polymers, water soluble mixed oxyalkylene polymers, and the polymeric form of ethylene glycol. Preferably, the one or more polyoxyhydrocarbyl compounds are poly(ethylene glycol) (PEG) or PEG derivatives. More preferably, PEG may vary in molecular weight from about 200 daltons to about 20,000 daltons.

In another aspect of the invention formulation suitable for oral administration, the pharmaceutically acceptable carrier comprises one or more polyglycolized lipids. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

The term "polyglycolized lipids" as used herein refers to mixtures of monoglycerides, diglycerides, or triglycerides and polyethyleneglycol monoesters and diesters formed by the partial alcoholysis of vegetable oil using PEG of 200 g/mol to 2,000 g/mol or by the esterification of fatty acids using PEG 200 g/mol to 2,000 g/mol and glycerols. Preferably these include GELUCIRE® 35/10, GELUCIRE® 44/14, GELUCIRE® 46/07, GELUCIRE® 50/13, GELUCIRE® 53/10, and LABRASOL®.

In another aspect of the invention formulation suitable for oral administration, the pharmaceutically acceptable carrier comprises one or more pharmaceutically acceptable surfactants. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

In an additional aspect of the invention formulation suitable for oral administration, the pharmaceutically acceptable carrier comprises one or more pharmaceutically acceptable granulating agents. A preferred embodiment of this aspect has the ionizable substituted indolinone be a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof. Suitable granulating agents include without limitation silicon dioxide, microcrystalline cellulose, starch, calcium carbonate, pectin, crospovidone, polyplasdone, and the like, and suitable combinations of two or more thereof.

In an additional aspect of the invention formulation suitable for oral administration, the pharmaceutically acceptable carrier comprises suitable combinations of two or more of the members of the group comprising one or more polyoxyhydrocarbyl compounds, one or more polyglycolized lipids, one or more surfactants, and one or more granulating agents. Preferably, the pharmaceutically acceptable carrier comprises one or more polyoxyhydrocarbyl compounds, one or more polyglycolized lipids, and one or more surfactants. These oral formulations have advantageous solubility characteristics and oral bioavailability, and allow for the oral administration of the ionizable substituted indolinones for testing.

In an additional aspect, the invention provides pharmaceutically acceptable compositions containing an ionizable substituted indolinone. Preferred pharmaceutically acceptable compositions of the present invention are selected from the group comprising the invention formulation suitable for oral administration, a hard gelatin capsule filled with the invention formulation suitable for oral administration, a soft gelatin capsule filled with the invention formulation suitable for oral administration, and a hard gelatin capsule filled with the invention formulation suitable for oral administration admixed with a granulating agent to form a dry solid composition. In preferred embodiments, a solution comprising the invention formulation suitable for oral administration is encapsulated in a soft elastic gelatin capsule (SEC) or a hard gelatin capsule.

A solid composition of the formulation can be prepared by mixing the invention formulation in a liquefied state with a pharmaceutically acceptable granulating agent or a mixture of pharmaceutically acceptable granulating agents.

In an additional aspect of the invention formulation suitable for oral administration, the formulation is solid and the pharmaceutically acceptable carrier comprises one or more pharmaceutically acceptable diluents, one or more pharmaceutically acceptable binders, one or more pharmaceutically acceptable disintegrants, one or more pharmaceutically acceptable surfactants, one or more pharmaceutically acceptable lubricants and one or more pharmaceutically acceptable flow enhancers. Preferably the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

Suitable pharmaceutically acceptable diluents include without limitation pregelantinized starch, lactose, monohydrate or lactose anhydrous, mannitol, microcrystalline cellulose, and the like, and suitable combinations of two or more thereof. Suitable pharmaceutically acceptable binders include without limitation polyvinylpyrrolidone, hydroxylpropyl cellulose, hydroxypropylmethylcellulose, starch, and the like, and suitable combinations of two or more thereof. Suitable pharmaceutically acceptable disintegrants include without limitation sodium starch glycollate, crosscarmellose, crospovidone, sodium carboxymethylcellulose, calcium carboxymethylcellulose, starch and the like, and suitable combinations of two or more thereof. Suitable pharmaceutically acceptable surfactants are as described herein, and further include without limitation sodium lauryl sulfate, cetylpyridinium chloride, polysorbate 80, polyoxyethylene stearates, and the like, and suitable combinations of two or more thereof. Suitable pharmaceutically acceptable lubricants include without limitation magnesium stearate, stearic acid, sodium stearyl fumarate, PEG (3,000–10,000), glyceryl behenate and the like, and suitable combinations of any two or more thereof. Suitable pharmaceutically acceptable flow enhancers include without limitation colloidal silicon dioxide, talc, and the like, and suitable combinations of any two or more thereof.

In another aspect of the invention formulation suitable for oral administration, the formulation is a solution and the pharmaceutically acceptable carrier comprises one or more polyoxyhydrocarbyl compounds, one or more surfactants and one or more buffers. Preferably the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and pharmaceutically active salts, prodrugs, derivatives, and analogs thereof.

In a further aspect of the invention formulation suitable for oral administration, the formulation is a suspension and the pharmaceutically acceptable carrier comprises one or more pharmaceutically acceptable suspending agents, one or more pharmaceutically acceptable salt solutions and one or more pharmaceutically acceptable surfactants. Preferably the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and pharmaceutically active salts, prodrugs, derivatives, and analogs thereof.

Suitable pharmaceutically acceptable suspending agents include without limitation povidone, carboxylmethycellulose (CMC) and hydroxypropylmethyl cellulose (HPMC).

In yet another aspect of the invention formulation suitable for oral administration, the formulation is a solution and the pharmaceutically acceptable carrier comprises one or more pharmaceutically acceptable oils, and one or more pharmaceutically acceptable surfactants. Preferably the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and pharmaceutically active salts, prodrugs, derivatives, and analogs thereof. In other preferred embodiments, each of the one or more pharmaceutically acceptable oils is a sesame oil, and each of the one or more pharmaceutically acceptable surfactants is an ethylene oxide copolymer (e.g., PLURONIC™ F68, and the like, as described above).

In yet a further aspect of the invention formulation suitable for oral administration, the pharmaceutically acceptable carrier comprises one or more pharmaceutically acceptable surfactants and one or more pharmaceutically acceptable oils. Preferably the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof. In a preferred embodiment, the pharmaceutically acceptable surfactant comprises ethylene oxide copolymer (e.g., PLURONIC™ F68, and the like) and the pharmaceutically acceptable oil comprises sesame oil.

In an additional aspect, the invention features a method of preparing a formulation for parenteral or oral administration comprising adding to a salt solution, formed in situ by admixing a molar equivalent of a base solution or an acid solution with an ionizable substituted indolinone, one or more polyoxyhydrocarbyl compounds and/or one or more buffers. In a preferred embodiment, both the one or more polyoxyhydrocarbyl compounds and the one or more buffers are added to the salt solution. Preferably, the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and the pharmaceutically active salts, prodrugs, derivatives, and analogs thereof.

In a preferred embodiment of the method of preparing a formulation, the acid solution is selected from the group consisting of hydrochloric acid, sulfuric acid, formic acid, lactic acid, malic acid, and the like, and suitable combinations of two or more hereof, and the base solution is selected from the group consisting of sodium hydroxide, ammonium hydroxide, meglumine, triethylamine, triethanolamine, and the like, and suitable combinations of two or more hereof. Preferably, the base solution is sodium hydroxide.

In another preferred embodiment of the method of preparing a formulation, the one or more polyoxyhydrocarbyl compounds is selected from the group consisting of polyethylene glycol 300, polyethylene glycol 400, propyleneglycol, glycerin, and the like, and suitable combinations of two or more hereof, although polyoxyhydrocarbyl compounds listed previously can also be used in some cases. Preferably, the one or more polyoxyhydrocarbyl compounds is polyethylene glycol 300.

In a further preferred embodiment of the method of preparing a formulation, the buffer pH is three pH units higher than the pka of the ionizable substituted indolinone or three pH units lower than the pkb of the ionizable substituted indolinone, and has a molarity between 0.01 M and 0.1 M. Preferably, the buffer is selected from the group consisting of acetate, citrate, phosphoric acid buffer, ascorbate, hydrochloric acid buffer, and Tris-HCl buffer, and the like, and suitable combinations of two or more hereof. Alternatively, the buffer is selected from the group consisting of sodium phosphate, sodium carbonate, sodium hydroxide, glutamate, glycine, Tris base buffers, and the like, and suitable combinations of two or more hereof.

In a further preferred embodiment of the method of preparing a formulation, the method also includes sterilizing the solution. Preferably, the sterilizing is done by filtration.

Thus, a particular embodiment of the method of preparing a formulation aspect of the invention features a method of preparing a formulation, the method comprising adding to a salt solution, formed in situ via addition of a molar equivalent of sodium hydroxide to 3-[2,4-dimethyl-5-(2-oxo-1,2-dihydro-indol-3-ylidenemethyl)-1H-pyrrol-3-yl]-propionic acid, polyethylene glycol 300 and a sodium phosphate buffer. In preferred embodiments of this method of preparing a formulation, the method also includes adding benzyl alcohol to the salt solution, and/or sterilizing the resulting formulation by filtration.

In an additional aspect, the invention features a method of preparing a formulation suitable for oral administration, the method comprising admixing an ionizable substituted indolinone, one or more pharmaceutically acceptable surfactants, and one or more pharmaceutically acceptable oils. Preferably, the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and pharmaceutically active salts, prodrugs, derivatives, and analogs thereof. In other preferred embodiments, each of the one or more pharmaceutically acceptable oils is a vegetable oil (e.g., sesame oil, and the like, as described above), and/or each of the one or more pharmaceutically acceptable surfactants is an ethylene oxide copolymer (e.g., PLURONIC™ F68, and the like, as described above).

Other components can also be added to the invention formulations to enhance their therapeutic effects. For example, the ionizable substituted indolinones may be further formulated in liposomes in addition to the above-mentioned components. Liposomes have been shown to enhance the delivery of compounds into cells. However, because the formulations have been shown to have a therapeutic effect with only the components described herein, formulations of the present invention may also "consist essentially of" or "consist of" these components.

In preferred embodiments of the invention, the formulations are effective in treating or preventing an abnormal condition in a patient in need of such treatment. The patient is preferably a mammal and more preferably a human. In a highly preferred embodiment, the formulations are parenteral. Parenteral administration includes intravenous, subcutaneous, intraperitoneal, intramuscular, intraosseous, and intramedullary injection, and the like, and suitable combinations of two or more hereof.

The term "preventing" as used herein refers to administering the formulation to a patient before the abnormal condition manifests itself in that patient.

The term "treating" as used herein refers to the method of the invention having a therapeutic effect and at least partially alleviating or abrogating the abnormal condition in the organism (e.g., patient).

The term "therapeutic effect" as used herein refers to inhibition of the abnormal condition. The term "therapeutic effect" also refers to the inhibition of factors causing or contributing to the abnormal condition. A therapeutic effect relieves to some extent one or more of the symptoms of the abnormal condition.

The term "mammal" as used herein preferably refers to the organisms of the class known as "mammalia", such as mice, rats, rabbits, guinea pigs, goats, sheep, horses, cows, dogs, cats, monkeys, apes, humans, and the like; more preferably dogs, cats, monkeys, apes, humans, and the like; and most preferably humans.

The term "abnormal condition" refers to a function in the cells or tissues of a patient that deviates from normal functions in that patient. An abnormal condition can relate to cell proliferation (e.g., be a cell proliferative disorder) as described herein.

The term "cell proliferative disorder" as used herein refers to a disorder where an excess cell proliferation of one or more subset of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the affected cells. Hyper-proliferative cell disorders include without limitation cancers, blood vessel proliferative disorders, fibrotic disorders, autoimmune disorders, and the like. Cell proliferative disorders suitable for treatment in accordance with the present invention include without limitation cancers (e.g., erythroblastoma, glioblastoma, meningioma, astrocytoma, melanoma, myoblastoma, breast cancers, gastric cancers, ovarian cancers, renal cancers, hepatic cancers, pancreatic cancers, bladder cancers, thyroid cancers, prostate cancers, colorectal cancers, solid tumor cancers, colon cancer, brain cancer, blood cancers, bone cancers, liver cancer, kidney cancer, stomach cancer, lung cancer, Kaposi's sarcoma, non-small cell lung cancer, skin cancer, and the like, non-small cell lung cancers, and the like).

In reference to the treatment of abnormal conditions caused, in whole or in part, by a cell proliferative disorder, a therapeutic effect refers to one or more of the following: (a) reducing tumor size; (b) inhibiting (e.g, slowing or stopping) tumor metastasis; (c) inhibiting tumor growth; and (d) relieving to some extent one or more of the symptoms associated with the abnormal condition.

Thus, the present invention features methods of preventing or treating an abnormal condition in a patient in need of treatment comprising: (a) diluting a parenteral formulation into a pharmaceutically acceptable solution, said parenteral formulation comprising an ionizable substituted indolinone, one or more polyoxyhydrocarbyl compounds, and a buffer; and (b) parenterally administering said diluted formulation to said patient. Preferably, the ionizable substituted indolinone is a pyrrole substituted 2-indolinone of Formula I having $R^9$ be -(alk$_1$)Z$_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid, and pharmaceutically active salts, prodrugs, derivatives, and analogs thereof.

In preferred embodiments of a method of preventing or treating an abnormal condition in a patient in need of treatment with a parenteral formulation, the ionizable substituted indolinone is solubilized by combining with a molar equivalent of a base solution or an acid solution. Preferably, the base solution is selected from the group consisting of sodium hydroxide, ammonium hydroxide, triethylamine, ethylenediamine, N-methyl-D-glucamine, choline, triethanolamine, and the like, and suitable combinations of two or more hereof, and the acid solution is selected from the group consisting of hydrochloric acid, sulfuric acid, formic acid, lactic acid, malic acid, succinic acid, acetic acid, methane sulfonic acid, benzene sulfonic acid, phosphoric acid, and the like, and suitable combinations of two or more hereof In yet other preferred embodiments of a method of preventing or treating an abnormal condition in a patient in need of treatment with a parenteral formulation, the one or more polyoxyhydrocarbyl compounds is selected from the group consisting of polyethylene glycol 300, polyethylene glycol 400, propyleneglycol, glycerin, and the like, and suitable combinations of two or more hereof. Preferably, the one or more polyoxyhydrocarbyl compounds is polyethylene glycol 300.

In other preferred embodiments of a method of preventing or treating an abnormal condition in a patient in need of treatment with a parenteral formulation, the buffer pH is three pH units higher than the pka of said ionizable substituted indolinone, or three pH units lower than the pkb of said ionizable substituted indolinone. Preferably, the buffer has a molarity between 0.01 M and 0.1 M, and is selected from the group consisting of acetate, citrate, phosphoric acid buffer, ascorbate, hydrochloric acid buffer, Tris-HCl buffer, and the like, and suitable combinations of two or more hereof. Alternatively, the buffer is selected from the group consisting of sodium phosphate, sodium carbonate, sodium hydroxide, glutamate, glycine, Tris base buffers, and the like, and suitable combinations of two or more hereof. Preferably, the buffer is sodium phosphate buffer.

In other preferred embodiments of a method of preventing or treating an abnormal condition in a patient in need of treatment with a parenteral formulation, the formulation also contains one or more pharmaceutically acceptable surfactants. Preferably, pharmaceutically acceptable surfactants include but are not limited to POLYSORBATE 80 and other polyoxyethylene sorbitan fatty acid esters, glyceryl monooleate, sorbitan monooleate, pluronic F68, lecithin, polyvinyl alcohol, ethylene oxide copolymers such as PLURONIC™ (a polyether) and TETRONIC™ (BASF), polyol moieties, sorbitan esters, and the like, and suitable combinations of two or more hereof. Preferably ethoxylated castor oils, such as CREMOPHOR EL®, are used for the formulation of hydrophobic pharmaceutical agents. In other preferred embodiments of a method of preventing or treating an abnormal condition in a patient in need of treatment with a parenteral formulation, the formulation also contains a pharmaceutically acceptable preservative. Preferably, the preservative is selected from the group consisting of benzyl alcohol, methyl paraben, ethyl paraben, phenol, and the like, and suitable combinations of two or more hereof. Most preferably, the preservative is benzyl alcohol.

In other preferred embodiments of a method of preventing or treating an abnormal condition in a patient in need of treatment with a parenteral formulation, the formulation also contains an antioxidant. Preferably, the antioxidant is selected from the group consisting of sodium meta-bisulfite EDTA, ascorbic acid, benzyl alcohol, and the like, and suitable combinations of two or more hereof, and preferably is benzyl alcohol.

In yet other preferred embodiments of a method of preventing or treating an abnormal condition in a patient in need of treatment with a parenteral formulation, the patient is a mammal, preferably a human.

Further, the present invention features methods of preventing or treating an abnormal condition in a patient in need of treatment comprising orally administering to the patient a formulation comprising an ionizable substituted indolinone, one or more pharmaceutically acceptable surfactants, and one or more pharmaceutically acceptable oils. Preferably, the ionizable substituted indolinone is a pyrrole substituted 2-indolinone of Formula I having $R^9$ be —$(alk_1)Z_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-2-oxo-1,2-dihydro-indol-3-ylidenemethyl)-1H-pyrrol-3-yl]-propionic acid, and pharmaceutically active salts, prodrugs, derivatives, and analogs thereof. In other preferred embodiments, each of the one or more pharmaceutically acceptable oils is a vegetable oil (e.g., sesame oil, and the like, as described above), and/or each of the one or more pharmaceutically acceptable surfactants is an ethylene oxide copolymer (e.g., PLURONIC™ F68, and the like, as described above).

Preferably, the hydrophobic pharmaceutical agent is a pyrrole substituted 2-indolinone of Formula I having $R^9$ be —$(alk_1)Z_1$, and each of $R^8$ and $R^{10}$ independently selected from the group consisting of hydrogen and unsubstituted lower alkyl. In a presently preferred aspect, the ionizable substituted indolinone is 3-[2,4-dimethyl-5-(2-oxo-1,2-dihydro-indol-3-ylidenemethyl)-1H-pyrrol-3-yl]-propionic acid (compound IV), and pharmaceutically active salts, prodrugs, derivatives, and analogs thereof.

Other features and advantages of the invention will be apparent from the following description of the preferred embodiments and from the claims.

DETAILED DESCRIPTION OF THE PREFERRED EMBODIMENTS

The instant invention features parenteral and oral formulations for indolinone compounds that are ionizable as free acids or free bases. In particular, the formulations aid the administration of indolinones that are ionizable as free acids or free bases to patients in need of treatment.

1. Properties of 3-[2,4-Dimethyl-5-(2-oxo-1,2-dihydro-indol-3-ylidenemethyl)-1H-pyrrol-3-yl]-propionic acid 3-[2,4-Dimethyl-5-(2-oxo-1,2-dihydro-indol-3-ylidenemethyl)-1H-pyrrol-3-yl]-propionic acid, is an indolinone compound that is a potent inhibitor of signal transduction via Flk-1/KDR, PDGF receptor, and FGF receptor. It is also efficacious in inhibiting SC growth of multiple tumor types and inhibited the growth of established tumors. This compound is a preferred compound for use in the formulations of the present invention. Properties of formulations comprising this compound are set forth in the experimental materials that follow.

2. Pharmaceutical Compositions and Uses

A compound or combination of the present invention, a prodrug thereof or a physiologically acceptable salt of either the compound or its prodrug, can be administered as such to a human patient or it can be administered in pharmaceutical compositions or formulations in which the foregoing materials are mixed with suitable carriers or excipient(s). Techniques for formulation and administration of drugs may be found in "Remington's Pharmacological Sciences," Mack Publishing Co., Easton, Pa., latest edition.

A. Routes of Administration

General

Suitable routes of administration may include, without limitation, oral, rectal, transmucosal or intestinal administration or intramuscular, subcutaneous, intramedullary, intrathecal, direct intraventricular intravenous, intraperitoneal, intranasal, or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

B. Composition/Formulation

General

Pharmaceutical compositions and formulations of the present invention may be manufactured by processes well known in the art; e.g., by means of conventional mixing, dissolving, granulating, dragee-making, levigating, emulsifying, encapsulating, entrapping or lyophilizing processes.

Pharmaceutical compositions and formulations for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations and formulations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol; cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinylpyrrolidone (PVP). If desired, disintegrating agents may be added, such as cross-linked polyvinylpyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions and formulations which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For buccal administration, the compositions and formulations may take the form of tablets or lozenges formulated in conventional manner.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions and formulations for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous-injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. The proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds and formulations may be delivered using a sustained-release system, such as semipermeable matrices of solid hydrophobic polymers containing the therapeutic agent. Various sustained-release materials have been established and are well (mown by those skilled in the art.

The pharmaceutical compositions and formulations herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the compounds of the invention may be provided as sans with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

3-[2,4-Dimethyl-5-(2-oxo-1,2-dihydro-indol-3-ylidenemethyl)-1H-pyrrol-3-yl]-propionic acid composition This compound may be formulated as any of the compositions and formulations described above. Presently preferred formulations, however, comprise 3-[2,4-Dimethyl-5-(2-oxo-1,2-dihydro-indol-3-ylidenemethyl)-1 H-pyrrol-3-yl]-propionic acid composition in sufficient sterile parenteral solution to afford a final concentration of about 10 mg/ml.

3. Dosage

A. General

Compounds, combinations, and pharmaceutical compositions and formulations suitable for use in the present invention include compositions wherein the active ingredients are contained in an amount sufficient to achieve the intended purpose; i.e., the modulation of protein kinase (PK) activity or the treatment or prevention of a PK-related disorder.

The above referenced protein kinase related disorder is selected from the group consisting of an EGFR related disorder, a PDGFR related disorder, an IGFR related disorder and a flk related disorder.

The above referenced protein kinase related disorder is a cancer selected from the group consisting of squamous cell carcinoma, sarcomas such as Kaposi's sarcoma, astrocytoma, glioblastoma, lung cancer, bladder cancer, colorectal cancer, gastrointestinal cancer, head and neck cancer, melanoma, ovarian cancer, prostate cancer, breast cancer, small-cell lung cancer and glioma in a further aspect of this invention.

The above referenced protein kinase related disorder is selected from the group consisting of diabetes, a hyperproliferation disorder, von Hippel-Lindau disease, restenosis, fibrosis, psoriasis, osteoarthritis, rheumatoid arthritis, an inflammatory disorder and angiogenesis in yet another aspect of this invention.

Additional disorders which may be treated or prevented using the compounds of this invention are immunological disorders such as autoimmune disease (AIDS) and cardiovascular disorders such as atherosclerosis.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition, (See e.g., Fingl, et al., 1975, in "The Pharmacological Basis of Therapeutics", Ch. 1 p.1).

Therapeutic compounds should be more potent in inhibiting receptor tyrosine kinase activity than in exerting a cytotoxic effect. A measure of the effectiveness and cell toxicity of a compound can be obtained by determining the therapeutic index; i.e., $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques as well(Mossman, 1983 *J. Immunol. Methods*, 65:55–63), by measuring the amount of LDH released (Korzeniewski and Callewaert, 1983, *J. Immunol. Methods*, 64:313; Decker and Lohmann-Matthes, 1988, *J. Immunol. Methods*, 115:61), or by measuring the lethal dose in animal models. Compounds with a large therapeutic index are preferred. Thus, in one aspect of the invention, a preferred dosage of the compounds, agents, combinations, and pharmaceutical compositions contemplated for use in the invention requires the therapeutic index of each active component to be greater than 2, preferably at least 10, more preferably at least 50.

Dosage amount and interval may be adjusted individually to provide plasma levels of the active species, which are sufficient to maintain the kinase modulating effects. These plasma levels are referred to as minimal effective concentrations (MECs). The MEC will vary for each compound but can be estimated from in vitro data; e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using NEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration end other procedures known in the art may be employed to determine the correct dosage amount and interval.

The amount of a composition administered will, of course, be dependent on the subject being treated, the severity of the affliction, the manner of administration, the judgment of the prescribing physician, etc.

B. 3-[2.4-Dimethyl-5-(2-oxo-1,2-dihydro-indol-3-ylidenemethyl)-1H-pyrrol-3-yl]-propionic acid.

Therapeutically Effective Amounts

In general, a "therapeutically effective amount" refers to that amount of an agent or its metabolite which is effective to prevent, alleviate, reduce or ameliorate symptoms of disease and/or the undesired side effects attributable to treatment of disease with another agent or its metabolite, or to prolong the survival of the patient being treated. More particularly, in reference to the treatment of cancer, a therapeutically effective amount refers to that amount which has the effect of (1) reducing the size of (or preferably eliminating) the tumor; (2) inhibiting (that is, slowing to some extent, preferably stopping) tumor metastasis; (3) inhibiting to some extent (that is slowing to some extent, preferably stopping) tumor growth; and/or, (4) relieving to some extent (or preferably eliminating) one or more symptoms associated with the cancer and/or one or more undesired side effects attributable to treatment of the cancer with another agent or its metabolite. Non-limiting examples of therapeutically effective amounts of particular agents and compounds contemplated for use in the present invention are further described below.

In addition to the above general definition, by a "therapeutically effective amount" of an agent is meant any amount administered in any manner and in any treatment regime as may be currently recognized in the medical arts or as may come about as the result of future developments regarding the use of these agents.

A "treatment regime" refers to specific quantities of the ionizable substituted indolinone contemplated for use in this invention) administered at set times in a set manner over an established time period.

When referring to "set times" of administration within a treatment regime, "consecutive days" means consecutive calendar days; i.e., Monday, Tuesday, Wednesday, etc. "Staggered" days means calendar days with other calendar days between them, e.g., without limitation, Monday, Wednesday, Saturday, etc.

Furthermore, with retard to a "therapeutically effective amount" of an ionizable substituted indolinone, the phrase refers to an amount of the compound sufficient to inhibit the growth, size and vascularization; i.e., angiogenesis and/or vasculogenesis, tumors during the recovery" periods, i.e., the periods in a treatment regime when no other chemotherapeutic agent is being administered to a patient.

Specific Amounts

Based on the pharmacological data obtained regarding 3-[2,4-Dimethyl-5-(2-oxo-1,2-dihydro-indol-3-ylidenemethyl)-1H-pyrrol-3-yl]-propionic acid composition (see above), the compound may be administered in doses ranging from about 1 mg/m$^2$ to about 3000 mg/m$^2$. In a presently preferred embodiment, the dosage is between about 50 mg/m$^2$ and about 2400 mg/m$^2$. In another preferred embodiment, therapeutically effective amounts of 3-[2,4-Dimethyl-5-(2-oxo-1,2-dihydro-indol-3-ylidenemethyl)-1H-pyrrol-3-yl]-propionic acid composition comprise from about 50 to about 800 mg/m$^2$. Of course, the dose would depend on a number of factors, including patient specific factor, e.g., weight, dosing regimen (e.g., frequency, route of administration, effect of food) etc.

The formulation(s) described in the above composition section may be administered to a patient at a rate of from about 0.1 to about 200 cc/hour The rate of administration for a particular patient is dependent on achieving therapeutically relevant plasma levels for the particular indication. The prescribing physician is skilled in making such as determination.

By "about," wherever the term appears herein, is meant ±10)%; i.e., about 175 cc/hour means from 157.5 cc/hour to 192.5 cc/hour, etc.

In a presently preferred embodiment, the 3-[2,4-Dimethyl-5-(2-oxo-1,2-dihydro-indol-3-ylidenemethyl)-1 H-pyrrol-3-yl]-propionic acid composition dose is administered during rest periods when no other agent is being administered to a patient.

B. Pharmaceutical Acceptable Carriers.

The following tables set forth the ranges of components useful in the inventive formulations.

All formulation components:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10% | 0.01–7.5% | 0.01–5.0% |
| Polyoxyhydrocarbyl Compounds | 5.0–70% | 5.0–45% | 15–45% |
| Buffer | 0–3% | 0–1.0% | 0–0.5% |
| Surfactant | 0–50.0% | 0–50.0% | 0–31.5% |
| Preservative | 0–3.0% | 0–2.0% | 0.5–2.0% |
| Antioxidant | 0–3.0% | 0–2.0% | 0.1–1.0% |
| Alcohol | 0–40.0% | 0–30.0% | |
| Oil | 5–75% | 10–25% | 15–20% |
| Granulating Agent | 10–95% | 20–60% | 30–50% |
| Diluent | 5–95% | 10–80% | 20–60% |
| Binder | 0–15% | 0–8% | 0–5% |
| Disintegrant | 1–20% | 4–15% | 4–10% |
| Lubricant | 0.3–2.0% | 0.5–1.5% | 1.0–1.5% |
| Flow Enhancer | 0–1.0% | 0.3–1.0% | 0.3–0.8% |
| Suspending Agent | 0–2.0% | 0–1.0% | 0–0.5% |

Indolinone+Polyoxyhydrocarbyl Compounds:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Polyoxyhydrocarbyl Compounds | 1.0–70.0% | 5.0–45% | 15.0–45.0% |

Indolinone+Buffer

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Buffer | 0.01M–1M | 0.05–0.5M | 0.2–0.5M |

Indolinone+Preservative:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Preservative | 0–3.0% | 0–2.0% | 0.5–2.0% |

Indolinone+Antioxidant:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Antioxidant | 0–3.0% | 0–2.0% | 0.1–1.0% |

Indolinone+Alcohol:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10% | 0.01–7.5% | 0.01–5.0% |
| Alcohol | 0–40.0% | 0–30.0% | 0–25.0% |

Indolinone+Oil:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 5–75% | 10–25% | 15% |
| Oil | 20–90% | 70–85% | 80% |

Indolinone+Surfactant:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Surfactant | 0–50.0% | 0–40.0% | 0–31.5% |

Indolinone+Granulating Agent:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 5–90% | 40–80% | 50–70% |
| Granulating Agent | 10–95% | 20–60% | 30–50% |

Indolinone+Polyoxyhydrocarbyl Compounds+Surfacant+Polyglycolized Lipids:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Polyoxyhydrocarbyl Compounds | 5.0–70% | 5–45% | 15.0–45.0% |
| Surfactant | 0–50% | 0–40% | 0–31.5 |

Indolinone+Surfactant+Diluent+Binder+Disintegrant+Lubricant+Flow Enhancer:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 5–90% | 10–80% | 15–75% |
| Surfactant | 0–10% | 0.1–8.0% | 1–5% |
| Binder | 5–95% | 15–85% | 20–75% |
| Disintegrant | 1–20% | 4–15% | 4–10% |
| Lubricant | 0.3–2.0% | 0.5–1.5% | 1.0–1.5% |
| Flow Enhancer | 0–1.0% | 0.3–1.0% | 0.3–0.8% |

Indolinone+Polyoxyhydrocarbyl Compounds+Buffer+Surfactant:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10.0% | 0.01–7.5% | 0.01–5.0% |
| Polyoxyhyrocarbyl Compounds | 5–70% | 5–45% | 15–45% |
| Buffer | 0–3% | 0–1% | 0–0.5% |
| Surfactant | 0–50% | 0–40% | 0–31.5% |

Indolinone+Surfactant+Salt Solution+Suspending Agent:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 0.01–10% | 0.01–7.5% | 0.01–5.0% |
| Surfactant | 0–50% | 0.1–1.0% | 0.1–0.5% |
| Salt Solution | 0.5–1% | 0.5–1% | 0.5–1% |
| Suspending Agent | 0–2% | 0–1% | 0–0.5% |

Indolinone+Surfactant+Oil:

| Component | Broadest Range of Component Concentration in Formulation | Preferred Range of Component Concentration in Formulation | Most Preferred Range of Component Concentration in Formulation |
|---|---|---|---|
| Ionizable Substituted Indolinone | 10–30% | 10–25% | 10–20% |
| Surfactant | 0–10% | 3–8% | 5% |
| Oil | 50–80% | 60–80% | 70–80% |

Method of Making Formulation comprising Indolinone+Polyoxyhydrocarbyl Compounds+Buffer:

| Component | Broadest Range of Component Concentration in Formulation Made By Method | Preferred Range of Component Concentration in Formulation Made By Method | Most Preferred Range of Component Concentration in Formulation Made By Method |
|---|---|---|---|
| Ionizable Substituted Indolinone | 0.01–10% | 0.01–7.5% | 0.01–5% |
| Polyoxyhydrocarbyl Compounds | 5–70% | 5–50% | 5–45% |
| Buffer | 0–3% | 0–1% | 0–0.05% |

Method of Making Formulation comprising Indolinone+Surfactant+Oil:

| Component | Broadest Range of Component Concentration in Formulation Made By Method | Preferred Range of Component Concentration in Formulation Made By Method | Most Preferred Range of Component Concentration in Formulation Made By Method |
|---|---|---|---|
| Ionizable Substituted Indolinone | 1–1000 mg | 10–900 mg | 50–750 mg |
| Surfactant | 1–100 mg | 10–90 mg | 45–55 mg |
| Oil | 10–1000 mg | 10–900 mg | 200–900 mg |

4. Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

Additional methods of preparing pharmaceutical formulations of the compounds, methods of determining the amounts of compounds to be administered to a patient, and modes of administering compounds to an organism are disclosed in U.S. application Ser. No. 08/702,232 by Tang, et al., and entitled "Indolinone Combinatorial Libraries and Related Products and Methods for the Treatment of Disease," filed Aug. 23, 1996, and International patent publication number WO 96/22976, by Buzzetti, et al., and entitled "Hydrosoluble 3-Arylidene-2-Oxindole Derivatives as Tyrosine Kinase Inhibitors," published Aug. 1, 1996, both of which are incorporated herein by reference in their entirety, including any drawings. Those skilled in the art will appreciate that such descriptions are applicable to the present invention and can be easily adapted to it.

SYNTHESIS EXAMPLES

The compounds of this invention, as well as the precursor 2-oxindoles and aldehydes, may be readily synthesized using techniques well known in the chemical arts. It will be appreciated by those skilled in the art that other synthetic pathways for forming the compounds of the invention are available and that the following is offered by way of example and not limitation.

A. General synthetic procedure.

The following general methodology may be employed to prepare the compounds of this invention:

The appropriately substituted 2-oxindole (1 equiv.), the appropriately substituted aldehyde (1.1 equiv.) and a base (0.1 equiv.) are mixed in a solvent (1–2 ml/mmol 2-oxindole) and the mixture is then heated for from about 2 to about 12 hours. After cooling, the precipitate that forms is filtered, washed with cold ethanol or ether and vacuum dried to give the solid product. If no precipitate forms, the reaction mixture is concentrated and the residue is triturated with dichloromethane/ether, the resulting solid is collected by filtration and then dried, The product may optionally be further purified by chromatography.

The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo(5.4.1]undec-7-one, pyrrolidine and piperidine.

Examples of inorganic bases are, without limitation, ammonia, alkali metal or alkaline earth hydroxides, phosphates, carbonates, bicarbonates, bisulfates and amides. The alkali metals include, lithium, sodium and potassium while the alkaline earths include calcium, magnesium and barium.

In a presently preferred embodiment of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principle of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through-hydrogen bonding. Examples of protic solvents include; without limitation, water and alcohols.

An "aprotic solvent" may be polar or non-polar but, in either case, does not contain acidic hydrogens and therefore is not capable of hydrogen bonding with solutes. Examples, without limitation, of non-polar, protic solvents, are pentane, hexane, benzene, toluene, methylene chloride and carbon tetrachloride. Examples of polar aprotic solvents are chloroform, tetrahydro-foran, dimethylsulfoxide and dimethylformamide.

In a presently preferred embodiment of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10 degrees Celsius of the indicated temperature, more preferably within 5 degrees Celsius of the indicated temperature and, most preferably, within 2 degrees Celsius of the indicated temperature. Thus, for example, by "about 75° C." is meant 75° C.±10° C., preferably 75° C.±5° C. and most preferably, 75° C.±2° C.

B. Synthetic methods used in the examples which follow:

Method A: Formylation of pyrroles

POCl (1,1 equiv.) is added dropwise to dimethylformamide (3 equiv.) at −10° C. followed by addition of the appropriate pyrrole dissolved in dimethylformamide. After stirring for two hours, the reaction mixture is diluted with H₂O and basified to pH 11 with 10 N KOH. The precipitate which forms is collected by filtration, washed with H₂O and dried in a vacuum oven to give the desired aldehyde.

Method B: Saponification of pyrrolecarboxylic acid esters

A mixture of a pyrrolecarboxylic acid ester and koh (1–4 equiv.) In etoh is refluxed until reaction completion is indicated by thin layer chromatography (tlc). The cooled reaction mixture is acidified to ph 3 with 1 n hcl. The precipitate which forms is collected by filtration, washed with h₂o and dried in a vacuum oven to give the desired pyrrolecarboxylic acid Method C: Amidation To a stirred solution of a pyrrolecarboxylic acid dissolved in dimethylformamide(0.3M) is added 1-ethyl-3-(3-dimethylamino propyl)carbodiimide (1.2 equiv.), 1-hydroxybenzotriazole (1.2 equiv.), and triethylamine (2 equiv.). The appropriate amine is added (1 equiv.) and the reaction stirred until completion is indicated by TLC. Ethyl seem is then added to the reaction mixture and the solution washed with saturated NaHCO₃ and brine (with extra salt), dried over MgSO₄ and concentrated to afford the desired amide.

Method D. Condensation of aldehydes and oxindoles containing carboxylic add substituents A mixture of the oxindole (1 equivalent), 1 equivalent of the aldehyde and 1–3 equivalents of piperidine (or pyrrolidine) in ethanol (0.4 M) is stirred at 90–100° C. until reaction completion is indicated by TLC. The mixture is than concentrated and the residue acidified with 2N HCl. The precipitate that forms is washed with H₂O and EtOH and then dried in a vacuum oven to give the product.

Method E: Condensation of aldehydes and oxindoles not containing carboxylic acid substituents A mixture of the oxindole (1 equivalent), 1 equivalent of the aldehyde and 1–3 equivalents of piperidine (or pyrrolidine) in ethanol (0.4 M) is stirred at 90–100° C. until reaction completion is indicated by TLC. The mixture is cooled to room temperature and the solid which forms is collected by vacuum filtration, washed with ethanol and dried to give the product. If a precipitate does not form upon cooling of the reaction mixture, the mixture is concentrated and purified by column chromatography.

C. Examples of oxindole syntheses

The following examples of the synthesis of representative oxindoles is not to be construed as limiting the scope of this invention in any manner whatsoever. Alternate routes to the oxindoles shown as well as other oxindoles to be used to make the compounds of this invention will become apparent to those skilled in the an based on the following disclosures. Such syntheses and oxindoles are within the scope and spirit of this invention.

5-Amino-2-oxindole

5-Nitro-2-oxindole (6.3 g) was hydrogenated in methanol over 10% palladium on carbon to give 3.0 g (60% yield) of the title compound as a white solid, 5-Bromo-2-oxindole 2-Oxindole (1.3 g) in 20 mL acetonitrile was cooled to −10° C. and 2.0 g N-bromosuccinimide was slowly added with stirring. The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 ml, of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl-acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried in a vacuum oven to afford the title compound.

5-Nitro-2-oxindole

2-Oxindole (6.5 g) was dissolved in 25 mL concentrated sulfuric acid and the mixture maintained at -10 to -15° C. while 2.1 mL of fuming nitric acid was added dropwise. After the addition of the nitric acid the reaction mixture was stirred at 0° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-vitro-2-oxindole.

5-Iodo-2-oxindole

2-Oxindole (82.9 g) was suspended in 630 mL of acetic acid with mechanical stirring and the mixture cooled to 10° C. in an ice water bath. Solid N-iodosuccinimide (175 g) was added in portions over 10 minutes. After the addition was complete the mixture was stirred for 1.0 hour at 10° C. The suspended solid, which had always been present, became very thick at this time. The solid was collected by vacuum filtration, washed with 100 mL of 50% acetic acid in water and then with 200 mL of water and sucked dry for 20 minutes in the funnel. The product was dried under vacuum to give 93.5 g (36%) of 5-iodo-2-oxindole containing about 5% 2-oxindole by proton NMR.

5-Methyl-2-oxindole

5-Methylisatin (15.0 g) and 60 mL of hydrazine hydrate were heated at 140 to 160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6N hydrochloric acid. After standing at room temperature for 2 days the precipitate was collected by vacuum filtration, washed with water and dried under vacuum to give 6.5 g (47% yield) of 5-methyl-2-oxindole.

5-Bromo-4-methyloxindole and 5,7-Dibromo-4-methyloxindole

4-Methyl-2-oxindole (5 g) in 40 mL of acetonitrile was treated with 7.26 g of N-bromosuccinimide and stirred at room temperature for 4 hours. Thin layer chromatography (ethyl acetate:hexane 1:2, silica gel) showed a mixture of 5-bromo (Rf 0.3) and 5,7-dibromo (Rf 0.5) products. Another 7,26 g of N-bromosuccinimide was added and the mixture stirred for 4 additional hours. The solid was collected by vacuum filtration, washed with 20 mL of acetonitrile and dried to give a 1:1 mixture of mono and dibromo compounds. The filtrate was concentrated and chromatographed on silica gel (ethyl acetate:hexane (1:2)) to give 1.67 g of 5-bromo-4-methyl-2-oxindole as a beige solid. The remaining 1:1 mixture of solids was recrystallized twice from glacial acetic acid to give 3.2 g of 5,7-dibromo-4-methyl-2-oxindole as a light orange solid. The filtrates from this material were chromatographed as above to give 0.6 g of 5-bromo-4-methyl-2-oxindole and 0.5 g of 5,7-dibromo-4-methyl-2-oxindole.

6-Fluoro-2-oxindole

Sodium hydride (2.6 g) and 14.5 g of dimethylmalonate was stirred and heated to 100° C. in 160 mL dimethylsulfoxide for 1.0 hour. The mixture was cooled to room temperature, 7.95 g of 2,5-difluoronitrobenzene were added and the mixture was stirred for 30 minutes. The mixture was then heated to 100° C. for 1.0 hour, cooled to room temperature and poured into 400 mL of saturated ammonium chloride solution. The mixture was extracted with 200 mL of ethyl acetate and the organic layer washed with brine, dried over anhydrous sodium sulfate and concentrated under vacuum. The residue was crystallized from methanol to give 24.4 g (80% yield) of dimethyl 4-fluoro-2-nitrophenylmalonate as a white solid, Rf 0.2 on thin layer chromatography (ethyl acetate:hexane 1:6, silica gel). The filtrate was concentrated and chromatographed on a column of silica gel (ethyl acetate:hexane 1:8) to give an additional 5.03 g of dimethyl 4-fluoro-2-nitro-phenylmalonate, for a total of 29.5 g (96% yield).

Dimethyl 4-fluoro-2-nitrophenylmalonate (5.0 g) was refluxed in 20 mL of 6N hydrochloric acid for 24 hours. The reaction was cooled and the white solid collected by vacuum filtration, washed with water and dried to give 3.3 g (87% yield) of 4-fluoro-2-nitrophenylacetic acid, Rf 0.6 on thin layer chromatography (ethyl acetate:hexane 1:2, silica gel).

4-Fluoro-2-nitrophenylacetatic acid (3.3 g) dissolved in 15 mL of acetic acid was hydrogenated over 0.45 g of 10% palladium on carbon at 60 psi $H_2$ for 2 hours. The catalyst was removed by filtration and washed with 15 mL of methanol. The combined filtrates were concentrated and diluted with water. The precipitate was collected by vacuum filtration, washed with water and dried to give 1.6 g (70% yield) of 6-fluoro-2-oxindole, Rf 0.24 on thin layer chromatography. The filtrate was concentrated to give a purple solid with an NNM spectrum similar to the first crop. Chromatography of the purple solid (ethyl acetate:hexane 1:2, silica gel) gave a second crop of 6-fluoro-2-oxindole as a white solid.

5-Aminosulfonyl-2-oxindole

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulphonyl-2-oxindole (50% yield) which was used without further purification.

5-Chlorosulphonyl-2-oxindole (2,1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Methylaminosulfonyl-2-oxindole

A suspension of 3.38 g of 5-chlorosulphonyl-2-oxindole in 10 mL 2M methylamine in tetrahydrofuran was stirred at room temperature for 4 hours during which time a white solid formed. The precipitate was collected by vacuum filtration, washed twice with 5 mL of water and dried under vacuum at 40° C. overnight to give 3.0 g (88% yield) of 5-methylaminosulfonyl-2-oxindole.

5-(4-Trifluoromethylphenylaminosolfonyl-2-oxindole

A suspension of 2.1 g of 5-chlorosulphonyl-2-oxindole, 1.6 g of 4-trifluoromethylaniline and 1.4 g of pyridine in 20 mL of dichloromethane was stirred at room temperature for 4 hours. The precipitate which formed was collected by vacuum filtration, washed twice with 5 mL of water and dried under vacuum at 40° C. overnight to give 2.4 g of crude product containing some impurities by thin layer chromatography. The crude product was chromatographed on silica gel eluting with ethyl acetate:hexane (1,2) to give 1.2 g (37% yield) of 5-(4-trifluoromethylphenyl-aminosulfonyl)-2-oxindole.

5-(Morphollaosulfonyl)-2-oxindole

A suspension of 2.3 g of 5chlorosulphonyl-2-oxindole and 2.2 g of morpholine in 50 mL of dichloromethane was stirred at room temperature for 3 hours. The white precipitate was collected by vacuum filtration, washed with ethyl acetate and hexane and dried under vacuum at 40° C. overnight to give 2.1 g (74% yield) of 5-(morpholinosulfonyl)-2-oxindole.

6-Trifluoromethyl-2-oxindole

Dimethylsulfoxide (330 mL) was added to 7.9 g of sodium hydride followed by dropwise addition of 43.6 g diethyloxalate. The mixture was heated to 100° C. for 1.0 hour and cooled to room temperature. 2-Nitro-4-trifluoromethyltoluene (31.3 g) was added, the reaction stirred for 30 minutes at room temperature and then heated to 100° C. for 1 hour. The reaction was cooled and poured into a mixture of saturated aqueous ammonium chloride, ethyl acetate and hexane. The organic layer was washed with saturated ammonium chloride, water and brine, dried, and concentrated to give dimethyl 2-(2-nitro-4-trifluoromethylphenyl)malonate.

The diester was dissolved in a mixture of 6.4 g of lithium chloride and 2.7 mL of water in 100 mL of dimethylsulfoxide and heated to 100° C. for 3 hours. The reaction was cooled and poured into a mixture of ethyl acetate and brine. The organic phase was washed with brine, dried with sodium sulfate, concentrated and chromatographed on silica gel (10% ethyl acetate in hexane). The fractions containing product were evaporated to give 25.7 g of methyl 2-nitro-4-trifluoromethylphenylacetate.

Methyl 2-nitro-4-trifluoromethylphenylacetate (26 mg) was hydrogenated over 10% palladium on carbon and then heated at 100° C. for 3 hours. The catalyst was removed by filtration and the solvent evaporated to give the title compound.

5-(2-Chloroethyl)oxindole

5-Chloroacetyl-2-oxindole(4.18 g) in 30 mL of trifluoroacetic acid in an ice bath was treated with 4.65 g of triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-2-oxindole as a reddish-brown solid.

5-Methoxycarbonyl-2-oxindole 5-iodo-2-oxindole (17 g) was refluxed with 2 g of palladium diacetate, 18.2 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on silica gel (30% ethyl acetate in hexane). The fractions containing product were concentrated and allowed to stand. The precipitated product was collected by vacuum filtration to give 0.8 g (7%) of the title compound as an off-white solid.

4-Carboxy-2-oxindole

A solution of trimethylsilyldiazomethane, in hexane (2M) was added dropwise to a solution of 2.01 g of 2-chloro-3-carboxy-nitrobenzene in 20 mL methanol at room temperature until no further gas evolution occurred. The excess trimethylsilyldiazo-methane was quenched with acetic acid. The reaction mixture was dried by rotary pump and the residue was further dried in a vacuum oven overnight. The product (2-chloro-3-methoxycarbonyl-nitrobenzene) was pure enough for the following reaction.

Dimethyl malonate (6.0 mL) was added to an ice-cold suspension of 2.1 g of sodium hydride in 15 mL of DMSO. The reaction mixture was then stirred at 100° C. for 1.0 h and then cooled to room temperature. 2-Chloro-3-methoxycarbonyl-nitrobenzene (2.15 g) was added to the above mixture in one portion and the mixture was heated to 100° C. for 1.5 h. The reaction mixture was then cooled to room temperature and poured into ice water, acidified to pH 5, and extracted with ethyl acetate. The organic layer was washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 mL of 6 N hydrochloric acid overnight. The mixture was concentrated to dryness and refluxed for 2 hours with 1.1 g of tin(II) chloride in 20 mL of ethanol. The mixture was filtered through Celite, concentrated and chromatographed on silica gel (ethyl acetate-:hexane:acetic acid) to give 0.65 g (37% yield) of 4-carboxy-2-oxindole as a white solid.

5-Carboxy-2-oxindole

2-Oxindole (6.7 g) was added to a stirred suspension of 23 g of aluminum chloride in 30 mL of dichloroethane in an ice bath. Chloroacetyl chloride (11.3 g) was slowly added and hydrogen chloride gas was evolved. After ten minutes of stirring, the reaction was warmed at 40 to 50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 93 g of 5-chloroacetyl-2-oxindole was stirred in 90 mL pyridine at 80 to 90° C. for 3 hours then cooled to room temperature. The precipitate was collected by vacuum filtration and washed with 20 mL ethanol. The solid was dissolved in 90 mL 2.5N sodium hydroxide and stirred at 70 to 80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

5-Carboxyethyl-2-oxindole

5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

5-Iodo-4-methyl-2-oxindole

To 2 g of 4-methyl-2-oxindole in 40 mL of glacial acetic acid in an ice bath was added 3.67 g N-iodosuccinimide. The mixture was stirred for 1 hour, diluted with 100 mL 50% acetic acid in water and filtered. The resulting white solid was dried under high vacuum to give 3.27 g (88% yield) of the title compound as an off white solid.

5-Chloro-4-methyl-2-oxindole

A suspension of 3.0 g of 4-methyl-2-oxindole was stirred in 50 mL of acetonitrile at room temperature while 3.3 g of N-chlorosuccinimide was added in portions. Trifluoroacetic acid (1 mL) was then added. The suspension was stirred at room temperature for 3 days during which time solid was always present. The white solid was collected by vacuum filtration, washed with a small amount of cold acetone and dried overnight in a vacuum oven at 40° C. to give 2.5 g (68%) of 5-chloro-4-methyl-2-oxindole.

5-Butyl-2-oxindole

Triethylsilane (1.3 g) was added to 1 g 4-butanoyl-1-oxindole in 20 mL of trifluoroacetic acid at room temperature and the solution stirred for 3 hours. The reaction was poured into ice water to give a red oil which solidified after standing. The solid was collected by vacuum filtration, washed with water and hexane and dried to give 1.7 g (91% yield) of the title compound as an off-white solid.

5-Ethyl-2-oxindole

To 5-Acetyl-2-oxindole (2 g) in 15 mL of trifluoroacetic acid in an ice bath was slowly added 1.8 g of triethylsilane; the reaction was then stirred at room temperature for 5 hours. One mL of triethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.

5-(Morpholin-4-ethyl)-2-oxindole

5-Chloroethyl-2-oxindole (2.3 g), 1.2 mL of morpholine and 1.2 ml, of diisopropylethylamine were heated overnight at 100° C. in 10 mL of dimethylsulfoxide. The mixture was cooled, poured into water and extracted with ethyl acetate. The organic layer was washed with brine, dried and evaporated. The residue was chromatographed on silica gel (5% methanol in chloroform) to give 0.9 g (31%) of the title compound as a white solid.

5-(4-Methoxycarbonylbenzamido)-2-oxindole

A mixture of 82.0 mg 5-amino-2-oxindole and 131.0 mg 4-methoxycarbonylbenzoyl chloride in pyridine was stirred at room temperature for 3 hr and poured into ice water. The precipitate was filtered, washed with water and dried in a vacuum oven to give 138.0 mg of 5-(4-methoxycarbonylbemzamido)-2-oxindole (81% yield).

5-(4-Carboxybenzamido)-2-oxindole 5-(4-Methoxycarbonylbenzamido)-2-oxindole (0.9 g) and 0.4 g of sodium hydroxide in 25 mL of methanol were refluxed for 3 hours. The mixture was concentrated, water added, and the mixture acidified with 6N hydrochloric acid. The precipitate was collected by vacuum filtration to give 0.75 g (87%) of the title compound as a white solid.

5-Methoxy-2-oxindole

Chloral hydrate (9.6 g) was dissolved in 200 mL of water containing 83 g of sodium sulfate. The solution was warmed to 60° C., a solution of 11.4 g of hydroxylamine hydrochloride in 50 mL of water was added and the mixture was held at 60° C. In a separate flask, 6.4 g of 4-anisidine and 4.3 mL of concentrated hydrochloric acid in 80 mL of water was warmed to 80° C. The first solution was added to the second and the mixture refluxed for 2 minutes after which it was cooled slowly to room temperature and then cooled in an ice bath. The tan precipitate was collected by vacuum filtration, washed with water and dried under vacuum to give 8.6 g (85% yield) of N-(2-hydroximino-acetyl)anisidine.

Concentrated sulfuric acid (45 mL) containing 5 mL of water was warmed to 60° C. and 8.6 g of N-(2-hydroximinoacetyl)anisidine was added in one portion. The stirred mixture was heated to 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid. 5-Methoxyisatin (5.0 g) and 30 mL of hydrazine hydrate were heated to reflux for 15 minutes. The reaction mixture was cooled to room temperature and 50 mL of water was added. The mixture was extracted 3 times with 25 mL of ethyl acetate each time, the organic layers combined, dried over anhydrous sodium sulfate and concentrated to give a yellow solid. The solid was stirred in ethyl acetate and 11 g of insoluble material was removed by vacuum filtration and saved. This material proved to be 2-hydrszinocmbonylmethyl-4-anisidine. The filtrate was concentrated and chromatographed on silica gel eluting with ethyl acetate:hexane (1:1) to give 0.7 g of 5-methoxy-2-oxindole as a yellow solid. The 11 g of 2-hydrazinocarbonylmethyl-4-anisidine was refluxed for 1 hour in 20 mL of 1N sodium hydroxide. The mixture was cooled, acidified to pH 2 with concentrated hydrochloric acid and extracted 3 times with 25 mL of ethyl acetate each time. The organic extracts were combined, washed with brine, dried over anhydrous sodium sulfate and concentrated to give 0.8 g of 5-methoxy-2-oxindole as a yellow solid. The combined yield was 1.5 g or 33%.

7-Azaozindole 3,3-Dibromo-7-azaoxindole (2.9 g) was dissolved in a mixture of 20 mL of acetic acid and 30 mL of acetonitrile. To the solution was added 6.5 g of zinc dust. The mixture was stirred for 2 hrs at room temperature. The solid was filtered from the mixture and the solvent evaporated. The residue was slurried with ethyl acetate. The ethyl acetate solution containing insoluble solid was passed through a short column of silica gel. The collected ethyl acetate solution was evaporated and the residue dried under vacuum to give 1.8 g (yield 91%) of 7-azaoxindole acetic acid salt.

5-Dimethylaminosulfonyl-2-oxindole

A suspension of 2.3 g 5-chlorosulphonyl-2-oxindole in 10 mL 2M dimethylamine in methanol was stirred at room temperature for 4 hours at which time a white solid formed. The precipitate was collected by vacuum filtration, washed with 5 mL of 1N sodium hydroxide and 5 mL of 1N hydrochloric acid and dried under vacuum at 40° C. overnight to give 19 g (79% yield) of 5-dimethylamino-sulfonyl-2-oxindole.

6-Phenyl-2-oxindole

Dimethyl malonate (10 mL) in 25 mL of dimethylsulfoxide was added dropwise to 3.5 g sodium hydride suspended in 25 mL dimethylsulfoxide and the mixture heated at 100° C. for 10 minutes. The mixture was cooled to room temperature and 4.7 g of 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give, as a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g of 3-nitrobiphenyl-4-acetic acid as a cream colored solid.

Iron powder (2.6 g) was added all at once to 4.5 g of 3-nitrobiphenyl-4-acetic acid in 40 mL of acetic acid. The mixture was refluxed for 2 hours, concentrated to dryness and taken up in ethyl acetate. The solids were removed by filtration and the filtrate washed twice with 1N hydrochloric acid and brine and dried over anhydrous sodium sulfate. The filtrate was concentrated to give 3.4 g (93% yield) of 6-phenyl-2-oxindole as a light brown solid.

6-(2-Methoxyphenyl)-2-oxindole

Tetrakis(triphenylphosphine)palladium (1 g) was added to a mixture of 5 g 2-methoxyphenylboronic acid, 6.6 g 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, then dried, and concentrated to give a dark green oil which solidified on standing, crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was heated at 100° C. for 15 minutes and cooled to room temperature. Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated sodium chloride solution and extracted twice with ethyl acetate. The extracts were combined, washed with saturated ammonium chloride, water and brine, dried over anhydrous sodium sulfate and concentrated to give crude dimethyl 2'-methoxy-3-nitrobiphenyl-4-malonate as a yellow oil.

Crude dimethyl 2'-methoxy-3-nitrobiphenyl-4-malonate was heated at 100° C. in 50 mL of 6 N hydrochloric acid for 24 hours and cooled. The precipitate was collected by filtration, washed with water and hexane, and dried to give 9.8 of 2'-methoxy-2-nitrobiphenyl-4acetic acid as a light tan solid.

Iron powder (5 g) was added in one portion of 9.8 g of 2'-methoxy-3-nitrobiphenyl-4-acetic acid in 50 mL of glacial acetic acid was heated to 100° C. for 3 hours. The reaction mixture was concentrated to dryness, sonicated in ethyl acetate and filtered to remove the insolubles. The filtrate was washed twice with 1N hydrochloric acid, water and then brine, dried over anhydrous sodium sulfate and concentrated. The residue was chromatographed on silica gel in ethyl acetate:hexane (1:2) to give 5.4 g of 6-(2-methoxyphenyl)-2-oxindole as a rose colored solid.

6-(3-Methoxyphenyl)-2-oxindole

Tetrakis(triphenylphosphine)palladium (0.8 g) was added to a mixture of 5 g 3-methoxyphenylboronic acid, 5 g 5-bromo-2-fluoro-nitrobenzoic and 11 mL of 2 M sodium carbonate solution in 100 mL of toluene. The mixture was refluxed for 2 hours, diluted with water and extracted with ethyl acetate. The ethyl acetate was washed with saturated sodium bicarbonate and brine and then dried and concentrated to give an oily solid. The solid was chromatographed on silica gel (ethyl acetate:hexane (1:6)) to give 4.3 g (77% yield) of 4-fluoro-3'-methoxy-3-nitrobiphenyl.

Dimethyl malonate (9.7 mL) was added dropwise to 2.0 g sodium hydride suspended in 50 mL dimethylsulfoxide. The mixture was heated to 100° C. for 35 minutes and cooled to room temperature. 4-Fluoro-2'-methoxy-3-nitrobiphenyl (4.2 g) in 50 mL dimethylsulfoxide was added and the mixture was heated at 100° C. for 1 hour. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude dimethyl 3'-methoxy-3-nitrobiphenyl-4-malonate was heated at 110° C. in 45 mL 6N hydrochloric acid for 4 days and then cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid (33:66:1) to give 3.0 g of 6-(3-methoxypheny)-2-oxindole as a pink solid.

6-(4-Methoxyphenyl)-2-oxindole

Tetrakis(triphenylphosphine)palladium (I g) was added to a mixture of 5 g of 4-methoxyphenylboronic acid, 6.6 g of 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, dried, and concentrated to give a brown oily solid. The solid was chromatographed on silica gel (5% ethyl acetate in hexane) to give crude 4-fluoro-4'-methoxy-3-nitrobiphenyl as a pale yellow solid.

Dimethyl malonate (10 mL) was added dropwise to 2.0 g of sodium hydride suspended in 60 mL of dimethylsulfoxide. The mixture was heated to 100° C. for 10 minutes and cooled to room temperature. Crude 4-fluoro-2'-methoxy-3-nitrobiphenyl (5.2 g) in 50 mL dimethylsulfoxide was added and the mixture was heated at 100° C. for 2 hours. The reaction mixture was cooled and quenched with 300 mL of saturated sodium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4malonate as a yellow oil.

Crude dimethyl 4'-methoxy-3-nitro-biphenyl-4-malonate was heated at 100° C. in 60 mL of 6N hydrochloric acid for 15 hours and cooled. The precipitate was collected by filtration, washed with water and hexane, and dried to give 7.2 g of crude 4'-methoxy-3nitrobiphenyl-4-acetic acid as a light tan solid.

Iron powder (3.6 g) was added in one portion to 7.2 g of 4'-methoxy-3-nitrobiphenyl-4-acetic acid in 50 mL of glacial acetic acid and heated at 100° C. overnight. The reaction mixture was concentrated to dryness, sonicated in ethyl acetate and filtered to remove the insolubles. The filtrate was washed twice with 1N hydrochloric acid and brine, dried over anhydrous sodium sulfate and concentrated to give 2.7 g of 6-(4-methoxyphenyl)-2-oxindole as a rose colored solid.

6-(3-Ethoxyphenyl)-2-oxindole

Tetrakis(triphenylphosphine)palladium (0.8 g) was added to a mixture of 4.2 g of 3-ethoxyphenylboronic acid, 5.0 g of 5-bromo-2-fluoronitrobenzene and 22 mL of 2 M sodium carbonate solution in 50 mL of toluene and 50 mL of ethanol. The mixture was refluxed for 2 hours, concentrated, water was added and the mixture was extracted twice with ethyl acetate. The ethyl acetate layer was washed with water and brine, then dried, and concentrated. The residue was chromatographed on silica gel (5% ethyl acetate in hexane) to give 5.3 g (90% yield) of crude 4-fluoro-3'-ethoxy-3-nitrobiphenyl as a yellow oil.

Dimethyl malonate (11.4 mL) was added dropwise to 4.0 g sodium hydride suspended in 20 mL dimethylsulfoxide. The mixture was heated to 100° C. for 10 minutes and then cooled to room temperature. Crude 4-fluoro-3'-ethoxy-3-nitrobiphenyl (5.3 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with water and brine and then dried over anhydrous sodium sulfate and concentrated to give crude dimethyl-3'-ethoxy-3-nitrobiphenyl-4-malonate as a yellow oil.

Crude dimethyl 3'-ethoxy-3-nitrobiphenyl-4-malonate was heated at 100° C. in 60 mL of 6N hydrochloric acid for 4 days and then cooled. The precipitate was collected by filtration, washed with water and hexane, and dried to give 4.7 g of crude 3'-ethoxy-3-nitrobiphenyl-4-acetic acid as a light tan solid.

Iron powder (2.4 g) was added in one portion to 4.6 g of 3'-ethoxy-3-nitrobiphenyl-4-acetic acid in 40 mL of glacial acetic acid and refluxed for 2 hours. The reaction mixture was concentrated to dryness, treated repeatedly with ethyl acetate and filtered to remove the insolubles. The filtrate was washed twice with 1N hydrochloric acid and brine and then dried over anhydrous sodium sulfate and concentrated to give 3.5 g (91% yield) of 6-(3-ethoxyphenyl)-2-oxindole as a light brown solid.

6-Bromo-2-oxindole

Dimethyl malonate (13 mL) was added dropwise to 2.7 g sodium hydride suspended in 20 mL dimethylsulfoxide. The mixture was heated to 100° C. for 10 minutes and then cooled to room temperature. 5-Bromo-2-fluoronitrobenzene (5.0 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate as a pale yellow oil.

Crude dimethyl 4-bromo-2-nitrophenylmalonate was heated at 110° C. in 40 mL of 6N hydrochloric acid for 24 hours and then cooled. The precipitate was collected by filtration, washed with water and dried to give 5.3 g (89% yield) of 4-bromo-2-nitro-phenylacetic acid as an off white solid.

4-Bromo-2-nitrophenylacetic acid (0.26 g), 0.26 g zinc powder and 3 mL 50% sulfuric acid in 5 mL of ethanol were heated at 100° C. overnight. The reaction mixture was filtered, diluted with a little acetic acid, concentrated to remove ethanol, diluted with water and extracted twice with ethyl acetate. The combined extracts were washed with brine, dried over anhydrous sodium sulfate and concentrated to give 0.19 g (90% yield) of 6-bromo-2-oxindole as a yellow solid.

5-Acetyl-2-oxindole

2-Oxindole (3 g) was suspended in 1,2-dichloroethane and 3.2 mL acetyl chloride were slowly added. The resulting suspension was heated to 50° C. for 5 hours, cooled, and poured into water. The resulting precipitate was collected by vacuum filtration, washed copiously with water and dried under vacuum to give 2.9 g (73% yield) of the title compound as a brown solid.

5-Butanoyl-2-oxindole

To 15 g aluminum chloride suspended in 30 mL 1,2-dichloro-ethane in an ice bath was added 7.5 g of 2-oxindole and then 12 g of butanoyl chloride. The resulting suspension was heated to 50° C. overnight. The mixture was poured into ice water and extracted 3 times with ethyl acetate. The combined ethyl acetate layers were washed with brine, dried over sodium sulfate, and concentrated to dryness to give a brown solid. The solid was chromatographed on silica gel (50% ethyl acetate in hexane) to give 3 g (25%) of the title compound as a yellow solid.

5-Cyanoethyl-2-oxindole

Potassium cyanide (2.0 g) was added to 15 mL of dimethyl-sulfoxide and heated to 90° C. 5-Chloroethyl-2-oxindole (3.0 g) dissolved in 5 mL dimethyl sulfoxide was added slowly with stirring, and the reaction heated to 150° C. for 2 hours. The mixture was cooled, poured into ice water and the precipitate collected by vacuum filtration, washed with water, dried and then chromatographed on silica gel (5% methanol in chloroform) to give 1.2 g (42% yield) of the title compound.

6-Morpholin-4-yl)-2-oxindole

6-Amino-2-oxindole (2.2 g), 4.0 g, 2,2'-dibromoethyl ether and 7.9 g sodium carbonate were refluxed in 20 ml ethanol overnight, concentrated and diluted with 50 ml of water. The mixture was extracted three times with 50 ml of ethyl acetate and the organic extracts combined, washed with 20 ml of brine, dried over anhydrous sodium sulfate and concentrated to dryness. The solid was chromatographed on a column of silica gel (ethyl acetate:hexane (1:1) containing 0.7% acetic acid) to give 1.2 g (37% yield) of the title compound as a beige solid.

6-(3-Trifluoroacetylphenyl)-2-oxindole

3-Aminophenylboronic acid (3.9 g), 5 g 5-bromo-2-fluoro-nitrobenzene, 0.8 g tetrakis(triphenylphosphine) palladium and 23 mL of 2 M sodium bicarbonate solution in 50 mL of toluene were refluxed under nitrogen for 2.5 hours. The reaction mixture was poured into 200 mL of ice water and the mixture extracted three times with 50 mL of ethyl acetate. The combined organic layers were washed with 50 mL of water and 20 mL of brine, dried over anhydrous sodium sulfate and concentrated to give 9.7 g (92% yield) of 2-fluoro-5-(3-aminophenyl)nitrobenzene as a dark brown oil.

Trifluoroacetic anhydride (5.4 mL) was slowly added to a stirred solution of 9.7 g 2-fluoro-5-(3-aminophenyl)-nitrobenzene and 5.3 mL of triethylamine in 50 mL of dichloromethane at 0° C. and the mixture was stirred for an additional 20 minutes. The mixture was concentrated and the residue chromatographed on a column of silica gel (10% ethyl acetate in hexane) to give 8.6 g (65% yield) of 2-fluoro-5-(3trifluoroacetamidophenyl)nitrobenzene as a pale orange oil which solidified on standing.

Dimethyl malonate (9.6 mL) was added dropwise to a stirred suspension of 3.2 g of 60% sodium hydride in mineral oil in 40 mL anhydrous dimethylsulfoxide under nitrogen. The mixture was stirred for 10 minutes and 2-fluoro-5-(3-trifluoroacetamido-phenyl)nitrobenzene in 20 mL dimethylsulfoxide was added. The resulting dark red mixture was heated to 100° C. for 2 hours. The reaction was quenched by pouring into 100 mL of saturated ammonium chloride solution and extracted twice with 50 mL of ethyl acetate. The organic phase was washed with 50 mL each of saturated ammonium chloride solution, water, and brine, dried over anhydrous sodium sulfate and concentrated to a yellow oil. The oil was chromatographed on a column of silica gel (ethyl acetate:hexane (1:4)) to give 4.4 g (50% yield) of dimethyl 2-[2-nitro-4-(3-trifluoroacetamido-phenyl)phenyl]-malonate as a pale yellow solid.

Dimethyl 2-[2-nitro-4-(3-trifluoroacetamidophenyl)-phenyl]malonate (4.4 g) was refluxed overnight in 50 mL 6N hydrochloric acid. The reaction mixture was cooled to room temperature and the solids were collected by vacuum filtration, washed with water, and dried under vacuum to give 2.7 g (73% yield) of 2-[2-nitro-4-(3-trifluoroacetamidophenyl)phenyl] acetic acid.

2-[2-Nitro-4-(3-trifluoroacetamidophenyl)phenyl]acetic acid (100 mg) and 50 mg iron powder in 3 mL acetic acid was heated at 100° C. for 2 hours. The reaction mixture was concentrated and the residue sonicated in 5 mL ethyl acetate. The insoluble solids were removed by vacuum filtration and the filtrate washed with 1N hydrochloric acid, water and brine, dried over anhydrous sodium sulfate and concentrated to give 10 mg (14% yield) of the title compound as a rose-colored solid.

5-Isopropylaminosulfonyl-2-oxindole

To a 100 mL flask charged with 27 mL chlorosulfonic acid was slowly added 13.3 g 2-oxindole. The reaction temperature was maintained below 30° C. during the addition. The reaction mixture was stirred at room temperature for 1.5 hour, heated to 68° C. for 1 hour, cooled, and poured into water. The precipitate which formed was filtered, washed with water and dried in a vacuum oven to give 11.0 g (50%) of 5-chlorosulfonyl-2-oxindole which was used without further purification.

A suspension of 3 g 5-chlorosulfonyl-2-oxindole, 1.15 g isopropylamine and 1.2 mL of pyridine in 50 mL of dichloromethane was stirred at room temperature for 4 hours during which time a white solid formed. The solid was collected by vacuum filtration, slurry-washed with hot ethanol, cooled, collected by vacuum filtration and dried under vacuum at 40° C. overnight to give 1.5 g (45%) of 5-isopropylaminosulfonyl-2-oxindole.

$^1$H NMR (360 MHz, DMSO-d6) δ 10.69 (s, br, 1H, NH), 7.63 (dd, J=2 and 8 Hz, 1H), 7.59 (d, J=2 Hz, 1H), 7.32 (d, J=7 Hz, 1H, NH—SO$_2$—), 6.93 (d, J=8 Hz, 1H), 3.57 (s, 2H), 3.14–3.23 (m, 1H, CH—(CH$_3$)$_2$), 0.94 (d, J=7 Hz, 6H, 2×CH$_3$).

5-Phenylaminosulfonyl-2-oxindole

A suspension of 5-chlorosulfonyl-2-oxindole (1.62 g, 7 mmol), aniline (0.782 mL, 8.4 mmol) and pyridine (1 mL) in dichloromethane (20 ml) was stirred at room temperature for 4 hours. The reaction mixture was diluted with ethyl acetate (300 mL) and acidified with 1N hydrochloric acid (16 mL). The organic layer was washed with sodium bicarbonate and brine, dried and concentrated. The residue was washed with ethanol (3 mL) and then chromatographed on silica gel eluting with methanol/dichloromethane 1:9 to give of 5-phenylaminosulfonyl-2-oxindole.

$^1$HNMR (360 MHz, DMSO-d6) δ 10.71 (s, br, 1H, NH), 10.10 (s, br, 1H, NH), 7.57–7.61 (m, 2H), 7.17–7.22 (m, 2H), 7.06–7.09 (m, 2H), 6.97–7.0 (m, 1H), 6.88 (d, J=8.4 Hz, 1H), 3.52 (s, 2H).

2-Oxo-2,3-dihydro-1H-indole-5-sulfonic acid pyridin-3-ylamide

A solution of 5-chlorosulfonyl-2-oxindole (3 g) and 3-aminopyridine (1.46 g) in pyridine (15 mL) was stirred at room temperature overnight at which time a brown solid was present. The solid was filtered, washed with ethanol and dried under vacuum to yield 1.4 g (38%) of 2-oxo-2,3-dihydro-1H-indole-5-sulfonic acid pyridin-3-ylamide.

$^1$HNMR (360 MHz, DMSO-d6) δ 10.74 (s, 1H, NH), 10.39 (s, 1H, SO$_2$NH), 8.27–8.28 (d, 1H), 8.21–8.23 (m, 1H), 7.59–7.62 (m, 2H), 7.44–7.68 (m, 1H ), 7.24–7.28 (m, 1H), 6.69–6.71 (d, 1H), 3.54 (s, 2H).

MS m/z (APCI+) 290.2.

5-Phenyloxindole

5-Bromo-2-oxindole (5 g, 23.5 mmol) was dissolved in 110 mL toluene and 110 mL ethanol with stirring and a little heat. Tetrakis(triphenylphosphine)palladium(0) (1.9 g, 1.6 mmol) was added followed by 40 mL (80 mmol) 2M aqueous sodium carbonate. To this mixture was added benzene boronic acid (3.7 g, 30.6 mmol) and the mixture was heated in a 100° C. oil bath for 12 hours. The reaction was cooled, diluted with ethyl acetate (500 mL), washed with saturated sodium bicarbonate (200 mL), water (200 mL), 1N HCl (200 mL) and brine (200 mL). The organic layer was dried over magnesium sulfate and concentrated to afford a brown solid. Trituration with dichloromethane afforded 3.8 g (77%) of 5-phenyl-2-oxindole as a tan solid.

$^1$H NMR (360 MHz, DMSO-d6) δ 10.4 (br s, 1H, NH), 7.57 (dd, J=1.8 and 7.2 Hz, 1H), 7.5 to 7.35 (m, 5H), 7.29 (m, 1H), 6.89 (d, J=8.2 Hz, 1H), 3.51 (s, 2H, CH$_2$CO).

MS m/z 209 [M$^+$].

In similar fashion, the following oxindoles can be prepared:

6-(3,5-Dichlorophenyl)-1,3-dihydroindol-2-one $^1$H NMR (360 MHz, DMSO-d6) δ 10.46 (br, 1H, NH), 7.64 (d, J=1.8 Hz, 2H), 7.57 (m, 1H), 7.27 (m, 2H), 7.05 (d, J=1.1 Hz, 1H), 3.5 (s, 2H).

MS-EI m/z 277/279 [M]$^+$.

6-(4-Butylphenyl)-1,3-dihydroindol-2-one $^1$H NMR (360 MHz, DMSO-d6) δ 10.39 (s, 1H, NH), 7.49 (d, J=8.0 Hz, 2H), 7.25 (d, J=8 Hz, 3H), 7.17 (dd, J=1.5 and 7.8 Hz, 1H), 6.99 (d, J=1.5 Hz, 1H), 3.48 (s, 2H, CH$_2$CO), 2.60 (t, J=7.5 Hz, 2 Hz, CH$_2$CH$_3$), 1.57 (m, 2H, CH$_2$), 1.32 (m, 2H, CH$_2$), 0.9 (t, J=7.5 Hz, 3H, CH$_3$).

6-(5-Isopropyl-2-methoxyphenyl)-1,3-dihydroindol-2-one $^1$H NMR (360 MHz, DMSO-d6) δ 10.29 (br s, 1H, NH), 7.16–7.21 (m, 2H), 7.08 (d, J=2.4 Hz, 1H), 6.97–7.01 (m, 2H), 6.89 (d, J=0.8 Hz, 1H), 3.71 (s, 3H, OCH$_3$), 3.47 (s, 2H, CH$_2$OH), 2.86 (m, 1H, CH(CH$_3$)$_2$), 1.19 (d, J=6.8 Hz, 6H, CH(CH$_3$)$_2$).

MS-EI m/z 281 [M]$^+$.

6-(4-Ethylphenyl)-1,3-dihydroindol-2-one $^1$H NMR (360 MHz, DMSO-d6) δ 10.39 (br s, 1H, NH), 7.50 (d, J=8.2 Hz, 2H), 7.28 (d, J=8.2 Hz, 2H), 7.25 (d, J=7.5 Hz, 1H), 7.17 (dd, J=1.6 & 7.5 Hz, 1H), 6.99 (d, J=1.6 Hz, 1H), 3.48 (s, 2H, CH$_2$CO), 2.63 (q, J=7.6 Hz, 2H, CH$_2$CH$_3$), 1.20 (t, J=7.6 Hz, 3H, CH$_2$CH$_3$).

MS-EI m/z 237 [M]$^+$.

6-(3-Isopropylphenyl)-1,3-dihydroindol-2-one $^1$H NMR (360 MHz, DMSO-d6) δ 10.37 (br s, 1H, NH), 7.43 (m, 1H), 7.35–7.39 (m, 1H), 7.17–7.27 (m, 3H), 7.01 (d, J=1.8 Hz, 1H), 3.49 (s, 2H, CH$_2$CO), 2.95 (m, 1H, CH(CH$_3$)$_2$), 1.24 (d, J=6.8 Hz, 6H, CH(CH$_3$)$_2$).

MS-EI m/z 251 [M]$^+$.

6-(2,4-Dimethoxyphenyl)-1,3-dihydroindol-2-one $^1$H NMR (360 MHz, DMSO-d6) δ 10.28 (br s, 1H, NH), 7.17 (m, 2H), 6.93 (dd, J=1.6 & 7.6 Hz, 1H), 6.86 (d, J=1.6 Hz, 1H), 6.63 (d, J=2.4 Hz, 1H), 6.58 (dd, J=2.4 & 8.5 Hz, 1H), 3.79 (s, 3H, OCH$_3$), 3.74 (s, 3H, OCH$_3$), 3.45 (s, 2H, CH$_2$CO).

MS-EI m/z 269 [M]$^+$.

6-Pyridin-3-yl-1,3-dihydroindol-2-one $^1$H NMR (360 MHz, DMSO-d6) δ 10.51 (s, 1H, NM), 8.81 (d, J=2.5 Hz, 1H), 8.55 (dd, J=1.8 and 5.7 Hz, 1H), 8 (m, 1H), 7.45 (dd, J=5.7 and 9.3 Hz, 1H), 7.3 (m, 2H), 7.05 (s, 1H), 3.51 (s, 2H, CH$_2$CO).

MS m/z 210 [M]$^+$.

2-Oxo-2,3-dihydro-1H-indole-4-carboxylic acid (3-chloro-4-ethoxyphenyl)amide

To a solution of 4-carboxy-2-oxindole (200 mg, 1.13 mmol) and 3-chloro-4-methoxyphenylamine (178 mg, 1.13 mmol) in dimethylformamide (15 mL) at room temperature was added benzotriazol-1-yloxytris(dimethylamino)phosphonium hexafluorophosphate (BOP reagent, 997 mg, 2.26 mmol) followed by 4-dimethylaminopyridine (206 mg, 1.69 mmol). The mixture was stirred at room temperature for 72 hours. The reaction was then diluted with ethyl acetate (300 mL), washed with saturated sodium bicarbonate (100 mL), water, 2N hydrochloric acid (100 mL), water (3×200 mL) and brine. It was then dried over magnesium sulfate and concentrated. The residue was triturated with ethyl acetate to give 2-oxo-2,3-dihydro-1H-iondole-4-carboxylic acid (3-chloro-4-methoxyphenyl)-amide as a pink solid.

$^1$HNMR (360 MHz, DMSO-d6) δ 10.50 (s, br, 1H, NH), 10.12 (s, br, 1H, NH), 7.9 (s, J=2.5 Hz, 1H), 7.62 (dd, J=2.5 & 9 Hz, 1H), 7.38 (d, J=7.6 Hz, 1H), 7.32 (t, J=7.6 Hz, 1H), 7.13 (d, J=9 Hz, 1H), 6.98 (d, J=7.6 Hz, 1H), 3.83 (s, 3H, OCH$_3$), 3.69 (s, 2H, CH$_2$).

MS-EI m/z 316 [M]$^+$.

D. Aldehydes

5-Formyl-2,4-dimethyl-1H-pyrrole-3-carboxylic acid t-Butyl-3-oxobutyrate (158 g, 1 mol) was dissolved in 200 mL of acetic acid in a 500 mL 3-neck round bottom flask equipped with a thermometer, addition funnel and mechanical stirring. The mixture was cooled in an ice bath to about 10° C. Sodium nitrite (69 g, 1 mol) was added over 75 minutes keeping the temperature under 15° C. The cold bath was removed and the mixture stirred for 30 minutes and then allowed to stand for 3.5 hours to give t-butyl-2-hydroxyimino-3-oxobutyrate.

Ethyl-3-oxobutyrate (130 g, 1 mol) was dissolved in 400 mL of acetic acid in a 2 L 3-neck round bottom flask equipped with a thermometer, an addition funnel, mechanical stirring and placed in an oil bath. Zinc dust (50 g, 0.76 mmol) was added and the mixture heated to 60° C. with stirring. The t-butyl-2-hydroxyimino-3-oxobutyrate solution prepared above was slowly added, the temperature of the reaction mixture being maintained at about 65° C. More zinc dust was then added (4×50 g, 3.06 mol) with the last portion added after all the t-butyl ester had been added. At the end of the additions the temperature was 64° C. The temperature was increased to 70–75° C., stirred for one hour and then poured into 5 L of water. The gray floating precipitate was collected by vacuum filtration and washed with 2 L of water to give 354 g of wet crude product. The crude product was dissolved in 1 L of hot methanol and filtered hot to remove zinc. The filtrate was cooled upon which a precipitate formed. The precipitate that was collected by vacuum filtration and dried to give 118 g of product. The filtrate was put in the refrigerator overnight uon which additional product precipitated. A total of 173.2 g of 3,5-dimethyl-1H-pyrrole-2,4-dicarboxylic acid 2-tert-butyl ester 4-ethyl ester was obtained.

3,5-Dimethyl-1H-pyrrole-2,4-dicarboxylic acid 2-tert-butyl ester 4-ethyl ester (80.1 g, 0.3 mol) and 400 mL trifluoroacetic acid were stirred for 5 minutes in a 2 L 3-neck round bottom flask equipped with mechanical stirring and warmed to 40° C. in an oil bath. The mixture was then cooled to −5° C. and triethyl orthoformate (67.0 g, 0.45 mol) was added all at once. The temperature increased to 15° C. The mixture was stirred for about 1 minute, removed from the cold bath and then stirred for 1 hour. The trifluoroacetic acid was removed by rotary evaporation and the residue put in the refrigerator where it solidified. The solid was dissolved by warming and poured into 500 g of ice. The mixture was extracted with 800 mL of dichloromethane to give a red solution and a brown precipitate, both of which were saved. The precipitate was isolated and washed with 150 mL of saturated sodium bicarbonate solution. The dichloromethane phase was also washed with 150 mL of sodium bicarbonate. The dichloromethane solution was then washed 3 more times with 100 mL of water. The dichloromethane solution was evaporated to dryness. The dark residue which remained was recrystallized twice from ethyl acetate containing Darco carbon black to give golden yellow needles. The brown precipitate was recrystallized from 350 mL ethyl acetate likewise containing Darco to give a yellow-red solid. All the recrystallized solids were combined and recrystallized from 500 mL of ethanol to give 37.4 g (63.9%) of 5-formyl-2,4-dimethyl-1H-pyrrole-3-carboxylic acid ethyl ester as yellow needles (mp 165.6–166.3° C., lit. 163–164° C.). The residue obtained after evaporatiing of the ethyl acetate and ethanol mother liquors were combined and recrystallized from 500 mL of ethanol to give a second crop (10.1 g) or product as dirty yellow needles.

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH 3. The solid which formed was collected by filtration, washed with water and dried in a vacuum oven overnight to give 1.6 g (93%) of 5-formyl-2,4-dimethyl-1H-pyrrole-3-carboxylic acid.

$^1$H NMR (300 MHz, DMSO-d6)δ: 12.09 (s, br, 2N, NH & COOH), 9.59 (s, 1H, CHO), 2.44 (s, 3H, CH$_3$), 2.40 (s, 3H, CH$_3$).

5-Formyl-2,4-diomethyl-1H-pyrrole-3-carboxylic acid (2-dimethylaminoethyl) amide To a mixture of 5-formyl-2,4-dimethyl-1H-pyrrole-3-carboxylic acid (1.67 g, 10 mmol) in dimethylformamide (10 mL) was added benzotriazol-1-yloxytris (dimethylamino)-phosphonium hexafluorophosphate (BOP reagent, 6 g, 13.5 mmol) followed by 3 mL diisopropyl-ethylamine. After stirring for 5 minutes, 1 mL of N,N-dimethylethylendiamine was added and the mixture was stirred at room temperature for 24 hours. To the reaction mixture was added 25 mL of 1N sodium hydroxide and 25 mL of brine. After stirring for 30 minutes, the reaction mixture was poured into water (100 mL) and extracted (3×200 mL) with 10% of methanol in dichloromethane. The organic layers were combined, dried over anhydrous sodium sulfate and evaporated using a rotary evaporator. The residue which remained was purified by chromatography (silica gel column, 5%–10% methanol in dichloromethane) to give 1 g (42%) of 5-formyl-2,4-dimethyl-1H-pyrrole-3-carboxylic acid (2-dimethylamino-ethyl)-amide.

$^1$H NMR (360 MHz, DMSO-d6) δ: 11.77 (s, 1H, NH), 9.53 (s, 1H, CHO), 7.34 (t, J=5.6 Hz, 1H, CONH), 3.27 (m, 2H, CONCH$_2$CH$_2$), 2.37 (t, J=6.8 Hz, 2H, CONCH$_2$CH$_2$), 2.35 (s, 3H, CH$_3$), 2.3 (s, 3H, CH$_3$), 2.17 (s, 6H, 2×CH$_3$). MS m/z 238.3 [M+1]$^+$.

3,5-dimethyl-4-(4-methyl-piperazine-1-carbonyl)-1H-pyrrole-2-carboxaldehyde

To a mixture of 5-formyl-2,4-dimethyl-1H-pyrrole-3-carboxylic acid (1.67 g, 10 mmol) in dimethylformamide (10 mL) was added benzotriazol-1-yloxytris (dimethylamino)-phosphonium hexafluorophosphate (BOP reagent, 6 g, 13.5 mmol) followed by 3 mL of diisopropy-lethylamine. After stirring for 5 minutes, 2 mL of 1-methylpiperazine was added and the mixture was stirred at room temperature for 24 hours. To the reaction was then added 25 mL of 1N sodium hydroxide and 25 mL of brine. After stirring for 30 minutes, the reaction mixture was poured into water (100 mL) and extracted (3×200 mL) with 10% of methanol in dichloromethane. The organic layers were combined, dried over anhydrous sodium sulfate and evaporated on a rotary evaporator. The residue which remained was purified by chromatography(silica gel column, 5%–10% of methanol in dichloromethane) to give 1 g (40%) of 3,5-dimethyl-4-(4-methyl-piperazine-1-carbonyl)-1H-pyrrole-2-carboxaldehyde.

$^1$H NMR (360 MHz, DMSO-d6)δ: 11.82 (s, 1H, NH), 9.50 (s, 1H, CHO), 3.14 (br m, 4H, 2×CH$_2$), 2.29 (br m, 4H, 2×CH$_2$), 2.19 (s, 3H, CH$_3$), 2.17 (s, 3H, CH$_3$), 2.14 (s, 3H, CH$_3$).

MS EI 249 [M]$^+$.

E. Synthesis of pyrrole substituted 2-indolinones

EXAMPLE 1 (FROM TABLE 1)

4-Methyl-5-(2-oxo-1,2-dihydroindol-3-ylidenemethyl)-1H-pyrrole-2-carboxylic Acid 4-Methyl-2-pyrrolecarboxylic acid ethyl ester (commercially available) was formylated using method A to give (73%) of 5-formyl-4-methyl-2-pyrrolecarboxylic acid ethyl ester. It was then hydrolysed using method B to give 5-formyl-4-methyl-1H-pyrrole-2-carboxylic acid (58%).

Oxindole (133 mg, 1 mmol) was condensed with 5-formyl-4-methyl-1H-pyrrole-2-carboxylic acid (153 mg) using method D to give 268 mg (100%) of the title compound as an orange-red solid.

$^1$HNMR (360 MHz, DMSO-d6) δ 13.84 (s, br, 1H, NH), 12.84 (s, br, 1H, COOH), 10.98 (s, br, 1H, NH), 7.82 (d, J=7.5 Hz, 1H), 7.67 (s, 1H, H-vinyl), 7.18 (t, J=7.5 Hz, 1H), 7.01 (t, J=7.5 Hz, 1H), 6.88 (d, J=7.5 Hz, 1H), 6.71 (d, J=2.2 Hz, 1H), 2.32 (s, 3H, CH$_3$).

MS (negative mode) 266.8 [M−1]$^+$.

EXAMPLE 2 (FROM TABLE 1)

4-Methyl-5-(1-methyl-2-oxo-1,2-dihydroindol-3-ylidenemethyl)-1H-pyrrole-2-carboxylic Acid 1-Methyl-1,3-dihydroindol-2-one (147 mg, 1 mmol) was condensed with 5-formyl-4-methyl-1H-pyrrole-2-carboxylic acid (153 mg) using method D to give 250 mg (86%) of the title compound.

$^1$HNMR (360 MHz, DMSO-d6) δ 13.82 (s, br, 1H, NH), 12.88 (s, br, 1H, 7.83 (d, J=7.5 Hz, 1H), 7.65 (s, 1H, H-vinyl), 7.26 (t, J=7.5 Hz, 1H), 7.02–7.09 (m, 2H), 6.70 (d, J=2.2 Hz, 1H), 2.32 (s, 3H, CH$_3$).

MS m/z 283.0 [M+1]$^+$.

EXAMPLE 3 (FROM TABLE 1)

4-Methyl-5-(2-oxo-1,2-dihydroindol-3-ylidenemethyl)-1H-pyrrole-2-carboxylic Acid Methyl Ester Oxoindole (105 mg, 0.79 mmol) was condensed with 5-formyl-4-methyl-1H-pyrrole-2-carboxylic acid methyl ester (110 mg, 0.67 mmol) using method E to give 153.2 mg (81%) of the title compound.

$^1$HNMR (360 MHz, DMSO-d6) δ 13.98 (s, br, 1H, NH), 10.97 (s, br, 1H, NH), 7.82 (d, J=7.6 Hz, 1H), 7.67 (s, 1H, H-vinyl), 7.2 (dt, J=1.2 & 7.7 Hz, 1H), 7.01 (dt, J=1.2, 7.7 Hz, 1H), 6.90 (d, J=7.6 Hz, 1H), 6.77 (d, J=2 Hz, 1H).

MS (ES) m/z 283 [M$^+$+1].

EXAMPLE 4 (FROM TABLE 1)

5-(5-Chloro-2-oxo-1,2-dihydroindol-3-ylidenemethyl)-4-methyl-1H-pyrrole-2-carboxylic Acid Ethyl Ester 5-Chloro-1,3-dihydroindol-2-one (2.22 g, 13.2 mmol) was condensed with 5-formyl-4-methyl-1H-pyrrole-2-carboxylic acid ethyl ester (2.43 g) using method E to give 4.1 g (94%) of the title compound as an orange solid.

$^1$HNMR (360 MHz, DMSO-d6) δ 13.95 (s, br, 1H, NH), 7.98 (d, J=2.2 Hz, 1H, H-4), 7.78 (s, 1H, H-vinyl), 7.18 (dd, J=2.2 & 8.3 Hz, 1H, H-6), 6.87 (d, J=8.3 Hz, 1H, H-7), 7.34 (d, J=1.8 Hz, 1H,H-3'), 4.27 (q, J=7.2 Hz, 2H,. OCH$_2$CH$_3$), 2.33 (s, 3H, CH$_3$), 1.29 (t, J=7.2 Hz, 3H, OCH$_2$CH$_3$).

MS-EI m/z 330 [M$^+$].

EXAMPLE 5 (FROM TABLE 1)

5-(5-Chloro-2-oxo-1,2-dihydroindol-3-ylidenemethyl)-4-methyl-1H-pyrrole-2-carboxylic Acid A mixture of 5-(5-chloro-2-oxo-1,2-dihydroindol-3-ylidenemethyl)-4-methyl-1H-pyrrole-2-carboxylic acid ethyl ester (1.3 g, 4 mmol) and potassium hydroxide in methanol (25 mL) and ethanol (25 mL) was heated to reflux for overnight. Insoluble materials were removed by filtration and the mixture was neutralized with 6N hydrochloric acid to give 0.876 g (70%) of the title compound.

$^1$H NMR (360 MHz, DMSO-d6) δ 13.80 (s, br, 1H, NH), 12.90 (s, br, 1H, COOH), 11.06 (s, br, 1H, NH), 8.02 (d, J=1.8 Hz, 1H, H-4), 7.81 (s, 1H, H-vinyl), 7.20 (dd, J=1.8 & 8.3 Hz, 1H, H-6), 6.89 (d, J=8.3 Hz, 1H, H-7), 6.72 (d, J=1.8 Hz, 1H, H-3'), 2.35 (s, 3H, CH$_3$).

MS-EI m/z 302 [M$^+$].

EXAMPLE 6 (FROM TABLE 1)

5-(5-Bromo-2-oxo-1,2-dihydroindol-3-ylidenemethyl)-4-methyl-1H-pyrrole-2-carboxylic Acid (3-pyrrolidin-1-yl-propyl)amide 5-Bromo-1,3-dihydroindol-2-one (0.16 g, 0.76 mmol) was condensed with 5-formyl-4-methyl-1H-pyrrole-2-carboxylic acid (3-pyrolidin-1-ylpropyl)amide (0.2 g, prepared by method C) to give 60 mg (17%) of the title compound as an orange solid.

$^1$H NMR (300 MHz, DMSO-d6) δ 13.61 (s, br, 1H, NH), 11.02 (s, br, 1H, NH), 8.42 (t, J=5.8 Hz, 1H, CONHCH$_2$), 8.12 (d, J=1.8 Hz, 1H, H-4), 7.78 (s, 1H, H-vinyl), 7.30 (dd, J=1.8 & 8.4 Hz, 1H, H-6), 6.82 (d, J=8.4 Hz, 1H, H-7), 6.77 (d, J=2.4 Hz, 1H, H-3'), 3.22–3.31 (m, 2H, CH$_2$), 2.38–2.43 (m, 6H, 3×CH$_2$), 2.35 (s, 3H, CH$_3$), 1.62–1.71 (m, 6H, 3×CH$_2$).

MS-EI m/z 456 and 458 [M$^+$−1 and M$^+$+2].

EXAMPLE 7 (FROM TABLE 1)

5-Bromo-2-oxo-1,2-dihydroindol-3-ylidenemethyl)-4-methyl-1H-pyrrole-2-carboxylic Acid (3-diethylamino-propyl)amide 5-Bromo-1,3-dihydroindol-2-one (0.16 g, 0.75 mmol) was condensed with 5-formyl-4-methyl-1H-pyrrole-2-carboxylic acid (3-diethylaminopropyl)amide (0.2 g, prepared by method C) to give 30 mg (8%) of the title compound as an orange solid.

$^1$HNMR (300 MHz, DMSO-d6) δ 13.61 (s, br, 1H, NH), 11.02 (s, br, 1H), NH), 8.40 (m, 1H, CONHCH$_2$), 8.12 (d, J=1.5 Hz, 1H, H-4), 7.78 (s, 1H, H-vinyl), 7.30 (dd, J=1.5 & 8.2 Hz, 1H, H-6), 6.82 (d, J=8.2 Hz, 1H, H-7), 6.78 (d, J=2.4 Hz, 1H, H-3'), 3.23 (m, 2H,, CH$_2$), 2.38–2.45 (m, 6H, CH$_2$ & N(CH$_2$CH$_3$)$_2$), 2.35 (s, 3H, CH$_3$), 1.61 (m, 2H, CH$_2$), 0.93 (t, J=7.1 Hz, 6H, N(CH$_2$CH$_3$)$_2$).

MS-EI m/z 458 and 460 [M$^+$−1 and M$^+$+2].

EXAMPLE 8 (FROM TABLE 1)

5-(5-Bromo-2-oxo-1,2-dihydroindol-3-ylidenemethyl)-1H-pyrrole-2-carboxylic Acid (2-diethylaminoethyl)amide 5-Bromo-1,3-dihydroindol-2-one (212 mg, 1 mmol) was condensed with 5-formyl-1H-pyrrole-2-carboxylic acid (2-diethylaminoethyl)amide (prepared from ethyl pyrrole-2-carboxylate by method A, B and then C) to give 162 mg (38%) of the title compound.

$^1$H NMR (300 MHz, DMSO-d6) δ 13.53 (s, br, 1H, NH), 11.06 (s, br, 1H, NH), 8.37 (t, 1H, CONHCH$_2$), 7.89 (m, 2H), 7.32 (dd, J=2.0 Hz, 1H), 6.96 (s, 1H), 6.80–6.84 (m, 2H), 3.3 (m, 2H, CH$_2$), 2.45–2.55 (m, 6H, N(CH$_2$CH$_3$)$_2$ & CH$_2$), 0.95 (t, J=7.2 Hz, 6H, N(CH$_2$CH$_3$)$_2$).

MS-EI m/z 430 and 432 [M$^+$–1 M$^+$+1].

EXAMPLE 9 (FROM TABLE 1)

5-(2-Oxo-6-phenyl-1,2-dihydroindol-3-ylidenemethyl)-1H-pyrrole-2-carboxylic Acid (2-diethylaminoethyl)amide 6-Phenyl-1,3-dihydroindol-2-one (209 mg, 1 mmol) was condensed with 5-formyl-1H-pyrrole-2-carboxylic acid (2-diethylaminoethyl)amide to give 182 mg (42%) of the title compound.

$^1$H NMR (300 MHz, DMSO-d6) δ 13.56 (s, br, 1H, NH), 11.06 (s, br, 1H, NH), 8.36 (t, 1H, CONHCH$_2$), 7.77 (s, 1H, H-vinyl), 7.73 (d, J=7.8 Hz, 1H), 7.64 (d, J=7.2 Hz, 2H), 7.46 (m, 2H), 7.32 (m, 2H), 7.11 (s, 1H), 6.96 (m, 1H), 6.80 (m, 1H), 3.31–3.32 (m, 2H, CH$_2$), 2.46–2.53 (m, 6H, N(CH$_2$CH$_3$)$_2$ & CH$_2$), 0.96 (t, J=6.9 Hz, 6H, N(CH$_2$CH$_3$)$_2$).

MS-EI m/z 428 [M$^+$].

EXAMPLE 10 (FROM TABLE 1)

5-(5-Bromo-2-oxo-1,2-dihydroindol-3-ylidenemethyl)-1H-pyrrole-2-carboxylic Acid (2-diethylaminoethyl)-methyl-amide 5-Bromo-1,3-dihydroindol-2-one (212 mg, 1 mmol) was condensed with 5-formyl-1H-pyrrole-2-carboxylic acid (2-diethylaminoethyl)methylamino to give 246 mg (55%) of the title compound.

$^1$H NMR (360 MHz, DMSO-d6) δ 13.54 (s, br, 1H, NH), 11.06 (s, br, 1H, NH), 7.90 (m, 2H), 7.33 (dd, J=1.8 & 8.4 Hz, 1H), 6.82–6.85 (m, 3H), 3.55 (s, br, 2H, CH$_2$), 3.25 (s, br, 3H, NCH$_3$), 2.57 (t, J=6.5 Hz, 2H, CH$_2$), 2.45 (m, 4H, N(CH$_2$CH$_3$)$_2$), 0.91 (m, 6H, N(CH$_2$CH$_3$)$_2$).

MS-EI m/z 444 and 446 [M$^+$–1 and M$^+$+1].

EXAMPLE 11 (FROM TABLE 1)

5-(2-Oxo-6-phenyl-1,2-dihydroindol-3-ylidenemethyl)-1H-pyrrole-2-carboxylic Acid (2-diethylaminoethyl)methylamide 6-Phenyl-1,3-dihydroindol-2-one (209 mg, 1 mmol) was condensed with 5-formyl-1H-pyrrole-2-carboxylic acid (2-diethylaminoethyl)methylamide to give 277 mg (63%) of the title compound.

$^1$H NMR (360 MHz, DMSO-d6) δ 13.58 (s, br, 1H, NH), 11.04 (s, br, 1H, NH), 7.78 (s,1H, H-vinyl), 7.73 (d, J=7.8 Hz, 1H), 7.64 (d, J=7.5 Hz, 2 Hz), 7.46 (m, 2H), 7.33–7.36 (m, 2H), 7.11 (s, 1H), 6.84 (m, 1H), 6.78 (m, 1H), 3.55 (s, br, 2H, CH$_2$), 3.25 (s, br, 3H, NCH$_3$), 2.58 (t, 2H, CH$_2$), 2.44 (m, 4H, N(CH$_2$CH$_3$)$_2$), 0.92 (m, 6H, N(CH$_2$CH$_3$)$_2$).

EXAMPLE 12 (FROM TABLE 1)

3-Methyl-5-(2-oxo-1,2-dihydroindol-3-ylidenemethyl)-1H-pyrrole-2-carboxylic acid (3-diethylaminopropyl)amide Oxindole (66.5 mg, 0.5 mmol) was condensed with 5-formyl-3-methyl-1H-pyrrole-2-carboxylic acid (3-diethylaminopropyl)amide (prepared from 3-formyl-3-methyl-1H-pyrrole-2-carboxylic acid ethyl ester by method B then C) to give 39 mg (21%) of the title compound.

$^1$H NMR (300 MHz, DMSO-d6) δ 13.34 (s, br, 1H, NH), 10.88 (s, br, 1H, NH), 7.62–7.67 (m, 3H), 7.17 (m, 1H), 6.99 (m, 1H), 6.87 (d, J=7.6 Hz, 1H), 6.63 (d, J=1 Hz, 1H), 3.26–3.32 (m, 2H, CH$_2$), 2.41–2.48 (m, 6H, CH$_2$ & N(CH$_2$CH$_3$)$_2$), 2.29 (s, 3H, CH$_3$), 1.63 (m, 2H, CH$_2$), 0.93 (t, J=7.2 Hz, 6H, N(CH$_2$CH$_3$)$_2$).

MS-EI m/z 380 [M$^+$].

EXAMPLE 13 (FROM TABLE 1)

5-(5-Bromo-2-oxo-1,2-dihydroindol-3-ylidenemethyl)-3-methyl-1H-pyrrole-2-carboxylic Acid (3-diethylamino-propyl)amide 5-Bromo-1,3-dihydroindol-2-one (106 mg, 0.5 mmol) was condensed with 5-formyl-3-methyl-1H-pyrrole-2-carboxylic acid (3-diethylaminopropyl)amide to give 35 mg (15%) of the title compound.

$^1$H NMR (300 MHz, DMSO-d6) δ 13.35 (s, br, 1H, NH), 11.00 (s, br, 1H, NH), 7.89 (d, J=1.9 Hz, 1H, H-4), 7.80 (s, 1H, H-vinyl), 7.74 (t, J=5.3 Hz, 1H, CONHCH$_2$), 7.31 (dd, J=1.9 & 8.4 Hz, 1H, H-6), 6.83 (d, J=8.4 Hz, 1H, H-7), 6.63 (s, 1H, H-3'), 3.26 (m, 2H, CH$_2$), 2.41–2.48 (m, 6H, CH$_2$ & N(CH$_2$CH$_3$)$_2$), 2.29 (s, 3H, CH$_3$), 1.63 (m, 2H, CH$_2$), 0.93 (t, J=7.1 Hz, 6H, N(CH$_2$CH$_3$)$_2$).

MS-EI m/z 458 and 460 [M$^+$–1 and M$^+$+1].

EXAMPLE 14 (FROM TABLE 1)

3-Methyl-5-(2-oxo-6-phenyl-1,2-dihydroindol-3-ylidenemethyl)-1H-pyrrole-2-carboxylic Acid (3-diethylaminopropyl)amide 6-Phenyl-1,3-dihydroindol-2-one (105 mg, 0.5 mmol) was condensed with 5-formyl-3-methyl-1H-pyrrole-2-carboxylic acid (3-diethylaminopropyl)amide to give 67.8 (30%) of the title compound.

$^1$H NMR (300 MHz, DMSO-d6) δ 13.37 (s, br, 1H, NH), 11.02 (s, br, 1H, NH), 7.23–7.73 (m, 11H), 3.29 (m, 2H, CH$_2$), 2.41–2.48 (m, 6H, CH$_2$ & N(CH$_2$CH$_3$)$_2$), 2.29 (s, 3H, CH$_3$), 1.64 (m, 2H, CH$_2$), 0.94 (t, J=7.0 Hz, 6H, N(CH$_2$-CH$_3$)$_2$).

MS-EI m/z 456 [M$^+$].

EXAMPLE 15 (FROM TABLE 1)

5-(5-Methoxy-2-oxo-1,2-dihydroindol-3-ylidenemethyl)-3-methyl-1H-pyrrole-2-carboxylic Acid (3-dimethylamino-propyl)amide 5-Methoxy-1,3-dihydroindol-2-one (82.5 mg, 0.5 mmol) was condensed with 5-formyl-3-methyl-1H-pyrrole-2-carboxylic acid (3-diethylaminopropyl)amide to give 80 mg (39%) of the title compound.

$^1$H NMR (300 MHz, DMSO-d6) δ 13.45 (s, br, 1H, NH), 10.70 (s, br, 1H, NH), 7.68–7.70 (m, 2H), 7.32 (d, J=1.8 Hz, 1H), 6.72–6.79 (m, 2H), 6.60 (s, 1H), 3.73 (s, 3H, OCH$_3$), 3.28 (m, 2H, CH$_2$), 2.41–2.48 (m, 6H, CH$_2$ & N(CH$_2$CH$_3$)$_2$), 2.29 (s, 3H, CH$_3$), 1.63 (m, 2H, CH$_2$), 0.93 (t, J=7.0 Hz, 6H, N(CH$_2$CH$_3$)$_2$).
MS m/z 410 [M$^+$].

EXAMPLE 16 (FROM TABLE 1)

5-(6-Methoxy-2-oxo-1,2-dihydroindol-3-ylidenemethyl)-3-methyl-1H-pyrrole-2-carboxylic Acid (3-diethylamino-propyl)amide 6-Methoxy-1,3-dihydroindol-2-one (82.5 mg, 0.5 mmol) was condensed with 5-formyl-3-methyl-1H-pyrrole-2-carboxylic acid (3-diethylaminopropyl)amide to give 63 mg (31%) of the title compound.

$^1$H NMR (300 MHz, DMSO-d6) δ 13.22 (s, br, 1H, NH), 10.86 (s, br, 1H, NH), 7.39–7.63 and 6.37–6.55 (m, 6H), 3.73 (s, 3H, OCH$_3$), 3.3 ((m, 2H, CH$_2$), 2.45 (m, 6H, CH$_2$ & N(CH$_2$CH$_3$)$_2$), 2.28 (s, 3H, CH$_3$), 1.63 (m, 2H, CH$_2$), 0.93 (m, 6H, N(CH$_2$CH$_3$)$_2$).
MS m/z 410 [M$^+$].

EXAMPLE 17 (FROM TABLE 1)

3-(5-Bromo-2-oxo-1,2-dihydroindol-3-ylidenemethyl)-4,5,6,7-tetrahydro-2H-isoindole-1-carboxylic Acid (2-diethylamino-ethyl)amide 4,5,6,7-Tetrahydro-2H-isoindole-1-carboxylic acid ethyl ester (May, Donald A.; Lash, Timothy D.; *J. Org. Chem.*, 1992, 57:18, 4820–4828) was formylated using method A then B to give 3-formyl-4,5,6,7-tetrahydro-2H-isoindole-1-carboxylic acid.

5-Bromo-1,3-dihydroindol-2-one (1.43 g, 6.8 mmol) was condensed with 3-formyl-4,5,6,7-tetrahydro-2H-isoindole-1-carboxylic acid (2-diethylaminoethyl)amide (1.97 g) to give 2.2 g (67%) of the title compound as a yellow-orange solid.

$^1$H NMR (360 MHz, DMSO-d6) δ 13.47 (s, 1H, NH), 11.0 (s, 1H, NH), 8.0 (d, 1H, NH), 7.70 (s, 1H, CH), 7.28 (dd, J=2.1 and 8.2 Hz, 1H, ArH), 7.16 (m, 1H, ArH), 6.8 (d, J=8.3 Hz, 1H, ArH), 3.3 (s, 2H, CONH), 2.5 (m, 6H, 3×NCH$_2$), 2.78 (br m, 2H, pyrrole CH$_2$), 2.72 (br m, 2H pyrroleCH$_2$), 1.7 (br m, 4H, N(CH$_2$CH$_3$)$_2$), 1.74 (br s, 4H, CH$_2$CH$_2$CH$_2$CH$_2$), 0.96 (t, J=7.4 Hz, 6H, N(CH$_2$CH$_3$)$_2$).
MS-EI m/z 484 and 486 [M$^+$−1 and M$^+$+1].

EXAMPLE 18 (FROM TABLE 1)

3-(5-Bromo-2-oxo-1,2-dihydroindol-3-ylidenemethyl)-4,5,6,7-tetrahydro-2H-isoindole-1-carboxylic Acid (3-diethylamino-propyl)amide 5-Bromo-1,3-dihydroindol-2-one (20 mg, 0.1 mmol) was condensed with 3-formyl-4,5,6,7-tetrahydro-2H-isoindole-1-carboxylic acid (3-diethylaminopropyl)amide (30 mg) to give 33 mg (46%) of the title compound as an orange solid.

$^1$H NMR (360 MHz, DMSO-d6) δ 10.9 (s, 1H, NH), 8.0 (m, 1H, NH), 7.68 (m, 1H, ArH), 7.4 (m, 1H, ArH), 7.29 (d, J=1.9 and 8.5 Hz, 1H, ArH), 6.8 (d, J=8 Hz, 1 H, ArH), 2.7 (br m, 4H, 2×NCH$_2$), 2.4 (m, 8H, 4×NCH$_2$), 1.7 (br m, 4H), N(CH$_2$CH$_3$)$_2$), 1.6 (br m, 2H, CH$_2$CH$_2$CH$_2$), 0.93 (t, J=7.4 Hz, 6H, N(CH$_2$CH$_3$)$_2$).
MS-EI m/z 499 and 501 [M$^+$ and M$^+$+2].

EXAMPLE 19 (FROM TABLE 1)

3-(5-Bromo-2-oxo-1,2-dihydroindol-3-ylidenemethyl)-4,5,6,7-tetrahydro-2H-isoindole-1-carboxylic Acid (3-pyrrolidin-1-ylpropyl)amide 5-Bromo-1,3-dihydroindol-2-one (80 mg, 0.4 mmol) was condensed with 3-formyl-4,5,6,7-tetrahydro-2H-isoindole-1-carboxylic acid (3-pyrrolidin-1-ylpropyl)amide (120 mg) to give 43 mg (22%) of the title compound as a tan-orange solid.

$^1$H NMR (360 MHz, DMSO-d6) δ 13.4 (s, 1H, NH), 10.9 (s, 1H, NH), 8.0 (m, 1H, NH), 7.69 (m, 1H, ArH), 7.49 (m, 1H, ArH), 7.28 (d, J=1.7 and 7.8 Hz, 1H, ArH), 6.8 (d, J=8 Hz, 1H, ArH), 3.3 (br m, 2H, 2×NCH$_2$), 2.8 (m, 4H, 2×pyrroleCH$_2$), 2.5 (br m, 4H, N(CH$_2$CH$_3$)$_2$), 1.6 (br m, 8H, 2×pyrroleCH$_2$CH$_2$, CH$_2$CH$_2$CH$_2$ and CONHCH$_2$).
MS-EI m/z 497 and 499 [M$^+$ and M$^+$+2].

EXAMPLE 20 (FROM TABLE 1)

3-(2-Oxo-6-pyridin-3-yl-1,2-dihydroindol-3-ylidenemethyl)-4,5,6,7-tetrahydro-2H-isoindole-1-carboxylic Acid (2-diethylaminoethyl)amide 6-Pyridin-3-yl-1,3-dihydroindol-2-one (60 mg, 0.4 mmol) was condensed with 3-formyl-4,5,6,7-tetrahydro-2H-isoindole-1-carboxylic acid (2-diethylaminoethyl)amide (80 mg) to give 50 mg (38%) of the title compound as a reddish solid.

$^1$H NMR (360 MHz, DMSO-d6) δ 13.4 (s, 1H, NH), 11 (s, 1H, NH), 8.9 (d, 1H, NH), 8.7 (dd, 1H, ArH), 8.1 (dd, 1H, ArH), 7.9 (d, 1H, ArH), 7.6 (s, 1H, CH), 7.5 (dd, 1H, ArH), 7.3 (dd, 1H, ArH),7.1 (m, 2H, ArH), 3.35 (m, 2H, CONHCH$_2$), 2.8 (m, 4H, 2×pyrroleCH$_2$), 2.5 (br m, 6H, N(CH$_2$CH$_3$)$_2$ and NCH$_2$), 1.75 (br s, 4H, 2×pyrroleCH$_2$CH$_2$), 0.9 (t, 6H, N(CH$_2$CH$_3$)$_2$).
MS-EI m/z 484 [M$^+$].

EXAMPLE 21 (FROM TABLE 1)

4-Benzoyl-5-(5-bromo-2-oxo-1,2-dihydroindol-3-ylidenemethyl)-3-methyl-1H-pyrrole-2-carboxylic Acid (3-diethylaminopropyl)amide To a mixture of benzoyl chloride (1 equiv.) and aluminum chloride (1 equiv.) in dichloromethane at 0° C. was added ethyl 3,5-dimethyl-2-pyrrolecarboxylate (1 equiv.). The mixture was stirred at 80° C. for 4 hr. The mixture was then extracted with ethyl acetate (EtOAc) and H$_2$O. The combined organic extracts were washed with saturated sodium bicarbonate and brine, dried and concentrated to give (51%) of 4-benzoyl-3,5-dimethyl-1H-pyrrole-2-carboxylic acid.

A mixture of 4-benzoyl-3,5-dimethyl-1H-pyrrole-2-carboxylic acid ethyl ester (4.13 g, 15.2 mmol) and ceric ammonium nitrate (33 g, 4equiv.) in 50 mL of tetrahydrofuran (THF):acetic acid (HOAc):H$_2$O 1:1:1 was refluxed overnight. The reaction mixture was then cooled, extracted with EtOAc and then basified to pH 9 with sodium carbonate. The organic layer was then washed with brine, dried (MgSO$_4$) and concentrated followed by colum chromatography to give 3.25 g (75%) of 4-benzoyl-5-formyl-3-methyl-1H-pyrrole-2-carboxylic acid ethyl ester as a yellow solid.

5-Bromo-1,3-dihydro-indol-2-one was condensed with 4-benzoyl-5-formyl-3-methyl-1H-pyrrole-2-carboxylic acid using method D to give 4-benzoyl-5-(5-bromo-2-oxo-1,2-dihydro-indol-3-ylidenemethyl)-3-methyl-1H-pyrrole-2-carboxylic acid.

The above carboxylic acid was then coupled with N,N-diethyl-1,3-propanediamine using method C to give the title compound.

$^1$H NMR (360 MHz, DMSO-d6) δ 7.96 (m, 1H, CONHCH$_2$), 7.76 (d, J=7.0 Hz, 2H), 7.68 (t, 1H), 7.56 (m, 2H), 7.40 (s, 2H), 7.33 (dd, J=1.6 & 8.3 Hz, 1H, H-6), 6.84 (d, J=8.3 Hz, 1H, H-7), 3.33 (m, 2H, CH$_2$), 2.42–2.46 (m, 6H, 3×CH$_2$), 2.10 (s, 3H, CH$_3$), 1.65 (m, 2H, CH$_2$), 0.94 (t, J=7.0 Hz, 6H, N(CH$_2$CH$_3$)$_2$).

MS Electron Impact m/z 564 [M$^+$1].

EXAMPLE 22 (FROM TABLE 1)

4-Benzoyl-5-(5-bromo-2-oxo-1,2-dihydroindol-3-ylidenemethyl)-3-methyl-1H-pyrrole-2-carboxylic Acid (3-morpholin-4-ylpropyl)amide $^1$H NMR (360 MHz, DMSO-d6) δ 14.10 (s, 1H, NH), 11.14 (br s, 1H, NH), 7.92 (m, 1H, CONHCH$_2$), 7.75 (m, 2H), 7.69 (t, 1H), 7.56 (m, 2H), 7.42 (m, 2H), 7.33 (dd, J=1.9 & 8.3 Hz, 1H, H-6), 6.85 (d, J=8.3 Hz, 1H, H-7), 3.56 (m, 4H, 2×CH$_2$), 3.33 (m, 2H, CH$_2$), 2.35 (m, 6H, 3×CH$_2$), 2.10 (s, 3H, CH$_3$), 1.70 (m, 2H), CH$_2$).

EXAMPLE 23 (FROM TABLE 1)

4-Benzoyl-3-methyl-5-(2-oxo-1,2-dihydroindol-3-ylidenemethyl)-1H-pyrrole-2-carboxylic Acid (3-pyrrolidin-1-ylpropyl)amide $^1$H NMR (300 MHz, DMSO-d6) δ 14.18 (s, 1H, NH), 11.14 (br s, 1H, NH), 8.01 (m, 1H, CONHCH$_2$), 7.74 (m, 1H), 7.67 (m, 1H), 7.55 (m, 1H), 7.32 (s, 1H, H-vinyl), 7.17 (m, 1H), 6.92 (m, 1H), 3.36 (m, 2H, CH$_2$), 2.44 (m, 6 H, 3×CH$_2$), 2.11 (s, 3H, CH$_3$), 1.65–1.75 (m, 6H, 3×CH$_2$).

MS Electron Impact m/z 482 [M$^+$].

EXAMPLE 24 (FROM TABLE 1)

4-Benzoyl-5-(5-bromo-2-oxo-1,2-dihydroindol-3-ylidenemethyl)-3-methyl-1H-pyrrole-2-carboxylic Acid (3-pyrrolidin-1-ylpropyl)amide $^1$H NMR (360 MHz, DMSO-d6) δ 14.01 (s, 1H, NH), 11.18 (br s, 1H, NH), 7.98 (m, 1H, CONHCH$_2$), 7.75 (m, 2H), 7.68 (m, 1H), 7.55 (m, 2H), 7.40 (m, 2H), 7.33 (dd, J=2.0 & 8.2 Hz, 1H, H-6), 6.84 (d, J=8.2 Hz, 1H, H-7), 3.34 (m, 2H, CH$_2$), 2.42–2.47 (m, 6H, 3×CH$_2$), 2.09 (s, 3H, CH$_3$), 1.70 (m, 2H, CH$_2$), 1.64 (m, 4H, 2×CH$_2$).

EXAMPLE 25 (FROM TABLE 1)

4-Benzoyl-3-methyl-5-(2-oxo-6-phenyl-1,2-dihydroindol-3-ylidenemethyl)-1H-pyrrole-2-carboxylic Acid (3-pyrrolidin-1-ylpropyl)amide $^1$H NMR (300 MHz, DMSO-d6) δ 14.15 (s, 1H, NH), 11.16 (br s, 1H, NH), 7.98 (m, 1H, CONHCH$_2$), 7.77 (d, J=7.7 Hz, 2H), 7.69 (m, 1H), 7.53–7.63 (m, 4H), 7.44 (m, 2H), 7.33–7.37 (m, 2H), 7.24 (s, 2H), 7.12 (s, 1H), 3.36 (m, 2H, CH$_2$), 2.43–2.48 (m, 6 H, 3×CH$_2$), 2.12 (s, 3H, CH$_3$), 1.74 (m, 2H, CH$_2$), 1.69 (m, 4H, 2×CH$_2$).

MS Electron Impact m/z 558 [M$^+$].

EXAMPLE 26 (FROM TABLE 1)

4-Benzoyl-5-(6-methoxy-2-oxo-1,2-dihydroindol-3-ylidenemethyl)-3-methyl-1H-pyrrole-2-carboxylic Acid (3-pyrrolidin-1-ylpropyl)amide $^1$H NMR (300 MHz, DMSO-d6) δ 13.99 (s, 1H, NH), 11.05 (br s, 1H, NH), 7.93 (m, 1H, CONHCH$_2$), 7.72 (m, 2H), 7.64 (m, 1H), 7.54 (m, 2H), 7.15 (s, 1H, H-vinyl), 7.04 (d, J=8.4 Hz, 1H, H-4), 6.51 (dd, J=2.3 & 8.4 Hz, 1H, H-5), 6.44 (d, J=2.3 Hz, 1H, H-7), 3.74 (s, 3H, OCH$_3$), 3.35 (m, 2H, CH$_2$), 2.42–2.46 (m, 6 H, 3×CH$_2$), 2.10 (s, 3H, CH$_3$), 1.72 (m, 2H, CH$_2$), 1.65 (m, 4H, 2×CH$_2$).
MS Electron Impact m/z 512 [M$^+$].

EXAMPLE 27 (FROM TABLE 1)

4-Benzoyl-5-(5-methoxy-2-oxo-1,2-dihydroindol-3-ylidenemethyl)-3-methyl-1H-pyrrole-2-carboxylic Acid (3-pyrrolidin-1-ylpropyl)amide $^1$H NMR (360 MHz, DMSO-d6) δ 14.24 (s, 1H, NH), 10.90 (br s, 1H, NH), 7.97 (m, 1H, CONHCH$_2$), 7.75 (d, J=7.2 Hz, 2H), 7.69 (m, 1H), 7.56 (m, 2H), 7.24 (s, 1H, H-vinyl), 6.79 (m, 2H), 6.66 (m, 1H), 3.67 (s, 3H, OCH$_3$), 3.34 (m, 2H, CH$_2$), 2.43–2.48 (m, 6 H, 3×CH$_2$), 2.14 (s, 3H, CH$_3$), 1.71 (m, 2H, CH$_2$), 1.66 (m, 4H, 2×CH$_2$).

MS Electron Impact m/z 512 [M$^+$].

EXAMPLE 28 (FROM TABLE 1)

4-Benzoyl-5-(5-fluoro-2-oxo-1,2-dihydroindol-3-ylidenemethyl)-3-methyl-1H-pyrrole-2-carboxylic Acid (3-pyrrolidin-1-ylpropyl)amide $^1$H NMR (300 MHz, DMSO-d6) δ 14.20 (s, 1H, NH), 11.14 (br s, 1H, NH), 8.03 (m, 1H, CONHCH$_2$), 7.75 (m, 2H), 7.68 (m, 1H), 7.55 (m, 2H), 7.38 (s, 1H, H-vinyl), 7.08 (m, 1H), 7.01 (m, 1H), 6.87 (m, 1H), 3.34 (m, 2H, CH$_2$), 2.42–2.48 (m, 6 H, 3×CH$_2$), 2.09 (s, 3H, CH$_3$), 1.70 (m, 2H, CH$_2$), 1.65 (m, 4H, 2×CH$_2$).

MS Electron Impact m/z 500 [M$^+$].

EXAMPLE 29c (FROM TABLE 1)

4-Acetyl-5-(5-bromo-2-oxo-1,2-dihydroindol-3-ylidenemethyl)-3-methyl-1H-pyrrole-2-carboxylic Acid (3-diethylaminopropyl)amide 5-Bromo-1,3-dihydro-indol-2-one was condensed with 4-acetyl-5-formyl-3-methyl-1H-pyrrole-2-carboxylic acid (3-diethylaminopropyl)amide (prepared from 4-acetyl-5-formyl-3-methyl-1H-pyrrole-2-carboxylic acid ethyl ester by method B then C) to give the title compound.

$^1$H NMR (300 MHz, DMSO-d6) δ 14.19 (s, 1H, NH), 11.19 (br s, 1H, NH), 8.15 (m, 1H, CONHCH$_2$), 8.11 (s, 1H, H-vinyl), 7.72 (d, J=1.8 Hz, 1H, H-4), 7.38 (dd, J=1.8 & 8.2 Hz, 1H, H-6), 6.87 (d, J=8.2 Hz, 1H, H-7), 3.27 (m, 2H, CH$_2$), 2.57 (s, 3H, CH$_3$CO), 2.46 (m, 9 H, CH$_3$ & 3×CH$_2$), 1.64 (m, 2H, CH$_2$), 0.93 (t, J=7.1 Hz, 6H, N(CH$_2$CH$_3$)$_2$).

EXAMPLE 30 (FROM TABLE 1)

4-Acetyl-5-(5-bromo-2-oxo-1,2-dihydroindol-3-ylidenemethyl)-3-methyl-1H-pyrrole-2-carboxylic Acid (3-pyrrolidin-1-ylpropyl)amide $^1$H NMR (300 MHz, DMSO-d6) δ 8.14 (m, 1H, CONHCH$_2$), 8.10 (s, 1H, H-vinyl), 7.70 (d, 1H, H-4), 7.36 (dd, J=1.6 & 8.1 Hz, 1H, H-6), 6.85 (d, J=8.1 Hz, 1H, H-7), 3.32 (m, 2H, CH$_2$), 2.57 (s, 3H, CH$_3$CO), 2.44 (s, 3H, CH$_3$), 2.35–2.48 (m, 6H, 3×CH$_3$), 1.65–1.71 (m, 6H, 3×CH$_2$).

MS m/z 499 & 501 [M$^+$] * [M$^+$+2].

EXAMPLE 31 (FROM TABLE 1)

4-Acetyl-5-(5-bromo-2-oxo-1,2-dihydroindol-3-ylidenemethyl)-3-methyl-1H-pyrrole-2-carboxylic Acid (3-morpholin-4-ylpropyl)amide $^1$H NMR (300 MHz, DMSO-d6) δ 14.20 (s, 1H, NH), 11.26 (br s, 1H, NH), 8.09 (m, 2H, H-vinyl & CONHCH$_2$), 7.73 (d, J=1.5 Hz, 1H, H-4), 7.38 (dd, J=1.5 & 8.3 Hz, 1H, H-6), 6.87 (d, J=8.3 Hz, 1H, H-7), 3.55 (m, 4H, 2×CH$_2$), 3.26 (m, 2H, CH$_2$), 2.57 (s, 3H, CH$_3$CO), 2.44 (s, 3H, CH$_3$), 2.35 (m, 6H, 3×CH$_3$), 1.68 (m, 2H, CH$_2$).

MS-EI m/z 514 & 516 [M$^+$−1] & [M$^+$+1].

EXAMPLE 32 (FROM TABLE 1)

4-Acetyl-5-(5-bromo-2-oxo-1,2-dihydroindol-3-ylidenemethyl)-3-methyl-1H-pyrrole-2-carboxylic acid (3-hydroxypropyl)amide $^1$H NMR (360 MHz, DMSO-d6) δ 14.17 (s, 1H, NH), 11.25 (br s, 1H, NH), 8.10 (s, 1H, H-vinyl), 8.03 (m, 1H, CONHCH$_2$), 7.71 (br s, 1H, H-4), 7.37 (br d, J=8.4 Hz, 1H, H-6), 6.87 (d, J=8.4 Hz, 1H, H-7), 4.51 (br s, 1H, OH), 3.51 (br s, 2H, CH$_2$), 3.36 (m, 2H, CH$_2$), 2.57 (s, 3H, CH$_3$CO), 2.43 (s, 3H, CH$_3$), 1.70 (m, 2H, CH$_2$).

MS-EI m/z 445 & 447 [M$^+$−1] & [M$^+$+1].

EXAMPLE 34 (FROM TABLE 1)

4-Acetyl-5-(5-bromo-2-oxo-1,2-dihydroindol-3-ylidenemethyl)-3-methyl-1H-pyrrole-2-carboxylic Acid (2-morpholin-4-ylethyl)amide $^1$H NMR (360 MHz, DMSO-d6) δ 14.19 (s, 1H, NH), 11.14 (br s, 1 H, NH), 8.10 (s, 1H, H-vinyl), 7.84 (m, 1H, CONHCH$_2$), 7.71 (d, J=1.8 Hz, 1H, H-4), 7.38 (dd, J=1.8 & 8.2 Hz, 1H, H-6), 6.87 (d, J=8.2 Hz, 1H, H-7), 3.58 (m, 4H, 2×CH$_2$), 3.40 (m, 2H, CH$_2$), 2.57 (s, 3H, CH$_3$CO), 2.49 (m, 4H, 2×CH$_2$), 2.45 (m, CH$_3$ & CH$_2$).

MS-EI m/z 500 & 502 [M$^+$−1] & [M$^+$+1].

EXAMPLE 35 (FROM TABLE 1)

4-Acetyl-5-(5-bromo-2-oxo-1,2-dihydroindol-3-ylidenemethyl)-3-methyl-1H-pyrrole-2-carboxylic Acid (2-pyrrolidin-1-ylethyl)amide $^1$H NMR (360 MHz, DMSO-d6) δ 14.17 (s, 1H, NH), 11.23 (s, 1H,, NH), 8.11 (s, 1H, H-vinyl), 7.91 (m, 1H, CONHCH$_2$), 7.73 (d, J=1.9 Hz, 1H, H-4), 7.39 (dd, J=1.9 & 8.3 Hz, 1H, H-6), 6.88 (d, J=8.3 Hz, 1H, H-7), 3.40 (m, 2H, CH$_2$), 2.62 (m, 2H, CH$_2$), 2.57 (s, 3H, CH$_3$CO), 2.49 (m, 4H, 2×CH$_2$), 2.44 (s, 3H, CH$_3$), 1.69 (m, 4H, 2×CH$_2$).

EXAMPLE 36 (FROM TABLE 1)

4-Acetyl-5-(4-bromo-2-oxo-1,2dihydroindol-3-ylidenemethyl)-3-methyl-1H-pyrrole-2-carboxylic Acid [2-(4-hydroxyphenyl)ethyl]amide $^1$H NMR (300 MHz, DMSO-d6) δ 14.21 (s, 1H, NH), 11.18 (s, 1H, OH), 9.09 (s, 1H, NH), 8.06–8.10 (m, 2H), 7.73 (s, 1H), 7.38 (d, J=7.8 Hz, 1H), 7.04 (d, J=7.1 Hz, 2H), 6.88 (d, J=7.8 Hz, 1H), 6.67 (d, J=7.1 Hz, 2H), 3.42 (m, 2H, CH$_2$), 2.72 (m, 2H, CH$_2$), 2.56 (s, 3H, CH$_3$CO), 2.37 (s, 3H, CH$_3$).

MS-EI m/z 507 & 509 [M$^+$−1] & [M$^+$1].

EXAMPLE 37 (FROM TABLE 1)

5-Bromo-2-oxo-1,2-dihydroindol-3-ylidenemethyl)-2-isopropyl-4-phenyl-1H-pyrrole-3-carboxylic Acid (3-diethylaminopropyl)amide A mixture of 2-aminoacetophenone hydrochloride (1 equiv.), ethyl isobutylacetate (1.2 equiv.) and sodium acetate (2.4 equiv.) in H$_2$O was stirred at 100° C. for 18 hours and then cooled to room temperature. The aqueous layer was decanted off and the oil was dissolved in ethyl acetate. It was then washed with water and brine and then dried to give (93%) of 2-isopropyl-4-phenyl-1H-pyrrole-3-carboxylic acid ethyl ester as a red brown oil.

$^1$H NMR (300 MHz, DMSO-d6) δ 11.21 (s, br, 1H, NH), 7.14–7.27 (m, 5H), 6.70 (d, J=2.7 Hz, 1H), 4.02 (q, J=7.1 Hz, 2H, OCH$_2$CH$_3$), 3.65 (m, 1H, CH(CH$_3$)$_2$), 1.22 (d, J=7.5 Hz, 6H, CH(CH$_3$)$_2$), 1.04 (t, J=7.1 Hz, 3H, OCH$_2$CH$_3$).

MS-EI m/z 257 [M$^+$].

The above pyrrole was formylated using method A to give (41%) 5-formyl-2-isopropyl-4-phenyl-1H-pyrrole-3-carboxylic acid ethyl ester as a reddish solid.

$^1$H NMR (300 MHz, DMSO-d6) δ 12.35 (s, br, 1H, NH), 9.14 (s, 1H, CHO), 7.36 (s, 5H), 3.96 (q, J=7.1 Hz, 2H, OCH$_2$CH$_3$), 3.74 (m, 1H, CH(CH$_3$)$_2$), 1.29 (d, J=6.9 Hz, 6H, CH(CH$_3$)$_2$), 0.90 (t, J=7.1 Hz, 3H, OCH$_2$CH$_3$).

MS-EI m/z 285 [M$^+$].

The pyrrolecarboxylic acid ester was hydrolysed using method B to give (57%) of 5-formyl-2-isopropyl-4-phenyl-1H-pyrrole-3-carboxylic acid as a beige solid.

$^1$H NMR (300 MHz, DMSO-d6) δ 12.28 (s, br, 1H, COOH), 12.02 (s, br, 1H, NH), 9.10 (s, 1H, CHO), 7.35 (s, 5H), 3.81 (m, 1H, CH(CH$_3$)$_2$), 1.28 (d, J=6.9 Hz, 6H, CH(CH$_3$)$_2$).

MS-EI m/z 257 [M$^+$].

5-Bromo-1,3-dihydroindol-2-one (120 mg, 0.31 mmol) was condensed with 5-formyl-2-isopropyl-4-phenyl-1H-pyrrole-3-carboxylic acid (3-diethylaminopropyl)amide (prepared by method C) to give 120 mg (71%) of the title compound.

$^1$H NMR (300 MHz, DMSO-d6) δ 14.23 (s, br, 1H, NH), 11.08 (s, br, 1H, NH), 7.38–7.55 (m, 7H, Ar-H & CONHCH$_2$), 7.30 (s, 1H, H-vinyl), 7.26 (dd, J=1.8 & 7.8 Hz, 1H), 6.85 (d, J=8.7 Hz, 1H), 3.36 (m, 1H, CH(CH$_3$)$_2$), 3.07 (m, 2H, CH$_2$), 2.34 (q, J=7.1 Hz, 4H, N(CH$_2$CH$_3$)$_2$), 2.22 (t, J=6.9 Hz, 2H, CH$_2$), 1.40 (m, 2H, CH$_2$), 1.31 (d, J=6.9 Hz, 6H, CH(CH$_3$)$_2$), 0.86 (t, J=7.1 Hz, 6H, N(CH$_2$CH$_3$)$_2$).

MS m/z 565.1 [M$^+$+1].

EXAMPLE 38 (FROM TABLE 1)

5-(5-Bromo-2-oxo-1,2-dihydroindol-3-ylidenemethyl)-2-isopropyl-4-phenyl-1H-pyrrole-3-carboxylic Acid (3-pyrrolidin-1-ylpropyl)amide 5-(5-bromo-2-oxo-1,2-dihydroindol-3-ylidenemethyl)-2-isopropyl-4-phenyl-1H-pyrrole-3-carboxylic acid (127 mg, 0.28 mmol) was condensed with 3-pyrrolidin-1-yl-propylamine (43 mg, 0.336 mmol) to give 140 mg (66%) of the title compound.

$^1$H NMR (300 MHz, DMSO-d6) δ 14.40 (s, br, 1H, NH), 7.38–7.47 (m, 7H), 7.23–7.27 (m, 2H), 6.84 (d, J=8.1 Hz, 1H), 3.36 (m, 1H, CH(CH$_3$)$_2$), 3.08 (m, 2H, CH$_2$), 2.30 (m, 4H, 2×CH$_2$), 2.20 (t, J=7.0 Hz, 2H, CH$_2$), 1.62 (m, 4H, 2×CH$_2$), 1.42 (t, J=7.0 Hz, 2H, CH$_2$), 1.31 (d, J=7.2 Hz, 6H, CH(CH$_3$)$_2$).

MS-EI m/z 560 and 562 [M$^+$−1 and M$^+$+1].

EXAMPLE 39 (FROM TABLE 1)

5-(5-Bromo-2-oxo-1,2-dihydroindol-3-ylidenemethyl)-2-isopropyl-4-phenyl-1H-pyrrole-3-carboxylic Acid (2-diethylaminoethyl)amide 5-Bromo-1,3-dihydroindol-2-one (57 g, 0.27 mmol) was condensed with 5-formyl-2-isopropyl-4-phenyl-1H-pyrrole- 3-carboxylic acid (2-diethylaminoethyl)amide (120 mg) to give 78 mg (53%) of the title compound as a yellow solid.

$^1$H NMR (300 MHz, DMSO-d6) δ 14.23 (s, br, 1H, NH), 11.09 (s, br, 1H, NH), 7.38–7.51 (m, 6H), 7.25–7.28 (m, 2H), 7.19 (t, 1H, CONHCH$_2$), 6.85 (d, J=7.8 Hz,1H), 3.43 (m, 1H, CH(CH$_3$)$_2$), 3.11 (m,2H,CH$_2$), 2.28–2.39 (m, 6H, N(CH$_2$CH$_3$)$_2$ & CH$_2$, 1.31 (d, J=6.9 Hz, CH(CH$_3$)$_2$), 0.85 (t, J=7.0 Hz, 6H, N(CH$_2$CH$_3$)$_2$.

MS-EI m/z 548 and 550 [M$^+$−1 and M$^+$+1].

EXAMPLE 40 (FROM TABLE 1)

5-(5-Bromo-2-oxo-1,2-dihydroindol-3-ylidenemethyl)-2-isopropyl-4-phenyl-1H-pyrrole-3-carboxylic Acid [3-(4-methylpiperazin-1-yl)propyl]amide 5-Bromo-1,3-dihydroindol-2-one (53 mg, 0.25 mmol) was condensed with 5-formyl-2-isopropyl-4-phenyl-1H-pyrrole-3-carboxylic acid [3-(4-methylpiperazin-1-yl)propyl]amide (300 mg to give 65 mg of the title compound.

$^1$H NMR (300 MHz, DMSO-d6) δ 14.22 (s, br, 1H, NH), 11.08 (s, br, 1H, NH), 7.23–7.50 (m, 9H), 6.85 (d, J=8.7 Hz, 1H), 3.37 (m, 1H, CH(CH$_3$)$_2$), 3.05 (m, 2H, CH$_2$), 2.24 (m, 8H, 4×CH$_2$), 2.11 (m, 5H, CH$_2$ & CH$_3$), 1.42 (m, 2H, CH$_2$), 1.31 (d, J=7.2 Hz, 6H, CH(CH$_3$)$_2$).

MS-EI m/z 589 and 591 [M$^+$−1 amd M$^+$+1].

EXAMPLE 41 (FROM TABLE 1)

5-(5-Bromo-2-oxo-1,2-dihydroindol-3-ylidenemethyl)-2-isopropyl-4-phenyl-1H-pyrrole-3-carboxylic acid 5-Bromo-1,3-dihydroindol-2-one (170 mg, 0.8 mmol) was condensed with 5-formyl-2-isopropyl-4-phenyl-1H-pyrrole-3-carboxylic acid (205 mg) using method D to give 210 mg (58%) of the title compound as a yellow solid.

$^1$HNMR (300 MHz, DMSO-d6) δ 14.31 (s, br, 1H, NH), 11.16 (s, br, 1H, NH), 7.26–7.44 (m, 7H), 7.11 (s, 1H, H-vinyl), 6.85 (d, J=7.8 Hz, 1H), 3.78 (m, 1H, CH(CH$_3$)$_2$), 1.34 (d, J=6.9 Hz, 6H, CH(CH$_3$)$_2$).

MS-EI m/z 452 [M$^+$+1].

EXAMPLE 42 (FROM TABLE 1)

5-(5-Bromo-2-oxo-1,2-dihydroindol-3-ylidenemethyl)-2-methyl-4-phenyl-1H-pyrrole-3-carboxylic acid (2-pyrrolidin-1-ylethyl)amide 5-Bromo-1,3-dihydroindol-2-one (44 mg, 0.21 mmol) was condensed with 5-formyl-2-methyl-4-phenyl-1H-pyrrole-3-carboxylic acid (2-pyrrolidin-3-ylethyl)amide (70 mg, prepared in the same manner as the isopropyl analog, above) to give 0.03 g (27%) of the title compound as a yellow solid.

$^1$HNMR (300 MHz, DMSO-d6) δ 13.87 (s, br, 1H, NH), 11.11 (s, br, 1H, NH), 7.36–7.51 (m, 6H), 7.26 (dd, J=1.8 & 8.1 Hz, 1H), 7.2 (s, 1H, H-vinyl), 7.09 (m, 1H, CONHCH$_2$), 6.83 (d, J=8.1 Hz, 1H), 3.17 (m, 2H, NCH$_2$), 2.48 (m, CH$_3$), 2.29–2.35 (m, 6H, 3×NCH$_2$), 1.59 (m, 4H, 2×CH$_2$).

MS-EI m/z 518 and 520 [M$^+$−1 and M$^+$+1].

EXAMPLE 43 (FROM TABLE 1)

5-[6-(2-Methoxyphenyl)-2-oxo-1,2-dihydroindol-3-ylidenemethyl]-2-methyl-4-phenyl-1H-pyrrole-3-carboxylic acid (2-pyrrolidin-1-ylethyl)amide 6-(2-Methoxyphenyl)-1,3-dihydroindol-2-one (50 mg, 0.21 mmol) was condensed with 5-formyl-2-methyl-4-phenyl-1H-pyrrole-3-carboxylic acid (2-pyrrolidin-1-ylethyl)amide (70 mg) to give 0.04 g (35%) of the title compound as a yellow-orange solid.

$^1$HNMR (300 MHz, DMSO-d6) δ 13.82 (s, br, 1H, NH), 11.02 (s, br, 1H, NH), 7.48 (m, 2H), 7.43 (m, 1H), 7.38 (m, 2H), 7.32 (m, 1H), 7.24 (m, 2H), 7.16 (s, 1H, H-vinyl), 7.08 (m, 2H), 7.03 (m, 1H), 7.0 (m, 2H), 3.74 (s, 3H, OCH$_3$), 3.19 (m, 2H, NCH$_2$), 2.49 (m, CH$_3$), 2.32–2.38 (m, 6H, 3×NCH$_2$), 1.59 (m, 4H, 2×CH$_2$).

MS-EI m/z 546 [M$^+$].

EXAMPLE 44 (FROM TABLE 1)

5-(5-Bromo-2-oxo-1,2-dihydroindol-3-ylidenemethyl)-2-methyl-4-phenyl-1H-pyrrole-3-carboxylic acid (2-dimethylaminoethyl)amide 5-Bromo-1,3-dihydroindol-2-one (46 mg, 0.22 mmol) was condensed with 5-formyl-2-methyl-4-phenyl-1H-pyrrole-3-carboxylic acid (2-dimethylaminoethyl)amide (65 mg) to give 60 mg (55%) of the title compound as a yellow solid.

$^1$HNMR (360 MHz, DMSO-d6) δ 13.86 (s, br, 1H, NH), 11.09 (s, br, 1H, NH), 7.47–7.49 (m, 2H), 7.38–7.41 (m, 4H), 7.26 (dd, J=2.2 & 8.3 Hz, 1H), 7.21 (s, 1H, H-vinyl), 7.04 (m, 1H, CONHCH$_2$), 6.77 (d, J=8.3 Hz, 1H), 3.15 (m, 2H, NCH$_2$), 2.48 (m, CH$_3$), 2.16 (t, J=6.8 Hz, 2H, 3×NCH$_2$), 2.02 (s, 6H, 2×NCH$_3$).

MS m/z 493 and 494.8 [M$^+$ and M$^+$+2].

EXAMPLE 45 (FROM TABLE 1)

5-[6-(2-Methoxyphenyl)-2-oxo-1,2-dihydroindol-3-ylidenemethyl]-2-methyl-4-phenyl-1H-pyrrole-3-carboxylic acid (2-dimethylaminoethyl)amide 6-(2-Methoxyphenyl)-1,3-dihydroindol-2-one (53 mg, 0.22 mmol) was condensed with 5-formyl-2-methyl-4-phenyl-1H-pyrrole-3-carboxylic acid (2-dimethylaminoethyl)amide (65 mg) to give 0.05 g (44%) of the title compound as an orange gum.

$^1$HNMR (300 MHz, DMSO-d6) δ 13.82 (s, br, 1H, NH), 11.02 (s, br, 1H, NH), 7.37–7.52 (m, 5H), 7.32 (m, 1H), 7.22–7.27 (m, 2H), 7.16 (s, 1H), 7.08 (m, 2H), 7.03 (m, 1H), 7.0 (m, 2H), 3.74 (s, 3H, OCH$_3$), 3.15 (m, 2H, NCH$_2$), 2.49 (m, CH$_3$), 2.16 (t, J=6.5 Hz, 2H, NCH$_2$), 2.02 (s, 6H, 2×NCH$_3$).

MS m/z 521 [M$^+$+1].

EXAMPLE 46 (FROM TABLE 1)

5-(5-Bromo-2-oxo-1,2-dihydroindol-3-ylidenemethyl)-2-methyl-4-phenyl-1H-pyrrole-3-carboxylic acid ethyl ester 5-Bromo-1,3-dihydroindol-2-one (60 mg, 0.29 mmol) was condensed with 5-formyl-2-methyl-4-phenyl-1H-pyrrole-3-carboxylic acid ethyl ester (75 mg) to give 78 mg (60%) of the title compound as an orange solid.

$^1$HNMR (360 MHz, DMSO-d6) δ 14.01 (s, br, 1H, NH), 11.13 (s, br, 1H, NH), 7.42–7.46 (m, 3H), 7.27–7.34 (m, 4H), 7.12 (s, 1H), 6.84 (dd, J=2.2 & 8.3 Hz, 1H), 3.99–4.03 (m, 2H, OCH$_2$CH$_3$), 2.61 (s, 3H, CH$_3$), 0.98–1.03 (m, 3H, OCH$_2$CH$_3$).

MS-EI m/z 450 and 452 [M$^+$−1 and M$^+$+1].

EXAMPLE 47 (FROM TABLE 1)

5-(5-Bromo-2-oxo-1,2-dihydroindol-3-ylidenemethyl)-2-methyl-4-phenyl-1H-pyrrole-3-carboxylic acid (3-diethylaminopropyl)amide 5-bromo-1,3-dihydroindol-2-one (0.47 g, 2.2 mmol) was condensed with 5-formyl-2-methyl-4-phenyl-1H-pyrrole-3- carboxylic acid (3-diethylaminopropyl)amide (0.75 g) to give 0.11 g (42%) of the title compound as an orange solid.

$^1$HNMR (300 MHz, DMSO-d6) δ 13.86 (s, br, 1H, NH), 7.42–7.46 (m, 3H), 7.37–7.50 (m, 7H), 7.24–7.28 (m, 2H), 6.83 (d, J=8.1 Hz, 1H), 3.09 (m, 2H, NCH$_2$), 2.45 (s, 3H, CH$_3$), 2.38 (q, J=7.1 Hz, 4H, 2xNCH$_2$CH$_3$), 2.26 (t, J=6.9 Hz, 2H, NCH$_2$), 1.42 (m, 2H, NCH$_2$), 0,87 (t, J=7.1 Hz, 6H, 2xNCH$_2$CH$_3$).

MS-EI m/z 535.0 and 537 [M$^+$ and M$^+$+2].

EXAMPLE 48 (FROM TABLE 1)

5-(5-Bromo-2-oxo-1,2-dihydroindol-3-ylidenemethyl)-2,4-dimethyl-1H-pyrrole-3-carboxylic acid (2-dimethylamino-ethyl)amide A mixture of tert-butyl 3-oxobutyrate and sodium nitrite (1 equiv.) in acetic acid was stirred at room temperature to give tert-butyl-2-hydroximino-3-oxobutyrate.

Ethyl-3-oxobutyrate (1 equiv.), zinc dust (3.8 equiv.) and the crude tert-butyl-2-hydroximino-3-oxobutyrate in acetic acid was stirred at 60° C. for 1 hr. The reaction mixture was poured into H$_2$O and the filtrate was collected to give (65%) 2-tert-butyloxycarbonyl-3,5-dimethyl-4-ethoxycarbonylpyrrole.

A mixture of 2-tert-butyloxycarbonyl-3,5-dimethyl-4-ethoxycarbonylpyrrole and triethyl orthoformate (1.5 equiv.) in trifluoroacetic acid was stirred at 15° C. for 1 hour. The reaction was concentrated and the residue was purified to give (64%) 2,4-dimethyl-3-ethoxycarbonyl-5-formylpyrrole as yellow needles.

2,4-Dimethyl-3-ethoxycarbonyl-5-formylpyrrole was hydrolyzed using method B to give (90%) 5-formyl-2,4-dimethyl-1H-pyrrole-3-carboxylic acid.

$^1$H NMR (360 MHz, DMSO-d6) δ 12 (br s, 2H, NH and CO$_2$H), 9.58 (s, 1H, CHO), 2.44 (s, 3H, CH$_3$), 2.40 (s, 3H, CH$_3$).

MS m/z 267 [M$^+$].

5-Bromo-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g, prepared by method C) using method B to give 0.3 g (83%) of the title compound as a yellow solid.

$^1$HNMR (360 MHz, DMSO-d6) δ 13.60 (s, br, 1H, NH), 10.94 (s, b, 1H, NH), 8.07 (d, J=1.8 Hz, 1H, H-4), 7.75 (s, 1H, H-vinyl), 7.44 (t, J=5.2 Hz, 1H, CONHCH$_2$), 7.24 (dd, J=1.8 & 8.4 Hz, 1H, H-6), 6.82 (d, J=8.4 Hz, 1H, H-7), 3.26–3.33 (m, 2H, NCH$_2$), 2.42 (s, 3H, CH$_3$), 2.41 (s, 3H, CH$_3$), 2.38 (t, J=6.7 Hz, 2H, NCH$_2$), 2.18 (s, 6H, N(CH$_3$)$_2$).

MS-EI m/z 430 and 432 [M$^+$–1 and M$^+$+1].

EXAMPLE 49 (FROM TABLE 1)

2,4-Dimethyl-5-(2-oxo-6-phenyl-1,2-dihydroindol-3-ylidenemethyl)-1H-pyrrole-3-carboxylic acid (2-dimethylaminoethyl)amide 6-Phenyl-1,3-dihydroindol-2-one (0.17 g, 0.8 mmol) was condensed with 5-formyl-2,4-dimethyl-1H-pyrrole-3-carboxylic acid (2-dimethylaminoethyl)amide (0.2 g) to give 0.13 g (36%) of the title compound as a yellow-orange solid.

$^1$HNMR (360 MHz, DMSO-d6) δ 13.59 (s, br, 1H, NH), 10.93 (, br, 1H, NH), 7.85 (d, J=7.92 Hz, 1H, H-4), 7.64–7.65 (m, 3H), 7.40–7.47 (m, 3H,), 7.32–7.36 (m, 1H, Ar-H), 7.30 (dd, J=1.6 & 7.9 Hz, 1H, H-5), 7.11 (d, J=1.6 Hz, 1H, H-7), 3.28–3.34 (m, 2H, NCH$_2$), 2.43 (s, 3H, CH$_3$), 2.41 (s, 3H, CH$_3$), 2.38 (t, J=6.8 Hz, 2H, NCH$_2$), 2.18 (s, 6H, N(CH$_3$)$_2$).

MS-EI m/z 428 [M$^+$].

EXAMPLE 50 (FROM TABLE 1)

5-(5-Chloro-2-oxo-1,2-dihydroindol-3-ylidenemethyl)-2,4-dimethyl-1H-pyrrole-3-carboxylic acid (2-dimethylamino-ethyl)amide 5-Chloro-1,3-dihydroindol-2-one (0.1 g, 0.6 mmol) was condensed with 5-formyl-2,4-dimethyl-1H-pyrrole-3-carboxylic acid (2-dimethylaminoethyl)amide (0.15 g) to give 0.22 g (90%) of the title compound as a yellow solid.

$^1$HNMR (300 MHz, DMSO-d6) δ 13.61 (s, br, 1H, NH), 10.98 (, br, 1H, NH), 7.96 (d, J=2.0 Hz, 1H, H-4), 7.75 (s, 1H, H-vinyl), 7.50 (t, J=5.5 Hz, 1H, CONHCH$_2$), 7.12 (dd, J=2.0 & 8.3 Hz, 1H, H-6), 6.86 (d, J=8.3 Hz, 1H, H-7), 3.26–3.31 (m, 2H, NCH$_2$), 2.42 (s, 3H, CH$_3$), 2.40 (s, 3H, CH$_3$), 2.36 (t, J=6.6 Hz, 2H, NCH$_2$), 2.17 (s, 6H, N(CH$_3$)$_2$).

MS-EI m/z 386 [M$^+$].

EXAMPLE 51 (FROM TABLE 1)

5-(5-Bromo-2-oxo-1,2-dihydroindol-3-ylidenemethyl)-2,4-dimethyl-1H-pyrrole-3-carboxylic acid (2-diethylamino-ethyl)amide 5-Bromo-1,3-dihydroindol-2-one (0.17 g, 0.8 mmol) was condensed with 5-formyl-2,4-dimethyl-1H-pyrrole-3-carboxylic acid (2-diethylaminoethyl)amide (0.2 g) to give 0.09 g (26%) of the title compound as a yellow solid.

$^1$HNMR (360 MHz, DMSO-d6) δ 13.61 (s, br, 1H, NH), 10.98 (, br, 1H, NH), 8.09 (d, J=1.7 Hz, 1H, H-4), 7.76 (s, 1H, H-vinyl), 7.42 (t, J=5.5 Hz, 1H, CONHCH$_2$), 7.24 (dd, J=1.7 & 8.0 Hz, 1H, H-6), 6.82 (d, J=8.0 Hz, 1H, H-7), 3.23–3.32 (m, 2H, NCH$_2$), 2.46–2.55 (m, 6H, 3xNCH$_2$), 2.43 (s, 3H, CH$_3$), 2.42 (s, 3H, CH$_3$), 0.96 (t, J=7.2 Hz, 6H, 2xNCH$_2$CH$_3$).

MS-EI m/z 485 and 460 [M$^+$–1 and M$^+$+1].

EXAMPLE 52 (FROM TABLE 1)

5-(5-Bromo-2-oxo-1,2-dihydroindol-3-ylidenemethyl)-2,4-dimethyl-1H-pyrrole-3-carboxylic acid (2-pyrrolidin-1-yl-ethyl)amide 5-Bromo-1,3-dihydroindol-2-one (0.09 g, 0.4 mmol) was condensed with 5-formyl-2,4-dimethyl-1H-pyrrole-3-carboxylic acid (2-pyrrolidin-1-ylethyl)amide (0.1 g) to give 0.14 g (81%) of the title compound as a yellow-orange solid.

$^1$HNMR (300 MHz, DMSO-d6) δ 13.61 (s, br, 1H, NH), 10.98 (, br, 1H, NH), 8.09 (d, J=1.9 Hz, 1H, H-4), 7.76 (s, 1H, H-vinyl), 7.53 (t, J=5.5 Hz, 1H, CONHCH$_2$), 7.24 (dd, J=1.9 & 8.5 Hz, 1H, H-6), 6.81 (d, J=8.5 Hz, 1H, H-7), 3.29–3.35 (m, 2H, NCH$_2$), 2.54 (t, J=6.9 Hz, 2H, NCH$_2$), 2.47 (m, under DMSO), 2.42 (s, 3H, CH$_3$), 2.40 (s, 3H, CH$_3$), 1.66–1.69 (m, 4H, 2xCH$_2$).

MS-EI m/z 456 and 458 [M$^+$–1 and M$^+$+1].

EXAMPLE 53 (FROM TABLE 1)

5-(5-Bromo-2-oxo-1,2-dihydroindol-3-ylidenemethyl)-2,4-dimethyl-1H-pyrrole-3-carboxylic acid (3-imidazol-1-yl-propyl)amide 5-Bromo-1,3-dihydroindol-2-one (0.09 g, 0.4 mmol) was condensed with 5-formyl-2,4-dimethyl-1H-pyrrole-3-carboxylic acid (3-imidazol-1-ylpropyl)amide (0.1 g) to give 0.1 g (59%) of the title compound as an orange solid.

$^1$HNMR (300 MHz, DMSO-d6) δ 13.63 (s, br, 1H, NH), 10.99 (, br, 1H, NH), 8.09 (d, J=2.2 Hz, 1H, H-4), 7.77 (s,

1H, H-vinyl), 7.71 (t, J=5.7 Hz, 1H, CONHCH$_2$), 7.65 (s, 1H, Ar-H), 7.25 (dd, J=2.2 & 8.4 Hz, 1H, H-6), 7.20 (s, 1H, Ar-H), 6.89 (s, 1H, Ar-H), 6.81 (d, J=8.4 Hz, 1H, H-7), 4.02 (t, J=6.7 Hz, 2H, NCH$_2$), 3.18 (q, J=6.7 Hz, 2H, NCH$_2$), 2.43 (s, 3H, CH$_3$), 2.41 (s, 3H, CH$_3$), 1.93 (m, 2H, CH$_2$).

MS-EI m/z 467 and 469 [M$^+$–1 and M$^+$+1].

EXAMPLE 54 (FROM TABLE 1)

5-[6-(2-Methoxyphenyl)-2-oxo-1,2-dihydroindol-3-ylidenemethyl]-2,4-dimethyl-1H-pyrrole-3-carboxylic acid (2-dimethylaminoethyl)amide 6-(2-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 0.06 g (100%) of the title compound as a yellow-orange gum.

$^1$HNMR (300 MHz, DMSO-d6) δ 13.60 (s, br, 1H, NH), 10.89 (s, br, 1H, NH), 7.79 (d, J=8.4 Hz, 1H), 7.63 (s, 1H, H-vinyl), 7.46 (t, J=5.5 Hz, 1H, CONHCH$_2$), 7.28–7.35 (m, 2H), 6.99–7.11 (m, 4H), 3.76 (s, 3H, OCH$_3$), 3.27–3.31 (m, 2H, NCH$_2$), 2.43 (s, 3H, CH$_3$), 2.39 (s, 3H, CH$_3$) 2.37 (m, 2H, NCH$_2$), 2.18 (s, 6H, N(CH$_3$)$_2$).

MS-EI m/z 458 [M$^+$].

EXAMPLE 55 (FROM TABLE 1)

5-[6-(3-Methoxyphenyl)-2-oxo-1,2-dihydroindol-3-ylidenemethyl]-2,4-dimethyl-1H-pyrrole-3-carboxylic acid (2-dimethylaminoethyl)amide 6-(3-Methoxyphenyl)-1,3-dihydroindol-2-one (30 mg, 0.13 mmol) was condensed with 5-formyl-2,4-dimethyl-1H-pyrrole-3-carboxylic acid (2-dimethylaminoethyl)amide (30 mg) to give 8 mg (14%) of the title compound as a yellow-orange solid.

$^1$HNMR (360 MHz, DMSO-d6) δ 13.59 (s, br, 1H, NH), 10.92 (s, br, 1H, NH), 7.84 (d, J=7.6 Hz, 1H), 7.65 (s, 1H, H-vinyl), 7.42 (m, 1H, CONHCH$_2$), 7.36 (d, J=7.8 Hz, 1H), 7.29 (dd, J=1.6 & 7.6 Hz, 1H), 7.20 (d, J=7.8 Hz, 1H), 7.14 (d, J=2.8 Hz, 1H), 7.11 (d, J=1.6 Hz, 1H), 6.91 (dd, J=2.8 & 7.8 Hz, 1H), 3.82 (s, 3H, OCH$_3$), 3.21–3.33 (m, 2H, NCH$_2$), 2.43 (s, 3H, CH$_3$), 2.40 (s, 3H, CH$_3$), 2.36–2.40 (m, 2H, NCH$_2$), 2.18 (s, 6H, N(CH$_3$)$_2$).

MS-EI m/z 485 [M$^+$].

EXAMPLE 56 (FROM TABLE 1)

2,4-Dimethyl-5-(2-oxo-5-phenyl-1,2-dihydroindol-3-ylidenemethyl)-1H-pyrrole-3-carboxylic acid (2-diethylaminoethyl)amide 5-Phenyl-1,3-dihydroindol-2-one (80 mg, 0.4 mmol) was condensed with 5-formyl-2,4-dimethyl-1H-pyrrole-3-carboxylic acid (2-diethylaminoethyl)amide (0.1 g) using method B to give 79 mg (46%) of the title compound.

$^1$HNMR (300 MHz, DMSO-d6) δ 13.66 (s, br, 1H, NH), 10.95 (, br, 1H, NH), 8.15 (d, J=1.2 Hz, 1H), 7.81 (s, 1H, H-vinyl), 7.71 (d, J=7.5 Hz, 1H), 7.40–7.47 (m, 4H), 7.31 (m, 1H), 6.95 (d, J=8.1 Hz, 1H), 3.2–3.31 (m, 2H, NCH$_2$), 2.46–2.55 (m, 6H, 3xNCH$_2$), 2.44 (s, 6H, 2xCH$_3$), 0.96 (t, J=7.4 Hz, 6H, 2xNCH$_2$CH$_3$).

MS-EI m/z 465 [M$^+$].

EXAMPLE 57 (FROM TABLE 1)

2,4-Dimethyl-5-(2-oxo-5phenyl-1,2-dihydroindol-3-ylidenemethyl)-1H-pyrrole-3-carboxylic acid (2-pyrrolidin-1-ylethyl)amide 5-Phenyl-1,3-dihydroindol-2-one (0.04 g, 0.2 mmol) was condensed with 5-formyl-2,4-dimethyl-1H-pyrrole-3-carboxylic acid (2-pyrrolidin-1-ylethyl)amide (0.04 g) to give the title compound as a yellow-orange solid.

$^1$HNMR (300 MHz, DMSO-d6) δ 13.65 (s, br, 1H, NH), 10.96 (, br, 1H, NH), 8.15 (d, J=1.0 Hz, 1H), 7.80 (s, 1H, H-vinyl), 7.71 (d, J=7.2 Hz, 2H), 7.49 (t, J=6.3 Hz, 1H, CONHCH$_2$), 7.41–7.46 (m, 3H), 7.31 (m, 1H), 6.95 (d, J=7.8 Hz, 1H), 4.08 (m, 4H, 2x NCH$_2$), 3.32 (m, 2H, NCH$_2$), 2.55 (t, J=7.1 Hz, 2H, NCH$_2$), 2.47 (m, under DMSO), 2.43 (s, 6H, 2xCH$_3$), 1.66 (m, 4H, 2xCH).

MS-EI m/z 454 [M$^+$].

EXAMPLE 58 (FROM TABLE 1)

2,4-Dimethyl-5-(2-oxo-5-phenyl-1,2-dihydroindol-3-ylidenemethyl)-1H-pyrrole-3-carboxylic acid (3-imidazol-1-ylpropyl)amide 5-Phenyl-1,3-dihydroindol-2-one (8 mg, 0.04 mmol) was condensed with 5-formyl-2,4-dimethyl-1H-pyrrole-3-carboxylic acid (3-imidazol-1-ylpyropyl)amide (10 mg) to give 10 mg (59%) of the title compound as an orange solid.

$^1$HNMR (300 MHz, DMSO-d6) δ 13.67 (s, br, 1H, NH), 10.96 (, br, 1H, NH), 8.16 (d, J=1.2 Hz, 1H), 7.81 (s, 1H, H-vinyl), 7.65–7.72 (m, 4H), 7.44 (m, 3H), 7.31 (m, 1H, CONHCH$_2$), 7.21 (s, 1H, Ar-H), 4.02 (t, J=6.5 Hz, 2H, NCH$_2$), 3.19 (q, J=6.5 Hz, 2H, CONHCH$_2$), 2.44 (s, 6H, 2xCH$_3$), 1.93 (m, 2H, CH$_2$CH), CH$_2$).

MS-EI m/z 465 [M$^+$].

EXAMPLE 59 (FROM TABLE 1)

2,4-Dimethyl-5-[2-oxo-6-phenyl-1,2-dihydroindol-3-ylidenemethyl)-1H-pyrrole-3-carboxylic acid (2-diethylaminoethyl)amide 6-Phenyl-1,3-dihydroindol-2-one (0.08 g, 0.4 mmol) was condensed with 5-formyl-2,4-dimethyl-1H-pyrrole-3-carboxylic acid (2-diethylaminoethyl)amide (0.1 g) to give 65 mg (38%) of the title compound as a yellow solid.

$^1$HNMR (300 MHz, DMSO-d6) δ 13.61 (s, br, 1H, NH), 10.99 (, br, 1H, NH), 7.86 (d, J=7.8 Hz, 1H), 7.62–7.66 (m, 3H), 7.40–7.47 (m, 3H), 7.28–7.36 (m, 2H), 7.10 (d, J=1.2 Hz, 1H), 3.26 (m, 2H, NCH$_2$), 2.46–2.55 (m, 6H, 3xNCH$_2$), 2.44 (s, 3H, CH$_3$), 2.41 (s, 3H, CH$_3$), 0.97 (t, J=7.2 Hz, 6H, 2xNCH$_2$CH$_3$).

MS-EI m/z 456 [M$^+$].

EXAMPLE 60 (FROM TABLE 1)

2,4-Dimethyl-5-(2-oxo-6-phenyl-1,2-dihydroindol-3-ylidenemethyl)-1H-pyrrole-3-carboxylic acid (2-pyrrolidin-1-ylethyl)amide 6-Phenyl-1,3-dihydroindol-2-one (30 mg, 0.15 mmol) was condensed with 5-formyl-2,4-dimethyl-1H-pyrrole-3-carboxylic acid (2-pyrrolidin-1-ylethyl)amide (40 mg) to give 5.9 mg (8.5%) of the title compound as a yellow-orange solid.

$^1$HNMR (300 MHz, DMSO-d6) δ 13.60 (s, br, 1H, NH), 10.99 (, br, 1H, NH), 7.86 (d, J=7.8 Hz, 1H), 7.63–7.66 (m, 3H), 7.51 (m, 1H, CONHCH$_2$), 7.45 (m, 2H), 7.28–7.36 (m, 2H), 7.10 (d, J=1.5 Hz, 1H), 3.31 (m, 6H, 3xNCH$_2$), 2.55 (t, J=6.6 Hz, 2H, NCH$_2$), 2.43 (s, 3H, CH$_3$), 2.40 (s, 3H, CH$_3$), 1.67 (m, 4H, 2xCH$_2$).

MS-EI m/z 454 [M$^+$].

EXAMPLE 61 (FROM TABLE 1)

2,4-Dimethyl-5-(2-oxo-6-phenyl-1,2-dihydroindol-3-ylidenemethyl)-1H-pyrrole-3-carboxylic acid (3-imidazol-1-ylpropyl)amide 6-Phenyl-1,3-dihydroindol-2-one (8 mg, 0.04 mmol) was condensed with 5-formyl-2,4-dimethyl-1H-pyrrole-3- carboxylic acid (3-imidazol-1-ylpropyl)amide (10 mg) to give 7.3 mg (43%) of the title compound as an orange solid.

$^1$HNMR (300 MHz, DMSO-d6) δ 13.62 (s, br, 1H, NH), 10.99 (, br, 1H, NH), 7.86 (d, J=8.2 Hz, 1H), 7.62–7.70 (m, 5H), 7.45 (m, 2H), 7.35 (m, 1H), 7.30 (dd, J=1.4 & 8.2 Hz, 1H), 7.21 (s, 1H), 71.0 (d, J=1.4 Hz, 1H), 6.89 (s, 1H), 4.02 (t, J=6.9 Hz, 2H, CH$_2$), 3.19 (m, 2H, NCH$_2$ CH$_2$), 2.43 (s, 3H, CH$_3$), 2.41 (s, 3H, CH$_3$), 1.93 (t, J=6.9 Hz, 2H, NCH$_2$).

MS-EI m/z 465 [M$^+$].

EXAMPLE 62 (FROM TABLE 1)

5-[6-(3,5-Dichlorophenyl)-2-oxo-1,2-dihydroindol-3-ylidenemethyl]-2,4-dimethyl-1H-pyrrole-3-carboxylic acid (2-diethylaminoethyl)amide 6-(3,5-Dichlorophenyl)-1,3-dihydroindol-2-one (64 mg, 0.23 mmol) was condensed with 5-formyl-2,4-dimethyl-1H-pyrrole-3-carboxylic acid (2-diethylaminoethyl)amide (60 mg) to give 53 mg (44%) of the title compound as a light brown solid.

$^1$HNMR (360 MHz, DMSO-d6) δ 13.62 (s, br, 1H, NH), 10.99 (s, 1H, NH), 7.89 (d, J=7.9 Hz, 1H, H-4), 7.69–7.71 (m, 3H), 7.55 (m, 1H, CONHCH$_2$), 7.37 (m, 2H), 7.14 (d, J=1.4 Hz, 1H, H-7), 3.27 (m, 2H, NCH$_2$), 2.48–2.58 (m, 6H, 3xNCH$_2$), 2.45 (s, 3H, CH$_3$), 2.42 (s, 3H, CH$_3$), 0.97 (t, J=6.8 Hz, 6H, 3xNCH$_2$CH$_3$).

MS m/z 526.9 [M$^+$+1].

EXAMPLE 63 (FROM TABLE 1)

2,4-Dimethyl-5-(2-oxo-6-pyridin-3-yl-1,2-dihydroindol-3-ylidenemethyl)-1H-pyrrole-3-carboxylic acid (2-diethylaminoethyl)amide 6-Pyridin-3-yl-1,3-dihydroindol-2-one (40 mg, 0.19 mmol) was condensed with 5-formyl-2,4-dimethyl-1H-pyrrole-3-carboxylic acid (2-diethylaminoethyl)amide (50 mg) give 29 mg (33%) of the title compound as a light orange solid.

$^1$HNMR (300 MHz, DMSO-d6) δ 13.62 (s, br, 1H, NH), 11.05 (s, br, 1H, NH), 8.86 (s, br, 1H), 8.53 (d, J=5.8 Hz, 1H), 8.04 (m, 1H), 7.91 (d, J=8.1 Hz, 1H), 7.70 (s, 1H, H-vinyl), 7.40–7.48 (m, 2H), 7.35 (d, J=7.5 Hz, 1H), 7.14 (s, 1H), 3.26 (m, 2H, NCH$_2$), 2.48–2.55 (m, 3xNCH$_2$), 2.42 (s, 3H, CH$_3$), 2.38 (s, 3H, CH$_3$), 0.96 (t, J=6.9 Hz, 6H, 2xNCH$_2$CH).

MS-EI m/z 457 [M$^+$].

EXAMPLE 64 (FROM TABLE 2)

2,4-Dimethyl-5-(2-oxo-6-pyridin-3-yl-1,2-dihydroindol-3-ylidenemethyl)-1H-pyrrole-3-carboxylic acid (2-pyrrolidin-1-ylethyl)amide 6-Pyridin-3-yl-1,3-dihydroindol-2-one (60 mg, 0.28 mmol) was condensed with 5-formyl-2,4-dimethyl-1H-pyrrole-3-carboxylic acid (2-pyrrolidin-1-ylethyl)amide (75 mg) to give 90 mg (71%) of the title compound as a light orange solid.

$^1$HNMR (300 MHz, DMSO-d6) δ 13.61 (s, br, 1H, NH), 11.05 (s, br, 1H, NH), 8.86 (d, J=1.5 Hz, 1H), 8.54 (dd, J=1.5 & 4.8 Hz, 1H), 8.05 (m, 1H), 7.91 (d, J=7.8 Hz, 1H), 7.70 (s, 1H, H-vinyl), 7.44–7.53 (m, 2H), 7.36 (dd, J=1.5 & 8.1 Hz, 1H), 7.15 (d, J=1.2 Hz, 1H), 3.33 (m, 2H, NCH$_2$), 2.47–2.57 (m, 6H, 3xNCH$_2$), 2.43 (s, 3H, CH$_3$), 2.41 (s, 3H, CH$_3$), 1.67 (m, 4H, 2xCH$_2$).

MS-EI m/z 455 [M$^+$]

EXAMPLE 65 (FROM TABLE 1)

2,4-Dimethyl-5-(2-oxo-6-pyridin-3-yl-1,2-dihydroindol-3-ylidenemethyl)-1H-pyrrole-3-carboxylic acid (3-dimethylaminopropyl)amide 6-Pyridin-3-yl-1,3-dihydroindol-2-one (42 mg, 0.2 mmol) was condensed with 5-formyl-2,4-dimethyl-1H- pyrrole-3-carboxylic acid (3-dimethylaminoproyl)amide (50 mg) to give 67 mg (75%) of the title compound as yellow-brown solid.

$^1$HNMR (360 MHz, DMSO-d6) δ 13.61 (s, br, 1H, NH), 11.00 (s, br, 1H, NH), 8.86 (s, br, 1H), 8.54 (s, br, 1H), 8.04 (m, 1H), 7.90 (d, J=8.0 Hz, 1H), 7.69 (s, 1H, H-vinyl), 7.63 (m, 1H), 7.45–7.48 (m, 1H), 7.35 (dd, J=1.7 & 8.0 Hz, 1H), 7.15 (d, J=1.7 Hz, 1H), 3.21–3.27 (m, 2H, NCH$_2$), 2.43 (s, 3H, CH$_3$), 2.41 (s, 3H, CH$_3$), 2.28 (m, 2H, NCH$_2$), 2.14 (s, 6H, 2xNCH$_3$), 1.64 (m, 2H, CH$_2$).

MS-EI m/z 443 [M$^+$].

EXAMPLE 66 (FROM TABLE 1)

2,4-Dimethyl-5-(2-oxo-5-phenyl-1,2-dihydroindol-3-ylidenemethyl)-1H-pyrrole-3-carboxylic acid (3-dimethylaminopropyl)amide 5-Phenyl-1,3-dihydroindol-2-one (67 mg, 0.32 mmol) was condensed with 5-formyl-2,4-dimethyl-1H-pyrrole-3-carboxylic acid (3-dimethylaminopropyl)amide (81 mg) to give 40 mg (28%) of the title compound as an orange solid.

$^1$HNMR (360 MHz, DMSO-d6) δ 13.66 (s, br, 1H, NH), 10.92 (s, br, 1H, NH), 8.14 (s, 1H), 7.79 (s, 1H), 7.71 (m, 2H), 7.62 (m, 1H), 7.44 (m, 3H), 7.32 (m, 1H), 6.95 (m, 1H), 3.33 (m, 2H, NCH$_2$), 2.43 (s, 6H, 2xCH$_3$), 2.27 (m, 2H, NCH$_2$), 2.13 (s, 6H, 2xNCH$_3$), 1.63 (m, 2H, CH$_2$).

MS-EI m/z 442 [M$^+$].

EXAMPLE 67 (FROM TABLE 1)

2,4-Dimethyl-5-(2-oxo-5-phenyl-1,2-dihydroindol-3-ylidenemethyl)-1H-pyrrole-3-carboxylic acid (3-diethylaminopropyl)amide 5-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.3 g (40%) of the title compound as a yellow-orange solid.

$^1$HNMR (360 MHz, DMSO-d6) δ 13.64 (s, 1H, NH), 10.91 (s, 1H, NH), 8.14 (d, J=1.4 Hz, 1H, ArH), 7.8 (s, 1H, ArH), 7.7 (dd, J=1.2 and 8.5 Hz, 2H, ArH), 7.6 (t, J=5.3 Hz, 1H, CONHCH$_2$), 7.4 (m, 3H, ArH), 7.3 (t, J=7.4 Hz, 1H, ArH), 6.9 (d, J=8.0 Hz, 1H, ArH), 3.2 (m, 2H, CONHCH$_2$), 2.5 (m, 12H, 3xNCH$_2$ and 2xCH$_3$), 1.61 (m, 2H, CH$_2$CH$_2$CH$_2$), 0.93 (t, J=6.7 Hz, 6H, NCH$_2$CH$_3$).

MS-EI m/z 470 [M$^+$].

EXAMPLE 68 (FROM TABLE 1)

2,4-Dimethyl-5-(2-oxo-6-phenyl-1,2-dihydroindol-3-ylidenemethyl)-1H-pyrrole-3-carboxylic acid (3-diethylaminopropyl)amide 6-Phenyl-1,3-dihydroindol-2-one (1.5 g, 7.16 mmol) was condensed with 5-formyl-2,4-dimethyl-1H-pyrrole-3-carboxylic acid (3-diethylaminopropyl)amide (2 g) to give 1.9 g (57%) of the title compound as an orange solid.

$^1$HNMR (360 MHz, DMSO-d6) δ 13.58 (s, 1H, NH), 10.94 (s, 1H, NH), 7.8 (d, J=7.9 Hz, 1H, ArH), 7.6 (m, 4H,

ArH), 7.4 (t, J=7.5 Hz, 2H, ArH), 7.3 (m, 2H), 7.1 (d, J=1.4 Hz, 1H, ArH), 3.2 (m, 2H, CONHCH$_2$), 2.5 (m, 12H, 3xNCH$_2$ and 2xCH$_3$), 1.61 (m, 2H, CH$_2$CH$_2$CH$_2$), 0.93 (t, J=6.7 Hz, 6H, NCH$_2$CH$_3$).

MS-EI m/z 470 [M$^+$].

EXAMPLE 69 (FROM TABLE 1)

3-[4-(3-Diethylaminopropylcarbamoyl)-3,5-dimethyl-1H-pyrrol-2-ylmethylene]-2-oxo-2,3-dihydro-1H-indole-4-carboxylic acid (3-chloro-4-methoxyphenyl)amide 2-Oxo-2,3-dihydro-1H-indole-4-carboxylic acid (3-chloro-4-methoxyphenyl)amide (1 g, 3.16 mmol) was condensed with 5-formyl-2,4-dimethyl-1H-pyrrole-3-carboxylic acid (3-diethylaminopropyl)amide (1 g, 3.58 mmol) to give 1.7 g (85%) of the title compound as a yellow-orange solid.

MS-EI m/z 578.2 [M$^+$].

EXAMPLE 70 (FROM TABLE 1)

5-(5-Bromo-2-oxo-1,2-dihydroindol-3-ylidenemethyl)-2,4-dimethyl-1H-pyrrole-3-carboxylic acid (3-diethylamino-propyl)amide 5-Bromo-1,3-dihydroindol-2-one (0.5 g, 2.36 mmol) was condensed with 5-formyl-2,4-dimethyl-1H-pyrrole-3-carboxylic acid (3-diethylaminopropyl)amide (0.51 g) to give 0.84 g of the title compound as a red-orange solid.

$^1$HNMR (360 MHz, DMSO-d6) δ 13.61 (s, 1H, NH), 10.99 (s, 1H, NH), 8.09 (d, J=1.8 Hz, 1H, ArH), 7.7 (m, 4H), 7.2 (dd, J=1.8 and 8.3 Hz, 2H, ArH), 6.8 (d, J=7.8 Hz, 1H, ArH), 3.3 (br s, 4H, 2xNCH$_2$), 3.2 (m, 2H, CONHCH$_2$), 2.6 (br s, 2H, NCH$_2$ and 2xCH$_3$), 2.4 (s, 6H, 2xCH$_3$), 1.66 (m, 2H, CH$_2$CH$_2$CH$_2$), 0.98 (t, J=7.1 Hz, 6H, NCH$_2$CH$_3$).

MS-EI m/z 472 and 474 [M$^+$−1 and M$^+$+1].

EXAMPLE 71 (FROM TABLE 1)

5-(5-Bromo-2-oxo-1,2-dihydroindol-3-ylidenemethyl)-2,4-diisopropyl-1H-pyrrole-3-carboxylic acid (2-diethylamino-ethyl)amide 5-Bromo-1,3-dihydroindol-2-one (100 mg, 0.47 mmol) was condensed with 5-formyl-2,4-diisopropyl-1H-pyrrole-3-carboxylic acid (2-diethylaminoethyl)amide (150 mg) to give 0.15 g (62%) of the title compound as a yellow-orange solid.

$^1$HNMR (300 MHz, DMSO-d6) δ 13.97 (s, 1H, NH), 10.95 (s, 1H, NH), 8.09 (d, J=1.3 Hz, 1H, ArH), 7.84 (m, 1H), 7.79 (s, 1H), 7.23 (dd, J=1.3 and 8.1 Hz, 1H, ArH), 6.8 (d, J=8.1 Hz, 1H, ArH), 3.5 (m, 1H, CH), 3.3 (m, 3H, CH and NHCH$_2$), 2.5 (br m, 6H, 3xNCH$_2$), 1.28 (d, J=6.9 Hz, 6H, 2xCH$_3$), 1.23 (d, J=6.6 Hz, 6H, 2xCH$_3$), 0.96 (m, 6H, 2xCH$_2$CH$_3$).

MS-EI m/z 514 and 516 [M$^+$−1 and M$^+$+1].

EXAMPLE 72 (FROM TABLE 1)

5-(5-Bromo-2-oxo-1,2-dihydroindol-3-ylidenemethyl)-2,4-diisopropyl-1H-pyrrole-3-carboxylic acid (3-diethylamino-propyl)amide 5-Bromo-1,3-dihydroindol-2-one (90 mg, 0.42 mmol) was conducted with 5-formyl-2,4-diisopropyl-1H-pyrrole-3-carboxylic acid (3-diethylaminopropyl)amine (140 mg) to give 54 mg (25%) of the title compound as red-brown solid.

$^1$HNMR (300 MHz, DMSO-d6) δ 13.98 (s, 1H, NH), 10.96 (s, 1H, NH), 8.09 (d, J=1.7 Hz, 2H), 7.78 (s, 1H, H-vinyl), 7.23 (dd, J=1.7 and 8.1 Hz, 1H, ArH), 6.82 (d, J=8.1 Hz, 1H, ArH), 3.5 (m, 1H, CH), 3.25 (m, 2H, NHCH$_2$), 3.15 (m, 1H, CH), 2.7 (br s, 6H, 3xNCH$_2$), 1.7 (br m, 2H, CH$_2$CH$_2$CH$_2$), 1.28 (d, J=6.9 Hz, 6H, 2xCH$_3$), 1.24 (d, J=5.9 Hz, 6H, 2xCH$_3$), 1.06 (m, 6H, 2xCH$_2$CH$_3$).

MS-EI m/z 528 and 530 [M$^+$−1 and M$^+$−1].

EXAMPLE 73 (FROM TABLE 1)

5-(5-Bromo-2-oxo-1,2-dihydroindol-3-ylidenemethyl)-2,4-diisopropyl-1H-pyrrole-3-carboxylic acid (3-pyrrolidin-1-ylpropyl)amide 5-Bromo-1,3-dihydroindol-2-one (130 mg, 0.6 mmol) was condensed with 5-formyl-2,4-diisopropyl-1H-pyrrole-3-carboxylic acid (3-pyrrolidin-1-ylpropyl)amide (150 mg, 0.45 mmol) to give 36 mg (15%) of the title compound as a tan-orange solid.

$^1$HNMR (300 MHz, DMSO-d6) δ 13.98 (s, 1H, NH), 10.97 (s, 1H, NH), 8.10 (d, J=1.6 Hz, 2H), 7.78 (s, 1H, H-vinyl), 7.23 (dd, J=1.6 and 7.6 Hz, 1H, ArH), 6.82 (d, J=7.6 Hz, 1H, ArH), 3.5 (m, 1H, CH), 3.25 (m, 2H, NHCH$_2$), 3.15 (m, 1H, CH), 2.7 (br s, 6H, 3xNCH$_2$), 1.7 (br m, 6H, 3xNCH$_2$CH$_2$), 1.28 (d, J=5.6 Hz, 6H, 2xCH$_3$), 1.24 (d, J=5.7 Hz, 6H, 2xCH$_3$).

MS-EI m/z 526 and 528 [M$^+$−1 and M$^+$+1].

EXAMPLE 74 (FROM TABLE 1)

5-(5-Bromo-2-oxo-1,2-dihydroindol-3-ylidenemethyl)-2,4-dimethyl-1H-pyrrole-3-carboxylic acid (pyridin-4-ylmethyl)-amide 5-Bromo-1,3-dihydroindol-2-one (170 mg, 0.8 mmol) was condensed with 5-formyl-2,4-dimethyl-1H-pyrrole-3-carboxylic acid (pyridin-4-ylmethyl)amide (200 mg) to give 14 mg(4%) of the title compound as a yellow solid.

$^1$HNMR (300 MHz, DMSO-d6) δ 13.67 (s, 1H, NH), 11.01 (s, br, 1H, NH), 8.51 (dd, J=1.6 & 4.3 Hz, 2H), 8.23 (t, J=6.0 Hz, 1H, CONHCH$_2$), 8.11 (d, J=1.9 Hz, 1H), 7.78 (s, 1H, H-vinyl), 7.31 (d, J=6.0 Hz, 2H), 7.25 (dd, J=1.9 & 8.1 Hz, 1H), 6.82 (d, J=8.1 Hz, 1H), 4.45 (d, J=6.0 Hz, 2H, NCH$_2$), 2.46 (s, 6H, 2xCH$_3$).

MS-EI m/z 450 and 452 [M$^+$−1 and M$^+$+1].

EXAMPLE 75 (FROM TABLE 1)

5-[6-(4-Butylphenyl)-2-oxo-1,2-dihydroindol-3-ylidenemethyl]-2,4-dimethyl-1H-pyrrole-3-carboxylic acid (2-pyrrolidin-1-ylethyl)amide 5-[6-(4-Butylphenyl)]-1,3-dihydroindol-2-one (50 mg, 0.19 mmol) was condensed with 5-formyl-2,4-dimethyl-1H-pyrrole-3-carboxylic acid (2-pyrrolidin-1-ylethyl)amide (50 mg) to give 74 mg (76%) of the title compound as an orange solid.

$^1$HNMR (360 MHz, DMSO-d6) δ 13.58 (s, 1H, NH), 10.93 (s, br, 1H, NH), 7.82 (d, J=7.9 Hz, 1H), 7.63 (s, 1H, H-vinyl), 7.54 (d, J=7.9 Hz, 2H), 7.46 (m, 1H, CONH), 7.26 (m, 3H), 7.09 (s, 1H), 3.30 (m, 2H, CH$_2$), 2.52–2.63 (m, 4H, 2xCH$_2$), 2.49 (m, 4H, 2xCH$_2$), 2.43 (s, 3H, CH$_3$), 2.40 (s, 3H, CH$_3$), 1.68 (m, 4H, 2xCH$_2$), 1.58 (m, 2H, CH$_2$), 1.34 (m, 2H, CH$_2$), 0.91 (t, J=7.2 Hz, 3H, CH$_2$CH$_2$).

MS-EI m/z 510 [M$^+$].

EXAMPLE 76 (FROM TABLE 1)

5-[6-(5-Isopropyl-2-methoxyphenyl)-2-oxo-1,2-dihydroindol-3-ylidenemethyl]-2,4-dimethyl-1H-pyrrole-3-carboxylic acid (2-pyrrolidin-1-ylethyl)amide 6-(5-Isopropyl-2-methoxyphenyl)-1,3-dihydroindol-2-one (50 mg, 0.17 mmol) was condensed with 5-formyl-2,4- dimethyl-1H-pyrrole-3-carboxylic acid (2-pyrrolidin-1-yl-ethyl)amide (45 mg) to give 67 mg (75%) of the title compound as an orange solid.

¹HNMR (360 MHz, DMSO-d6) δ 13.60 (s, 1H, NH), 10.82 (s, br, 1H, NH), 7.77 (d, J=7.9 Hz, 1H), 7.61 (s, 1H, H-vinyl), 7.45 (m, 1H, CONH), 7.0–7.19 (m, 5H), 3.73 (s, 3H, OCH₃), 3.32 (m, 2H, CH₂), 2.87 (m, 1H, CH(CH₃)₂), 2.56 (m, 2H, CH₂), 2.48 (m, 4H, 2xCH₂), 2.43 (s, 3H, CH₃), 2.40 (s, 3H, CH₃), 1.68 (m, 4H, 2xCH₂), 1.21 (d, J=6.8 Hz, 6H, CH(CH₃)₂).

MS m/z 527.2 [M⁺+1].

EXAMPLE 77 (FROM TABLE 1)

5-[6-(4-Ethylphenyl)-2-oxo-1,2-dihydroindol-3-ylidenemethyl]2,4-dimethyl-1H-pyrrole-3-carboxylic acid (2-pyrrolidin-1-ylethyl)amide 6-(4-Ethylphenyl)-1,3-dihydroindol-2-one (45 mg, 0.19 mmol) was condensed 5-formyl-2,4-dimethyl-1H-pyrrole-3-carboxylic acid (2-pyrrolidin-1-ylethyl)amide (50 mg) to give 60 mg (65%) of the title compound as a yellow-orange solid.

¹HNMR (300 MHz, DMSO-d6) δ 13.59 (s, 1H, NH), 10.96 (s, br, 1H, NH), 7.83 (d, J=8.4 Hz, 1H), 7.64 (s, 1H, H-vinyl), 7.51–7.56 (m, 3H), 7.25–7.30 (m, 3H), 7.08 (d, J=1 Hz, 1H), 3.31 (m, 2H, CH₂), 2.63 (m, 2H, CH₂CH₃), 2.55 (m, 2H, CH₂), 2.49 (m, 4H, 2xCH₂), 2.42 (s, 3H, CH₃), 2.40 (s, 3H, CH₃), 1.67 (m, 4H, 2xCH₂), 1.20 (t, J=7.5 Hz, 3H, CH₂CH₃).

MS-EI m/z 482 [M⁺].

EXAMPLE 78 (FROM TABLE 1)

5-[6-(2,4-Dimethoxyphenyl)-2-oxo-1,2-dihydroindol-3-ylidenemethyl]2,4-dimethyl-1H-pyrrole-3-carboxylic acid (2-pyrrolidin-1-ylethyl) amide 6-(2,4-Dimethyloxyphenyl)-1,3-dihydroindol-2-one (51 mg, 0.19 mmol) was condensed with 5-formyl-2,4-dimethyl-1H-pyrrole-3-carboxylic acid (2-pyrrolidin-1-ylethyl)amide (50 mg) to give 30 mg (31%) of the title compound as an orange solid.

¹HNMR (300 MHz, DMSO-d6) δ 13.59 (s, 1H, NH), 10.86 (s, br, 1H, NH), 7.75 (d, J=7.8 Hz, 1H), 7.60 (s, 1H, H-vinyl), 749 (m, 1H, CONH), 7.22 (d, J=8.4 Hz, 1H), 7.03 (m, 1H), 6.97 (s, 1H), 6.58–6.65 (m, 2H), 3.79 (s, 3H, OCH₃), 3.76 (s, 3H, OCH₃), 3.33 (m, 2H, CH₂), 2.55 (m, 2H, CH₂), 2.50 (m, 4H, 2xCH₂), 2.42 (s, 3H, CH₃), 2.39 (s, 3H, CH₃), 1.67 (m, 4H, 2xCH₂).

MS-EI m/z 514 [M⁺].

EXAMPLE 79 (FROM TABLE 1)

5-[6-(3-Isopropylphenyl)-2-oxo-1,2-dihydroindol-3-ylidenemethyl]-2,4-dimethyl-1H-pyrrole-3-carboxylic acid (2-pyrrolidin-1-ylethyl)amide 6-(3-Isopropylphenyl)-1,3-dihydroindol-2-one (48 mg, 0.19 mmol) was condensed with 5-formyl-2,4-dimethyl-1H-pyrrole-3-carboxylic acid (2-pyrrolidin-1-ylethyl)amide (50 mg) to give 59 mg (63%) of the title compound as an orange solid.

¹HNMR (300 MHz, DMSO-d6) δ 13.63 (s, 1H, NH), 10.97 (s, br, 1H, NH), 7.87 (d, J=7.8 Hz, 1H), 7.68 (s, 1H, H-vinyl), 7.24–7.55 (m, 6H), 7.13 (s, 1H), 3.34 (m, 2H, CH₂), 3.30 (m, 1H, CH(CH₃)₂), 2.60 (m, 2H, CH₂), 2.50 (m, 4H, 2xCH₂), 2.45 (s, 3H, CH₃), 2.43 (s, 3H, CH₃), 1.70 (m, 4H, 2xCH₂), 1.27 (d, J=6.9 Hz, 6H, CH(CH₃)₂).

MS-EI m/z 496 [M⁺].

EXAMPLE 80 (FROM TABLE 1)

5-(5-Fluoro-2-oxo-1,2-dihydroindol-3-ylidenemethyl)-2,4-dimethyl-1H-pyrrole-3-carboxylic acid (2-diethylamino-ethyl)amide 5-Fluoro-1,3-dihydroindol-2-one (0.54 g 3.8 mmol) was condensed with 5-formyl-2,4-dimethyl-1H-pyrrole-3-carboxylic acid (2-diethylaminoethyl)amide to give 0.83 g (55%) of the title compound as a yellow green solid.

¹HNMR (360 MHz, DMSO-d6) δ 13.66 (s, 1H, NH), 10.83 (s, br, 1H, NH), 7.73 (dd, J=2.5 & 9.4 Hz, 1H), 7.69 (s, 1H, H-vinyl), 7.37 (t, 1H, CONHCH₂CH₂), 6.91 (m, 1H), 6.81–6.85 (m, 1H), 3.27 (m, 2H, CH₂), 2.51 (m, 6H, 3xCH₂), 2.43 (s, 3H, CH₃), 2.41 (s, 3H, CH₃), 0.96 (t, J=6.9 Hz, 6H, N(CH₂CH₃)₂).

MS-EI m/z 398 [M⁺].

EXAMPLE 81 (FROM TABLE 1)

3-[4-(2-Diethylaminoethylcarbamoyl)-3,5-dimethyl-1H-pyrrol-2-ylmethylene]-2-oxo-2,3-dihydro-1H-indole-6-carboxylic acid 2-Oxo-2,3-dihydro-1H-indole-6-carboxylic acid (80 mg, 0.45 mmol) was condensed with 5-formyl-2,4-dimethyl-1H-pyrrole-3-carboxylic acid (2-diethylaminoethyl)amide to give 210 mg (92%) of the title compound as a yellow orange solid.

¹HNMR (360 MHz, DMSO-d6) δ 13.6 (s, 1H, NH), 7.76 (d, J=8.0 Hz, 1H), 7.66 (s, 1H, H-vinyl), 7.57 (dd, J=1.5 & 8.0 Hz, 1H), 7.40–7.42 (m, 2H), 3.28 (m, 2H, CH₂), 2.88 (m, H-piperidine), 2.54 (m, 6H, 3xCH₂), 2.44 (s, 3H, CH₃), 2.40 (s, 3H, CH₃), 1.56 (m, H-piperidine), 0.97 (t, J=6.98 Hz, 6H, N(CH₂CH₃)₂).

MS m/z 424 [M⁺].

EXAMPLE 82 (FROM TABLE 1)

5-(5-Dimethylsulfamoyl-2-oxo-1,2-dihydroindol-3-ylidenemethyl)-2,4-dimethyl-1H-pyrrole-3-carboxylic acid (2-pyrrolidin-1-ylethyl)amide 2-Oxo-2,3-dihydro-1H-indole-5-sulfonic acid dimethylamide (90 mg, 0.38 mmol) was condensed with 5-formyl-2,4-dimethyl-1H-pyrrole-3-carboxylic acid (2-pyrrolidin-1-ylethyl)amide (100 mg) to give 100 mg (54%) of the title compound as a yellow solid.

¹HNMR (360 MHz, DMSO-d6) δ 13.65 (s, 1H, NH), 11.30 (s, br, 1H, NH), 8.25 (d, 1H), 7.92 (s, 1H, H-vinyl), 7.48–7.53 (m, 2H), 7.07 (d, J=8.2 Hz, 1H), 3.33 (m, 2H, CH₂), 2.61 (s, 6H, N(CH₃)₂), 2.56 (t, 2H, CH₃), 2.49 (m, 4H, 2xCH₂), 2.45 (s, 3H, CH₃), 2.44 (s, 3H, CH₃), 1.67 (m, 4H, 2xCH₂).

MS-EI m/z 485 [M⁺].

EXAMPLE 83 (FROM TABLE 1)

5-[5-(3-Chlorophenylsulfamoyl)-2-oxo-1,2-dihydroindol-3-ylidenemethyl]2,4-dimethyl-1H-pyrrole-3-carboxylic acid (2-pyrrolidin-1-ylethyl) amide 2-Oxo-2,3-dihydro-1H-indole-5-sulfonic acid (3-chlorophenyl)amide (120 mg, 0.38 mmol) was condensed with 5-formyl-2,4-dimethyl-1H-pyrrole-3-carboxylic acid (2-pyrrolidin-1-ylethyl)amide (100 mg) to give 150 mg (69%) of the title compound as a yellow orange solid.

$^1$HNMR (360 MHz, DMSO-d6) δ 13.55 (s, 1H, NH), 11.26 (br s, 1H, NH), 10.30 (br s, 1H, NH), 8.26 (d, 1H), 7.79 (s, 1H, H-vinyl), 7.51–7.57 (m, 2H), 7.22 (t, J=8.1 Hz, 1H), 7.15 (m, 1H), 7.07 (m, 1H), 7.0 (m, 2H), 3.44 (m, 2H, CH$_2$), 2.57 (t, J=7.0 Hz, 2H, CH$_2$), 2.49 (m, 4H, 2xCH$_2$), 2.44 (s, 3H, CH$_3$), 2.43 (s, 3H, CH$_3$), 1.68 (m, 4H, 2xCH$_2$).

MS m/z 568 [M$^+$].

EXAMPLE 84 (FROM TABLE 1)

2,4-Dimethyl-5-[2-oxo-5-(pyridin-3-ylsulfamoyl)-1,2-dihydroindol-3-ylidenemethyl]-1H-pyrrole-3-carboxylic acid (2-pyrrolidin-1-ylethyl)amine 2-Oxo-2,3-dihydro-1H-indole-5-sulfonic acid pyridin-3-ylamide (110 mg, 0.38 mmol) was condensed with 5-formyl-2,4-dimethyl-1H-pyrrole-3-carboxylic acid (2-pyrrolidin-1-ylethyl)amide (100 mg) to give 150 mg (74%) of the title compound as an orange solid.

$^1$HNMR (360 MHz, DMSO-d6) δ 13.58 (s, 1H, NH), 8.21 (d, J=2.0 Hz, 2H), 8.04 (m, 1H), 7.76 (s, 1H, H-vinyl), 7.49–7.54 (m, 2H), 7.41 (m, 1H), 7.14 (m, 1H), 6.94 (d, J=8.5 Hz, 1H), 3.33 (m, 2H, CH$_2$), 2.56 (t, J=7.06 Hz, 2H, CH$_2$), 2.49 (m, 4H, 2xCH$_2$), 2.43 (s, 6H, 2xCH$_3$), 1.68 (m, 4H, 2xCH$_2$).

MS m/z 535 [M$^+$].

EXAMPLE 85 (FROM TABLE 1)

3-[3,5-Dimethyl-4-(4-methylpiperazine-1-carboxyl)-1H-pyrrol-2-ylmethylene]-4-(2-hydroxyethyl)-1,3-dihydroindol-2-one 4-(2-Hydroxyethyl)-1,3-dihydroindol-2-one (71 mg, 0.4 mmol) was condensed with 3,5-dimethyl-4-(4-methylpiperazine-1-carbonyl)-1H-pyrrole-2-carbaldehyde to give 90 mg (55%) of the title compound as an orange solid.

$^1$HNMR (300 MHz, DMSO-d6) δ 14.25(s, 1H, NH), 10.88 (s, 1H, NH), 7.57 (s, 1H, H-vinyl), 7.03 (m, 1H), 6.75–6.82 (m, 2H), 4.86 (m, 1H, OH), 3.70 (m, 2H, CH$_2$), 3.04 (m, 2H, CH$_2$), 2.48 (m, 4H, 2xCH$_2$), 2.28 (br s, 7), 2.19 (s, 3H, CH$_3$), 2.18 (s, 3H, CH$_3$).

MS m/z (+ve) 4.09.3 [M$^+$].

EXAMPLE 86 (FROM TABLE 1)

3-[3,5-Diethyl-4-(4-methylpiperazine-1-carbonyl)-1H-pyrrol-2-ylmethylene]-2-oxo-2,3-dihydro-1H-indole-5-sulfonic acid phenylamide 2-Oxo-2,3-dihydro-1H-indole-5-sulfonic acid phenylamide (110 mg, 0.4 mmol) was condensed with 3,5-dimethyl-4-(4-methylpiperazine-1-carbonyl)-1H-pyrrole-2-carbaldehyde (100 mg) to give 50 mg (24%) of the title compound as a yellow solid.

$^1$HNMR (300 MHz, DMSO-d6) δ 13.52 (s, 1H, NH), 11.26 (s, 1H, NH), 10.08 (s, 1H, NH), 8.21 (d, J=1.6 Hz, 1H), 7.75 (s, 1H, H-vinyl), 7.50 (dd, J=1.6 & 8.3 Hz, 1H), 7.19 (m, 2H), 7.10 (m, 2H), 6.97 (m, 2H), 2.49 (m, 4H, 2xCH$_2$), 2.28 (m, 10H, 2xCH$_3$ & 2xCH$_2$), 2.18 (s, 3H, CH$_3$).

MS-EI m/z 519 [M$^+$].

EXAMPLE 87 (FROM TABLE 1)

5-(5-Dimethylsulfamoyl-2-oxo-1,2-dihydroindol-3-ylidenemethyl)-2,4-dimethyl-1H-pyrrole-3-carboxylic acid (2-diethylaminoethyl)amide 2-Oxo-2,3-dihydro-1H-indole-5-sulfonic acid dimethylamide (90 mg, 0.38 mmol) was condensed with 5-formyl-2,4-dimethyl-1H-pyrrole-3-carboxylic acid (2-diethylaminoethyl)amide (100 mg) to give 80 mg (43%) of the title compound as a yellow solid.

$^1$HNMR (300 MHz, DMSO-d6) δ 11.30 (s, 1H, NH), 8.27 (d, J=1.7 Hz, 1H), 7.94 (s, 1H, H-vinyl), 7.49 (dd, J=1.7 & 8.0 Hz, 1H), 7.44 (m, 1H, CONHCH$_2$CH$_2$), 7.07 (d, J=8.0 Hz, 1H), 3.26 (m, 2H, CH$_2$), 2.60 (s, 6H, N(CH$_3$)$_2$), 2.53 (m, 2H, CH$_2$), 2.45–2.50 (m, 10H, 2xCH$_3$ & N(CH$_2$CH$_3$)$_2$, 0.96 (t, J=7.2 Hz, 6H, N(CH$_2$CH$_3$)$_2$).

MS-EI m/z 487 [M$^+$].

EXAMPLE 88 (FROM TABLE 1)

5-[5-(3-Chlorophenylsulfamoyl)-2-oxo-1,2-dihydroindol-3-yldienemethyl]-2,4-dimethyl-1H-pyrrole-3-carboxylic acid (2-diethylaminoethyl) amide 2-Oxo-2,3-dihydro-1H-indole-5-sulfonic acid (3-chlorophenyl)amide (120 mg, 3.8 mmol) was condensed with 5-formyl-2,4-dimethyl-1H-pyrrole-3-carboxylic acid (2diethylaminoethyl)amide (100 mg) to give 80 mg (37%) of the title compound as a yellow solid.

$^1$HNMR (360 MHz, DMSO-d6) δ 13.55 (s, 1H, NH), 11.24 (s, 1H, NH), 10.29 (s, 1H, NH), 8.25 (d, J=1.87 Hz, 1H), 7.79 (s, 1H, H-vinyl), 7.52 (dd, J=1.87 & 8.3 Hz, 1H), 7.42 (m, 1H, CONHCH$_2$CH$_2$), 7.22 (t, J=8.02 Hz, 1H), 7.15 (t, J=2 Hz, 1H), 7.08 (m, 1H), 7.0 (m, 2H), 3.27 (m, 2H, CH$_2$), 2.48–2.57 (m, 6H, 3xCH$_2$), 2.45 (s, 3H, CH$_3$), 2.44 (s, 3H, CH$_3$), 0.97 (t, J=7.0 Hz, 6H, N(CH$_2$CH$_3$)$_2$).

MS m/z 570.1 [M$^+$].

EXAMPLE 95 (FROM TABLE 1)

3-(2-Oxo-5-phenyl-1,2-dihydroindol-3-ylidenemethyl)-4,5,6,7-tetrahydro-2H-isoindole-1-carboxylic acid ethyl ester $^1$HNMR (360 MHz, DMSO-d6) δ 13.74 (s, 1H, NH), 11.00 (s, 1H, NH), 8.13 (d, J=1.7 Hz, 1H), 7.74 (s, 1H, H-vinyl), 7.70 (d, J=7.7 Hz, 2H), 7.49 (dd, J=1.7 & 8.0 Hz, 1H), 7.44 (t, J=7.7 Hz, 2H), 7.32 (m, 1H), 6.96 (d, J=8.0 Hz, 1H), 4.26 (q, J=7.0 Hz, 2H, OCH$_2$CH$_3$), 2.79 (m, 2H, CH$_2$), 2.72 (m, 2H, CH$_2$), 1.73 (m, 4H, 2xCH$_2$), 1.30 (t, J=7.0 Hz, 3H, OCH$_2$CH$_3$).

MS-EI m/z 412 [M$^+$].

EXAMPLE 99 (FROM TABLE 1)

3-(2-Oxo-5-phenylsulfamoyl-1,2-dihydroindol-3-ylidenemethyl)-4,5,6,7-tetrahydro-2H-isoindole-1-carboxylic acid ethyl ester $^1$HNMR (360 MHz, DMSO-d6) δ 13.64 (s, 1H, NH), 11.33 (s, 1H, NH), 10.07 (s, 1H, NH), 8.24 (d, J=1.8 Hz, 1H), 7.74 (s, 1H, H-vinyl), 7.57 (dd, J=1.8 & 8.0 Hz, 1H), 7.21 (t, J=7.6 Hz, 2H), 7.11 (d, J=7.6 Hz, 2H), 6.99 (d, J=8.0 Hz, 1H), 6.98 (d, J=7.6 Hz, 1H), 4.27 (q, J=7.0 Hz, 2H, OCH$_2$CH$_3$), 2.80 (m, 2H, CH$_2$), 2.73 (m, 2H, CH$_2$), 1.73 (m, 4H, 2xCH$_2$), 1.30 (t, J=7.0 Hz, 3H, OCH$_2$CH$_3$).

MS-EI m/z 491 [M$^+$].

EXAMPLE 109 (FROM TABLE 1)

3-[3-(Morpholine-4-carbonyl)-4,5,6,7-tetrahydro-2H-isoinodol-1-ylmethylene]-2-oxo-2,3-dihydro-1H-indole-6-carboxylic acid $^1$HNMR (360 MHz, DMSO-d6) δ 13.60 (s, 1H, NH), 12.75 (br s, 1H, COOH), 11.08 (s, 1H, NH), 7.85 (d, J=7.8

Hz, 1H), 7.71 (s, 1H, H-vinyl), 7.62 (dd, J=1.4 & 7.8 Hz, 1H), 7.41 (d, J=1.4 Hz, 1H), 3.65 (m, 4H, 2xCH$_2$), 3.55 (m, 4H, 2xCH$_2$), 2.81 (m, 2H, CH$_2$), 2.54 (m, 2H, CH$_2$) 1.73 (m, 4H, 2XCH$_2$).

MS-EI m/z 421 [M$^+$].

EXAMPLE 112 (FROM TABLE 1)

5-Bromo-3-[3-(pyrrolidine-1-carbonyl)-4,5,6,7-tetrahydro-2H-isoindol-1-ylmethylene]-1,3-dihydro-indol-2-one $^1$HNMR (360 MHz, DMSO-d6) δ 13.56 (s, 1H, NH), 11.00 (s, 1H, NH), 8.05 (d, J=1.8 Hz, 1H), 7.74 (s, 1H, H-vinyl), 7.28 (dd, J=1.3 & 8.3 Hz, 1H), 6.83 (d, J=8.3 Hz, 1H), 3.57 (m, 4H, 2xCH$_2$), 2.79 (m, 2H, CH$_2$), 2.65 (m, 2H, CH$_2$), 1.88 (m, 4H, 2xCH$_2$), 1.71 (m, 4H, 2xCH$_2$).

MS-EI m/z 439 & 441 [M$^+$−1] & M$^+$+1].

EXAMPLE 114 (FROM TABLE 1)

3-(3-Dimethylcarbamoyl-4,5,6,7-tetrahydro-2H-isoindol-1-ylmethylene)-2-oxo-2,3-dihydro-1H-indole-6-carboxylic acid $^1$-HNMR (360 MHz, DMSO-d6) δ 13.60 (s, 1H, NH), 12.72 (br s, 1H, COOH), 11.05 (s, 1H, NH), 7.85 (d, J=7.9 Hz, 1H), 7.72 (s, 1H, H-vinyl), 7.6 (dd, J=1.3 & 7.9 Hz, 1H), 7.42 (d, J=1.3 Hz, 1H), 3.03 (s, 6H, N(CH$_3$)$_2$), 2.81 (m, 2H, CH$_2$), 2.55 (m, 2H, CH$_2$), 1.73 (m, 4H, 2xCH).

MS-EI m/z 379 [M$^+$].

EXAMPLE 115 (FROM TABLE 1)

4-Methyl-5-(5-methylsulfamoyl-2-oxo-1,2-dihydro-indol-3-ylidenemethyl)-1H-pyrrole-3-carboxylic acid $^1$HNMR (300 MHz, DMSO-d6) 13.56 (br s, 1H, NH), 8.24 (d, J=1.5 Hz, 1H), 7.86 (s, 1H, H-vinyl), 7.74 (d, J=2.96 Hz, 1H), 7.56 (dd, J=1.5 & 8.1 Hz, 1H), 7.20 (br m, 1H, NHCH$_3$), 7.03 (d, J=8.1 Hz, 1H), 2.57 (s, 3H, CH$_3$), 2.41 (s, 3H, CH$_3$).

MS-EI m/z 361 [M$^+$].

EXAMPLE 116 (FROM TABLE 1)

{[4-Methyl-5-(4-methyl-5-methylsulfamoyl-2-oxo-1,2-dihydro-indol-3-ylidenemethyl)-1H-pyrrole-3-carbonyl]-amino}-acetic acid ethyl ester 4-Methyl-1H-pyrrole-3-carboxylic acid ethyl ester (lit. ref. D. O. Cheng, T. L. Bowman and E. LeGroff; J. Heterocyclic Chem.; 1976, 13; 1145–1147) was formylated using method A, hydrolyzed using method B followed by amidation (method C) to give [(5-formyl-4-methyl-1H-pyrrole-3-carbonyl)-amino]-acetic acid ethyl ester.

5-Methyl-5-methylaminosulfonyl-2-oxindole (50 mg, 0.21 mmol) was condensed with [(5-formyl-4-methyl-1H-pyrrole-3-carbonyl)-amino]-acetic acid ethyl ester (100 mg, 0.42 mmol) and piperidine (0.1 mL) in ethanol (2 mL) to give 50 mg (52%) of the title compound.

$^1$HNMR (360 MHz, DMSO-d6) δ 13.59 (s, 1H, NH), 11.29 (v.br. s, 1H, NH-CO), 8.33 (t, J=5.8 Hz, 1H, CONHCH$_2$), 7.83 (d, J=3.11 Hz, 1H), 7.80 (s, 1H, H-vinyl), 7.71 (d, J=8.5 Hz, 1H), 7.34 (br m, 1H, NCH$_3$), 6.89 (d, J=8.5 Hz, 1H), 4.11 (q, J=7.1 Hz, 2H, OCH$_2$CH$_3$), 3.92 (d, J=5.8 Hz, 2H, GlyCH$_2$), 2.86 (s, 3H, CH$_3$), 2.48 (s, 3H, CH$_3$), 2.42 (d, J=4.71 Hz, 3H, HNCH$_3$), 1.20 (t, J=7.1 Hz, 3H, OCH$_2$CH$_3$).

MS-EI m/z 460 [M$^+$].

EXAMPLE 117 (FROM TABLE 1)

{[4-Methyl-5-(5-methylsulfamoyl-2-oxo-1,2-dihydro-indol-3-ylidenemethyl)-1H-pyrrole-3-carbonyl]-amino}-acetic acid ethyl ester A mixture of 5-methylaminosulfonyl-2-oxindole (0.06 g, 0.22 mmol), [(5-formyl-4-methyl-1H-pyrrole-3-carbonyl)-amino]-acetic acid ethyl ester (0.075 g, 0.27 mmol) and piperidine (2 drops) in ethanol (5 mL) was heated in a sealed tube at 90° C. for 12 hrs. After cooling, the precipitate was collected by vacuum filtration, washed with ethanol, triturated with dichloromethane/ether and dried to give 0.035 g (36%), of the title compound as a yellowish brown solid.

$^1$H NMR (360 MHz, DMSO-d6) δ 13.6 (s, 1H, NH), 11 (v.br. s, 1H, NH-CO), 8.30 (t, J=5.7 Hz, 1H, CONHCH$_2$), 8.25 (d, J=1.2 Hz, 1H), 7.88 (s, 1H, H-vinyl), 7.84 (d, J=3.3 Hz, 1H), 7.57 (dd, J=1.9 & 8.5 Hz, 1H), 7.14 (br m, 1H, NHCH$_3$), 7.04 (d, J=8.5 Hz, 1H), 4.11 (q, J=6.7 Hz, 2H, OCH$_2$CH$_3$), 3.92 (d, J=5.7 Hz, 2H, GlyCH$_2$), 2.55 (s, 3H, CH$_3$), 2.41 (m, 3H, NCH$_3$), 1.20 (t, J=6.7 Hz, 3H, OCH$_2$CH$_3$).

MS m/z 446 [M$^+$].

EXAMPLE 118 (FROM TABLE 1)

{[4-Methyl-5-(5-methylsulfamoyl-2-oxo-1,2-dihydro-indol-3-ylidenemethyl)-1H-pyrrole-3-carbonyl]-amino}-acetic acid A mixture of [(5-formyl-4-methyl-1H-pyrrole-3-carbonyl)-amino]-acetic acid ethyl ester (0.142 g, 0.59 mmol) and 1N NaOH (1.2 mL) in methanol (10 mL) was stirred at room temperature for 1 hr. The reaction was concentrated and the residue was condensed with 5-methylaminosulfonyl-2-oxindole (0.13 g, 0.48 mmol) and piperidine (0.12 mL) in ethanol (12 mL) to give 0.11 g (52%) of the title compound.

$^1$HNMR (300 MHz, DMSO-d6) δ 13.98 (br s, 1H, NH), 8.17 (s, 1H), 7.80 (s, 1H), 7.75 (d, J=3.1Hz, 1H), 7.51 (dd, J=2. & 8.2 Hz, 1H), 7.21 (m on br s, 2H), 6.97 (d, J=8.1 Hz, 1H), 3.41 (d, J=4.2 Hz, 2H, CH$_2$NH), 2.54 (s, 3H, pyrrole-CH$_3$), 2.39 (s, 3H, ArCH$_3$).

MS m/z 417 [M−1]$^+$.

EXAMPLE 120 (FROM TABLE 1)

5-Methyl-2-(2-oxo-1,2-dihydro-indol-3-ylidenemethyl)-1H-pyrrole-3-carboxylic acid $^1$HNMR (300 MHz, DMSO-d6) δ 13.77 (br s, 1H, NH), 12.49 (s, 1H, COOH), 11.07 (s, 1H, NH), 8.39 (s, 1H, H-vinyl), 7.43 (d, J=7.47 Hz, 1H), 7.20 (t, J=7.47 Hz, 1H), 7.03 (t, J=7.47 Hz, 1H), 6.91 (d, J=7.47 Hz, 1H), 6.49 (d, J=1.53 Hz, 1H), 2.34 (s, 3H, CH$_3$).

MS m/z 269 [M+H]$^+$.

EXAMPLE 121 (FROM TABLE 1)

5-Methyl-2-(2-oxo-1,2-dihydro-indol-3-ylidenemethyl)-1H-pyrrole-3-carboxylic acid ethyl ester $^1$HNMR (300 MHz, DMSO-d6) δ 13.79 (s, 1H, NH), 11.08 (s, 1H, NH), 8.31 (s, 1H, H-vinyl), 7.45 (d, J=7.52 Hz, 1H), 7.20 (t, J=7.52 Hz, 1H), 7.03 (t, J=7.52 Hz, 1H), 6.91 (d, J=7.52 Hz, 1H), 6.50 (d, J=2.1 Hz, 1H), 4.26 (q, J=7.2

Hz, 2H, OCH$_2$CH$_3$), 2.33 (s, 3H, CH$_3$), 1.32 (t, J=7.2 Hz, 3H, OCH$_2$CH$_3$).

MS m/z 297.1 [M+H]$^+$.

EXAMPLE 122 (FROM TABLE 1)

2-(5-Bromo-2-oxo-1,2-dihydroindol-3-ylidenemethyl)-5-methyl-1H-pyrrole-3-carboxylic acid ethyl ester $^1$HNMR (360 MHz, DMSO-d6) δ 13.72 (s, 1H, NH), 11.16 (s, 1H, NH), 8.29 (s, 1H, H-vinyl), 7.53 (d, J=2.0 Hz, 1H), 7.35 (dd, J=2.0 & 8.05 Hz, 1H), 6.87 (t, J=8.05 Hz, 1), 6.53 (d, J=2.4 Hz, 1H), 4.28 (q, J=7.03 Hz, 2H, OCH$_2$CH$_3$), 2.35 (s, 3H, CH$_3$), 1.33 (t, J=7.03 Hz, 3H, OCH$_2$CH$_3$).

MS m/z 375 & 377 [M+H]$^+$.

EXAMPLE 123 (FROM TABLE 1)

2-(5-Bromo-2-oxo-1,2-dihydroindol-3-ylidenemethyl)-5-methyl-1H-pyrrole-3-carboxylic acid $^1$HNMR (300 MHz, DMSO-d6) δ 13.72 (s, 1H, NH), 12.57 (s, 1H, COOH), 11.19 (s, 1H, NH), 8.36 (s, 1H-vinyl), 7.51 (d, J=1.4 Hz, 1H), 7.34 (dd, J=1.4 & 8.17 Hz, 1H), 6.87 (t, J=8.17 Hz, 1H), 6.52 (d, J=2.5 Hz, 1H), 2.35 (s, 3H, CH$_3$).

MS m/z 347 & 349 [M+H]$^+$.

EXAMPLE 124 (FROM TABLE 1)

2-(5-Bromo-2-oxo-1,2-dihydroindol-3-ylidenemethyl)-5-methyl-1H-pyrrole-3-carboxylic acid (2-pyrrolidin-1-ylethyl)-amide To a solution of 2-formyl-5-methyl-1H-pyrrole-3-carboxylic acid (250 mg, 1.63 mmol) in dimethylformamide (3 mL) was added 1-ethyl-3-(3-dimethylaminopropyl) carbodiimide (376 mg, 1.2 equiv.), 1-hydroxybenzotriazole (265 mg, 1.2 equiv.), triethylamine (0.45 mL, 2 equiv.) and 1-(2-aminoethyl)pyrrolidine (0.23 mL, 1.1 equiv.). After stirring at room temperature overnight, the reaction was diluted with saturated sodium bicarbonate and brine (with extra salt) and extracted with 10% methanol in dichloromethane. The combined organic layers were washed with brine, dried over anhydrous sodium sulfate and concentrated to give 130 mg of 2-formyl-5-methyl-1H-pyrrole-3-carboxylic acid (2-pyrrolidin-1-yl-ethyl)-amide.

A mixture of 5-bromo-2-oxindole (106 mg, 0.5 mmol), 2-formyl-5-methyl-1H-pyrrole-3-carboxylic acid (2-pyrrolidin-1-yl-ethyl)-amide (125 mg, 1 equiv.) and piperidine (0.2 mL) in ethanol (2 mL) was heated in a sealed tube at 80° C. for 1 hr and then cooled. The precipitate which formed was collected by vacuum filtration, washed with ethanol and ethyl acetate and dried to give the title compound as an orange solid.

$^1$HNMR (300 MHz, DMSO-d6) δ 13.62 (s, 1H, NH), 11.06 (br s, 1H, NH), 8.56 (s, 1H, H-vinyl), 8.15 (m, 1H, CONHCH$_2$), 7.48 (d, J=1.8 Hz, 1H), 7.31 (dd, J=1.8 & 7.9 Hz, 1H), 6.86 (d, J=7.9 Hz, 1H), 6.60 (d, J=2.3 Hz, 1H), 3.35 (m, 2H, HNCH$_2$CH$_2$), 2.56 (t, J=6.91 Hz, 2H, HNCH$_2$CH$_2$), 2.35 (s, 3H, CH$_3$), 1.67 (m, 4H, 2xCH$_2$).

MS m/z 443/445 [M$^+$ and M$^+$+2].

EXAMPLE 125 (FROM TABLE 1)

2-(5-Bromo-2-oxo-1,2-dihydroindol-3-ylidenemethyl)-5-methyl-1H-pyrrole-3-carboxylic acid (2-diethylaminoethyl)-amide To a solution of 2-formyl-5-methyl-1H-pyrrole-3-carboxylic acid (320 mg, 2.1 mmol) in dimethylformamide (3 mL) was added 1-ethyl-3-(3-dimethylaminopropyl) carbodiimide (483 mg, 1.2 equivl.), 1-hydroxybenzotriaole (340 mg, 1.2 equiv.), triethylamine (0.59 mL, 2 equiv.) and N,N-diethylethylenediamine (0.32 mL, 1.1 equiv.). After stirring at room temperature overnight, the reaction was diluted with saturated sodium bicarbonate and brine (with extra salt) and extracted with 10% methanol in dichloromethane. The combined organic layers were washed with brine, dried over anhydrous sodium sulfate and concentrated to give 2-formyl-5-methyl-1H-pyrrole-3-carboxylic acid (2-diethylaminoethyl)-amide.

A mixture of 5-bromo-2-oxindole (106 mg, 0.5 mmol), 2-formyl-5-methyl-1H-pyrrole-3-carboxylic acid (2-diethylamino-ethyl)-amide (126 mg, 1 equiv.) and piperidine (0.2 mL) in ethanol (2 mL) was heated in a sealed tube at 80° C. for 1 hr and then cooled. The precipitate was collected by vacuum filtration, washed with ethanol and ethyl acetate and dried to give the title compound as an orange solid.

$^1$HNMR (360 MHz, DMSO-d6) δ 13.62 (s, 1H, NH), 11.11 (br s, 1H, NH), 8.54 (s, 1H, H-vinyl), 8.1 (m, 1H, CONHCH$_2$), 7.49 (d, J=2.2 Hz, 1H), 7.31 (dd, J=2.2 & 8.3 Hz, 1H), 6.86 (d, J=8.3 Hz, 1H), 6.58 (d, J=2.24 Hz, 1H), 3.31 (m, 2H, HNCH$_2$CH$_2$), 2.59 (m, 6H, 3xCH$_2$), 2.36 (s, 3H, CH$_3$), 0.99 (t, J=6.8 Hz, 6H, N(CH$_2$CH$_3$)$_2$).

MS m/z 445/447 [M$^+$ and M$^+$+2].

EXAMPLE 1 (FROM TABLE 3)

3-[5-(5-Chloro-2-oxo-1,2-dihydroindol-3-ylidenemethyl)-4-methyl-1H-pyrrol-3-yl]-propionic acid 4-(2-Carboxyethyl)-2-formyl-3-methylpyrrole (4.5 g), 4.2 g of 5-chloro-2-oxindole, and 2.9 mL of piperidine in 50 mL of ethanol were heated to 95° C. for 5 hours. The reaction mixture was collected and concentrated. The residue was suspended in acetone and the yellow precipitate was filtered, washed with cold ethanol, 2 N aqueous hydrochloric acid and water to pH 6 then dried in a vacuum oven overnight to give 7.2 g of the title compound (88%) as a yellow solid.

$^1$HNMR (360 MHz, DMSO-d6): δ 13.31 (s, br, 1H, NH-1'), 12.06 (s, br, 1H, COOH), 10.88 (s, br, 1H, NH-1), 7.93 (d, J=1.88Hz, 1H, H-4), 7.75 (s, 1H, H-vinyl), 7.19 (d, J=3.1 Hz, 1H, H-2'), 7.1 (dd, b, J=1.88, 8.40 Hz, 1H, H-6), 6.84 (d, J=8.40 Hz, 1H, H-7), 2.65 (t, J=7.44 Hz, 2H, CH$_2$CH$_2$COOH), 2.46 (t, J=7.44 Hz, 2H, CH$_2$CH$_2$COOH), 2.28 (s, 3H, CH$_3$).

EXAMPLE 2 (FROM TABLE 3)

3-[5-(6-Methoxy-2-oxo-1,2-dihydroindol-3-ylidenemethyl)-4-methyl-1H-pyrrol-3-yl]-propionic acid 4-(2-Carboxyethyl)-2-formyl-3-methylpyrrole (190 mg), 163 mg of 6-methoxy-2-oxindole, and 2 drops of piperidine in 2 mL of ethanol were heated to 90° C. for 3 hours. The reaction mixture was cooled and concentrated. The residue was suspended in 6 N aqueous hydrochloric acid. The precipitate was filtered, washed with water to pH 6 and dried in a vacuum oven to give 140 mg of the title compound (43%) as a brown solid.

$^1$HNMR (360 MHz, DMSO-d6): δ 13.1 (s, br, 1H, NH-1'), 12.04 (s, br, 1H, COOH), 10.76 (s, br, 1H, NH-1), 7.63 (d, J=8.29 Hz, 1H, H-4), 7.46 (s, 1H, H-vinyl), 7.07 (d, J=3.03 Hz, 1H, H-2'), 6.55 (dd, J=2.32, 8.29 Hz, 1H, H-5), 6.43 (d, J=2.32 Hz, 1H, H-7), 3.74 (s, 3H, OCH$_3$), 2.63 (t, J=7.31 Hz, 2H, CH$_2$CH$_2$COOH), 2.45 (t, J=7.31 Hz, 2H, CH$_2$CH$_2$COOH), 2.23 (s, 3H, CH$_3$); MS m/z. (relative intensity, %) 327 ([M+1]$^+$, 100).

EXAMPLE 3 (FROM TABLE 3)

3-[5-(5-Chloro-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (220 mg), 147 mg 5-chloro-2-oxindole, and 2 drops of piperidine in 2 mL of ethanol were heated to 90° C. for 3 hours. The reaction mixture was cooled and concentrated. The residue was suspended in 6 N of aqueous hydrochloric acid. The precipitate was filtered, washed with water to pH 6 and dried in a vacuum oven to give 172 mg of the title compound (50%) as a brown solid.

$^1$HNMR (360 MHz, DMSO-d6), δ 13.42 (s, br, 1H, NH-1'), 12.03 (s, br, 1H, COOH), 10.80 (s, br, 1H, NH-1), 7.87 (d, J=2.06Hz, 1H, H-4), 7.67 (s, 1H, H-vinyl), 7.06 (dd, J=2.06, 8.3Hz, 1H, H-6), 6.83 (d, J=8.3 Hz, 1H, H-7), 2.64 (t, J=7.6 Hz, 2H, CH$_2$CH$_2$COOH), 2.34 (t, J=7.6 Hz, 2H, CH$_2$CH$_2$COOH), 2.29 (s, 3H, CH$_3$), 2.27 (s, 3H, CH$_3$); MS m/z (relative intensity, %) 345 ([M+1]$^+$, 64).

EXAMPLE 4 (FROM TABLE 3)

3-[4-Methyl-5-(2-oxo-1,2-dihydroindol-3-ylidenemethyl)-1H-pyrrol-3-yl]-propionic acid Sodium metal (1.5 g) was placed in a 3 L 3-neck round bottom flask equipped with a thermometer, reflux condenser and mechanical stirring and placed in an oil bath. Absolute ethanol (1 L) was added with stirring. When the sodium had dissolved, 350 g of pentan-2,4-dione was added all at once and then 310 g of ethyl acrylate added over 30 minutes. The mixture was refluxed for 2.5 hours and then allowed to cool to room temperature overnight. Glacial acetic acid (3 mL) was added and the solvent removed by rotary evaporation. The residue was filtered through a pad of diatomaceous earth and distilled in a wiped film still at 0.1 mm. The distillate was redistilled using a 10 inch vacuum jacketed Vigreux column to give 518 g of ethyl 5-acetyl-4-oxohexanoate, BP 84–92° C. at 0.2–0.7 mm.

To a 5 L three-neck flask equipped with a thermometer and a mechanical stirrer and heated on a steam bath was added 350 g ethyl 5-acetyl-4-oxohexanoate, 329 g ethyl aminomalonate hydrochloride, 133 g sodium acetate and 1.2 L acetic acid. The mixture was heated to 99° C. over 37 minutes. By 62° C., carbon dioxide evolution was already rapid. After a total of 35 minutes at 99° C. gas, CO$_2$ evolution had greatly slowed. After another hour, the mixture was cooled, sodium chloride removed by vacuum filtration, and the solvent evaporated. The residue was mixed with 1 L of cold water. The precipitate was collected by vacuum filtration, washed with 400 mL water, and dissolved in 1 L of hot 95% ethanol. The solution was treated with 20 g of Darco G-60, hot-filtered, and cooled to room temperature. The crystalline solid was collected by vacuum filtration, washed twice on the filter with 200 mL of 50% ethanol and dried under vacuum at 70° C. to give 285 g (64% yield) of 2-ethoxycarbonyl-4-(2-ethoxycarbonylethyl)-3,5-dimethylpyrrole. The filtrate was refrigerated overnight to give another 53.1 g (11.9% yield) of product for a total yield of 75.9%).

2-Ethoxycarbonyl-4-(2-ethoxycarbonylethyl)-3,5-dimethylpyrrole (285 g) and 3500 mL of ethyl ether was placed in a 5 L, 3 neck flask equipped with a mechanical stirrer, a reflux condenser and an addition funnel and cooled in an ice bath. Sulfuryl chloride (435 g) was added dropwise over 145 minutes. As the addition proceeded the mixture turned cloudy and green, then cleared. At the end of the addition the mixture was clear and faintly yellow. The mixture was stirred for 1 additional hour and then heated to reflux for 1 hour. The mixture was cooled and rotary evaporated, diluted with 1500 mL of ether, and rotary evaporated again. The dilution and evaporation was repeated again. The residue was added to 8 L of water containing 802 g of acetic acid and 535 g of sodium hydroxide. The mixture was briefly heated to 85° C. and then allowed to cool overnight with stirring. The aqueous layer, which contained solids, was separated and extracted with 800 mL of ether. The solids and the ether layer were added to 2.5 L of water containing 300 g of sodium carbonate, stirred for 1 and filtered to remove a small amount (~7 g) of solid. Sulfurous acid (137 g) was added to the mixture and the resulting precipitate washed twice with 250 mL of water and dried under vacuum to give 56.4 g of product. Sulfurous acid (92 g) was added to the filtrate and the resulting precipitate washed twice with 0.5 L of water and dried under vacuum to give 220 g of product for a total of 276.4 g (86.8% yield) of 2-carboxy-5-ethoxycarbonyl-3-(2-ethoxycarbonylethyl)-4-methylpyrrole.

2-Carboxy-5-ethoxycarbonyl-3-(2-ethoxycarbonylethyl)-4-methylpyrrole (50.5 g) and 400 ml 10% sodium hydroxide solution was heated to 180° C. in a Parr autoclave for 90 minutes. This process was repeated 4 more times until a total of 252.2 g of 2-carboxy-5-ethoxycarbonyl-3-(2-ethoxycarbonylethyl)-4-methylpyrrole had been treated. The five solutions were combined and rotary evaporated to a volume of about 1.8 L of thick black residue. The mixture was cooled to 10° C. in a water bath and 50% sulfuric acid was slowly added so as to keep the temperature at <20° C. until the pH was 2. Ethyl ether (1400 mL) was added, the mixture filtered and the precipitate saved. The precipitate was extracted in a Soxhlet extractor with 500 mL of ether. The combined ether layers were washed with 250 mL water followed by 150 mL of water. The combined water layers were back extracted with 150 mL of ether. All the ether layers were rotary evaporated and the residue dried to give 123.5 g of 3-(2-carboxyethyl)-4-methylpyrrole.

3-(2-Carboxyethyl)-4-methylpyrrole (123 g) was mixed with 1500 mL of ethyl ether and 250 mL of methanol in a magnetically stirred receiver flask. A separate 3 L, 3 neck round bottom flask was equipped with magnetic stirring, a distillation head and condenser leading to the inlet of the receiver flask, and heated in a water bath. Into the 3 L flask was placed 240 g of Diazald dissolved in 1800 mL of ethyl ether and a solution of 73 g of potassium hydroxide dissolved in 360 mL of 95% ethanol and 112 mL of water. The 3L flask was stirred and heated to 65–75° C. in a water bath and the diazomethane-ether mixture was distilled into the stirred receiver flask over about 2.5 hours. Ethyl ether (200 mL) was added to the 3 L flask and the distillation continued until complete. The receiver flask was stirred for another 30 minutes and then 10 mL of acetic acid was added. The mixture was extracted twice with 500 mL of water, then twice with 200 mL of saturated sodium bicarbonate. The ether layer was dried over anhydrous sodium sulfate and distilled to leave a dark fluid residue. The residue was distilled twice through a 4 inch Vigreux column and once through a 10 inch vacuum-jacketed Vigreux column to give 108 g (80.6% yield) of 3-(2-ethoxycarbonylethyl)-4-methylpyrrole. BP 108–113° C. at 0.5 mm.

Dimethylformamide was charged to a 500 mL, 3 neck round bottom flask equipped with mechanical stirring, a thermometer and a dropping funnel and maintained under a nitrogen atmosphere. The flask was cooled to 0° C. and 58.4 mL of phosphorus oxychloride was added dropwise over 80 minutes. Dichloroethane (280 mL) was added and the mixture allowed to warm to room temperature and then cooled to −10° C. 3-(2-methoxycarbonyl-ethyl)-4-methylpyrrole (55.7 g) dissolved in 80 mL dichloroethane was added dropwise over 1 hour and the mixture stirred for another 35 minutes. The mixture was rotary evaporated at <30° C. The fluid residue was poured into 2700 mL of ice-cold 2 N sodium hydroxide solution. The resulting solution was heated to 88° C. over 20 minutes and then maintained at this temperature for an additional 30 minutes. The solution was cooled to ambient temperature and extracted with 200 mL of ethyl ether. The aqueous solution was cooled to 0° C. and acidified to pH 3:5 by slowly adding about 1350 mL of 5 N hydrochloric acid. The yellow precipitate was collected by vacuum filtration, washed four times with 100 mL of water, and dried in a vacuum oven at ambient temperature to give 54.4 g (90.2% yield) of crude 4-(2-carboxyethyl)-2-formyl-3-methylpyrrole.

The crude material was placed in a refluxing mixture of 425 mL of ethanol and 700 mL of ethyl ether and hot filtered to remove an insoluble residue, which was retained. The filtrate was put in the freezer and the resulting precipitate collected by vacuum filtration and washed with 50 mL of ether. The filtrate was used to again extract the insoluble residue, hot filtered and put in the freezer. The resulting precipitate and the first precipitate were combined to give 26.1 g of 4-(2-carboxyethyl)-2-formyl-3-methylpyrrole as a brown powder, MP 149.0–150.3° C. The filtrate was combined with the filtrate from a previous preparation and concentrated to give 43 g of a brown solid. The solid was put into a refluxing mixture of 500 ml ether and 100 mL ethanol, filtered. The filtrate treated with Norit at reflux and hot filtered again. The filtrate was put in the freezer to give 3 additional crops of 4-(2-carboxyethyl)-2-formyl-3-ethylpyrrole, 7.7 g, MP 148–151° C., 3.2 g MP 128–134° C. and 4.1 g, MP 148.2–150.0° C.

4-(2-Carboxyethyl)-2-formyl-3-methylpyrrole (9.0 g) and 6.0 g of 2-oxindole in 50 mL of ethanol were heated to 70° C. in a 250 mL, 3-neck round bottom flask equipped with a thermometer, a reflux condenser and magnetic stirring. When most of the solids had dissolved, 4.5 g of piperidine was slowly added and the mixture refluxed for 4 hours. Acetic acid (12 mL) was slowly added resulting in a copious precipitate. The mixture was refluxed for 5 minutes, cooled to room temperature and the precipitate collected by vacuum filtration and washed with 30 mL of ethanol. The precipitate was slurry-washed at reflux in 30 mL of ethanol, cooled to room temperature, collected by vacuum filtration, washed with 20 mL of ethanol and dried under vacuum to give 11.9 g (80% yield) of 3-[4-(2-carboxyethyl)-3-methylpyrrol-2-methylidenyl]-2-indolinone, SU6663, as an orange solid.

$^1$HNMR (360 MHz, DMSO-d6): δ 13.29 (s, br, 1H, NH-1'), 12.05 (s, br, 1H, COOH), 10.78 (s, br, 1H, NH-1), 7.73 (d, J=7.43 Hz, 1H, H-4), 7.61 (s, 1H, H-vinyl), 7.13 (d, J=2.75 Hz, 1H, H-2'), 7.10 (t, J=7.43 Hz, 1H, H-6), 6.97 (t, J=7.43 Hz, 1H, H-5), 6.85 (d, J=7.43 Hz, 1H, H-7), 2.64 (t, J=7.38 Hz, 2H, CH$_2$CH$_2$COOH), 2.46 (t, J=7.38 Hz, 2H, CH$_2$CH$_2$COOH), 2.25 (s, 3H, CH$_3$); MS m/z (relative intensity, %), 297 ([M+1]$^+$, 100).

EXAMPLE 5 (FROM TABLE 3)

3-[2,4-dimethyl-5-(2-oxo-1,2-dihydroindol-3-ylidenemethyl)-1H-pyrrol-3-yl]-propionic acid 2,4-dimethyl-5-ethoxycarbonyl-3-(2-ethoxycarbonyl-ethyl)-pyrrole (1.07 kg) and 3.2 L 5 N sodium hydroxide were mechanically stirred in a 12 L three-neck round bottom flask equipped with a reflux condenser and an addition funnel and heated in an oil bath. The mixture was refluxed for 3 hours after which time the internal temperature was 96° C., all solids were dissolved and thin layer chromatography showed hydrolysis to be complete. The heating bath was removed and the mixture cooled to 50° C. in a water bath. 12N Hydrochloric acid (~1.3 L) was slowly added. After about 50% of the acid was added gas evolution began and the temperature reached 60° C. As more acid was added, gas evolution increased and a yellow precipitate formed. The final pH was adjusted to 3.5 with hydrochloric acid. The mixture was cooled in an ice bath to 8° C. The solids were collected by vacuum filtration, washed twice with 0.5 L of distilled water and dried for 48 hours in a vacuum oven at 55–60° C. to give 677 g (101% yield) of 3-(2-carboxyethyl)-2,4-dimethylpyrrole.

$^1$HNMR (d$_6$-DMSO) δ 11.9 (s, 1H, COOH), 9.9(s, 1H, NH), 6.2(s, 1H, aromatic), 2.5 (t, 2H, CH$_2$), 2.2 (t, 2H, CH$_2$), 2.0(s, 3H, CH$_3$), 1.9(s, 3H, CH$_3$); MP 134–136° C.

Dimethylformamide (28.5 g) in 250 mL of dichloromethane in a 1 L three neck round bottom flask equipped with magnetic stirring, a thermometer and a dropping funnel was cooled in an ice-salt bath to −1° C. Phosphorus oxychloride (59.3 g) was placed in the dropping funnel and slowly added to the reaction mixture. The funnel was flushed with 25 mL of dichloromethane to be sure all the phosphorus oxychloride. The maximum temperature reached by the mixture was 5° C. The mixture was stirred for 15 minutes at which time the temperature was −3° C. Solid 3-(2-Carboxyethyl)-2,4-dimethylpyrrole (32.6 g) was added in portions over 15 minutes. The maximum temperature reached by the mixture was 7° C. The reddish-black mixture was stirred for 30 minutes more and then heated to reflux for 1 hour. The mixture was cooled to 15° C. and 300 mL of water was added leading to a vigorous reaction during which the temperature increased. The mixture was stirred and cooled to 22° C. and the layers separated and saved. The organic layer was extracted with 100 mL of water and the aqueous layers combined and washed with 50 ml of dichloromethane. The organic layers were discarded. The aqueous layer was adjusted to pH 11 with ~180 mL of 10 N sodium hydroxide. The temperature increased to 40° C. The mixture was stirred for 30 minutes at which time the temperature was 27° C. The mixture was acidified to pH 2 with ~120 mL of 10 N hydrochloric acid which increased the temperature to 30° C. Ethyl acetate (150 mL) was added and the mixture was stirred to extract the product. During stirring a considerable amount of black solid appeared on top of the water layer. The ethyl acetate layer was separated and the aqueous layer and solid was extracted twice with 100 mL of ethyl acetate. The solid still present was collected by vacuum filtration, washed thoroughly with water and dried under vacuum at 40° C. to give 12 g (31% yield) of 3-(2-carboxyethyl)-2,4-dimethyl-5-formylpyrrole as a brownish-black solid. Thin layer chromatography (dichloromethane:acetic acid, 95:5, silica gel) showed a spot at Rf 0.7 and a colored spot at the origin. The ethyl acetate layers were combined, dried over anhydrous sodium sulfate, and evaporated to a brownish-black solid which was dried under vacuum at 40° C. to give 21 g (55% yield, total yield 86%) of 3-(2-carboxyethyl)-2,4-dimethyl-5-formylpyrrole, identical in appearance to the previous solid by thin layer chromatography.

Alternatively, dimethylformamide (124 mL) in 750 mL of dichloromethane in a 5 L three-neck round bottom flask equipped with mechanical stirring, a thermometer and a dropping funnel was cooled in an ice-salt bath to −9° C. Phosphorus oxychloride (114 mL) was added rapidly via the dropping funnel which was flushed into the reaction mixture with 50 mL of dichloromethane. The maximum temperature reached by the mixture was −4° C. Solid 3-(2-carboxyethyl)-2,4-dimethylpyrrole (133.6 g) was added in portions over 20 minutes. The maximum temperature reached by the mixture was 3° C. The dark reddish mixture was heated to reflux for 1 minute and then cooled to −1° C. The mixture was cooled to 1° C. and 800 mL of ice water was rapidly added. The maximum temperature reached was 15° C. The organic layer was separated and discarded. The aqueous layer was slowly adjusted to pH 12–13 with ~800 mL of 10 N potassium hydroxide, adding ice to control the temperature. The temperature increased to 37° C. The mixture was stirred for 90 minutes at ambient temperature at which time thin layer chromatography showed only a trace of light-colored material at the origin with the product at Rf 0.3. The mixture was cooled to 0° C. The mixture was acidified to pH 3 with ~600 mL of 10 N hydrochloric acid ice being added to control the temperature. The maximum temperature reached was 10° C. The mixture was stirred for 1 hour in the cold. The solid was collected by vacuum filtration, washed 4 times with 100 mL of water and dried under vacuum at 50–60° C. to give 140.6 g (90% yield) of 3-(2-carboxyethyl)-2,4-dimethyl-5-formylpyrrole as a brown solid.

$^1$HNMR ($d_6$-DMSO): δ 12.0(s, 1H, COOH), 11.3(s, 1H, NH), 9.4(s, 1H, CHO), 2.6 (t, 2H, $CH_2$), 2.3 (t, 2H, $CH_2$), 2.2(s, 3H, $CH_3$), 2.1(s, 3H, $CH_3$). MP 145–147° C.

3-(2-Carboxyethyl)-2,4-dimethyl-5-dormylpyrrole-(18.2 g) and 11.7 g 2-oxindole were dissolved in 100 mL of ethanol by heating in a 250 mL round bottom flask equipped with a magnetic stirrer and a reflux condenser in an oil bath. Pyrrolidine (7.0 g) was added and the reaction mixture refluxed for 2 hours at which time a large quantity of brown-black solid was present. Thin layer chromatography (ethyl acetate:ethanol:acetic acid 96:2:2, silica gel) showed the absence of oxindole starting material. Eight mL of acetic acid was added and the mixture refluxed for 15 minutes. The thick mixture was diluted with 50 mL of ethanol and cooled to 10° C. The solid was collected by vacuum filtration and washed with 50 mL of ethanol. The solid was stirred in 125 ml of ethanol at reflux for 10 minutes, cooled to 10° C., collected by vacuum filtration and washed with 50 mL of ethanol. The product was dried overnight at 45° C. under vacuum to give 25.5 g (88% yield) of 3-[2,4-dimethyl-3-(2-carboxyethyl) pyrrol-5-methylidenyl]-2-indolinone as an orange solid.

Alternatively, a mixture of 3-(5-formyl-2,4-dimethyl-1H-pyrrol-3-yl)-propionic acid (10 g, 51 mmol), 2-oxindole (6.5 g, 49 mmol) and sodium hydroxide (40 g, 58 mmol) dissolved in 50 ml of water was stirred at 50° C. for 4 hours. The reaction mixture was cooled to room temperature, filtered and the filtrate acidified with to pH 3 with 12 N hydrochloric acid. The solid which precipitated was collected by vacuum filtration, washed with 10 ml of water and dried under vacuum overnight. The crude solid slurry washed with hot ethanol twice. The solid was then collected by vacuum filtration, washed with 10 ml of ethanol and dried under vacuum to give 13.8 g (91%) of 3-[2,4-dimethyl-5-(2-oxo-1,2-dihydro-indol-3-ylidenemethyl)-1H-pyrrol-3-yl]-propionic acid.

$^1$HNMR (360 MHz, DMSO-d6): δ 13.38 (s, br, 1H, NH-1'), 12.05 (s, br, 1H, COOH), 10.70 (s, br, 1H, NH-1), 7.69 (d, J=7.39 Hz, 1H, H-4), 7.53 (s, 1H, H-vinyl), 7.06 (t, J=7.39 Hz, 1H, H-6), 6.95 (t, J=7.39 Hz, 1H, H-5), 6.85 (d, J=7.39 Hz, 1H, H-7), 2.63 (t, J=7.45 Hz, 2H, $CH_2CH_2COOH$), 2.34 (t, J=7.45 Hz, 2H, $CH_2CH_2COOH$), 2.28 (s, 3H, $CH_3$), 2.24 (s, 3H, $CH_3$); MS m/2 (relative intensity, %) 311 ([M+1]$^+$, 100).

EXAMPLE 6 (FROM TABLE 3)

3-[5-(5-Bromo-2-oxo-1,2-dihydroindol-3-ylidenemethyl)-4-methyl-1H-pyrrol-3-yl]-propionic acid 2-Oxindole (53.3 g) was suspended in 640 mL acetonitrile and the mixture cooled to 7° C. in an ice bath with mechanical stirring. Solid N-bromosuccinimide (74.8 g) was added in portions over 20 minutes. After about one-third of the N-bromosuccinimide had been added (over 5 minutes), the temperature had increased to 12° C. The addition was halted until the temperature of the mixture had dropped to 10° C. The addition was resumed keeping the temperature below 12° C. After the addition was complete, the mixture was stirred for 1 hour at 10° C. and then for 1 additional hour during which the mixture was allowed to warm to ambient temperature. The precipitate was collected by vacuum filtration, washed with 80 mL of ethanol and sucked dry for 20 minutes in the filtration funnel to give product containing 6.4% of 2-oxindole by HPLC. The solid was suspended in 1440 mL of denatured ethanol and slurry-washed by stirring and refluxing for 5 minutes at which time most of the solid had dissolved. The mixture was cooled in an ice bath to 13° C. The solid product was collected by vacuum filtration, washed with 80 mL of ethanol and dried under vacuum to give 57.7 g (68.0%) of 5-bromo-2-oxindole containing 1.13% 2-oxindole by HPLC. Slurry-washing with 30% less ethanol gave a better yield (88%) but contained more 2-oxindole (1.76%).

$^1$HNMR (360 MHz, DMSO-d6): δ 10.44 (s, br, 1H, NH-1), 7.32–7.36 (m, 2H), 6.76 (d, J=8.50 Hz, 1H, H-7), 3.5 (s, 2H, $CH_2$); MS m/z 212.1/214.1 ($M^+$/[M+2]$^+$).

4-(4-(2-Carboxyethyl)-2-formyl-3-methylpyrrole (90 mg), 106 mg 5-bromo-2-oxindole, and 75 μL piperidine in 2 mL ethanol were heated to 95° C. for 5 hours. The reaction mixture was cooled and concentrated. The residue was suspended in 2 N aqueous hydrochloric acid. The precipitate was filtered, washed with water to pH 6 and dried in a vacuum oven to give 120 mg (64%) of the title compound as a brown solid.

$^1$HNMR (360 MHz, DMSO-d6): δ 13.31 (s, br, 1H, NH-1'), 12.06 (s, br, 1H, COOH), 10.90 (s, br, 1H, NH-1), 8.06 (s, br, 1H, H-4), 7.75 (s, 1H, H-vinyl), 7.23 (d, br, J=8.50 Hz, 1H, H-6), 7.19 (d, J=2.84 Hz, 1H, H-2'), 6.80 (d, br, J=8.50 Hz, 1H, H-7), 2.65 (t, J=7.65 Hz, 2H, $CH_2CH_2COOH$), 2.46 (t, J=7.65 Hz, 2H, $CH_2CH_2COOH$), 2.28 (s, 3H, $CH_3$); MS m/z 375.1/377.2 ($M^+$/[M+2]$^+$).

EXAMPLE 7 (FROM TABLE 3)

3-[5-(5-Iodo-2-oxo-1,2-dihydroindol-3-ylidenemethyl)-4-methyl-1H-pyrrol-3-yl]-propionic acid 2-Oxindole (82.9 g) was suspended in 630 mL acetic acid and the moisture was mechanically stirred and cooled to 10° C. in an ice water bath. Solid N-iodosuccinimide (175 g) was added in portions over 10 minutes. After the addition was complete the mixture was stirred for 1 hour at 10° C. The suspended solid which was always present became very thick at this time. The solid was collected by vacuum filtration, washed with 100 mL of 50% acetic acid in water and then with 200 mL of water and sucked dry for 20 minutes in the filtration funnel. The product was dried under vacuum to give 93.5 g (36%) of 5-iodo-2-oxindole containing about 5% 2-oxindole by proton NMR.

$^1$HNMR (360 MHz, DMSO-d6): δ 10.45 (s, 1H, NH-1), 7.49 (s, 1H, H-4), 7.48 (d, J=8.10 Hz, 1H, H-6), 6.64 (d, J=8.10 Hz, 1H, H-7), and 3.46 (s, 2H, CH$_2$-3); MS m/z 258 [M−1]$^+$.

4-(2-Carboxyethyl)-2-formyl-3-methylpyrrole (90 mg), 130 mg 5-iodo-2-oxindole, and 75 L piperidine in 2 mL ethanol were heated at 95° C. for 5 hours. The reaction mixture was cooled and concentrated. The residue was suspended in 2 N aqueous hydrochloric acid. The precipitate was filtered, washed with water to pH 6 and dried in a vacuum oven to give 162 mg (77%) of the title compound as a brown solid.

$^1$HNMR (360 MHz, DMSO-d6): δ 13.30 (s, br, 1H, NH-1'), 12.06 (s, br, 1H, COOH), 10.88 (s, br, 1H, NH-1), 8.18 (s, br, 1H, H-4), 7.73 (s, 1H, H-vinyl), 7.40 (d, br, J=8.03 Hz, 1H, H-6), 7.19 (d, J=2.94 Hz, 1H, H-2'), 6.69 (d, br, J=8.03 Hz, 1H, H-7), 2.65 (t, J=7.40 Hz, 2H, CH$_2$CH$_2$COOH), 2.46 (t, J=7.40 Hz, 2H, CH$_2$CH$_2$COOH), 2.28 (s, 3H, CH$_3$); MS m/z 423 [M+1]$^+$.

EXAMPLE 8 (FROM TABLE 3)

3-[4-Methyl-5-(4-methyl-2-oxo-1,2-dihydroindol-3-ylidenemethyl)-1H-pyrrol-3-yl]-propionic acid Diethyl oxalate (30 mL) in 20 mL dry ether was added with stirring to 19 g potassium eethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternatively with 10% sodium hydroxide and 30% hydrogen peroxide until the dark red color was no longer present. The solid was filtered and the filtrate acidified with 6 N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of 4-methyl-2-oxindole as a white solid.

$^1$HNMR (360 MHz, DMSO-d6): δ 10.27 (s, br, 1H, NH-1), 7.06 (t, J=7.71 Hz, 1H, H-6), 6.74 (d, J=7.73 Hz, H-5), 6.63 (d, J=7.73 Hz, 1H, H-7), 3.36 (s, 2H, CH$_2$), 2.18 (s, 3H, CH$_3$).

4-(2-Carboxyethyl)-2-formyl-3-methylpyrrole (90 mg), 74 mg 4-methyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 80 mg (52%) of the title compound as a brown solid.

$^1$HNMR (360 MHz, DMSO-d6): δ 13.33 (s, br, 1H, NH-1'), 10.84 (s, br, 1H, NH-1), 7.54 (s, 1H, H-vinyl), 7.12 (d, J=2.0 Hz, 1H, H-2'), 7.01 (t, J=7.75 Hz, 1H, H-6), 6.79 (d, J=7.75 Hz, H-5), 6.74 (d, J=7.75 Hz, 1H, H-7), 2.64 (t, J=7.65 Hz, 2H, CH$_2$CH$_2$COOH), 2.57 (s, 3H, CH$_3$), 2.42 (t, J=7.65 Hz, 2H, CH$_2$CH$_2$COOH), 2.19 (s, 3H, CH$_3$); MS m/z (relative intensity, %) 311 ([M+1]$^+$, 100).

EXAMPLE 9 (FROM TABLE 3)

3-[4-Methyl-5-(5-methyl-2-oxo-1,2-dihydroindol-3-ylidenemethyl)-1H-pyrrol-3-yl]-propionic acid 5-Methylisatin (15.0 g) and 60 mL hydrazine hydrate were heated at 140–160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6 N hydrochloric acid. After standing at room temperature for 2 days the precipitate was collected by vacuum filtration, washed with water and dried under vacuum to give 6.5 g (47% yield) of 5-methyl-2-oxindole.

$^1$HNMR (360 MHz, DMSO-d6): δ 10.20 (s, br, 1H, NH-1), 6.99 (s, 1H, H-4), 6.94 (d, J=8.11 Hz, 1H, H-6), 6.68 (d, J=8.11 Hz, 1H, H-7), 3.39 (s, 2H, CH$_2$-3), and 2.22 (s, 3H, CH$_3$-5).

4-(2-Carboxyethyl)-2-formyl-3-methylpyrrole (90 mg), 74 mg 5-methyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 65 mg (42%) of the title compound as a brown solid.

$^1$HNMR (360 MHz, DMSO-d6): δ 13.30 (s, br, 1H, NH-1'), 12.05 (s, br, 1H, COOH), 10.67 (s, br, 1H, NH-1), 7.57 (s, 2H, H-vinyl, H-4), 7.12 (d, J=2.65 Hz, 1H, H-2'), 6.91 (d, J=7.82 Hz, 1H, H-6), 6.74 (d, J=7.82 Hz, 1H, H-7), 2.65 (t, J=6.94 Hz, 2H, CH$_2$CH$_2$COOH), 2.46 (t, J=6.94 Hz, 2H, CH$_2$CH$_2$COOH), 2.30 (s, 3H, CH$_3$), 2.25 (s, 3H, CH$_3$); MS m/z (relative intensity, %), 311 ([M+1]$^+$, 100).

EXAMPLE 10 (FROM TABLE 3)

3-[5-(5,6-dimethoxy-2-oxo-1,2-dihydroindol-3-ylidenemethyl)-4-methyl-1H-pyrrol-3-yl]-propionic acid 4-(2-Carboxyethyl)-2-formyl-3-methylpyrrole (90 mg), 97 mg 5,6-dimethoxy-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 104 mg (58%) of the title compound as a brown solid.

$^1$HNMR (360 MHz, DMSO-d6): δ 13.19 (s, br, 1H, NH-1'), 12.05 (s, br, 1H, COOH), 10.53 (s, br, 1H, NH-1), 7.46 (s, 1H), 7.41 (s, 1H), 7.02 (s, 1H, H-2'), 6.45 (s, 1H), 3.74 (s, 3H, OCH$_3$), 3.70 (s, 3H, OCH$_3$), 2.59 (t, J=7.43 Hz, 2H, CH$_2$CH$_2$COOH), 2.44 (t, J=7.43 Hz, 2H, CH$_2$CH$_2$COOH), 2.22 (s, 3H, CH$_3$); MS m/z 357 [M+1]$^+$.

EXAMPLE 11 (FROM TABLE 3)

3-[5-(6-Chloro-2-oxo-1,2-dihydroindol-3-ylidenemethyl)-4-methyl-1H-pyrrol-3-yl]-propionic acid 4-(2-Carboxyethyl)-2-formyl-3-methylpyrrole (200 mg), 167.6 mg 6-chloro-2-oxindole, and 166 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 246 mg (74%) of the title compound as a brown solid.

$^1$HNMR (360 MHz, DMSO-d6): δ 13.22 (s, br, 1H, NH-1'), 12.09 (s, br, 1H, COOH), 10.95 (s, br, 1H, NH-1), 7.78 (d, J=7.95 Hz, 1H, H-4), 7.66 (s, 1H, H-vinyl), 7.18 (d, J=2.64 Hz, 1H, H-2'), 7.01 (dd, J=1.90, 7.95 Hz, 1H, H-5), 6.86 (d, J=1.90 Hz, 1H, H-7), 2.65 (t, J=7.14 Hz, 2H, $CH_2CH_2COOH$), 2.45 (t, J=7.14 Hz, 2H, $CH_2CH_2COOH$), 2.26 (s, 3H, $CH_3$).

EXAMPLE 12 (FROM TABLE 3)

3-[4-(2-Carboxyethyl)-3-methyl-1H-pyrrol-2-ylmethylene]-2-oxo-2,3-dihydro-1H-indole-5-carboxylic acid methyl ester 5-Iodo-2-oxindole (17 g) was refluxed with 2 g palladium diacetate, 18.2 triethylamine, 150 mL methanol, 15 mL dimethylsulfoxide and 2.6 g DPPP in an atmosphere saturated with carbon monoxide. After 24 hours, the reaction mixture was filtered to remove the catalyst and the filtrate was concentrated. The concentrate was chromatographed on silica gel using 30% ethyl acetate in hexane. The fractions containing product were concentrated and allowed to stand. The product precipitated and collected by vacuum filtration to give 0.8 g (7%) of 5-methoxycarbonyl-2-oxindole as an off-white solid.

$^1$HNMR (360 MHz, DMSO-d6) δ 10.70 (s, br, 1H, NH-1), 7.83 (dd, J=1.77, 8.29 Hz, 1H, H-6), 7.77 (s, br, 1H, H-4), 6.89 (d, J=8.29 (Hz, 1H, H-7), 3.80 (s, 3H, $COOCH_3$-5), 3.51 (s, 2H, $CH_2$-3).

4-(2-Carboxyethyl)-2-formyl-3-methylpyrrole (90.6 mg), 88.6 mg 5-methoxycarbonyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 123 mg (69%) of the title compound as a yellow solid.

$^1$HNMR (360 MHz, DMSO-d6): δ 13.27 (s, br, 1H, NH-1'), 12.0 (s, vbr, 1H, COOH), 11.16 (s, br, 1H, NH-1), 8.36 (s, br, 1H, H-4), 7.80 (s, 1H, H-vinyl), 7.40 (dd, J=1.80, 8.14 Hz, 1H, H-6), 7.20 (d, J=2.91 Hz, 1H, H-5'), 6.96 (d, J=8.14 Hz, 1H, H-7), 3.84 (s, 3H, $COOCH_3$), 2.66 (t, J=7.55 Hz, 2H, $CH_2CH_2COOH$), 2.46 (t, J=7.55 Hz, 2H, $CH_2CH_2COOH$), 2.30 (s, 3H, $CH_3$); MS m/z (relative intensity, %) 355 ([M+1]$^+$, 100).

EXAMPLE 13 (FROM TABLE 3)

3-[4-(2-Carboxy-ethyl)-3-methyl-1H-pyrrol-2-ylmethylene]-2-oxo-2,3-dihydro-1H-indole-5-carboxylic acid 2-Oxindole (6.7 g) was added to a stirred suspension of 23 g aluminum chloride in 30 mL dichloroethane in an ice bath. Chloroacetyl chloride (11.3 g) was slowly added and hydrogen chloride gas was evolved. After ten minutes of stirring, the reaction was warmed to 40 . 50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g 5-chloroacetyl-2-oxindole was stirred in 90 mL pyridine at 80–90° C. for 3 hours then cooled to room temperature. The precipitate was collected by vacuum filtration and washed with 20 mL of ethanol. The solid was dissolved in 90 mL of 2.5 N sodium hydroxide and stirred at 70–80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

$^1$HNMR (360 MHz, DMSO-d6) δ 12.56 (s, br, 1H, COOH-5), 10.70 (s, 1H, NH-1), 7.82 (dd, J=1.57, 7.79 Hz, 1H, H-6), 7.74 (s, br, 1H, H-4), 6.87 (d, J=7.79 Hz, 1H, H-7), and 3.53 (s, 2H, $CH_2$-3). MS m/z (relative intensity, %), 178 ([M+1]$^+$, 100).

4-(2-Carboxyethyl)-2-formyl-3-methylpyrrole (90.6 mg), 88.6 mg 5-carboxy-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven. The crude product was purified by chromatography on a silica gel column using ethyl acetate-hexane-acetic acid as the eluant to give 51 mg(30%) of the title compound as a yellow solid.

$^1$HNMR (360 MHz, DMSO-d6): δ 13.27 (s, br, 1H, NH-1), 12.28 (s, vbr, 2H, 2×COOH), 11.11 (s, br, 1H, NH-1), 8.34 (d, J=1.36 Hz, 1H, H-4), 7.78 (s, 1H, H-vinyl), 7.40 (dd, J=1.36, 8.20 Hz, 1H, H-6), 7.19 (d, J=3.07 Hz, 1H, H-5'), 6.93 (d, J=8.20 Hz, 1H, H-7), 2.65 (d, J=7.56 Hz, 2H, $CH_2CH_2COOH$), 2.46 (t, J=7.56 Hz, 2H, $CH_2CH_2COOH$), 2.29 (s, 3H, $CH_3$); MS m/z 341.0 [M+1]$^+$.

EXAMPLE 14 (FROM TABLE 3)

3-[4-Methyl-5-(2-oxo-5-sulfamoyl-1,2-dihydroindol-3-ylidene-methyl)-1H-pyrrol-3-yl]-propionic acid To a 100 mL flask charged with 27 mL of chlorosulfonic acid was added slowly 13.3 g 2-oxindole. The reaction temperature was maintained below 30° C. during the addition. After the addition, the reaction mixture was stirred at room temperature for 1.5 hr, heated to 68° C. for 1 hr, cooled and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL ammonium hydroxide in 10 mL ethanol and stirred at room temperature overnight. The mixture was concentrated and the solid collected by vacuum filtration to give 0.4 g (20% yield) of 5-aminosulfonyl-2-oxindole as an off-white solid.

$^1$HNMR (360 MHz, DMSO-d6); δ 10.67 (s, 1H, NH-1), 7.63–7.66 (m, 2H, H-4,6), 7.13 (s, 2H, 5-$SO_2NH_2$), 6.91 (d, J=8.04 Hz, 1H, H-7), and 3.56 (s, 2H, $CH_2$-3); MS m/z (relative intensity, %) 211 ([M–1]$^+$, 100).

4-(2-Carboxyethyl)-2-formyl-3-methylpyrrole (90.6 mg), 106 mg 5-aminosulfonyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 132 mg (70%) of the title compound as a yellow solid.

$^1$HNMR (360 MHz, DMSO-d6); δ 13.28 (s, br, 1H, NH-1'), 12.0 (s, vbr, 1H, COOH), 11.15 (s, br, 1H, NH-1), 8.20 (d, J=1.60 Hz, 1H, H-4), 7.73 (s, 1H, H-vinyl), 7.59 (dd, J=1.60, 8.17 Hz, 1H, H-6), 7.22 (d, J=2.85 Hz, 1H, H-2'), 7.10 (s, 2H, $NH_2$), 6.98 (d, J=8.17 Hz, 1H, H-7), 2.67 (t, J=7.41 Hz, 2H, $CH_2CH_2COOH$), 2.46 (t, J=7.41 Hz, 2H, $CH_2CH_2COOH$), and 2.29 (s, 3H, $CH_3$).

EXAMPLE 15 (FROM TABLE 3)

3-[4-Methyl-5-(5-methylsulfamoyl-2-oxo-1,2-dihydroindol-3-ylidenemethyl)-1H-pyrrol-3-yl]-propionic acid A suspension of 3.38 g of 5-chlorosulfonyl-2-oxindole in 10 mL 2 M methylamine in tetrahydrofuran was stirred at room temperature for 4 hours at which time a white solid was present. The precipitate was collected by vacuum filtration, washed twice with 5 mL of water and dried under vacuum at 40° C. overnight to give 3.0 g (88% yield) of 5-methylaminosulfonyl-2-oxindole.

$^1$HNMR (300 MHz, DMSO-d6): δ 10.87 (s, br, 1H, NH-1), 7.86 (s, br, 1H, 5-SO$_2$NHCH$_3$), 7.61 (d, J=7.80 Hz 1H, H-6), 7.32 (d, J=4.67 Hz, 1H, H-4), 6.97 (d, J=7.80 Hz, 1H, H-7), 2.53 (s, 2H, CH$_2$-3), and 2.36 (s, 3H, 5-SO$_2$NHCH$_3$); MS m/z (relative intensity, %) 226 (M$^+$, 100).

4-(2-Carboxyethyl)-2-formyl-3-methylpyrrole (90.6 mg), 113 mg 5-methylaminosulfonyl-2-oxindole, and 75 µL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 163 mg (83%) of the title compound as a yellow solid.

$^1$HNMR (360 MHz, DMSO-d6): δ 13.30 (s, br, 1H, NH-1'), 12.0 (s, vbr, 1H, COOH), 11.19 (s, br, 1H, NH-1), 8.18 (d, J=1.64 Hz, 1H, H-4), 7.80 (s, 1H, H-vinyl), 7.53 (dd, J=1.64, 8.17 Hz, 1H, H-6), 7.23 (d, J=2.80 Hz, 1H, H-2'), 7.13 (q, J=5.15 Hz, 1H, NHCH$_3$), 7.02 (d, J=8.17 Hz, 1H, H-7), 3.84 (s, 3H, COOCH$_3$), 2.66 (t, J=7.54 Hz, 2H, CH$_2$CH$_2$COOH), 2.47 (t, J=7.54 Hz, 2H, CH$_2$CH$_2$COOH), 2.41 (d, J=5.15 Hz, 3H, NCH$_3$), 2.30 (s, 3H, CH$_3$); MS m/z 390 [M+1]$^+$.

EXAMPLE 16 (FROM TABLE 3)

3-{3-[4-(2-Carboxy-ethyl)-3-methyl-1H-pyrrol-2-ylmethylene]-2-oxo-2,3-dihydro-1H-indol-5-yl}-propionic acid 5-Chloroacetyl-2-oxindole (4.18 g) in 30 mL trifluoroacetic acid in an ice bath was treated with 4.65 g triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-2-oxindole as a reddish-brown solid.

Potassium cyanide (2.0 g) was added to 15 mL dimethylsulfoxide and heated to 90° C. 5-Chloroethyl-2-oxindole (3.0 g) dissolved in 5 mL of dimethylsulfoxide was added slowly with stirring, and the reaction heated to 150° C. for 2 hours. The mixture was cooled, poured into ice water and the precipitate collected by vacuum filtration, washed with water, and dried to give crude product. The crude material was chromatographed on silica gel using 5% methanol in chloroform to give 1.2 g (42% yield) of the title compound.

5-Cyanoethyl-2-oxindole (4.02 g) in 10 mL water containing 25 mL of concentrated hydrochloric acid was refluxed for 4 hours. The mixture was cooled, water added and the resulting solid collected by vacuum filtration, washed with water and dried to give 1.9 g (44% yield) of 5-carboxyethyl-2-oxindole as a yellow solid.

$^1$HNMR (360 MHz, DMSO-d6): δ 12.00 (s, br, 1H, 5-CH$_2$CH$_2$COOH), 10.21 (s, 1H, NH-1), 7.05 (s, 1H, H-4), 6.99 (d, J=8.68 Hz, 1H, H-6), 6.69 (d, J=8.68 Hz, 1H, H-7), 3.40 (s, 2H, CH$_2$-3), 2.74 (t, J=7.44 Hz, 2H, 5-CH$_2$CH$_2$COOH), and 2.46 (t, J=7.44 Hz, 2H, —CH$_2$CH$_2$COOH).

4-(2-Carboxyethyl)-2-formyl-3-methylpyrrole (90.6 mg), 102.6 mg 5-carboxyethyl-2-oxindole and 75 µL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight. The crude solid was purified by chromatography a silica gel column eluting with ethyl acetate-hexane-acetic acid to give 121 mg (66%) of the title compound as a yellow solid.

$^1$HNMR (360 MHz, DMSO-d6): δ 13.30 (d, J=2.38 Hz, 1H, NH-1'), 12.0 3 (s, vbr, 2H, 2×COOH), 10.68 (s, br, 1H, NH-1), 7.63 (s, 1H, H-4), 7.59 (s, 1H, H-vinyl), 7.12 (d, J=2.64 Hz, 1H, H-2'), 6.96 (dd, J=1.22, 7.93 Hz, 1H, H-6), 6.75 (d, J=7.93 Hz, 1H, H-7), 2.81 (t, J=7.75 Hz, 2H, CH$_2$CH$_2$COOH), 2.65 (t, J=7.75 Hz, 2H, CH$_2$CH$_2$COOH), 2.55 (t, J=7.75 Hz, 2H, CH$_2$CH$_2$COOH), 2.46 (t, J=7.42 Hz, CH$_2$CH$_2$COOH), and 2.26 (s, 3H, CH$_3$).

EXAMPLE 17 (FROM TABLE 3)

3-[5-(5-Ethyl-2-oxo-1,2-dihydro-indol-3-ylidenemethyl)-4-methyl-1H-pyrrol-3-yl]-propionic acid 2-Oxindole (3 g) was suspended in 1,2-dichloroethane and slowly treated with 3.2 mL acetyl chloride. The resulting suspension was heated to 50° C. for 5 hours, cooled, and poured into water. The resulting precipitate was collected by vacuum filtration, washed copiously with water and dried under vacuum to give 2.9 g (73% yield) of 5-Acetyl-2-oxindole as a brown solid.

5-Acetyl-2-oxindole (2 g) in 15 mL trifluoroacetic acid in an ice bath was slowly treated with 1.8 g triethylsilane and then stirred at room temperature for 5 hours. One mL of triethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.

$^1$HNMR (360 MHz, DMSO-d6): δ 10.25 (s, br, NH-1), 7.03 (s, 1H, H-4), 6.97 (d, J=8.05 Hz, 1H, H-6), 6.69 (d, J=8.05 Hz, 1H, H-7), 3.40 (s, 2H, CH$_2$-3), 2.51 (q, J=7.69 Hz, 2H, CH$_2$CH$_3$-5), and 1.12 (t, J=7.42 Hz, 3H, CH$_2$CH$_3$-5).

4-(2-Carboxyethyl)-2-formyl-3-methylpyrrole (90.6 mg), 80.5 mg 5-ethyl-2-oxindole, and 75 µL of piperidine in 2 mL of ethanol were heated at 95° C. for 5 hours. The reaction mixture was cooled and concentrated. The residue was suspended in 6 N of aqueous hydrochloric acid. The precipitate was filtered, washed with water to pH 6 and dried in a vacuum oven overnight. The crude solid was purified by a chromatography on a silica gel column eluting with ethyl acetate-hexane-acetic acid to give 52 mg (32%) of the title compound.

$^1$HNMR (360 MHz, DMSO-d6): δ 13.31 (s, br, 1H, NH-1'), 12.0 4(s, vbr, 1H, COOH), 10.66 (s, 1H, NH-1), 7.59 (s, 2H, H-4 and H-vinyl), 7.11 (d, J=3.29 Hz, 1H, H-2'), 6.94 (d, J=7.85 Hz, 1H, H-6), 6.75 (d, J=7.85 Hz, 1H, H-7), 2.65 (t, J=7.66 Hz, 2H, CH$_2$CH$_2$COOH), 2.57 (q, J=7.83 Hz, 2H, CH$_3$CH$_2$), 2.46 (t, J=7.66 Hz, CH$_2$CH$_2$COOH), 1.20 (t, J=7.83, 3H, CH$_3$CH$_2$), 2.26 (s, 3H, CH$_3$); MS m/z 325 [M+1]$^+$.

EXAMPLE 18 (FROM TABLE 3)

3-[5-(5-Methoxy-2-oxo-1,2-dihydroindol-3-ylidenemethyl)-4-methyl-1H-pyrrol-3-yl]-propionic acid Chloral hydrate (9.6 g) was dissolved in 200 mL water containing 83 g sodium sulfate. The solution was warmed to 60° C., a solution of 11.4 g hydroxylamine hydrochloride in 50 mL water was added and the mixture was held at 60° C. In a separate flask, 6.4 g 4-anisidine and 4.3 mL concentrated hydrochloric acid in 80 mL of water and was warmed to 80° C. The first solution was added to the second and the resulting mixture was refluxed for 2 minutes, cooled slowly to room temperature, and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL water was warmed to 60° C. and 8.6 g N-(2-hydroximinoacetyl) anisidine was added in one portion. The stirred mixture was heated at 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid.

5-Methoxyisatin (5.0 g) and 30 mL hydrazine hydrate were heated to reflux for 15 minutes. The reaction mixture was cooled to room temperature and 50 mL water was added. The mixture was extracted 3 times with 25 mL of ethyl acetate, the organic layers were combined, dried over anhydrous sodium sulfate and concentrated to give a yellow solid. The solid was stirred in ethyl acetate and 1.1 g of insoluble material removed by vacuum filtration and saved. This material proved to be 2-hydrazino-carbonylmethyl-4-anisidine. The filtrate was concentrated and chromatographed on silica gel eluting with ethyl acetate:hexane 1:1 to give 0.7 g of 5-methoxy-2-oxindole as a dirty yellow solid. The 1.1 g of 2-hydrazinocarbonylmethyl-4-anisidine was refluxed for 1 hour in 20 mL of 1 N sodium hydroxide. The mixture was cooled, acidified to pH 2 with concentrated hydrochloric acid and extracted 3 times with 25 mL of ethyl acetate. The organic extracts were combined, washed with brine, dried over anhydrous sodium sulfate and concentrated to give 0.8 g of 5-methoxy-2-oxindole as a dirty yellow solid. The combined yield was 1.5 g or 33%.

$^1$HNMR (360 MHz, DMSO-d6): δ 10.13 (s, 1H, NH-1), 6.84 (s, 1H, H-4), 6.72 (d, J=8.68 Hz, 1H, H-6), 6.69 (d, J=8.68 Hz, 1H, H-7), 3.68 (s, 3H, OCH$_3$-5), 3.41 (s, 2H, CH$_2$-3). MS m/z (relative intensity, %) 163 ([M+1]$^+$, 100).

4-(2-Carboxyethyl)-2-formyl-3-methylpyrrole (90 mg), 82 mg of 5-methoxy-2-oxindole, and 2 drops piperidine in 2 mL of ethanol were heated at 95° C. overnight. The reaction mixture was cooled and concentrated. The residue was suspended in 6 N aqueous hydrochloric acid. The precipitate was filtered, washed with water to pH 6 and dried in a vacuum oven overnight to give 110 mg (67%) of the title compound as a brown solid.

$^1$HNMR (360 MHz, DMSO-d6): δ 13.38 (s, br, 1H, NH-1'), 12.03 (s, vbr, 1H, COOH), 10.57 (s, 1H, NH-1), 7.63 (s, 1H, H-vinyl), 7.42 (d, J=2.46 Hz, 1H, H-4), 7.12 (d, J=3.08 Hz, 1H, H-2'), 6.74 (d, J=8.26 Hz, 1H, H-6), 6.75 (dd, J=2.46, 8.26 Hz, 1H, H-7), 3.77 (s, 3H, OCH$_3$), 2.65 (t, J=7.40 Hz, 2H, CH$_2$CH$_2$COOH), 2.46 (t, J=7.40 Hz, CH$_2$CH$_2$COOH), 2.27 (s, 3H, CH$_3$); MS m/z (relative intensity, %) 327 ([M+1]$^+$, 100).

EXAMPLE 19 (FROM TABLE 3)

3-[5-(5-Bromo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 106 mg 5-bromo-2-oxindole, and 75 μL piperidine in 3 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight to give 171 mg (88%) of the title compound as an orange solid.

$^1$HNMR (360 MHz, DMSO-d6): δ 12.04 (s, vbr, 1H, COOH), 10.80 (s, br, 1H, NH-1), 8.0 (d, J=2.06 Hz, 1H, H-4), 7.67 (s, 1H, H-vinyl), 7.19 (dd, J=2.06, 8.40 Hz, 1H, H-6), 6.79 (d, J=8.40 Hz, 1H, H-7), 2.65 (t, J=7.63 Hz, 2H, CH$_2$CH$_2$COOH), 2.35 (t, J=7.63 Hz, 2H, CH$_2$CH$_2$COOH), 2.29 (s, 3H, CH$_3$), 2.27 (s, 3H, CH$_3$); MS m/z (relative intensity, %) 389 ([M+1]$^+$, 100).

3-[5-(5-Iodo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 130 mg 5-iodo-2-oxindole, and 75 μL piperidine in 3 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight to give 155 mg (71%) of the title compound as an orange solid.

$^1$HNMR (360 MHz, DMSO-d6): δ 13.41 (s, br, 1H, NH-1'), 12.03 (s, br, 1H, COOH), 10.79 (s, br, 1H, NH-1), 8.12 (d, J=1.70 H z, 1H, H-4), 7.65 (s, 1H, H-vinyl), 7.36 (dd, J=1.70, 7.93 H z, 1H, H-6), 6.79 (d, J=7.93 Hz, 1H, H-7), 2.64 (t, J=7.76 Hz, 2H, CH$_2$CH$_2$COOH), 2.34 (t, J=7.76 Hz, 2H, CH$_2$CH$_2$COOH), 2.29 (s, 3H, CH$_3$), 2.27 (s, 3H, CH$_3$); MS m/z (relative intensity, %) 437 ([M+1]$^+$, 100).

EXAMPLE 20 (FROM TABLE 3)

3-[5-(5-Iodo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 130 mg 5-iodo-2-oxindole, and 75 μL of piperidine in 3 mL of ethanol were stirred at 95° C. for 5 hours. The reaction mixture was cooled and concentrated. The residue was suspended in 6N aqueous hydrochloric acid. The precipitate was filtered, washed with water to pH 6 and dried in a vacuum oven overnight to give 155 mg of the title compound (71%) as an orange solid.

$^1$HNMR (360 MHz, DMSO-d6) δ 13.41 (s, br, 1H, NH-1'), 12.03 (s, br, 1H, COOH), 10.79 (s, br, 1H, NH-1), 8.12 (d, J=1.70 Hz, 1H, H-4), 7.65 (s, 1H, H-vinyl), 7.36 (dd, J=1.70, 7.93 Hz, 1H, H-6), 6.79 (d, J=7.93 Hz, 1H, H-7), 2.64 (t, J=7.76 Hz, 2H, CH$_2$CH$_2$COOH), 2.34 (t, J=7.76 Hz, 2H, CH$_2$CH$_2$COOH), 2.29 (s, 3H, CH$_3$), 2.27 (s, 3H, CH$_3$). MS m/z (relative intensity, %) 437 ([M+1]$^+$, 100).

EXAMPLE 21 (FROM TABLE 3)

3-[2,4-Dimethyl-5-(4-methyl-2-oxo-1,2-dihydroindol-3-ylidene-methyl)-1H-pyrrol-3-yl]-propionic acid 3-(2-Carboxyethyl)-2,4-dimethyl-5-formylpyrrole (97.5 mg), 74 mg 4-methyl-2-oxindole and 75 μL piperidine in 3 mL of ethanol were heated at 95° C. for 5 hours. The reaction mixture was cooled and concentrated. The residue was suspended in 6 N of aqueous hydrochloric acid. The precipitate was filtered, washed with water to pH 6 and dried in a vacuum oven overnight to give 60 mg (37%) of the title compound as a green solid.

¹HNMR (360 MHz, DMSO-d6): δ 13.41 (s, br, 1H, NH-1'), 12.03 (s, br, 1H, COOH), 10.72 (s, br, 1H, NH-1), 7.50 (s, 1H, H-vinyl), 7.01 (t, J=7.82 Hz, 1H, H-6), 6.79 (d, J=7.82 H z, H-5), 6.74 (d, J=7.82 Hz, 1H, H-7), 2.64 (t, J=7.76 Hz, 2H, $CH_2CH_2COOH$), 2.56 (s, 3H, $CH_3$), 2.34 (t, J=7.76 Hz, 2H, $CH_2CH_2COOH$), 2.29 (s, 3H, $CH_3$), 2.18 (s, 3H, $CH_3$); MS m/z (relative intensity, %) 325 ([M+1]$^+$, 100).

EXAMPLE 22 (FROM TABLE 3)

3-[2,4-Dimethyl-5-(5-methyl-2-oxo-1,2-dihydroindol-3-ylidenemethyl)-1H-pyrrol-3-yl]-propionic acid 3-(2-Carboxyethyl)-2,4-dimethyl-5-formylpyrrole (97.5 mg), 74 mg 5-methyl-2-oxindole, and 75 μL piperidine in 3 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight to give 104 mg (64%) of the title compound as a yellow solid.

¹HNMR (360 MHz, DMSO-d6): δ 13.38 (s, br, 1H, NH-1'), 12.02 (s, br, 1H, COOH), 10.57 (s, br, 1H, NH-1), 7.52 (s, br, 1H, H-4), 7.50 (s, 1H, H-vinyl), 6.87 (d, J=7.86 Hz, 1H, H-6), 6.73 (d, J=7.86 Hz, 1H, H-7), 2.63 (t, J=7.49 Hz, 2H, $CH_2CH_2COOH$), 2.34 (t, J=7.49 Hz, 2H, $CH_2CH_2COOH$), 2.29 (s, 3H, $CH_3$), 2.28 (s, 3H, $CH_3$), and 2.24 (s, 3H, $CH_3$); MS m/z (relative intensity, %) 325 ([M+1]$^+$, 66).

EXAMPLE 23 (FROM TABLE 3)

3-[5-(6-Hydroxy-2-oxo-1,2-dihydroindol-3-ylidenemethyl)-2,4-dimethyl-1H-pyrrol-3-yl]-propionic acid 3.26 g 6-methoxy-2-oxindole in 60- mL dichloromethane was cooled to −2° C. and 40 mL 1 M boron tribromide solution in dichloromethane was added dropwise. The reaction mixture was stirred in an ice bath for 1 hour and then at room temperature for 1 hour. It was then poured into ice water and extracted with ethyl acetate. The organic layer was washed with water and brine, dried over anhydrous sodium sulfate, concentrated, the precipitate which formed filtered and then dried in a vacuum oven overnight to give 2.56 g of the 6-hydroxy-2-oxindole (86% yield).

¹HNMR (360 MHz, DMSO-d6): δ 10.13 (s, 1H, NH-1), 9.22 (s, 1H, OH-6), 6.93 (d, J=7.76 Hz, 1H, H-4), 6.27–6.31 (m, 2H, H-5,7), and 3.29 (s, 2H, $CH_2$-3); MS m/z 150 [M+1]$^+$.

3-(2-carboxyethyl)-2,4-dimethyl-5-formylpyrrole (82 mg), 63 mg 6-hydroxy-2-oxindole, and 48 μL piperidine in 2 mL of ethanol were heated at 90° C. for two days. The reaction mixture was cooled, concentrated, and purified by silica gel column chromotography eluting with ethyl acetate-hexane-acetic acid to give 55 mg (40%) of the title compound as an dark brown solid.

¹HNMR (360 MHz, DMSO-d6): δ 13.10 (s, br, 1H, NH-1'), 12.0 (s, vbr, 1H, COOH), 10.51 (s, br, 1H, NH-1), 9.41 (s, 1H, OH), 7.44 (d, J=7.83, 1H, H-4), 7.29 (s, 1H, H-vinyl), 6.37 (dd, J=2.16, 7.83 Hz, 1H, H-5), 6.33 (d, J=2.16 Hz, 1H, H-7), 2.62 (t, J=7.75 Hz, 2H, $CH_2CH_2COOH$), 2.32 (t, J=7.75 Hz, 2H, $CH_2CH_2COOH$), 2.25 (s, 3H, $CH_3$), 2.20 (s, 3H, $CH_3$); MS m/z 325 [M+1]$^+$.

EXAMPLE 24 (FROM TABLE 3)

3-[5-(6-Methoxy-2-oxo-1,2-dihydroindol-3-ylidenemethyl)-2,4-dimethyl-1H-pyrrol-3-yl]-propionic acid 3-(2-carboxyethyl)-2,4-dimethyl-5-formylpyrrole (97.5 mg), 82 mg 6-methoxy-2-oxindole and 2 drops piperidine in 2 mL of ethanol were heated at 95° C. for overnight. The reaction mixture was cooled and concentrated. The residue was suspended in 2 N aqueous hydrochloric acid. The precipitate was filtered, washed with water to pH 6 and dried in a vacuum oven overnight to give 130 mg (76%) of the title compound as a yellow solid.

¹HNMR (360 MHz, DMSO-d6): δ 13.15 (s, br, 1H, NH-1'), 11.75 (s, vbr, 1H, COOH), 10.65 (s, br, 1H, NH-1), 7.58 (d, J=8.27, 1H, H-4), 7.29 (s, 1H, H-vinyl), 6.37 (dd, J=2.26, 8.27 Hz, 1H, H-5), 6.33 (d, J=2.26 Hz, 1H H-7), 3.74 (s, 3H, $OCH_3$), 2.62 (t, J=7.67 Hz, 2H, $CH_2CH_2COOH$), 2.33 (t, J=7.67 Hz, 2H, $CH_2CH_2COOH$), 2.26 (s, 3H, $CH_3$), and 2.22 (s, 3H, $CH_3$); MS m/z (relative intensity, %) 341 ([M+1]$^+$, 100).

EXAMPLE 25 (FROM TABLE 3)

3-[5-(6-Hydroxy-2-oxo-1,2-dihydroindol-3-ylidenemethyl)-4-methyl-1H-pyrrol-3-yl]-propionic acid 4-(2-carboxyethyl)-2-formyl-3-methylpyrrole (543 mg), 450 mg 6-hydroxy-2-oxindole, and 450 μL piperidine in 10 mL of ethanol were heated at 90° C. overnight. The reaction mixture was cooled and concentrated. The residue was suspended in 2 N aqueous hydrochloric acid. The precipitate was filtered, washed with water to pH 6 and dried in a vacuum oven overnight to give a brown solid.

¹HNMR (360 MHz, DMSO-d6): δ 13.05 (s, br, 1H, NH-1'), 10.60 (s, br, 1H, NH-1), 9.4 (s, 1H, OH), 7.49 (d, J=8.08, 1H, H-4), 7.35 (s, 1H, H-vinyl), 7.02 (d, J=3.22 Hz, 1H, H-2'), 6.38 (dd, J=2.28, 8.08 Hz, 1H, H-5), 6.32 (d, J=2.28 Hz, 1H, H-7), 2.62 (t, J=7.67 Hz, 2H, $CH_2CH_2COOH$), 2.44 (t, J=7.67 Hz, 2H, $CH_2CH_2COOH$), and 2.21 (s, 3H, $CH_3$); MS m/z (relative intensity, %) 313 ([M+1]$^+$, 60).

EXAMPLE 26 (FROM TABLE 3)

3-[5-(6-Hydroxy-2-oxo-1,2-dihydroindol-3-ylidenemethyl)-4-methyl-1H-pyrrol-3-yl]-propionic acid 3,5-dimethoxy-benzyl ester 3-[5-(6-Hydroxy-2-oxo-1,2-dihydroindol-3-ylidenemethyl)-4-methyl-1H-pyrrol-3-yl]-propionic acid (100 mg), 56 mg 3,5-dimethoxy-benzylchloride and 207 mg potassium carbonate in 2 mL anhydrous dimethylformamide were heated at 90° C. overnight. The reaction mixture was cooled, poured into water and extracted with ethyl acetate. The organic layer was washed with water and brine, dried over anhydrous sodium sulfate, and concentrated. The crude product was purified by chromatography on a silica gel column eluting with ethyl acetate-hexane-acetic acid to give 39 mg of the title compound as a brown solid.

¹HNMR (360 MHz, DMSO-d6): δ 13.06 (s, br, 1H, NH-1'), 10.60 (s, br, 1H, NH-1), 9.4 (s, br, 1H, OH), 7.49 (d, J=8.03, 1H, H-4), 7.35 (s, 1H, H-vinyl), 7.01 (d, J=3.08 Hz, 1H, H-2'), 6.47 (d, J=2.29 Hz, 2H, aromatic), 6.42 (t, J=2.29 Hz, 1H, aromatic), 6.38 (dd, J=2.15, 8.03 Hz, 1H, H-5), 6.33 (d, J=2.15 Hz, 1H, H-7), 5.01 (s, 2H, $CH_2$-Ph), 3.70 (s, 6H, 2×$OCH_3$), 2.59–2.72 (m, 4H, $CH_2CH_2COOH$), and 2.20 (s, 3H, $CH_3$).

EXAMPLE 27 (FROM TABLE 3)

3-{5-[6-(3-Methoxy-phenyl)-2-oxo-1,2-dihydroindol-3-ylidenemethyl]-2,4-dimethyl-1H-pyrrol-3-yl}-propionic acid Tetrakis(triphenylphosphine)palladium (0.7 g) was added to a mixture of 5 g of 3-methoxyphenylboronic acid, 3.8 g 5-bromo-2-fluoronitrobenzene and 11 mL 2 M sodium carbonate solution in 100 mL of toluene. The mixture was refluxed for 2 hours, diluted with water and extracted with ethyl acetate. The ethyl acetate was washed with saturated sodium bicarbonate and then brine, dried, and concentrated to give an oily solid. The solid was chromatographed on silica gel using ethyl acetate:hexane (1:6) to give 4.3 g (77% yield) of 4-fluoro-3'-methoxy-3-nitrobiphenyl.

Dimethyl malonate (9.7 mL) was added dropwise to 2.0 g of sodium hydride suspended in 50 mL of dimethylsulfoxide. The mixture was heated at 100° C. for 35 minutes and then cooled to room temperature. 4-Fluoro-2'-methoxy-3-nitrobiphenyl (4.2 g) in 50 mL dimethylsulfoxide was added and the mixture was heated to 100° C. for 1 hours. The reaction mixture was cooled and quenched with 300 mL of saturated ammonium chloride solution and extracted twice with ethyl acetate. The extracts were combined, washed with brine, dried over anyhydrous sodium sulfate and concentrated to give crude dimethyl 3'-methoxy-3-nitrobiphenyl-4-malonate as a pale yellow solid.

Crude 3'-methoxy-3-nitro-biphenyl-4-malonate was heated at 110° C. in 45 mL of 6 N hydrochloric acid for 4 days and cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid 33:66:1 to give 3.0 g (75% yield based on 4-fluoro-3'-methoxy-3-nitrobiphenyl) of 6-(3-methoxypheny)-2-oxindole as a pink solid.

$^1$HNMR (360 MHz, DMSO-d6): δ 10.39 (s, br, 1H, NH), 7.35 (t, J=7.85 Hz, 1H), 7.26 (d, J=7.78 Hz, 1H), 7.19 (dd, J=1.22, 7.8 HZ, 1H), 7.13–7.16 (m, 1H), 7.09–7.1 (m, 1H), 7.01 (d, J=1.48 Hz, 1H), 6.90–6.93 (m, 1H), 3.8 (s, 3H, OCH3), 3.49 (s, 2H, CH2); MS m/z (relative intensity, %) 240.0 ([M+1]$^+$, 100).

3-(2-Carboxyethyl)-2,4-dimethyl-5-formylpyrrole (117 mg), 120 mg 6-(3-methoxyphenyl)-2-oxindole and 3 drops piperidine in 3 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 190 mg (91%) of the title compound as a brown solid.

$^1$HNMR (360 MHz, DMSO-d6): δ 13.38 (s, br, 1H, NH-1'), 12.04 (s, br, 1H, COOH), 10.79 (s, br, 1H, NH-1), 7.77 (d, J=8.05, 1H, H-4), 7.58 (s, 1H, H-vinyl), 7.27 (dd, J=1.49, 8.05 Hz, 1H, H-5), 7.09 (d, J=1.49 Hz, 1H, H-7), 6.89–7.59 (m, 4H), 3.81 (s, 3H, OCH$_3$), 2.65 (t, J=7.62 Hz, 2H, CH$_2$CH$_2$COOH), 2.35(t, J=7.62 Hz, 2H, CH$_2$CH$_2$COOH), 2.30 (s, 3H, CH$_3$), and 2.27 (s, 3H, CH$_3$); MS m/z (relative intensity, %) 417 ([M+1]$^+$, 75).

EXAMPLE 28 (FROM TABLE 3)

3-[5-(6-Bromo-2-oxo-1,2-dihydroindol-3-ylidenemethyl)-4-methyl-1H-pyrrol-3-yl]-propionic acid Dimethyl malonate (13 mL) was added dropwise to 2.7 g sodium hydride suspended in 20 mL dimethylsulfoxide. The mixture was heated to 100° C. for 10 minutes and cooled to room temperature. 5-Bromo-2-fluoronitrobenzene (5.0 g) in 25 mL dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate as a pale yellow oil.

Crude dimethyl 4-bromo-2-nitrophenylmalonate was heated at 110° C. in 40 mL of 6 N hydrochloric acid for 24 hours and cooled. The precipitate was collected by filtration, washed with water and dried to give 5.3 g (89% yield) of 4-bromo-2-nitrophenylacetic acid as an off white solid.

4-Bromo-2-nitrophenylacetic acid 0.26 g), 0.26 g zinc powder and 3 mL 50% sulfuric acid in 5 mL ethanol was heated at 100° C. overnight. The reaction mixture was filtered, diluted with a little acetic acid, concentrated to remove ethanol, diluted with water and extracted twice and ethyl acetate. The combined extracts were washed with brine, dried over anhydrous sodium sulfate and concentrated to give 0.19 g (90% yield) of 6-bromo-2-oxindole as a yellow solid.

$^1$HNMR (360 MHz, DMSO-d6): δ 10.45 (s, br, 1H, NH-1), 7.14 (d, J=7.89 Hz, 1H, H-4), 7.09 (dd, J=1.53, 7.89 Hz, 1H, H-5), 6.93 (d, J=1.53 Hz, 1H, H-7), and 3.43 (s, 2H, CH$_2$-3); MS m/z (relative intensity, %) 210 ([M−2]$^+$, 100) and 212 (M$^+$, 100).

4-(2-carboxyethyl)-2-formyl-3-methylpyrrole (90 mg), 106 mg 6-bromo-2-oxindole, and 3 drops piperidine in 3 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 172 mg (92%) of the title compound as a yellow solid.

$^1$HNMR (360 MHz, DMSO-d6): δ 13.22 (s, br, 1H, NH-1'), 12.04 (s, br, 1H, COOH), 10.92 (s, br, 1H, NH-1), 7.73 (d, J=8.37, 1H, H-4), 7.67 (s, 1H, H-vinyl), 7.18 (d, J=3.22 Hz, 1H, H-2'), 7.14 (dd, J=1.33, 8.37 Hz, 1H, H-5), 6.99 (d, J=1.33 Hz, 1H, H-7), 2.64 (t, J=8.39 H z, 2H, CH$_2$CH$_2$COOH), 2.46 (t, J=7.39 Hz, 2H, CH$_2$CH$_2$COOH), 2.25 (s, 3H, CH$_3$); MS (APCI) m/z 375.0 [M+1]$^+$.

EXAMPLE 29 (FROM TABLE 3)

3-{5-[6-(3-Methoxy-phenyl)-2-oxo-1,2-dihydroindol-3-ylidenemethyl]-4-methyl-1H-pyrrol-3-yl}-propionic acid 4-(2-carboxyethyl)-2-formyl-3-methylpyrrole (90.5 mg), 120 mg 6-(3-methoxyphenyl)-2-oxindole, and 3 drops piperidine in 3 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 195 mg (97%) of the title compound as a brown solid.

$^1$HNMR (360 MHz, DMSO-d6): δ 13.29 (s, br, 1H, NH-1'), 12.07 (s, br, 1H, COOH), 10.88 (s, br, 1H, NH-1), 7.82 (d, J=7.77, 1H, H-4), 7.65 (s, 1H, H-vinyl), 7.27 (dd, J=1.41, 7.77 H z, 1H, H-5), 7.09 (d, J=1.41 Hz, 1H, H-7), 6.89–7.36 (m, 5H), 3.82 (s, 3H, OCH$_3$), 2.65 (t, J=7.55 Hz, 2H, CH$_2$CH$_2$COOH), 2.47 (t, J=7.55 Hz, 2H, CH$_2$CH$_2$COOH), 2.27 (s, 3H, CH$_3$); MS (APCI) m/z 401 [M−1]$^+$.

EXAMPLE 30 (FROM TABLE 3)

3-{5-[6-(3-Ethoxy-phenyl)-2-oxo-1,2-dihydroindol-3-ylidenemethyl]-2,4-dimethyl-1H-pyrrol-3yl}-propionic acid Tetrakis(triphenylphosphine)palladium (0.8 g) was added to a mixture of 4.2 g of 3-ethoxyphenylboronic acid, 5.0 g 5-bromo-2-fluoronitrobenzene and 22 mL 2 M sodium carbonate solution in 50 mL toluene and 50 mL ethanol. The mixture was refluxed for 2 hours and then concentrated. Water was added and the mixture was extracted twice with ethyl acetate. The combined ethyl acetate layers were washed with water and brine brine, then dried and concentrated. The residue was chromatographed on silica gel using 5% ethyl acetate in hexane to give 5.3 g (90% yield) of crude 4-fluoro-3'-ethoxy-3-nitrobiphenyl as a yellow oil.

Dimethyl malonate (11.4 mL) was added dropwise to 4.0 g sodium hydride suspended in 20 mL dimethylsulfoxide. The mixture was heated to 100° C. for 10 minutes and cooled to room temperature. Crude 4-fluoro-3'-ethoxy-3-nitrobiphenyl (5.3 g) in 25 mL dimethylsulfoxide was added and the mixture was heated at 100° C. for 2 hours. The reaction mixture was cooled, quenched with 300 mL of saturated amonium chloride solution and extracted three times with ethyl acetate. The extracts were combined, washed with water and brine, dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate was heated at 100° C. in 60 mL 6 N hydrochloric acid for a total of 4 days and cooled. The precipitate was collected by filtration, washed with water and hexane and dried to give 4.7 g (77% yield based on 5-bromo-2-fluoronitrobenzene) of crude 3'-ethoxy-3-nitrobiphenyl-4-acetic acid as a light tan solid.

Iron chips (2.4 g) were added in one portion to 4.6 g 3'-ethoxy-3-nitrobiphenyl-4-acetic acid in 40 mL glacial acetic acid and the mixture refluxed for 2 hours. The reaction mixture was concentrated to dryness, treated repeatedly with ethyl acetate and filtered to remove insoluble material. The filtrate was washed twice with 1 N hydrochloric acid then with brine, dried over anhydrous sodium sulfate and concentrated to give 3.5 g (91% yield) of 6-(3-ethoxyphenyl)-2-oxindole as a light brown solid.

$^1$HNMR (360 MHz, DMSO-d6): δ 10.4 (s, br, 1H, NH), 7.33 (t, J=8.4 Hz, 1H, H-3'), 7.35 (d, J=7.77 Hz, 1H), 7.19 (dd, J=1.3, 7.66 HZ, 1H), 7.13 (d, J=7.69 Hz, 1H), 7.07–7.08 (m, 1H), 7.0 (s, br, 1H), 6.9 (dd, J=2.82, 8.08 Hz, 1H), 4.08 (q, J=7 H z, 2H, OEt), 3.49 (s, 2H, CH2), 1.34 (t, J=7 Hz, 3H, OEt); MS m/z (relative intensity, %) 254.2 ([M+1]$^+$, 100).

3-(2-carboxyethyl)-2,4-dimethyl-5-formylpyrrole (97.6 mg), 127 mg 6-(3-ethoxyphenyl)-2-oxindole, and 2 drops piperidine in 2 mL ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 227 mg of the title compound (~100%) as a brown solid.

$^1$H-NMR (360 MHz, DMSO-d6): δ 13.38 (s, br, 1H, NH-1'), 12.06 (s, br, 1H, COOH), 10.81 (s, br, 1H, NH-1), 7.77 (d, J=7.97, 1H, H-4), 7.58 (s, 1H, H-vinyl), 7.26 (dd, J=1.35, 7.97 Hz, 1H, H-5), 7.08 (d, J=1.35 Hz, 1H, H-7), 6.87–7.36 (m, 4H), 4.09 (q, J=7.0 Hz, 2H, CH$_3$CH$_2$), 2.65 (t, J=7.54 Hz, 2H, CH$_2$CH$_2$COOH), 2.47 (t, J=7.54 Hz, 2H, CH$_2$CH$_2$COOH), 2.30 (s, 3H, CH$_3$), 2.26 (s, 3H, CH$_3$), 1.34 (t, J=7.0 Hz, 3H, CH$_3$CH$_2$); MS m/z (relative intensity, %) 431 ([M+1]$^+$,21).

EXAMPLE 31 (FROM TABLE 3)

3-{5-[6-(3-Ethoxy-Phenyl)-2-Oxo-1,2-Dihydroindol-3-Ylidenemethyl]-4-methyl-1H-Pyrrol-3-Yl}-Propionic Acid 4-(2-carboxyethyl)-2-formyl-3-methylpyrrole (90.5 mg), 127 mg 6-(3-ethoxyphenyl)-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 200 mg (96%) of the title compound as a brown solid.

$^1$HNMR (360 MHz, DMSO-d6): δ 13.29 (s, br, 1H, NH-1'), 12.07 (s, vbr, 1H, COOH), 10.88 (s, br, 1H, NH-1), 7.82 (d, J=7.97, 1H, H-4), 7.65 (s, 1H, H-vinyl), 7.28 (dd, J=1.20, 7.97 Hz, 1H, H-5), 7.08 (d, J=1.20 Hz, 1H, H-7), 6.87–7.36 (m, 5H), 4.09 (q, J=6.98 Hz, 2H, CH$_3$CH$_2$), 2.65 (t, J=7.47 Hz, 2H, CH$_2$CH$_2$COOH), 2.47 (t, J=7.47 Hz, 2H, CH$_2$CH$_2$COOH), 2.27 (s, 3H, CH$_3$), 1,34 (t, J=6.98 Hz, 3H, CH$_3$CH$_2$).

EXAMPLE 32 (FROM TABLE 3)

3-[2,4-Dimethyl-5-(2-Oxo-6-Phenyl-1,2-Dihydroindol-3-Ylidenemethyl)-1H-Pyrrol-3-Yl]-Propionic Acid Tetrakis(triphenylphosphine)palladium (0.8 g) was added to a mixture of 3.1 g of benzeneboronic acid, 5 g 5-bromo-2-fluoronitrobenzene and 22 mL 2 M sodium carbonate solution in 50 mL toluene and 50 mL ethanol. The mixture was refluxed for 2 hours, concentrated, and the residue extracted twice with ethyl acetate. The ethyl acetate layer was washed with water and brine, dried, and concentrated to give a yellow oil. The oil was chromatographed on silica gel using 5% ethyl acetate in hexane to give 4.75 g (96% yield) of 4-fluoro-3-nitrobiphenyl as a yellow oil.

Dimethyl malonate (10 mL) in 25 mL of dimethylsulfoxide was added dropwise to 3.5 g sodium hydride suspended in 25 mL dimethylsulfoxide and the mixture was heated at 100° C. for 10 minutes. The mixture was cooled to room temperature and 4.7 g 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g (80% based on 4-fluoro-3-nitrobiphenyl) of 3-nitrobiphenyl-4-acetic acid as a cream colored solid.

Iron chips (2.6 g) were added all at once to 4.5 g 3-nitrobiphenyl-4-acetic acid in 40 mL acetic acid. The mixture was refluxed for 2 hours, concentrated to dryness and taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

$^1$HNMR (360 MHz, DMSO-d6): δ 10.4 (s, br, 1H, NH-1), 7.57–7.6 (m, 2H), 7.42–7.46 (m, 2H), 7.32–7.37 (m, 1H), 7.27 (d, J=7.7, 1H, H-4), 7.19 (dd, J=1.6, 7.7 Hz, 1H, H-5), 7.01 (d, J=1.6 Hz, 1H, H-7), 3.49 (s, 2H, CH$_2$); MS m/z (relative intensity, %) 210 ([M+1]$^+$, 100).

3-(2-carboxyethyl)-2,4-dimethyl-5-formylpyrrole (97.6 mg), 105 mg 6-phenyl-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 138 mg (71%) of the title compound as a brown solid.

$^1$HNMR (360 MHz, DMSO-d6): δ 13.38 (s, br, 1H, NH-1'), 12.05 (s, br, 1H, COOH), 10.81 (s, br, 1H, NH-1), 7.78 (d, J=7.84, 1H, H-4), 7.58 (s, 1H, H-vinyl), 7.25–7.63 (m, 6H), 7.09 (s, br, 1H, H-7), 2.64 (t, J=7.71 Hz, 2H, CH$_2$CH$_2$COOH), 2.35 (t, J=7.71 Hz, 2H, CH$_2$CH$_2$COOH), 2.30 (s, 3H, CH$_3$), and 2.26 (s, 3H, CH$_3$); MS m/z (relative intensity, %) 387 ([M+1]$^+$, 100).

EXAMPLE 33 (FROM TABLE 3)

3-[4-Methyl-5-(2-Oxo-6-Phenyl-1,2-Dihydro-Indol3-Ylidenemethyl)-1H-Pyrrol-3-Yl]-Propionic Acid 4-(2-Carboxyethyl)-2-formyl-3-methylpyrrole (90.5 mg), 105 mg 6-phenyl-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 146 mg (78%) of the title compound as a brown solid.

$^1$HNMR (360 MHz, DMSO-d6): δ 13.29 (s, br, 1H, NH-1'), 12.01 (s, vbr, 1H, COOH), 10.89 (s, br, 1H, NH-1), 7.83 (d, J=7.92, 1H, H-4), 7.65 (s, 1H, H-vinyl), 7.30–7.65 (m, 5H), 7.16 (d, J=2.83 Hz, 1H, H-2'), 7.28 (dd, J=1.58, 7.92 Hz, 1H, H-5), 7.09 (d, J=1.58 Hz, 1H, H-7), 2.66 (t, J=7.76 Hz, 2H, CH$_2$CH$_2$COOH), 2.45 (t, J=7.76 Hz, 2H, CH$_2$CH$_2$CH$_2$COOH), and 2.27 (s, 3H, CH$_3$); MS m/z (relative intensity, %) 373 ([M+1]$^+$, 100).

EXAMPLE 34 (FROM TABLE 3)

3-{5-[6-(4-Methoxy-Phenyl)-2-Oxo-1,2-Dihydroindol-3-Ylidenemethyl]-4-Methyl-1H-Pyrrol-3-Yl}-Propionic Acid Tetrakis(triphenylphosphine)palladium (1 g) was added to a mixture of 5 g 4-methoxyphenylboronic acid, 6.6 g 5-bromo-2-fluoronitrobenzene and 30 mL 2 M sodium carbonate solution in 50 mL toluene and 50 mL ethanol. The mixture was refluxed for 2 hours, concentrated, and the residue extracted twice with ethyl acetate. The ethyl acetate layer was washed with water and brine, dried, and concentrated to give a brown oily solid. The solid was chromatographed on silica gel using 5% ethyl acetate in hexane to give crude 4-fluoro-4'-methoxy-3-nitrobiphenyl as a pale yellow solid.

Dimethyl malonate (10 mL) was added dropwise to 2.0 g of sodium hydride suspended in 60 mL dimethylsulfoxide. The mixture was heated to 100° C. for 10 minutes and cooled to room temperature. Crude 4-fluoro-2'-methoxy-3-nitrobiphenyl (5.2 g) in 50 mL dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium choride, water and brine, dried over anhydrous sodium sulfate and concentrated to give crude dimethyl 4'-methoxy-3-nitrobiphenyl-4-malonate as a yellow oil.

Crude 4'-methoxy-3-nitro-biphenyl-4-malonate was heated at 100° C. in 60 mL 6 N hydrochloric acid for 15 hours and cooled. The precipitate which formed was collected by filtration, washed with water and hexane, and dried to give 7.2 g of crude 4'-methoxy-3-nitrobiphenyl-4-acetic acid as a light tan solid.

Iron chips (3.6 g) were added in one portion to 7.2 g 4'-methoxy-3-nitrobiphenyl-4-acetic acid in 50 mL glacial acetic acid and heated at 100° C. overnight. The reaction mixture was concentrated to dryness, sonicated in ethyl acetate and filtered to remove the insolubles. The filtrate was washed twice with 1 N hydrochloric acid, then with brine, dried over anhydrous sodium sulfate and concentrated to give 2.7 g (54% yield based on 5-bromo-2-fluoronitrobenzene) of 6-(4-methoxyphenyl)-2-oxindole as a rose colored solid.

$^1$HNMR (360 MHz, DMSO-d6): δ 10.38 (s, br, 1H, NH-1), 7.52 (d, J=9 Hz, 2H), 7.23 (d, J=7.3 Hz, 1H, H-4), 7.14 (d,d, J=1.38, 7.3 Hz, 1 H, H-5), 7.0 (d, J=9 Hz, 2H), 6.96 (d, J=1.38 Hz, 1H, H-7), 3.78 (s, 3H, OCH$_3$), 3.47 (s, 2H, CH$_2$); MS m/z (relative intensity, %) 214.0 ([M+1]$^+$, 100).

4-(2-Carboxyethyl)-2-formyl-3-methylpyrrole (90.5 mg), 120 mg 6-(4-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 118 mg (59%) of the title compound as a brown solid.

$^1$HNMR (360 MHz, DMSO-d6): δ 13.26 (s, br, 1H, NH-1'), 10.83 (s, br, 1H, NH-1), 7.78 (d, J=8.07 Hz, 1H, H-4), 7.61 (s, 1H, H-vinyl), 7.56 (d, J=8.97 Hz, 2H), 7.22 (dd, J=1.44, 8.07 Hz, 1H, H-5), 7.13 (d, J=3.09 Hz, 1H, H-2'), 7.04 (d, J=1.44 Hz, 1 H, H-7), 7.0 (d, J=8.97 Hz, 2H), 3.79 (s, 3H, OCH$_3$), 2.65 (t, J=7.54 Hz, 2H, CH$_2$CH$_2$COOH), 2.44 (t, J=7.54 Hz, 2H, CH$_2$CH$_2$COOH), and 2.27 (s, 3H, CH$_3$); MS m/z (relative intensity, %) 404 ([M+1]$^+$, 100).

EXAMPLE 35 (FROM TABLE 3)

3-{5-[6-(4-Methoxy-phenyl)-2-Oxo-1,2-Dihydroindol-3-Ylidenemethyl]-2,4-Dimethyl-1H-Pyrrol-3-Yl}-Propionic Acid 3-(2-Carboxyethyl)-2,4-dimentyl-5-formylpyrrole (98 mg), 120 mg 6-(4-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 118 mg (57%) of the title compound as a brown solid.

$^1$HNMR (360 MHz, DMSO-d6): δ 13.35 (s, br, 1H, NH-1'), 12.02 (s, br, 1H, COOH), 10.75 (s, br, 1H, H-1), 7.73 (d, J=6.75 Hz, 1H H-4), 7.56 (d, J=9.01 Hz, 2H), 7.54 (s, 1H, H-vinyl), 7.21 (dd, J=1.59, 6.75 Hz, 1H, H-5), 7.04 (d, J=1.59 Hz, 1H, H-7), 7.01 (d, J=9.01 Hz, 2H), 3.79 (s, 3H, OCH$_3$), 2.65 (t, J=7.54 Hz, 2H, CH$_2$CH$_2$COOH), 2.35 (t, J=7.54 Hz, 2H, CH$_2$CH$_2$COOH), 2.29 (s, 3H, CH$_3$), and 2.26 (s, 3H, CH$_3$); MS m/z (relative intensity, %) 417 ([M+1]$^+$, 100).

EXAMPLE 36 (FROM TABLE 3)

3-{5-[6-(2-Methoxy-Phenyl)-2-Oxo-1,2-Dihydroindol-3-Ylidenemethyl]-4-Methyl-1H-Pyrrol-3-Yl}-Propionic Acid Tetrakis(triphenylphosphine)palladium (1 g) was added to a mixture of 5 g of 2-methoxyphenylboronic acid, 6.6 g 5-bromo-2-fluoronitrobenzene and 30 mL 2 M sodium carbonate solution in 50 mL toluene and 50 mL ethanol. The mixture was refluxed for 2 hours, concentrated, and the residue extracted twice with ethyl acetate. The combined ethyl acetate layers were washed with water and brine, dried, and concentrated to give a dark green oil which solidified on standing give crude 4-fluoro-2'-methoxy-3-nitrobiphenyl.

Dimethyl malonate (14 mL) was added dropwise to 2.9 g of sodium hydride suspended in 50 mL dimethylsulfoxide. The mixture was heated to 100° C. for 15 minutes and cooled to room temperature.

Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated ammonium chloride solution and extracted twice with ethyl acetate. The extracts were combined, washed with saturated ammonium choride, water, and brine, dried over anhydrous sodium sulfate and concentrated to give crude dimethyl 2'-methoxy-3-nitrobiphenyl-4-malonate as a yellow oil.

Crude 2'-methoxy-3-nitrobiphenyl-4-malonate was heated at 100° C. in 50 mL 6 N hydrochloric acid for 24 hours and cooled. The precipitate was collected by filtration, washed with water and hexane, and dried to give 9.8 g of 2'-methoxy-2-nitrobiphenyl-4-acetic acid as a light tan solid.

Iron chips (5 g) were added in one portion to 9.8 g 2'-methoxy-3-nitrobiphenyl-4-acetic acid in 50 mL glacial acetic acid and the mixture was heated at 100° C. for 3 hours. The reaction mixture was concentrated to dryness, sonicated in ethyl acetate and filtered to remove the insolubles. The filtrate was washed twice with 1 N hydrochloric acid, water and brine, dried over anhydrous sodium sulfate and concentrated. The residue was chromatographed on silica gel using ethyl acetate:hexane 1:2 to give 5.4 g (69% yield based on 5-bromo-2-fluoronitrobenzene) of 6-(2-methoxyphenyl)-2-oxindole as a rose colored solid.

$^1$HNMR (360 MHz, DMSO-d6): δ 10.32 (s, br, 1H, NH), 7.29–7.34 (m, 1H), 7.19–7.25 (m, 2H), 7.08 (d, J=8 Hz, 1H, H-4), 6.97–7.02 (m, 2H), 6.91 (d, J=1.05 Hz, 1H, H-7), 3.8 (s, 3H, OCH$_3$), 3.47 (s, 2H, CH$_2$); MS m/z (relative intensity, %) 239.8 ([M+1]$^+$).

4-(2-Carboxyethyl)-2-formyl-3-methylpyrrole (217 mg), 239 mg 6-phenyl-2-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 348 mg (86%) of the title compound as a brown solid.

$^1$HNMR (360 MHz, DMSO-d6): δ 13.29 (s, br, 1H, NH-1'), 11.59 (s, br, 1H, COOH), 10.78 (s, br, 1H, NH-1), 7.75 (d, J=8.13 Hz, 1H, H-4), 7.62 (s, 1H, H-vinyl), 7.0–7.34 (m, 7H), 3.76 (s, 3H, OCH$_3$), 2.66 (t, J=7.46 Hz, 2H, CH$_2$CH$_2$COOH), 2.46 (t, J=7.46 Hz, 2H, CH$_2$CH$_2$COOH), and 2.27 (s, 3H, CH$_3$); MS m/z (relative intensity, %) 401 ([M+1]$^+$, 100).

EXAMPLE 37 (FROM TABLE 3)

3-{5-[6-(2-Methoxy-Phenyl)-2-Oxo-1,2-Dihydroindol-3-Ylidenemethyl]-2,4Dimethyl-1H-Pyrrol-3-Yl}-Propionic Acid 3-(2-Carboxyethyl)-2,4-dimentyl-5-formylpyrrole (234 mg), 239 mg 6-(2-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight.

The crude solid was purified by chromatography on a silica gel column eluting with ethyl acetae:hexane 1:1 containing 0.1% acetic acid to give 182 mg (44%) of the title compound as a brown solid.

$^1$HNMR (360 MHz, DMSO-d6): δ 13.38 (s, br, 1H, NH-1'), 12.0 (s, br, 1H, COOH), 10.7 (s, br, 1H, NH-1), 7.71 (d, J=7.74 Hz, 1H, H-4), 7.55 (s, 1H, H-vinyl), 7.0–7.33 (m, 6H), 3.76 (s, 3H, OCH$_3$), 2.65 (t, J=7.6 Hz, 2H, CH$_2$CH$_2$COOH), 2.35 (t, J=7.6 Hz, 2H, CH$_2$CH$_2$COOH), 2.3 (s, 3H, CH$_3$), and 2.26 (s, 3H, CH$_3$); MS (APCI neg) m/z (relative intensity, %) 415 ([M–1], 100).

EXAMPLE 38 (FROM TABLE 3)

3-[2,4-Dimethyl-5-(6-Morpholin-4-Yl-2-Oxo-1,2-Dihydroindol-3-Ylidenemethyl)-1H-Pyrrol-3-Yl]-Propionic Acid Tin chloride dihydrate (225 g) was added to a solution of 2,4-dinitrophenylacetic acid (22.6 g) in ethanol (450 mL). The mixture was heated at 90° C. for 10 hours. The reaction mixture was cooled and basified to pH 11 with 12M sodium hydroxide. The solids were removed by filtration and the filtrate was concentrated. The residue was treated with ethanol (300 mL). The insolubles were filtered and washed with ethanol (5×60 mL). The combined ethanol washes were evaporated and dried under vacuum to give 15 g of 6-amino-2-oxindole as a brown powder.

$^1$HNMR (360 MHz, DMSO-d6): δ 10.03 (s, br, NH), 6.78 (d, J=8.55 Hz, 1H, H-4), 6.09–6.11 (m, 2H), 4.95 (s, br, 2H, NH$_2$), 3.22 (s, 2H, H-3); MS (+APCI) m/z (relative intensity, %) 147 ([M–1]$^+$, 100).

6-Amino-2-oxindole (2.2 g), 4.0 g 2,2'-dibromoethyl ether and 7.9 g sodium carbonate were refluxed overnight in 20 ml of ethanol, concentrated and diluted with 50 ml of water. The mixture was extracted three times with 50 ml ethyl acetate, the organic extracts were combined, washed with 20 ml of brine, dried over anhydrous sodium sulfate and concentrated to dryness. The solid was chromatographed on a column of silica gel eluting with ethyl acetate-:hexane 1:1 containing 0.7% acetic acid to give 1.2 g (37% yield) of 6-(morpholin-4-yl)-2-oxindole as a beige solid.

$^1$HNMR (360 MHz, DMSO-d6): δ 10.2 (s, br, 1H, NH-1), 7.02 (d, J=7.87 Hz, 1H, H-4), 6.47 (dd, J=2.11, 7.87 Hz, 1H, H-5), 6.37 (d, J=2.11 Hz, 1H, H-7), 3.69–3.72 (m, 4H), 3.32 (s, 2H, CH$_2$), 3.01–3.04 (m, 4H); MS m/z (relative intensity, %) 219 ([M+1]$^+$, 100).

3-(2-Carboxyethyl)-2,4-dimentyl-5-formylpyrrole (3.3 g), 4 g 6-(morpholin-4-yl)-2-oxindole and 1.8 mL piperidine in 60 mL of ethanol were heated at 90° C. for 7 hours. The reaction mixture was cooled and concentrated. The residue was suspended in 6 N aqueous hydrochloric acid. The precipitate was filtered, washed with water to pH 6 and dried in a vacuum oven overnight. The resulting solid was purified by chromatography on a silica gel column eluting with ethyl acetate-hexane-acetic acid to give 2.78 g (38% yield) of the title compound as a brown solid.

$^1$HNMR (360 MHz, DMSO-d6): δ 13.13 (s, br, 1H, NH-1'), 12.02 (s, br, 1H, COOH), 10.57 (s, br, 1H, NH-1), 7.52 (d, J=8.46 Hz, 1H, H-4), 7.32 (s, 1H, H-vinyl, 6.58 (dd, J=1.99, 8.46 Hz, 1H, H-5), 6.41 (d, J=1.99 Hz, 1H, H-7), 3.71–3.74 (m, 4H), 3.06–3.09 (m, 4H, 2.62 (t, J=7.57 Hz, 2H, CH$_2$CH$_2$COOH), 2.33 (t, J=7.57 Hz, 2H, CH$_2$CH$_2$COOH), 2.26 (s, 3H, CH$_3$), and 2.21 (s, 3H, CH$_3$); MS m/z (relative intensity, %) 396 ([M+1]$^+$, 100).

EXAMPLE 39 (FROM TABLE 3)

3-[5-(5-Chloro-4-Methyl-2-Oxo-1,2-Dihydroindol-3-Ylidenemethyl)-2,4-Dimethyl-1H-Pyrrol-3-Yl]-Propionic Acid A suspension of 3.0 g 4-methyl-2-oxindole was stirred in 50 mL acetonitrile at room temperature while 3.3 g of N-chloro-succinimide was added in portions. Trifluoroacetic acid (1 mL) was then added. The suspension was stirred at room temperature for 3 days during which time solids were always present. The white solid was collected by vacuum filtration, washed with a small amount of cold acetone and dried overnight in a vacuum oven at 40° C. to give 2.5 g (68%) of 5-chloro-4-methyl-2-oxindole.

$^1$HNMR (360 MHz, DMSO-d6): δ 10.38 (s, br, 1H, NH), 7.19 (d, J=8 Hz, 1H, aromatic), 6.64 (d, J=8 Hz, 1H, aromatic), 3.46 (s, 2H, H-3), 2.19 (s, 3H, $CH_3$).

3-(2-Carboxyethyl)-2,4-dimethyl-5-formylpyrrole (98 mg), 91 mg 5-chloro-4-methyl-2-oxindole and 2 drops piperidine in 2 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 100 mg of the title compound.

$^1$HNMR (360 MHz, DMSO-d6): δ 13.47 (s, br, 1H, NH-1'), 12.03 (s,br, 1H, COOH), 10.83 (s, br, 1H, NH-1), 7.61 (s, 1H, H-vinyl), 7.14 (d, J=8.17 Hz, 1H, aromatic), 6.74 (d, J=8.17 Hz, 1H, aromatic), 2.64 (s, 3H, $CH_3$), 2.64 (t, J=7.62 Hz, 2H, $CH_2CH_2COOH$), 2.34 (t, J=7.62 Hz, 2H, $CH_2CH_2COOH$), 2.3 (s, 3H, $CH_3$), and 2.20 (s, 3H, $CH_3$).

EXAMPLE 40 (FROM TABLE 3)

3-[5-(5-Chloro-4Methyl-2-Oxo-1,2-Dihydroindol-3-Ylidenemethyl)-4-Methyl-1H-Pyrrol-3-Yl]-Propionic Acid 4-(2-Carboxyethyl)-2-formyl-3-methylpyrrole (91 g), 91 mg 5-chloro-4-methyl-2-oxindole and 2 drops piperidine in 2 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 95 mg of the title compound.

$^1$HNMR (360 MHz, DMSO-d6): δ 13.36 (s, br, 1H, NH-1'), 11.98 (s,br, 1H, COOH), 10.92 (s, br, 1H, NH-1), 7.68 (s, 1H), 7.19 (d, J=7.14 Hz, 1H, aromatic), 7.17 (s, 1H), 6.75 (d, J=7.14 Hz, 1H, aromatic), 2.66 (s, 3H, $CH_3$-4), 2.66 (t, J=7.51 Hz, 2H, $CH_2CH_2COOH$), 2.45 (t, J=7.51 Hz, 2H, $CH_2CH_2COOH$), 2.45 (t, J=7.51 Hz, 2H, $CH_2CH_2COOH$), 2.21 (s, 3H, $CH_3$); MS m/z (relative intensity, %) 345 ([M+1]$^+$, 100).

EXAMPLE 41 (FROM TABLE 3)

3-[2,4-Dimethyl-5-(2-Oxo-1,2-Dihydroindol-3-Ylidenemethyl)-1H-Pyrrol-3-Yl]-Propionic Acid, Sodium Salt A suspension of 8 g of 3-[2,4-dimethyl-5-(2-oxo-1,2-dihydroindol-3-ylidenemethyl)-1H-pyrrol-3-yl]-propionic acid in 60 mL of water was added to 0.98 g of sodium hydroxide in 10 ml of water. The mixture was stirred at RT for 30 minutes and filtered. The filtrate was frozen and lyophilized to give 8 g of the title compound.

Alternatively, a suspension of 117 g of 318-005 in 470 mL of water was added to 16.47 g of sodium hydroxide in 74 mL water. The mixture was stirred at room temperature for 15 minutes and filtered. The filtrate was added to 210 mL of ethanol and the resulting precipitate which formed was collected by suction filtration. After drying, a total of 106 g of the title compound was obtained.

$^1$HNMR (360 MHz, DMSO-d6): δ 13.34 (s, br 1H, NH-1'), 10.82 (s, br, 1H, NH-1), 7.65 (d, J=7.52 Hz, 1H, H-4), 7.5 (s, 1H, H-vinyl), 7.04 (t, J=7.52 Hz, 1H, H-6), 6.93 (t, J=7.52 Hz, 1H, H-5), 6.85 (d, J=7.52 Hz, 1H, H-7), 2.55 (t, J=6.95 Hz, 2H, $CH_2CH_2COOH$), 2.28 (s, 3H, $CH_3$), 2.24 (s, 3H, $CH_3$), and 1.99 (t, J=6.95 Hz, 2H, $CH_2CH_2COOH$).

EXAMPLE 42 (FROM TABLE 3)

3-[3,5-Dimethyl-4-(3-Morpholin-4-Ylpropyl)-1H-Pyrrol-2-Ylmethylene]-1,3-Dihydroindol-2-One Step 1: To a suspension of 3-(2,4-dimethyl-1H-pyrrol-3-yl)-propionic acid (10 g, 60.8 mmol) in 60 ml of dichloromethane was added 1,1'-carbonyldiimidazole (11.6 g, 71.8 mmol) followed morpholine (5.5 ml, 60.8 mmol) and N,N-diisopropylethylamine (Hunig's base, 10 ml, 60.8 mmol). The dark red reaction mixture was stirred at room temperature overnight and poured into ice water. The organic layer was washed with brine until the wash had a pH of about 6, dried over anhydrous sodium sulfate, and concentrated. The crude product was purified on a silica gel column eluting with dichloromethane-methanol (98:2) to give 13.84 g (96%) of 3-(2,4-dimethyl-1H-pyrrol-3-yl)-1-morpholin-4-yl-propan-1-one.

Step 2: To a suspension of lithium aluminum hydride (2.67 g, 70 mmol) in tetrahydrofuran (100 ml) was added dropwise a solution of 3-(2,4-dimethyl-1H-pyrrol-3-yl)-1-morpholin-4-yl-propan-1-one (13.84 g, 59 mmol) in tetrahydrofuran (50 ml). The reaction mixture was stirred at 80° C. for 1 hour and cooled ins an ice bath. Ice was added to the reaction mixture slowly until gas evolution ceased. A few drops of 2N sodium hydroxide were added and the reaction mixture was stirred at room temperature for 30 minutes. The reaction mixture was then extracted with ethyl acetate, dried over anhydrous sodium sulfate and concentrated to give 10.37 g (79%) of 4-[3-(2,4-dimethyl-1H-pyrrol-3-yl)-propyl]-morpholine as a light brown oil which was used without further purification.

Step 3: To an ice-cooled solution of N,N-dimethylformamide (5.5 ml, 70 mmol) in dichloromethane (30 ml) was dropwise added phosphorus oxychloride (6.5 ml, 70 mmol). When the addition was complete, the reaction mixture was stirred at room temperature for 15 minutes after which a solution of 3,5-dimethyl-4-(3-morpholin-4-yl-propyl)-1H-pyrrole-2-carboxaldehyde (10.37 g, 46.6 mmol) in dichloromethane (20 ml) was added dropwise at 0° C. The final reaction mixture was refluxed at 60° C. for 4 hours and then cooled in an ice bath. Ice was slowly added to the reaction mixture followed by addition of 2 N sodium hydroxide until a pH to 12 was reached. The reaction mixture was stirred at room temperature for 30 min, and then extracted with ethyl acetate. The organic layer was washed with brine, dried over anhydrous sodium sulfate and concentrated to give crude product which was purified on a silica gel column eluting with dichloromethane-methanol-ammonium hydroxide (9.5:0.5) to give 4.57 g (39%) of 3,5-dimethyl-4-(3-morpholin-4-yl-propyl)-1H-pyrrole-2-carbaldehyde as a dark red oil:

$^1$HNMR (360 MHz, DMSO-d6) δ 11.34 (s, br, 1H, NH-1), 9.40 (s, 1H, CHO-2), 3.55 (t, J=4.68 Hz, 4H, O($CH_2CH_2$)$_2$

NCH$_2$CH$_2$CH$_2$-4), 2.28–2.34 (m, 6H, O(CH$_2$CH$_2$)$_2$ NCH$_2$CH$_2$CH$_2$-4), 2.21 (t, J=7.10 Hz, 2H, O(CH$_2$CH$_2$)$_2$ NCH$_2$CH$_2$CH$_2$-4) CH$_3$-3), 2.19 (s, 3H, CH$_3$-5), 2.14 (s, 3H, CH$_3$-3'), 1.51 (quint, J=7.10 Hz, 2H, O(CH$_2$CH$_2$)$_2$ NCH$_2$CH$_2$CH$_2$-4), MS m/z (relative intensity, %) 251 ([M+1]$^+$, 100).

Step 4: A mixture of 1,3-dihydroindol-2-one (133 mg, 1.0 mmol), 3,5-dimethyl-4-(3-morpholin-4-yl-propyl)-1H-pyrrole-2-carboxaldehyde (250 mg, 1.0 mmol) and 3 drops pyrrolidine in 2.0 ml of ethanol was refluxed at 90° C. for 4 hours and then cooled to room temperature. The precipitate was filtered, washed with cold ethanol and hexane, and dried in a vacuum oven overnight to give 308.9 mg (85%) of 3-[3,5-dimethyl-4-(3-morpholin-4-yl-propyl)-1H-pyrrol-2-ylmethylene]-1,3-dihydroindol-2-one as a yellow solid:

$^1$HNMR (360 MHz, DMSO-d$_6$) δ 13.37 (s, 1H, NH-1'), 10.71 (s, 1H, NH-1), 7.68 (d, J=7.47 Hz, 1H, H-4), 7.53 (s, 1H, H-vinyl), 7.06 (dt, J=7.47 Hz, 1H, H-6), 6.94 (dt, J=7.74 Hz, 1H, H-5), 6.84 (d, J=7.47 Hz, 1H, H-7), 3.55 (t, J=4.37 Hz, 4H, O(CH$_2$CH$_2$)$_2$NCH$_2$CH$_2$CH$_2$-4'), 2.40 (t, J=7.31 Hz, 2H, O(CH$_2$CH$_2$)$_2$NCH$_2$CH$_2$CH$_2$-4'), 2.31 (t, J=4.37 Hz, 4H, O(CH$_2$CH$_2$)$_2$NCH$_2$CH$_2$CH$_2$-4'), 2.28 (s, 3H, CH$_3$-3'), 2.23 (s, 3H, CH$_3$-5'), 2.23 (t, J=7.31 Hz, 2H, O(CH$_2$CH$_2$)$_2$NCH$_2$CH$_2$CH$_2$-4'), 1.56 (quint., J=7.31 Hz, 2H, O(CH$_2$CH$_2$)$_2$NCH$_2$CH$_2$CH$_2$-4'), MS m/e (relative intensity, %) 365 (M$^+$·, 100).

EXAMPLE 43 (FROM TABLE 3)

5-Bromo-3-[3,5-Dimethyl-4-(3-Morpholin-4-Yl-Propyl)-1H-Pyrrol-2-Ylmethylene]-1,3-Dihydroindol-2-One A mixuture of 5-bromo-1,3-dihydroindol-2-one (212 mg, 1.0 mmol), 3,5-dimethyl-4-(3-morpholin-4-yl-propyl)-1H-pyrrole-2-carbaldehyde (250 mg, 1.0 mmol) and 3 drops pyrrolidine in 2.0 ml of ethanol was refluxed at 90° C. for 4 hours and then cooled to room temperature. The precipitate was filtered, washed with cold ethanol and hexane and dried in a vacuum oven overnight to give 399.8 mg (90%) of 5-bromo-3-[3,5-dimethyl-4-(3-morpholin-4-yl-propyl)-1H-pyrrol-2-ylmethylene]-1,3-dihydroindol-2-one as a red solid:

$^1$HNMR (300 MHz, DMSO-d$_6$) δ 13.43 (s, 1H, NH-1'), 10.81 (s, 1H, NH-1), 7.99 (d, J=2.07 Hz, 1H, H-4), 7.66 (s, 1H, H-vinyl), 7.18 (dd, J=2.07, 7.58 Hz, 1H, H-6), 6.79 (d, J=7.58 Hz, 1H, H-7), 3.55 (t, J=4.39 Hz, 4H, O(CH$_2$CH$_2$)$_2$NCH$_2$CH$_2$CH$_2$-4'), 2.40 (t, J=7.32 Hz, 2H, O(CH$_2$CH$_2$)$_2$NCH$_2$CH$_2$CH$_2$-4'), 2.31 (t, J=4.39 Hz, 4H, O(CH$_2$CH$_2$)$_2$NCH$_2$CH$_2$CH$_2$-4'), 2.29 (s, 3H, CH$_3$-3'), 2.26 (s, 3H, CH$_3$-5'), 2.23 (t, J=7.32 Hz, 2H, O(CH$_2$CH$_2$)$_2$NCH$_2$CH$_2$CH$_2$-4'), 1:56 (quint., J=7.32 Hz, 2H, O(CH$_2$CH$_2$)$_2$NCH$_2$CH$_2$CH$_2$-4'), MS m/e (relative intensity, %) 443 (M$^+$·, 100), 445 ([M+2]$^+$, 100).

EXAMPLE 44 (FROM TABLE 3)

3-[3,5-Dimethyl-4-(3-Morpholin-4-Yl-Propyl)-1H-Pyrrol-2-Ylmethylene]-6-Phenyl-1,3-dihydroindol-2-One Using the procedure of Example 2, an 88% yield of the title compound was obtained as a yellow solid:

$^1$HNMR (300 MHz, DMSO-d$_6$) δ 13.37 (s, 1H, NH-1'), 10.81 (s, 1H, NH-1), 7.77 (d, J=8.20 Hz, 1H, H-4), 7.62 (d, J=7.39 Hz, 2H, H-2",6"), 7.58 (s, 1H, H-vinyl), 7.44 (t, J=7.39 Hz, 2H, H-3",5"), 7.32 (t, br, J=7.39 Hz, 1H, H-4"), 7.26 (dd, J=1.49, 8.29 Hz, 1H, H-5), 7.09 (d, J=1.49 Hz, 1H, H-7), 3.56 (t, J=4.48 Hz, 4H, O(CH$_2$CH$_2$)$_2$NCH$_2$CH$_2$CH$_2$-4'), 2.41 (t, J=7.18 Hz, 2H, O(CH$_2$CH$_2$)$_2$NCH$_2$CH$_2$-4'), 2.31 (t, J=4.48 Hz, 4H, O(CH$_2$CH$_2$)$_2$NCH$_2$CH$_2$-4'), 2.29 (s, 3H, CH$_3$-3'), 2.26 (s, 3H, CH$_3$-5'), 2.24 (t, J=7.18 Hz, 2H, O(CH$_2$CH$_2$)$_2$NCH$_2$CH$_2$CH$_2$-4'), (quint., J=7.18 Hz, 2H, O(CH$_2$CH$_2$)$_2$NCH$_2$CH$_2$CH$_2$-4'), MS m/e (relative intensity, %) 441 (M$^+$·, 100),

EXAMPLE 45 (FROM TABLE 3)

3-[3,5-Dimethyl-4-(3-Morpholin-4-Yl-Propyl)-1H-Pyrrol-2-Ylmethylene]-6-(2-Methoxyphenyl)-1,3-Dihydroindol-2-One Using the procedure of Example 2, an 86% yield of the title compound was obtained as a yellow solid:

$^1$HNMR (300 MHz, DMSO-d$_6$) δ 13.37 (s, 1H, NH-1'), 10.72 (s, 1H, NH-1), 7.71 (d, J=7.79 Hz, 1H, H-4), 7.55 (s, 1H, H-vinyl), 7.27–7.34 (m, 2H), 6.98–7.10 (m, 4H), 3.76 (s, 3H, OCH$_3$-2"), 3.56 (t, J=4.50 Hz, 4H, O(CH$_2$CH$_2$)$_2$NCH$_2$CH$_2$CH$_2$-4'), 2.41 (t, J=7.12 Hz, 2H, O(CH$_2$CH$_2$)$_2$NCH$_2$CH$_2$CH$_2$-4'), 2.21–2.31 (m, 6H, O(CH$_2$CH$_2$)$_2$NCH$_2$CH$_2$CH$_2$-4'), 2.29 (s, 3H, CH$_3$-3'), 2.25 (s, 3H, CH$_3$-5'), 1.57 (quint., J=7.12 Hz, 2H, O(CH$_2$CH$_2$)$_2$NCH$_2$CH$_2$CH$_2$-4'), MS m/e (relative intensity, %) 471 (M$^+$·, 100).

EXAMPLE 46 (FROM TABLE 3)

3-[3,5-Dimethyl-4-(3-Morpholin-4-Yl-Propyl)-1H-Pyrrol-2-Ylmethylene]-6-(3-Methoxyphenyl)-1,3-Dihydroindol-2-One Using the procedure of Example 2, an 87% yield of the title compound was obtained as a yellow solid.

$^1$HNMR (300 MHz, DMSO-d$_6$) δ 13.38 (s, 1H, NH-1'), 10.80 (s, 1H, NH-1), 7.76 (d, J=7.93 Hz, 1H, H-4), 7.57 (s, 1H, H-vinyl), 7.35 (t, J=8.08 Hz, 1H, H-5"), 7.26 (dd, J=1.73, 7.93 Hz, 1H, H-5), 7.18 (d, br, J=8.08 Hz, 1H, H-4"), 7.13 (t, br, J=1.94 Hz, 1H, H-2"), 7.08 (d, J=1.73 Hz, 1H, H-7), 6.90 (dd, J=1.94, 8.08 Hz, 1H, H-6"), 3.81 (s, 3H, OCH$_3$-3"), 3.56 (t, J=4.38 Hz, 4H, O(CH$_2$CH$_2$)$_2$NCH$_2$CH$_2$CH$_2$-4'), 2.41 (t, J=7.19 Hz, 2H, O(CH$_2$CH$_2$)$_2$NCH$_2$CH$_2$CH$_2$-4'), 2.31 (t, J=4.38 Hz, 4H, O(CH$_2$CH$_2$)$_2$NCH$_2$CH$_2$CH$_2$-4'), 2.29 (s, 3H, CH$_3$-3'), 2.26 (s, 3H, CH$_3$-5'), 2.24 (t, J=7.19 Hz, 2H, O(CH$_2$CH$_2$)$_2$NCH$_2$CH$_2$CH$_2$-4'), 1.56 (quint., J=7.19 Hz, 2H, O(CH$_2$CH$_2$)$_2$NCH$_2$CH$_2$CH$_2$-4'), MS m/e (relative intensity, %) 471 (M$^+$·, 100).

EXAMPLE 47 (FROM TABLE 3)

3-[3,5-Dimethyl-4-(3-Morpholin-4-Yl-Propyl)-1H-Pyrrol-2-Ylmethylene]-6-(4-Methoxyphenyl)-1,3-Dihydroindol-2-One Using the method of Example 2, a 52% yield of the title compound was obtained as a yellow solid:

$^1$HNMR (300 MHz, DMSO-d$_6$) δ 13.35 (s, 1H, NH-1'), 10.77 (s, 1H, NH-1), 7.72 (d, J=7.97 Hz, 1H, H-4), 7.55 (d, J=8.57 Hz, 2H, H-2",6"), 7.54 (s, 1H, H-vinyl), 7.20 (dd, J=1.35, 7.97 Hz, 1H, H-5), 7.04 (d, J=1.35 Hz, 1H, H-7), 6.99 (d, J=8.57 Hz, 1H, H-3",5"), 3.78 (s, 3H, OCH$_3$-4"), 3.55 (t, J=4.57 Hz, 4H, O(CH$_2$CH$_2$)$_2$NCH$_2$CH$_2$CH$_2$-4'), 2.40 (t, J=6.97 Hz, 2H, O(CH$_2$CH$_2$)$_2$NCH$_2$CH$_2$CH$_2$-4'), 2.40 (t, J=6.97 Hz, 2H, O(CH$_2$CH$_2$)$_2$NCH$_2$CH$_2$CH$_2$-4'), 2.30 (t, J=4.57 Hz, 4H, O(CH$_2$CH$_2$)$_2$NCH$_2$CH$_2$CH$_2$-4') 2.28 (s, 3H, CH$_3$-3'), 2.24 (s, 3H, CH$_3$-5'), 2.23 (t, J=6.97 Hz, 2H, O(CH$_2$CH$_2$)$_2$NCH$_2$CH$_2$CH$_2$-4'), 1.55 (quint., J=6.97 Hz, 2H, O(CH$_2$CH$_2$)$_2$NCH$_2$CH$_2$CH$_2$-4'), MS m/e (relative intensity, %) 471 (M$^{+\cdot}$, 100).

EXAMPLE 48 (FROM TABLE 3)

3-[4-(3-Dimethylaminopropyl)-3,5-Dimethyl-1H-Pyrrol-2-Ylmethylene]-1,3-Dihydroindol-2-One Using Steps 1,2, and 3 of Example 1, a 63% yield of 4-(3-dimethylaminopropyl)-3,5-dimethyl-1H-pyrrole-2-carboxaldehyde as a dark red oil:

$^1$HNMR (360 MHz, DMSO-d$_6$) δ 11.33 (s, br, 1H, NH-1), 9.40 (s, 1H, CHO-2), 2.30 (t, J=7.42 Hz, 2H, (CH$_3$)$_2$NCH$_2$CH$_2$CH$_2$-4), 2.18 (s, 3H, CH$_3$-3), 2.15 (t, J=7.42 Hz, 2H, (CH$_3$)$_2$NCH$_2$CH$_2$CH$_2$-4), 2.14 (s, 3H, CH$_3$-5), 2.10 (s, 6H, (CH$_3$)$_2$NCH$_2$CH$_2$CH$_2$-4), 1.47 (quint., J=7.42 Hz, 2H, (CH$_3$)$_2$NCH$_2$CH$_2$CH$_2$-4), MS m/z (relative intensity, %) 208 ([M+1]$^{+\cdot}$, 100).

Using Stet 4 of Example 1, a 52% yield of the title compound was obtained as a yellow solid:

$^1$HNMR (360 MHz, DMSO-d$_6$) δ 13.38 (s, 1H, NH-1'), 10.70 (s, 1H, NH-1), 7.68 (d, J=7.54 Hz, 1H, H-4), 7.53 (s, 1H, H-vinyl), 7.06 (t, J=7.54 Hz, 1H, H-6), 6.94 (t, J=7.54 Hz, 1H, H-5), 6.85 (d, J=7.54 Hz, 1H, H-7), 2.38 (t, J=7.25 Hz, 2H, (CH$_3$)$_2$NCH$_2$CH$_2$CH$_2$-4'), 2.27 (s, 3H, CH$_3$-3'), 2.23 (s, 3H, CH$_3$-5'), 2.17 (t, J=7.25 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.52 (quint., J=7.25 Hz, 2H, (CH$_3$)$_2$NCH$_2$CH$_2$CH$_2$-4'), MS m/z (relative intensity, %) 323 (M$^{+\cdot}$, 100).

EXAMPLE 49 (FROM TABLE 3)

5-Bromo-3-[4-(3-Dimethylaminopropyl)-3,5-Dimethyl-1H-Pyrrol-2-Ylmethylene]-1,3-Dihydroindol-2-One Using the procedure of Example 2, a 71% yield of the title compound was obtained as a red solid:

$^1$HNMR (360 MHz, DMSO-d$_6$) δ 13.42 (s, 1H, NH-1'), 10.81 (s, 1H, NH-1), 7.98 (d, J=1.89 Hz, 1H, H-4), 7.66 (s, 1H, H-vinyl), 7.17 (dd, J=1.89, 8.23 Hz, 1H, H-6), 6.79 (d, J=8.23 Hz, 1H, H-7), 2.38 (t, J=7.23 Hz, 2H, (CH$_3$)$_2$NCH$_2$CH$_2$CH$_2$-4'), 2.27 (s, 3H, CH$_3$-3'), 2.25 (s, 3H, CH$_3$-5'), 2.16 (t, J=7.23 Hz, 2H, (CH$_3$)$_2$NCH$_2$CH$_2$CH$_2$-4'), 2.10 (s, 6H, (CH$_3$)$_2$NCH$_2$CH$_2$CH$_2$-4'), 1.51 (quint., J=7.23 Hz, 2H, (CH$_3$)$_2$NCH$_2$CH$_2$CH$_2$-4'), MS m/z (relative intensity, %) 401 ([M−1]$^{+\cdot}$, 100) and 403 ([M+1]$^{+\cdot}$, 100).

EXAMPLE 50 (FROM TABLE 3)

3-[4-(3-Dimethylaminopropyl)-3,5-Dimethyl-1H-pyrrol-2-Ylmethylene]-6-Phenyl-1,3-Dihydroindol-2-One Using the procedure of Example 2, an 83% yield of the title compound was obtained as an orange solid:

$^1$HNMR (360 MHz, DMSO-d$_6$) δ 13.38 (s, 1H, NH-1'), 10.81 (s, 1H, NH-1), 7.77 (d, J=7.82 Hz, 1H, H-4), 7.62 (d, J=7.59 Hz, 2H, H-2",6"), 7.58 (s, 1H, H-vinyl), 7.44 (t, J=7.59 Hz, 2H, H-3.41,5"), 7.32 (t, J=7.59 Hz, 1H, H-4"), 7.27 (dd, J=1.11, 7.82 Hz, 1H, H-5), 7.09 (d, J=1.11 Hz, 1H, H-7), 2.39 (t, J=7.18 Hz, 2H, (CH$_3$)$_2$NCH$_2$CH$_2$CH$_2$-4'), 2.29 (s, 3H, CH$_3$-3'), 2.25 (s, 3H, CH$_3$-5'), 2.17 (t, J=7.18 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.53 (quint., J=7.18 Hz, 2H, (CH$_3$)$_2$NCH$_2$CH$_2$CH$_2$-4'), MS m/z (relative intensity, %) 399 (M$^{+\cdot}$, 100).

EXAMPLE 51 (FROM TABLE 3)

3-[4-(3-Dimethylaminopropyl)-3,5-Dimethyl-1H-Pyrrol-2-Ylmethylene]-6-(2-Methoxyphenyl)-1,3-Dihydroindol-2-One Using the procedure of Example 2, an 83% yield of the title compound was obtained as a yellow solid:

$^1$HNMR (360 MHz, DMSO-d$_6$) δ 13.38 (s, 1H, NH-1'), 10.72 (s, 1H, NH-1), 7.70 (d, J=8.06 Hz, 1H, H-4), 7.55 (s, 1H, H-vinyl), 7.28–7.36 (m, 2H, H-4",5"), 7.14 (d, J=8.32 Hz, 1H, H-6"), 7.04 (dd, J=1.21, 8.06 Hz, 1H, H-5), 6.99 (d, J=7.42 Hz, 1H, H-3"), 6.99 (d, J=1.21 Hz, 1H, H-7), 3.76 (s, 3H, OCH$_3$-2"), 2.39 (t, J=7.24 Hz, 2H, (CH$_3$)$_2$NCH$_2$CH$_2$CH$_2$-4'), 2.28 (s, 3H, CH$_3$-3'), 2.25 (s, 3H, CH$_3$-5+), 2.18 (t, J=7.24 Hz, 2H, (CH$_3$)$_2$NCH$_2$CH$_2$CH$_2$-4'), 2.11 (s, 6H, CH$_3$)$_2$NCH$_2$CH$_2$CH$_2$-4'), 1.53 (quint., J=7.24 Hz, 2H, (CH$_3$)$_2$NCH$_2$CH$_2$CH$_2$-4'), MS m/z (relative intensity, %) 429 (M$^{+\cdot}$, 100).

EXAMPLE 52 (FROM TABLE 3)

3-[4-(3-Dimethylaminopropyl)-3,5-Dimethyl-1H-Pyrrol-2-Ylmethylene]-6-(3-Methoxyphenyl)-1,3-Dihydroindol-2-One Using the procedure of Example 2, an 83% yield of the title compound was obtained as a red solid:

$^1$HNMR (360 MHz, DMSO-d$_6$) δ 13.38 (s, 1H, NH-1'), 10.80 (s, 1H, NH-1), 7.60 (d, J=8.06 Hz, 1H, H-4), 7.57 (s, 1H, H-vinyl), 7.35 (t, J=8.15 Hz, 1H, H-5"), 7.26 (dd, J=1.39, 8.06 Hz, 1H, H-5), 7.19 (d, br, J=8.15 Hz, H-6"), 7.13 (m, 1H, H-2"), 7.09 (d, J=1.39 Hz, 1H, H-7), 6.90 (dd, J=2.57, 8.15 Hz, 1H, H-4"), 3.81 (s, 3H, OCH$_3$-3"), 2.39 (t, J=7.17 Hz, 2H, (CH$_3$)$_2$NCH$_2$CH$_2$CH$_2$-4'), 2.29 (s, 3H, CH$_3$-3'), 2.25 (s, 3H, CH$_3$-5'), 2.17 (t, J=7.17 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.53 (quint., J=7.17 Hz, 2H, (CH$_3$)$_2$NCH$_2$CH$_2$CH$_2$-4'), MS m/z (relative intensity, %) 429 (M$^{+\cdot}$, 100).

EXAMPLE 53 (FROM TABLE 3)

3-[4-(3-Dimethylaminopropyl)-3,5-Dimethyl-1H-Pyrrol-2-Ylmethylene]-6-(4-Methoxyphenyl)-1,3-Dihydroindol-2-One Using the procedure of Example 2, an 83% yield of the title compound was obtained as a brown solid:

$^1$HNMR (360 MHz, DMSO-d$_6$) δ 13.35 (s, 1H, NH-1'), 10.77 (s, 1H, NH-1), 7.73 (d, J=7.82 Hz, 1H, H-4), 7.56 (d, J=8.83 Hz, 2H, H-2",6"), 7.54 (s, 1H, H-vinyl), 7.20 (dd, J=1.64, 7.82 Hz, 1H, H-5), 7.04 (d, J=1.64 Hz, H-7), 7.00 (d, J=8.83 Hz, 2H, H-3",5), 3.78 (s, 3H, OCH$_3$-4"), 2.39 (t, J=7.24 Hz, 2H, (CH$_3$)$_2$NCH$_2$CH$_2$CH$_2$-4'), 2.28 (s, 3H, CH$_3$-3'), 2.25 (s, 3H, CH$_3$-5'), 2.17 (t, J=7.24 Hz, 2H(CH$_3$)$_2$NCH$_2$CH$_2$CH$_2$-4'), 2.11 (s, 6H, (CH$_3$)$_2$NCH$_2$CH$_2$CH$_2$-4'), 1.52 (quint., J=7.24 Hz, 2H, (CH$_3$)$_2$NCH$_2$CH$_2$CH$_2$-4'), MS m/z (relative intensity, %) 429 (M$^{+\cdot}$, 100).

EXAMPLE 54 (FROM TABLE 3)

5-Chloro-3-[4-(3-Dimethylaminopropyl)-3,5-Dimethyl-1H-Pyrrol-2-Ylmethylene]-1,3-Dihydroindol-2-One Using the procedure of Example 2, a 53% yield of the title compound was obtained as a brown solid:

$^1$HNMR (360 MHz, DMSO-d$_6$) δ 13.43 (s, 1H, NH-1'), 10.84 (s, 1H, NH-1), 7.87 (d, J=1.85 Hz, 1H, H-4), 7.66 (s, 1H, H-vinyl), 7.05 (dd, J=1.85, 8.15 Hz, 1H, H-6), 6.83 (d, J=8.15 Hz, 1H, H-7), 2.36–2.45 (m, 4H, (CH$_3$)$_2$NCH$_2$CH$_2$CH$_2$-4'), 2.30 (s, 6H, (CH$_3$)$_2$NCH$_2$CH$_2$CH$_2$-4'), 2.28 (s, 3H, CH$_3$-3'), 2.26 (s, 3H, CH$_3$-5'), 1.58 (quint., J=7.52 Hz, 2H, (CH$_3$)$_2$NCH$_2$CH$_2$CH$_2$-4'), MS m/z (relative intensity, %) 357 ([M−1]$^{+\cdot}$, 100).

EXAMPLE 55 (FROM TABLE 3)

6-Chloro-3-[4-(3-Dimehtylaminopropyl)-3,5-Dimethyl-1H-Pyrrol-2-Ylmethylene]-1,3-Dihydroindol-2-One Using the procedure of Example 2, a 77% yield of the title compound was obtained:

MS EI 357 [M−1]$^+$.

EXAMPLE 56 (FROM TABLE 3)

3-[4(3Dimethylaminopropyl)-3,5-Dimethyl-1H-Pyrrol-2-Ylmethylene]-5-Methoxy-1,3-Dihydroindol-2-One Using the procedure of Example 2, a 77% yield of the title compound was obtained:

MS EI 353 [M]$^+$.

EXAMPLE 57 (FROM TABLE 3)

3-[4-(3-Dimethylaminopropyl)-3,5-Dimethyl-1H-Pyrrol-2-Ylmethylene]-6-Methoxy-1,3-Dihydroindol-2-One Using the procedure of Example 2, a 74% yield of the title compound was obtained.

EXAMPLE 58 (FROM TABLE 3)

3-[4-(3-Dimethylaminopropyl)-3,5-Dimethyl-1H-Pyrrol-2-Ylmethylene]-5-Methyl-1,3-Dihydroindol-2-One Using the procedure of Example 2, a 45% yield of the title compound was obtained:

MS EI 337 [M]$^+$.

EXAMPLE 59 (FROM TABLE 3)

3-[4-(3-Dimethylaminopropyl)-3,5-Dimethyl-1H-Pyrrol-2-Ylmethylene]-4-Methyl-1,3-Dihydroindol-2-One Using the procedure of Example 2, a 99% yield of the title compound was obtained:

$^1$HNMR (300 MHz, DMSO-d$_6$) δ 13.45 (s, br, 1H, NH), 7.50 (s, 1H, H-vinyl), 6.98 (t, J=8.1 Hz, 1H, H-6), 6.76 (t, J=8.1 Hz, 2H, H-5 & H-7), 2.88 (m, 2H), CH$_2$), 2.64 (s, 6H, 2×CH$_3$), 2.56 (s, 3H, CH$_3$), 2.43 (t, J=7.4 Hz, 2H, CH$_2$), 2.29 (s, 3H, CH$_3$), 2.19 (s, 3H, CH$_3$), 1.65–1.75 (m, 2H, CH$_2$), MS EI 337 [M]$^+$.

EXAMPLE 60 (FROM TABLE 3)

3-[4(3Dimehtylaminopropyl)-3,5-Dimethyl-1H-Pyrrol-2-Ylmethylene]-4-(2-Hydroxy-Ethyl)-1,3-Dihydroindol-2-One Using the method of Example 2, a 98% yield of the title compound was obtained.

EXAMPLE 61 (FROM TABLE 3)

3-[4-(3-Dimethylaminopropyl)-3,5-Dimethyl-1H-Pyrrol-2-Ylmethylene]-2-Oxo-2,3-Dihydro-1H-Indole-5-Sulfonic Acid Amide Using the procedure of Example 2, a 59% yield of the title compound was obtaind:

$^1$HNMR (300 MHz, DMSO-d$_6$) δ 13.41 (s, 1H, NH-1'), 11.12 (s, 1H, NH-1), 8.16 (d, J=1.78 Hz, 1H, H-4), 7.66 (s, 1H, H-vinyl), 7.55 (dd, J=1.78, 8.18 Hz, 1H, H-6), 7.11 (s, br, 2H, H$_2$NSO$_2$-5), 6.98 (d, J=8.18 Hz, 1H, H-7), 2.47–2.50 (m, 2H, (CH$_3$)$_2$NCH$_2$CH$_2$CH$_2$-4'), 2.41 (t, J=7.37 Hz, 2H, (CH$_3$)$_2$NCH$_2$CH$_2$CH$_2$-4'), 2.36 (s, 6H, (CH$_3$)$_2$NCH$_2$CH$_2$CH$_2$-4'), 2.30 (s, 3H, CH$_3$-3'), 2.28 (s, 3H, CH$_3$-5'), 1.61 (quint., J=7.37 Hz, 2H, (CH$_3$)$_2$NCH$_2$CH$_2$CH$_2$-4').

EXAMPLE 62 (FROM TABLE 3)

3-[4-(3-Dimethylaminopropyl)-3,5-Dimethyl-1H-Pyrrol-2-Ylmethylene]-2-Oxo-2,3-Dihydro-1H-Indole-5-Sulfonic Acid Isopropylamide Using the method of Example 2, a 64% yield of the title compound was obtained:

MS EI 444 [M]$^+$.

EXAMPLE 63 (FROM TABLE 3)

3-[4-(3-Dimehtylaminopropyl)-3,5-Dimethyl-1H-Pyrrol-2-Ylmethylene]-5-(Morpholine-4-Sulfonyl)-1,3-Dihydroindol-2-One Using the procedure of Example 2, a 90% yield of the title compound was obtained.

MS EI 472 [M]$^+$.

EXAMPLE 64 (FROM TABLE 3)

3-[4-(3-Dimethylaminopropyl)-3,5-Dimethyl-1H-Pyrrol-2-Ylmethylene]-2-Oxo-2,3-Dihydro-1H-Indole-5-Sulfonic Acid Dimethylamide Using the method of claim 2, a 92% yield of the title compound was obtained:

$^1$HNMR (300 MHz, DMSO-d$_6$) δ 13.5 (s, br, 1H, NH), 12.21 (s, br, 1H, NH), 8.18 (d, J=1.8 Hz, 1H, H-4), 7.84 (s, 1H, H-vinyl), 7.44 (dd, J=1.8, 8.4 Hz, 1H, H-6), 7.05 (d, J=8.4 Hz, 1H, H-7), 2.59 (s, 6H, 2×CH$_3$), 2.59–2.64 (m, 2H, CH$_2$), 2.44 (s, 6H, 2×CH$_3$), 2.38–2.44 (m, 2H, CH$_2$), 2.31 (s, 6H, 2×CH$_3$), 1.59–1.69 (m, 2H, CH$_2$),

MS EI 430 [M]$^+$.

BIOLOGICAL EVALUATION EXAMPLES

The examples given below are not limiting and are merely representative of various aspects and features of the present invention. The examples demonstrate parenteral and oral formulations, methods of making such formulations and uses of the formulations. The ionizable free acid, 3-[2,4-Dimethyl-5-(2-oxo-1,2-dihydro-indol-3-ylidenemethyl)-1H-pyrrol-3-yl]-propionic acid, is used as a representative example for the genus of ionizable free acids and free bases.

EXAMPLE 1

In Vivo Efficacy of 3-[2,4-Dimethyl-5-(2-Oxo-1,2-Dihydro-Indol-3-Ylidenemethyl)-1H-Pyrrol-3-Yl]-propionic Acid The ability of 3-[2,4-Dimethyl-5-(2-oxo-1,2-dihydro-indol-3-ylidenemethyl)-1H-pyrrol-3-yl]-propionic acid to inhibit subcutaneous (SC) growth of multiple tumor types in athymic mice was evaluated.

Experimental Procedures
Tumor Cell Lines

C6, SKOV3 and A431 cell lines were purchased from the Americal Type Culture Collection (Rockville, Md.). SF763 and SF767 cells were obtained from Dr. Michael Berens (Barrow Neurological Institute). SF763T, SF767T, and SKOV3TP5 are tumor-derived sublines of SF763, SF767, and SKOV3 cells, respectively.

SF763T, SF767T, and SKOV3TP5 were derived by implanting the parental cells SC into BALB/c nu/nu mice. Tumors that displayed desirable growth characteristics were resected and finely minced in a sterile petri dish.

For the SF763T and SF767T cell lines, two to five mL of appropriate medium was added to the slurry and the tumor pieces were further mechanically teased apart. The resulting suspension was placed into tissue culture flasks and incubated with the appropriate culture medium supplemented with 100 units/mL penicillin G sodium and 100 $\mu$g/mL streptomycin sulfate (Gibco, Grand Island, N.Y.). Medium was changed every two to three days. After three to five passages, the antibiotic supplements were removed and the cells maintained in antibiotic-free medium.

For the SKOV3TP5 cells, fragments of resected tumors were injected SC into mice for in vivo passaging. This procedure was repeated five times before cells were returned to culture as described above.

Cell Culture

All reagents and media for cell culture were obtained from Life Technologies, Inc. (Gaithersburg, Md.). C6 cells were cultured in Ham's F-10 supplemented with 5% FBS and 2 mM L-glutamine. A375, A431 and EpH4-VEGF1 cells were cultured in DMEM supplemented with 10% FBS and 2 mM L-glutamine. SKOV3TP5 cells were cultured in McCoy's 5A medium supplemented with 10% FBS and 2 mM L-glutamine. Calu-6, SF763T and SF767T cells were cultured in MEM supplemented with 10% FBS, 2 mM L-glutamime, 1 mM sodium pyruvate and 0.1 mM MEM non-essential amino acids. All cell cultures were maintained at 37° C. in a humidified atmosphere of 5–10% $CO_2$.

Subcutaneous Xenograft Models in Athymic Mice

Experiments were conducted in accordance with Instutitional Animal Care and Use Committee (IACUC) guidelines as listed under protocol SAF029. Tumor cell lines (0.6–10× $10^6$ cells/animal; n=8–20 animals/group) were implanted SC in the hindflank region of 8–12 week old BALB/c nu/nu female mice. With the exception of experiments where the efficacy of 3-[2,4-Dimethyl-5-(2-oxo-1,2-dihydro-indol-3-ylidenemethyl)-1H-pyrrol-3-yl]-propionic acid on established tumors was evaluated, treatment with either 3-[2,4-Dimethyl-5-(2-oxo-1,2-dihydro-indol-3-ylidenemethyl)-1H-pyrrol-3-yl]-propionic acid or vehicle commenced one day post-implantation.

For parenteral dosing, animals received a 50 $\mu$L IP bolus injection of either 3-[2,4-Dimethyl-5-(2-oxo-1,2-dihydro-indol-3-ylidenemethyl)-1H-pyrrol-3-yl]-propionic acid in DMSO or DMSO alone for the indicated number of days. In most experiments, compound was administered daily. In the dosing regimen studies, compound was administered according to the schedules outlined in Table 2.

For oral administration, 3-[2,4-Dimethyl-5-(2-oxo-1,2-dihydro-indol-3-ylidenemethyl)-1H-pyrrol-3-yl]-propionic acid was delivered by oral gavage (PO) at 200 mg/kg in a Labrasol®-containing vehicle.

Tumor growth was measured using venier calipers. Tumor volumes were calculated as the produce of length x width x height. Statistical analysis was carried out using Student's t-test.

Results

Significant inhibition of SC tumor growth of Calu-6 (human lung carcinoma) cells in BALB/c nu/nu mice was observed following IP administration of 3-[2,4-Dimethyl-5-(2-oxo-1,2-dihydro-indol-3-ylidenemethyl)-1H-pyrrol-3-yl]-propionic acid at 75 and 100 $\mu$mg/kg/day. At the conclusion of the experiment (Day 25), inhibition of tumor growth was 79 to 86% compared to vehicle-treated control animals, and mortality was 12.5% at both doses.

In subsequent experiments, 3-[2,4-Dimethyl-5-(2-oxo-1,2-dihydro-indol-3-ylidenemethyl)-1H-pyrrol-3-yl]-propionic acid was administered IP to mice which had received implants of tumor xenografts representing several different tissue origins. The results of these studies are summarized in Table 1.

TABLE 1

Effect of IP administered
3-[2,4-Dimethyl-5-(2-oxo-1,2-dihydro-indol-3-ylidenemethyl)-1H-pyrrol-3-yl]-propionic acid
on SC growth of a panel of tumor xenografts
in BALB/c nu/nu mice

| Test Facility Number | Cell Line | Tumor Type | Compound Dose (mg/kg/d) | % Inhibition @ (day) | P value | % Mortality |
|---|---|---|---|---|---|---|
| E01591 | A375 | human melanoma | 75* | 56 (29) | 0.0386 | 0 |
| E01592 | C6 | rat glioma | 100 | 65 (18) | 0.0004 | 12.5 |
| E01606 | SF763T | human glioma | 75 | 48 (21) | 0.0037 | 12.5 |
| E01607 | SF767T | human glioma | 75 | 46 (21) | 0.0041 | 12.5 |

TABLE 1-continued

Effect of IP administered
3-[2,4-Dimethyl-5-(2-oxo-1,2-dihydro-indol-3-ylidenemethyl)-1H-pyrrol-3-yl]-
propionic acid
on SC growth of a panel of tumor xenografts
in BALB/c nu/nu mice

| Test Facility Number | Cell Line | Tumor Type | Compound Dose (mg/kg/d) | % Inhibition @ (day) | P value | % Mortality |
|---|---|---|---|---|---|---|
| E01668 | SKOV3TP5 | human ovarian | 75 | 9 (25) | ns | 25 |
| E01656 | A431 | human epidermal | 100 | 84 (24) | <0.0001 | 12.5 |
| E01661 | EpH4-VEGF1 | murine epithelial | 75 | 34 (18) | 0.0339 | 0 |

Table 1. Daily administration (except where indicated by *, dosed 3x/week) at the indicated doses (mg/kg/day) in DMSO began one day post-implantation. Percent inhibition compared to the vehicle-treated control group was calculated on the indicated days post-implantation. P values were calculated by comparing mean tumor size of the treated group to mean tumor size of the vehicle control group using the Student's t-test. ns = not significant (P > 0.05).

Including the Calu-6 data depicted in Table 1, 3-[2,4-Dimethyl-5-(2-oxo-1,2-dihydro-indol-3-ylidenemethyl)-1H-pyrrol-3-yl]-propionic acid significantly inhibited the SC growth of 6 to 7 tumor cell lines tested, representing tumors of skin, brain, and lung origin. These results suggest that 3-[2,4-Dimethyl-5-(2-oxo-1,2-dihydro-indol-3-ylidenemethyl)-1H-pyrrol-3-yl]-propionic acid inhibits the in vivo growth of multiple tumor types when administered systemically in a daily regimen.

The studies described above demonstrated that 3-[2,4-Dimethyl-5-(2-oxo-1,2-dihydro-indol-3-ylidenemethyl)-1H-pyrrol-3-yl]-propionic acid was efficacious at inhibiting the growth of several tumor types in vivo if drug administration began one day post-implantation. In the clinical scenario, this might simulate therapy on re-growth of tumors following tumor shrinkage by surgical resection or chemotherapy, or following metastasis of cancer.

To evaluate the efficacy of 3-[2,4-Dimethyl-5-(2-oxo-1,2-dihydro-indol-3-ylidenemethyl)-1H-pyrrol-3-yl]-propionic acid as first line therapy, that is, its effect on tumors that are already established, tumors were implanted and allowed to grow to a measurable size (approximately 100 mm$^3$) prior to initiation of drug administration.

C6 cells were implanted SC into athymic mice on day zero. When measurable tumors had developed in a majority of the animals (Day 7), they were divided into 3 groups: Group 1 received daily IP administration of compound (75 mg/kg/day) from Day 7 through Day 16; Group 2 received daily IP administration of compound (75 mg/kg/day) from Day 7 through Day 22, and Group 3 received daily IP administration of DMSO from Day 7 though Day 16. On Day 16, all Group 3 animals were humanely sacrificed due to tumor burden (mean tumor diameter approximately 1300 mm$^3$), and the growth of tumors in Groups 1 and 2 was monitored until the mean tumor burden of each group reached 1300 mm$^3$.

The results demonstrate that 3-[2,4-Dimethyl-5-(2-oxo-1,2-dihydro-indol-3-ylidenemethyl)-1H-pyrrol-3-yl]-propionic acid was efficacious even when the onset of administration was delayed until measurable tumors were present. Furthermore, there was a finite window of efficacy (Days 7 through 21, Group 1) that was not significantly prolonged by continued dosing beyond Day 16 (Group 2).

To assist in the development of a clinical dosing plan, dosing regimen studies were conducted to determine if tumor growth could be inhibited by dosing less frequently than daily. The results are summarized in Table 2. For comparison, the results obtained with daily dosing are included.

TABLE 2

In vivo dosing regimen studies with IP administered 3-[2,4-Dimethyl-5-(2-oxo-1,2-dihydro-indol-3-ylidenemethyl)-1H-pyrrol-3-yl]-propionic acid

| Test Facility Number | Dose (mg/kg) | Dosing Regimen | % Inhibition (at day) | P Value |
|---|---|---|---|---|
| E01592 | 50 | Daily | 27 (18) | ns |
| E01592 | 75 | Daily | 53 (18) | 0.002 |
| E01592 | 100 | Daily | 65 (18) | 0.004 |
| E01590 | 25 | Daily x 5 | 1 (18) | ns |
| E01590 | 50 | Daily x 5 | 68 (18) | 0.0000 |
| E01590 | 75 | Daily x 5 | 54 (18) | 0.0004 |
| E01590 | 50 | Twice weekly | 36 (19) | 0.0175 |
| E01590 | 75 | Twice weekly | 26 (19) | ns |
| E01590 | 100 | Twice weekly | 38 (19) | 0.0188 |
| E01590 | 50 | Three times weekly | 25 (18) | ns |
| E01590 | 75 | Three times weekly | 29 (18) | ns |
| E01590 | 100 | Three times weekly | 40 (18) | 0.0042 |
| E01605 | 100 | Daily x 5 followed by Once weekly | 42 (15) | 0.0327 |
| E01605 | 150 | Daily x 5 followed by once weekly | 51 (15) | 0.0128 |

Table 2. C6 cells were implanted SC in BALB/c nu/nu mice. Beginning one day post-implantation, animals received the indicated doses of compound, administered IP according to the schedules indicated. Control animals were dosed with vehicle (DMSO) according to the same schedules. Tumor volumes were measured and percent inhibition was calculated as described in the legend to FIG. 1. n = 8–16 aninals/group. ns = not significant (P > 0.05).

These data suggest that 3-[2,4-Dimethyl-5-(2-oxo-1,2-dihydro-indol-3-ylidenemethyl)-1H-pyrrol-3-yl]-propionic acid can be delivered using a dosing regimen that is less frequent than daily administration. For example, doses of 50 to 75 mg/kg delivered Daily x5 yielded efficacy similar to that seen when 100 mg/kg was administered Daily x7. Also, a dose of 100 mg/kg was administered twice weekly or three times weekly yielded statistically significant tumor growth inhibition of approximately 40%. The daily administration of 3-[2,4-Dimethyl-5-(2-oxo-1,2-dihydro-indol-3-ylidenemethyl)-1H-pyrrol-3-yl]-propionic acid is not necessary to achieve significant efficacy in preclinical models.

The efficacy of 3-[2,4-Dimethyl-5-(2-oxo-1,2-dihydro-indol-3-ylidenemethyl)-1H-pyrrol-3-yl]-propionic acid by the oral route of administration was examined in the C6 (rat glioma) SC xenograft model in athymic mice. Beginning one day post-implantation, compound (200 mg/kg/day in solution in a Labrasol®-containing vehicle) was administered to mice PO. Tumor growth was measured using venier calipers and tumor volumes were calculated as the product of length x width x height.

In this SC xenograft model, significant inhibition of tumor growth occurred following oral treatment of mice with 3-[2,4-Dimethyl-5-(2-oxo-1,2-dihydro-indol-3-ylidenemethyl)-1H-pyrrol-3-yl]-propionic acid at 200 mg/kg/day. On Day 18 post-implantation, tumor growth was inhibited by 82% compared to vehicle-treated animals, with only 10% mortality. These data demonstrate that 3-[2,4-Dimethyl-5-(2-oxo-1,2-dihydro-indol-3-ylidenemethyl)-1H-pyrrol-3-yl]-propionic acid effectively inhibited tumor growth when administered PO

EXAMPLE 2

Preformulation Studies

Preformulation studies evaluate the physico-chemical properties of the compound and enable formulation development of the compound.

Solubility Profile

Solubility was determined at room temperature by shaking an excess amount of 3-[2,4-Dimethyl-5-(2-oxo-1,2-dihydro-indol-3-ylidenemethyl)-1H-pyrrol-3-yl]-propionic acid in solvent for over 24 hours. The solution was filtered, appropriate dilutions made and the concentration of the compound in the supernatant was analyzed by a reverse phase HPLC method. The results are tabulated in Table 3.

TABLE 3

Solubility of 3-[2,4-Dimethyl-5-(2-oxo-1,2-dihydro-indol-3-ylidenemethyl)-1H-pyrrol-3-yl]-propionic acid

| Solvent | Solubility (mg/mL) |
| --- | --- |
| Water* | 0.03 |
| 0.1 N HCl | <0.0001 |
| 0.1 N NaOH* | 20.8 |
| pH 6 buffer** | 0.002 |
| pH 7 buffer** | 0.009 |
| pH 8 buffer** | 0.085 |
| pH 9 buffer** | 1.60 |
| PEG-300* | 6.8 |
| 15% PEG 300 in pH 8.2 buffer** | 1.4 |
| 30% PEG 300 in pH 8.2 buffer** | 3.2 |
| 15% PEG 300, 1% Benzyl alcohol in pH 8.2 buffer** | 1.8 |
| 30% PEG 300, 1% Benzyl alcohol in pH 8.2 buffer** | 3.7 |
| 10% Propylene glycol in pH 8.2 buffer** | 0.4 |
| 2% aqueous Polysorbate - 80 | 0.13 |
| Ethanol | 1.2 |
| Methanol | 0.6 |
| 2% Polysorbate - 80 | 0.13 |

*Average solubility of 3 lots.
** Average of 2 lots.
Buffer pH 6–8.2 is 0.1 M phosphate buffer; buffer pH 9 is 0.1 M borate buffer pH Solubility Profile The solubility of two lots of 3-[2,4-Dimethyl-5-(2-oxo-1,2-dihydro-indol-3-ylidenemethyl)-1H-pyrrol-3-yl]-propionic acid was determined at pH 6.0, 6.5, 7.0, 7.5 and 8.0 of phosphate buffer and pH 9 of borate buffer. The results are indicated in Table 4 and show that the solubility increases with pH. Ionic strength of the solution and common ion effect can affect solubility.

TABLE 4

Solubility of 3-[2,4-Dimethyl-5-(2-oxo-1,2-dihydro-indol-3-ylidenemethyl)-1H-pyrrol-3-yl]-propionic acid as a function of pH

| pH of Buffer | Average pH at Equilibrium | Average Solubility (mg/mL) |
| --- | --- | --- |
| 6.0 | 6.06 | 0.0024 |
| 6.5 | 6.52 | 0.004 |
| 7.0 | 6.96 | 0.009 |
| 7.4 | 7.39 | 0.019 |
| 8.0 | 8.06 | 0.085 |
| 8.2 | n/t | 0.13 |
| 9.0 | 8.79 | 1.6 |

Buffer pH 6–8.2 was 0.1 M phosphate buffer; buffer pH 9 was 0.1 M borate buffer. "pH at equilibrium" was measured after 24 hours of equilibration, just before analysis. n/t = not tested.

Ionization Constant, pKa, and Partition Coefficient, Log P

3-[2,4-Dimethyl-5-(2-oxo-1,2-dihydro-indol-3-ylidenemethyl)-1H-pyrrol-3-yl]-propionic acid is a hydrophobic ionizable weak acid. The pKa is 5.02. Log P and Log D (at pH 7.4) are 3.85 and 1.5, respectively. pKa, Log P, and Log D values were determined by potentiometric titration at Robertson Microlit Laboratories, New Jersey. pKa was calculated using the Seiler method.

TABLE 5

Solubility of In situ 3-[2,4-dimethyl-5-(2-oxo-1,2-dihydro-indol-3-ylidenemethyl)-1H-pyrrol-3-yl]-propionic acid salt formation

| Salt | Solubility mg/ml | pH |
| --- | --- | --- |
| Sodium | 23.9 | 8.56 |
| Ammonium | 3.85 | 9.2 |
| Ethylenediamine | 7.1 | 9.3 |
| Choline | 6.5 | 8.2 |
| Meglumine | 7.9 | 9.3 |
| Buffer pH 8 (free acid) | 0.085 | 8.06 |
| Buffer pH 8.8 (free acid) | 1.6 | 8.8 |
| Sodium salt | 17–25 | 8.6–8.9 |

The preformulation studies indicated that the aqueous solubility of the compound could be enhanced about 1000 times by a situ salt formation (e.g., the sodium salt has a solubility of about 25 mg/ml in comparison to the free acid which is about 30 µg/ml). This strategy was used in the formulation development.

EXAMPLE 3

Parenteral Formulations of Ionizable Substituted Indolinone Compounds

To be used as a parenteral formulation, and especially an intravenous formulation, a high aqueous solubility of the drug candidate is desirable. The solubility of 3-[2,4-Dimethyl-5-(2-oxo-1,2-dihydro-indol-3-ylidenemethyl)-1H-pyrrol-3-yl]-propionic acid was enhanced several folds by salt formation. The sodium salt of 3-[2,4-Dimethyl-5-(2-oxo-1,2-dihydro-indol-3-ylidenemethyl)-1H-pyrrol-3-yl]-propionic acid has a solubility of 20 mg/mL compared to the less than 0.1 mg/mL of the free acid. The solubility of 3-[2,4-Dimethyl-5-(2-oxo-1,2-dihydro-indol-3-ylidenemethyl)-1H-pyrrol-3-yl]-propionic acid was either enhanced by using the sodium salt of 3-[2,4-Dimethyl-5-(2-oxo-1,2-dihydro-indol-3-ylidenemethyl)-1H-pyrrol-3-yl]-propionic acid or by in situ salt formation using acid equivalents of sodium hydroxide during manufacture of the formulation.

Following salt formation, the formulation was buffered with various solutions, including glutamate, glycine, tris-phosphate and sodium hydroxide solutions, at pH ranging from 8–9 at different buffer strengths (0.01, 0.05, and 0.1 M). Some water miscible cosolvents like PEG-300 in varying amounts (0% to 40%) were used to enhance the solubility and to stabilize the formulation. Addition of other solubilizers, such as Polysorbate 80, was also tested.

The composition of an exemplary formulation are given in Table 6, below. The formulation if it does not contain any Cremophor® or Polysorbate-80 should be diluted 1:1 (one part formulation to 1 part IV fluid) with intravenous fluid such as sterile water for injection, containing 0.45% sodium chloride, before administration. The dilution is much higher (1:1 to 1:50) depending on the concentration of Polyethoxylated 35 Castor Oil (Cremophor® EL) and Polysorbate-80 These parenteral formulations can also be administered orally.

Stir until homogenous.

Add Benzyl Alcohol.

Stir until homogenous.

Qs with phosphate buffer, pH 8–9.0, preferably pH 8.2

Filter through 0.2 μm nylon filter (disposable Nalgene filter unit).

Preparation of 0.05 M Phosphate Buffer pH 8.2:

Prepare 0.05 M sodium phosphate monobasic (monohydrate) solution to give solution 1.

Prepare 0.05 M sodium phosphate dibasic (anhydrous) solution to give solution 2.

Mix solution 1: solution 2 (0.034:1) to give pH 8.2 phosphate buffer. Check pH and adjust to 8.2 with either solution 1 or solution.

TABLE 6

Parenteral Formulation Composition

| Component | **Concentration Percent(w/v) Formula 1 | **Concentration Percent(w/v) Formula 2 |
|---|---|---|
| *3-[2,4-Dimethyl-5-(2-oxo-1,2-dihydro-indol-3-ylidenemethyl)-1H-pyrrol-3-yl]-propionic acid | 0.05–1.5 | 0.05–5.0 |
| Polyethylene Glycol 300, NF | Most Preferred 30.0% More preferably 1.0–70.0% Preferably 10–50 | Most Preferred 45.0% More preferably 1.0–70.0% Preferably 25–65% |
| Benzyl Alcohol, USP/NF | Most Preferred 1.0% More preferably 0–3.0% Preferably 0.9–2.0% | Most Preferred 1.0% More preferably 0–3.0% Preferably 0.9–2.0% |
| Polyethoxylated 35 castor oil (Cremophor ® EL) or Polysorbate 80 | Most Preferred 0% More preferably 0–50% Preferably 0–10% | Most Preferred 31.5% More preferably 0–50% Preferably 0–31.5% |
| Sodium Phosphate Dibasic, anhydrous, USP/NF | Most Preferred 0.47% More preferably 0–1.0% Preferably 0.3–0.5% | Most Preferred 0% More preferably 0–1.0% Preferably 0.3–0.5% |
| Sodium Phosphate Monobasic, monohydrate, USP/NF | Most Preferred 0.016% More preferably 0–0.25% Preferably 0.01–0.02% | Most Preferred 0% More preferably 0–0.25% Preferably 0.01–0.02% |
| Water for Injection, USP | QS to 100% | QS to 1.0 mL |
| pH adjustment by NaoH or HCl | More preferably 7.5–10.0% Preferably 9.0–9.5% | More preferably 7.5–10.0% Preferably 9.0–9.5% |

**drug conc. equivalent to 12 mg/mL of 3-[2,4-Dimethyl-5-(2-oxo-1,2-dihydro-indol-3-ylidenemethyl)-1H-pyrrol-3-yl]-propionic acid. *When the free acid is used to manufacture the formulation, a 1:1 molar equivalent of sodium hydroxide is added for in situ salt formation. Values in the first level of parenthesis represent concentration ranges according to preferred embodiments of the invention. The second level of parenthesis are the most preferred embodiments of the invention.

EXAMPLE 4

Parenteral Formulation Procedures

Batch size 100 mL

Prepare 100 mL, 0.05 M Phosphate buffer, pH 8.0–9.0, preferably pH 8.2 using sodium phosphate monobasic (monohydrate) and sodium phosphate dibasic (anhydrous).

Weigh the sodium salt of 3-[2,4-dimethyl-5-(2-oxo-1,2-dihydro-indol-3-ylidenemethyl)-1H-pyrrol-3-yl]-propionic acid the free. If using the free acid (3-[2,4-dimethyl-5-(2-oxo-1,2-dihydro-indol-3-ylidenemethyl)-1H-pyrrol-3-yl]-propionic acid), add a molar equivalent of sodium hydroxide.

Add 50–60 mL 0.05 M Phosphate buffer.

Stir until dissolved on a magnetic stirrer.

Add PEG-300 to this mixture. If the formulation contains Cremophor or surfactant, add it after the addition of PEG-300.

EXAMPLE 5

Oral Administration-Oil Suspension

The formulation described below enhance the oral bioaviability of COMPOUND IV in beagle dogs, a preclinical absorption model. At higher doses in fasted conditions, bioavailability studies in beagle dogs indicated that COMPOUND IV coiuld have a low bioavailability due to its poor solubility.

Two oral oil suspension formulations of COMPOUND IV (50 mg/gm-formulation $F_3$ and 250 mg/gm) were developed and evaluated in dogs for oral bioavailability. Both formulations contain 50 mg/gm of Pluroanic F-68. The formulation at 50 mg/gm of COMPOUND IV contains 900 mgs of sesame oil and the one that contains 250 mg/gm of COMPOUND IV contains 700 mgs of sesame oil.

Another formulation composed of as high as 750 mg/gm drug load of COMPOUND IV (formulation $F_4$) was developed using wet granulation. The formulation contains 200 mgs sesame oil. An emulsion of oil in water was prepared with 50 mg/gm PLURONIC™ F68 as emulsion agent and used as granulating liquid.

| Example of Composition. (50 mg/gm to 750 mg/gm) | | |
|---|---|---|
| Composition | Formulation $F_3$ | Formulation $F_4$ |
| COMPOUND IV | 50 mg | 750 mg |
| Pluronic | 50 mg | 50 mg |
| Sesame Oil | 900 mg | 290 ms |

| | Mean AUC (fasted) (mcg*min/ml) | |
|---|---|---|
| | | sd |
| Tablet (wet granulated) | 471 | 478 |
| Oil Suspension (50 mg/g) | 919 | 230 |
| Hi load Oil suspension (250 mg/g) | 927 | 308 |

AUC refers to the area under the curve of the plasma concentration time curve and represents oral bioavilability (BA). Higher AUC indicates higher BA. The table indicates that the oil suspensions provide higher BA than a conventional wet granulated tablet.

EXAMPLE 6

Development of Preferred Formulations

The following formulation screening experiments identified preferred formulations.

Experiments were designed to screen various granulations of 3-[2,4-Dimethyl-5-(2-oxo-1,2-dihydro-indol-3-ylidenemethyl)-1H-pyrrol-3-yl]-propionic acid made using different proportions of components and the active pharmaceutical ingredient, with respect to their in vitro dissolution performance, as capsule dosage form. A total of 16 formulations were manufactured at 10 g scale each. These are listed in Table 9. Each formulation was tested for a period of 45 minutes.

TABLE 9

Composition of Granulations (formulation)

| | Amount of excipient in granulations (gms) | | | | | | | | |
|---|---|---|---|---|---|---|---|---|---|
| Ingredients | 1 | 2 | 3 | 4 | 5 | 6 | 7 | 8 | 9 |
| Compound III | 2 | 2 | 2 | 2 | 2 | 2 | 2 | 2 | 2 |
| Pregelatinized Starch | 0 | 0 | 0 | 0 | 5.68 | 5.31 | 5.25 | 5.47 | 0 |
| Fast-flo Lactose | 5.68 | 5.31 | 5.25 | 5.47 | 0 | 0 | 0 | 0 | 6.46 |
| Mannitol | 1.89 | 1.77 | 1.75 | 1.83 | 1.89 | 1.77 | 1.75 | 1.82 | 0.72 |
| Crosscarmellose sodium | 0 | 0.8 | 0.8 | 0 | 0.4 | 0 | 0 | 0.4 | 0 |
| Sodium starch glycolate | 0.4 | 0 | 0 | 0.4 | 0 | 0.8 | 0.8 | 0 | 0.8 |
| Sodium lauryl sulfate | 0 | 0.1 | 0 | 0.1 | 0 | 0.1 | 0 | 0.1 | 0 |
| Magnesium stearate | 0.025 | 0.025 | 0.2 | 0.2 | 0.025 | 0.025 | 0.2 | 0.2 | 0.025 |
| Total Blend | 10 | 10 | 10 | 10 | 10 | 10 | 10 | 10 | 10 |

| | Amount of excipient in granulations (gms) | | | | | | |
|---|---|---|---|---|---|---|---|
| Ingredients | 10 | 11 | 12 | 13 | 14 | 15 | 16 |
| Compound III | 2 | 2 | 2 | 2 | 2 | 2 | 2 |
| Pregelatinized Starch | 0 | 0 | 0 | 6.45 | 6.73 | 6.66 | 6.21 |
| Fast-flo Lactose | 6.73 | 6.66 | 6.21 | 0 | 0 | 0 | 0 |
| Mannitol | 0.75 | 0.74 | 0.69 | 0.72 | 0.75 | 0.74 | 0.69 |
| Crosscarmellose sodium | 0.4 | 0.4 | 0 | 0.8 | 0 | 0 | 0.8 |
| Sodium starch glycolate | 0 | 0 | 0.8 | 0 | 0.4 | 0.4 | 0 |
| Sodium lauryl sulfate | 0.1 | 0 | 0.1 | 0 | 0.1 | 0 | 0.1 |
| Magnesium stearate | 0.025 | 0.2 | 0.2 | 0.025 | 0.025 | 0.2 | 0.2 |
| Total Blend | 10 | 10 | 10 | 10 | 10 | 10 | 10 |

Based on the in-vitro dissolution performance of these granulations, the preferred 4 were identified and these are listed in Table 11. The four preferred dormulations listed in Table 11 were evaluated for stability. These formulations can be encapsulated in different size capsules (e.g., 0, 1, 2, 3 or 4) or tabletted at different strengths.

TABLE 11

Clinical Capsule Formulation Candidates

| Excipients | Amount of excipient in granulations (% w/w) | | | |
|---|---|---|---|---|
| | $F_5$ (Dry) | $F_6$ (Dry) | $F_7$ (Dry) | $F_8$ (Wet) |
| Compound III[1] | 28.0 | 28.0 | 28.0 | 28.0 |
| Pregelatinized Starch[2] | 0 | 60.0 | 0 | 30.0 |
| Fast-flo Lactose[2] | 65.5 | 0 | 33.5 | 0 |
| Lactose monohydrate regular grade[2] | 0 | 0 | 0 | 33.5 |
| Mannitol[2] | 0 | 6.0 | 0 | 0 |
| Microcrystalline cellulose[2] | 0 | 0 | 32.0 | 0 |
| Polyvinylpyroolidone[3] | 0 | 0 | 0 | 2.0 |
| Crosscarmellose sodium[4] | 4.0 | 4.0 | 4.0 | 4.0 |
| Sodium lauryl sulfate[5] | 1.0 | 1.0 | 0 | 1.0 |
| Cetylpyridinium chloride[3] | 0 | 0 | 1.0 | 0 |
| Magnesium stearate[6] | 1.0 | 0.5 | 1.0 | 1.0 |
| Colloidal silcon dioxide[7] | 0.5 | 0.5 | 0.5 | 0.5 |
| Total Blend | 100 | 100 | 100 | 100 |

Note:
[1] active ingredient;
[2] diluent;
[3] binder;
[4] disintegrant;
[5] wetting agent;
[6] lubricant;
[7] flow enhancer The data suggest that formulations according to the present invention have improved stability and have increased bioavailability. The in vivo data suggest that the formulations are effective in treating PK related disorders such as tumor growth.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments and are exemplary and are not intended as limitations on the scope of the invention. Changes therein and other uses will occur to those skilled in the art which are encompassed within the spirit of the invention and are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. A formulation suitable for parenteral or oral administration, said formulation comprising an ionizable substituted indolinone of Formula (I):

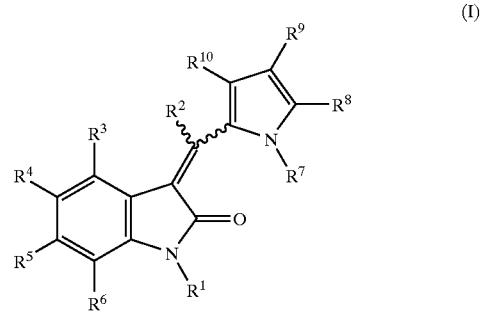

wherein
R$^1$ is selected from the group consisting of hydrogen, alkyl, alkenyl, alkynyl, cycloalkyl, aryl, hydroxy, alkoxy, C-carboxy, O-carboxy, acetyl, C-amido, C-thioamido, sulfonyl and trihalomethanesulfonyl;

R$^2$ is selected from the group consisting of hydrogen, halo, alkyl, cycloalkyl, aryl, heteroaryl and heteroalicyclic;

R$^3$, R$^4$, R$^5$ and R$^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —NR$^{11}$R$^{12}$;

R$^{11}$ and R$^{12}$ are independently selected from the group consisting of hydrogen, alkyl, cycloalkyl, aryl, heteroaryl, carbonyl, acetyl, sulfonyl, trifluoromethanesulfonyl and, combined, a five- or six-member heteroalicyclic ring;

R$^3$ and R$^4$, R$^4$ and R$^5$, or R$^5$ and R$^6$ may combine to form a six-member aryl ring, a methylenedioxy group or an ethylenedioxy group;

R$^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl;

R$^9$ is -(alk$_1$)Z, wherein Alk$_1$ is selected from the group consisting of alkyl, alkenyl or alkynyl, and Z is a polar group;

R⁸ and R¹⁰ are independently selected from hydrogen and unsubstituted lower alkyl;
one or more polyoxyhydrocarbyl compounds; and
a pharmaceutically acceptable carrier therefor;
wherein said ionizable substituted indolinone is solubilized by combining said indolinone with a molar equivalent of a base solution or an acid solution.

2. The formulation of claim 1, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

3. The formulation of claim 1, wherein said formulation is suitable for parenteral administration.

4. The formulation of claim 3, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

5. The formulation of claim 1, wherein each of said one or more polyoxyhydrocarbyl compounds is independently selected from the group consisting of water soluble carbohydrates, water soluble carbohydrate derivatives, water soluble polypeptides, water soluble polymers, water soluble mixed oxyalkylene polymers, the polymeric forms of ethylene glycol, and combinations thereof.

6. The formulation of claim 1, wherein each of said one or more polyoxyhydrocarbyl compounds is independently selected from the group consisting of polyethylene glycol 300, polyethylene glycol 400, propyleneglycol, glycerin, and combinations thereof.

7. The formulation of claim 1, wherein said base solution is selected from the group consisting of sodium hydroxide, ammonium hydroxide, triethylamine, ethylenediamine, N-methyl-D-glucamine, choline, and triethanolamine.

8. The formulation of claim 1, wherein said acid solution is selected from the group consisting of hydrochloric acid, sulfuric acid, formic acid, lactic acid, malic acid, succinic acid, acetic acid, methane sulfonic acid, benzene sulfonic acid, and phosphoric acid.

9. The formulation of claim 1, wherein said pharmaceutically acceptable carrier further comprises one or more buffers.

10. The formulation of claim 9, wherein each of said one or more buffers is independently selected from the group consisting of acetate, citrate, phosphoric acid buffer, ascorbate, hydrochloric acid buffer, Tris-HCl buffer, sodium phosphate, sodium carbonate, sodium hydroxide, flutamate, glycine, and Tris base buffers.

11. The formulation of claim 9, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

12. The formulation of claim 1, wherein said pharmaceutically acceptable carrier further comprises one or more pharmaceutically acceptable surfactants.

13. The formulation of claim 12, wherein each of said one or more pharmaceutically acceptable surfactants is independently selected from the group consisting of pharmaceutically acceptable non-ionic surfactants and pharmaceutically acceptable anionic surfactants.

14. The formulation of claim 12, wherein each of said one or more pharmaceutically acceptable surfactants is a non-ionic surfactant independently selected from the group consisting of polyoxyethylenepolypropylene glycols, polyoxyethylene castor oil derivatives, polyoxyethyleneglycerol oxystearate.

15. The formulation of claim 12, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

16. The formulation of claim 1, wherein said pharmaceutically acceptable carrier further comprises one or more pharmaceutically acceptable preservatives.

17. The formulation of claim 16, wherein each of said one or more pharmaceutically acceptable preservatives is independently selected from the group consisting of benzyl alcohol, methyl paraben, ethyl paraben, and phenol.

18. The formulation of claim 16, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

19. The formulation of claim 1, wherein said pharmaceutically acceptable carrier further comprises one or more antioxidants.

20. The formulation of claim 19, wherein each of said one or more antioxidants is independently selected from the group consisting of sodium meta-bisulfite, EDTA, ascorbic acid, and benzyl alcohol.

21. The formulation of claim 19, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

22. The formulation of claim 1, wherein said pharmaceutically acceptable carrier further comprises one or more pharmaceutically acceptable alcohols.

23. The formulation of claim 22, wherein each of said one or more pharmaceutically acceptable alcohols is independently selected from the group consisting of ethanol, benzyl alcohol, propylene glycol, 2-(2-ethoxyethoxy)ethanol, and glycerol.

24. The formulation of claim 22, wherein said pharmaceutically acceptable carrier further comprises an amount of pharmaceutically acceptable aqueous solution effective to prevent hemolysis on parenteral administration to a patient in need thereof.

25. The formulation of claim 22, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

26. The formulation of claim 1, wherein said pharmaceutically acceptable carrier further comprises one or more pharmaceutically acceptable oils.

27. The formulation of claim 26, wherein each of said one or more pharmaceutically acceptable oils is independently selected from the group consisting of mineral oils, vegetable oils, fractionated coconut oils, sesame oil, propyleneglycol monolaurate, and mixed triglycerides with caprylic acid and capric acid.

28. The formulation of claim 26, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

29. The formulation of claim 1, wherein said formulation is suitable for oral administration.

30. The formulation of claim 29, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

31. The formulation of claim 29, wherein each of said one or more polyoxyhydrocarbyl compounds is independently selected from the group consisting of water soluble carbohydrates, water soluble carbohydrate derivatives, water soluble polypeptides, water soluble polymers, water soluble mixed oxyalkylene polymers, and the polymeric forms of ethylene glycol.

32. The formulation of claim 29, wherein said pharmaceutically acceptable carrier comprises one or more polyglycolized lipids.

33. The formulation of claim 32, wherein each of said one or more polyglycolized lipids is independently selected from the group consisting of monoglycerides, diglycerides, triglycerides, polyethyleneglycol monoesters, and polyethyleneglycol diesters.

34. The formulation of claim 32, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

35. The formulation of claim 29, wherein said pharmaceutically acceptable carrier comprises one or more pharmaceutically acceptable surfactants.

36. The formulation of claim 35, wherein each of said one or more pharmaceutically acceptable surfactants is independently selected from the group consisting of non-ionic surfactants and pharmaceutically acceptable anionic surfactants.

37. The formulation of claim 35, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

38. The formulation of claim 29, wherein said pharmaceutically acceptable carrier comprises one or more pharmaceutically acceptable granulating agents.

39. The formulation of claim 38, wherein each of said pharmaceutically acceptable granulating agents is selected from the group consisting of silicon dioxide, microcrystalline cellulose, starch, calcium carbonate, pectin, crospovidone, water, alcohol and polyplasdone or a combination of any of the proceeding.

40. The formulation of claim 38, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

41. The formulation of claim 29, wherein said pharmaceutically acceptable carrier comprises two or more of the members of the group consisting of one or more polyoxyhydrocarbyl compounds, one or more polyglycolized lipids, one or more sufactants, and one or more granulizing agents.

42. The formulation of claim 41, wherein said pharmaceutically acceptable carrier comprises one or more polyoxyhydrocarbyl compounds, one or more polyglycolized lipids, and one or more surfactants.

43. The formulation of claim 29, wherein said formulation is solid, and wherein said pharmaceutically acceptable carriers comprise one or more pharmaceutically acceptable diluents, one or more pharmaceutically acceptable binders, one or more pharmaceutically acceptable disintegrants, one or more pharmaceutically acceptable surfactants, one or more pharmaceutically acceptable lubricants, and one or more pharmaceutically acceptable flow enhancers.

44. The formulation of claim 43, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

45. The formulation of claim 43, wherein each of said one or more pharmaceutically acceptable diluents is selected from the group consisting of pregelatinized starch, lactose monohydrate, lactose, monohydrate regular grade, mannitol, calcium phosphate and microcrystalline cellulose.

46. The formulation of claim 43, wherein each of said one or more pharmaceutically acceptable binders is selected from the group consisting of polyvinylpyrrolidone, hydroxypropylmethyl cellulose, hydroxypropylcellulose and starch.

47. The formulation of claim 43, wherein each of said one or more pharmaceutically acceptable disintegrants is selected from the group consisting of crosscarmellose sdoium, sodium starch glycolate, gospovidone, and starch.

48. The formulation of claim 43, wherein each of said one or more pharmaceutically acceptable surfactants is selected from the group consisting of sodium lauryl sulfate, polysorbate and cetylpyridinium chloride.

49. The formulation of claim 43, wherein each of said one or more pharmaceutically acceptable lubricants is selected from the group consisting of magnesium stearate, sodium stearyl fumarate, glyceryl behenate and stearic acid.

50. The formulation of claim 43, wherein each of said one or more pharmaceutically acceptable flow enhancers is selected from the group consisting of colloidal silicon dioxide and talc.

51. The formulation of claim 29, wherein said formulation is a solution, and wherein said pharmaceutically acceptable carrier comprises one or more polyoxyhydrocarbyl compounds, one or more surfactants, and one or more buffers.

52. The formulation of claim 51, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

53. The formulation of claim 51, wherein said polyoxyhydrocarbyl compound is selected from the group consisting of water soluble carbohydrates, water soluble carbohydrate derivatives, water soluble polypeptides, water soluble polymers, water soluble mixed oxyalkylene polymers, the polymeric forms of ethylene glycol, and combinations thereof.

54. The formulation of claim 51, wherein said surfactant is selected from the group consisting of pharmaceutically acceptable non-ionic surfactants and pharmaceutically acceptable anionic surfactants.

55. The formulation of claim 51, wherein said buffer is selected from the group consisting of acetate, citrate, phosphoric acid buffer, ascorbate, hydrochloric acid buffer, Tris-HCl buffer, sodium phosphate, sodium carbonate, sodium hydroxide, glutamate, glycine, and Tris base buffers.

56. The formulation of claim 29, wherein said formulation is an aqueous suspension, and wherein said pharmaceutically acceptable carrier comprises a suspending agent and a surfactant.

57. The formulation of claim 56, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

58. The formulation of claim 56, wherein said suspending agent is selected from the group consisting of carboxymethylcellulose, hydroxypropylmethylcellulose, povidone and starch.

59. The formulation of claim 56, wherein said surfactant is selected from the group consisting of pharmaceutically acceptable non-ionic surfactants and pharmaceutically acceptable anionic surfactants.

60. The formulation of claim 29, wherein said pharmaceutically acceptable carrier comprises one or more pharmaceutically acceptable surfactants and one or more pharmaceutically acceptable oils.

61. The formulation of claim 60, wherein said ionizable substituted indolinone is 3-[2,4-dimethyl-5-(2-oxo-1,2-dihydro-indol-3-ylidenemethyl)-1H-pyrrol-3-yl]-propionic acid or an analog thereof.

62. The formulation of claim 61, wherein said pharmaceutically acceptable surfactant comprises an ethylene oxide copolymer and said pharmaceutically acceptable oil comprises sesame oil.

63. The formulation of claim 62, wherein said ionizable substituted indolinone is present in a concentration selected from the range of about 50 mg/gm to about 750 mg/gm.

64. The formulation of claim 62, wherein said ionizable substituted indolinone is present in a concentration selected from the range of about 50 mg/gm to about 500 mg/gm.

65. The formulation of claim 62, wherein said ionizable substituted indolinone is present in a concentration selected from the range of about 50 mg/gm to about 200 mg/gm.

66. A pharmaceutically acceptable composition comprising a hard gelatin capsule whose filing comprises the formulation of claim 29.

67. A pharmaceutically acceptable composition comprising a soft gelatin capsule whose filing comprises the formulation of claim 29.

68. A pharmaceutically acceptable composition comprising a hard gelatin capsule whose filing comprises the formulation of claim 38.

69. A method of preparing a formulation comprising adding to a salt solution, formed in situ by admixing a molar equivalent of a base solution or an acid solution with an ionizable substituted indolinone of Formula (I):

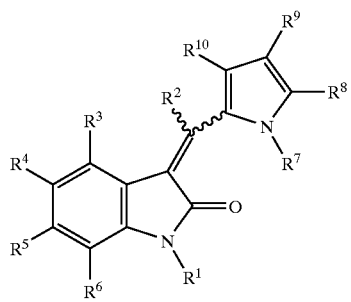

(I)

wherein
$R^1$ is selected from the group consisting of hydrogen, alkyl, alkenyl, alkynyl, cycloalkyl, aryl, hydroxy, alkoxy, C-carboxy, O-carboxy, acetyl, C-amido, C-thioamido, sulfonyl and trihalomethanesulfonyl;
$R^2$ is selected from the group consisting of hydrogen, halo, alkyl, cycloalkyl, aryl, heteroaryl and heteroalicyclic;
$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —$NR^{11}R^{12}$;
$R^{11}$ and $R^{12}$ are independently selected from the group consisting of hydrogen, alkyl, cycloalkyl, aryl, heteroaryl, carbonyl, acetyl, sulfonyl, trifluoromethanesulfonyl and, combined, a five- or six-member heteroalicyclic ring;
$R^3$ and $R^4$, $R^4$ and $R^5$, or $R^5$ and $R^6$ may combine to form a six-member aryl ring, a methylenedioxy group or an ethylenedioxy group;
$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl;
$R^9$ is -(alk$_1$)Z, wherein Alk$_1$ is selected from the group consisting of alkyl, alkenyl or alkynyl, and Z is a polar group;
$R^8$ and $R^{10}$ are independently selected from hydrogen and unsubstituted lower alkyl,
one or more polyoxyhydrocarbyl compounds and/or one or more buffers.

70. The method of claim 69, wherein both said one or more polyoxyhydrocarbyl compounds and said one or more buffers are added to said salt solution.

71. The method of claim 69, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

72. A method of making a formulation suitable for oral administration comprising admixing an ionizable substituted indolinone of Formula (I):

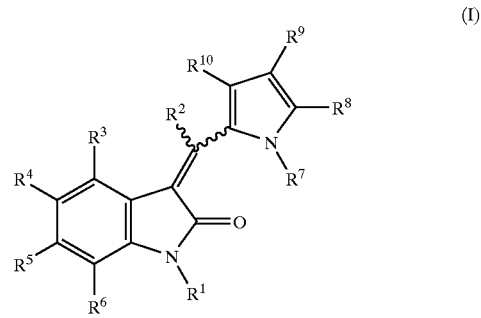

(I)

wherein
$R^1$ is selected from the group consisting of hydrogen, alkyl, alkenyl, alkynyl, cycloalkyl, aryl, hydroxy, alkoxy, C-carboxy, O-carboxy, acetyl, C-amido, C-thioamido, sulfonyl and trihalomethanesulfonyl;
$R^2$ is selected from the group consisting of hydrogen, halo, alkyl, cycloalkyl, aryl, heteroaryl and heteroalicyclic;
$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethane-sulfonamido, carbonyl, C-carboxy, O-carboxy, C-amido, N-amido, cyano, nitro, halo, O-carbamyl, N-carbamyl, O-thiocarbamyl, N-thiocarbamyl, amino and —$NR^{11}R^{12}$;

$R^{11}$ and $R^{12}$ are independently selected from the group consisting of hydrogen, alkyl, cycloalkyl, aryl, heteroaryl, carbonyl, acetyl, sulfonyl, trifluoromethanesulfonyl and, combined, a five- or six-member heteroalicyclic ring;

$R^3$ and $R^4$, $R^4$ and $R^5$, or $R^5$ and $R^6$ may combine to form a six-member aryl ring, a methylenedioxy group or an ethylenedioxy group;

$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl;

$R^9$ is -(alk$_1$)Z, wherein Alk$_1$ is selected from the group consisting of alkyl, alkenyl or alkynyl, and Z is a polar group;

$R^8$ and $R^{10}$ are independently selected from hydrogen and unsubstituted lower alkyl;

one or more pharmaceutically acceptable surfactants; and one or more pharmaceutically acceptable oils.

73. The method of claim 72, wherein said ionizable substituted indolinone is 3-[2,4-dimethyl-5-(2-oxo-1,2-dihydro-indol-3-ylidenemethyl)-1H-pyrrol-3-yl]-propionic acid, or a pharmaceutically acceptable salt, prodrug, derivative, or analog thereof.

* * * * *

UNITED STATES PATENT AND TRADEMARK OFFICE
CERTIFICATE OF CORRECTION

PATENT NO. : 6,878,733 B1 Page 1 of 1
APPLICATION NO. : 09/716332
DATED : April 12, 2005
INVENTOR(S) : Shenoy et al.

It is certified that error appears in the above-identified patent and that said Letters Patent is hereby corrected as shown below:

On the Title page,

Item [*] Notice and item 45: Subject to any disclaimer, the term of this patent is extended or adjusted under 35 USC 154(b) by (295) days Delete the phrase "by 295" and insert -- by 415 days--

Signed and Sealed this

Twenty-seventh Day of November, 2007

JON W. DUDAS
*Director of the United States Patent and Trademark Office*